United States Patent [19]
Katz et al.

[11] Patent Number: 5,824,513
[45] Date of Patent: Oct. 20, 1998

[54] RECOMBINANT DNA METHOD FOR PRODUCING ERYTHROMYCIN ANALOGS

[75] Inventors: Leonard Katz, Waukegan; Stefano Donadio; James B. McAlpine, both of Libertyville, all of Ill.

[73] Assignee: Abbott Laboratories, Abbott Park, Ill.

[21] Appl. No.: 642,734

[22] Filed: Jan. 17, 1991

[51] Int. Cl.⁶ .................. C12P 19/62; A61N 31/335; C12N 15/52; C12N 15/76
[52] U.S. Cl. .................. 435/76; 435/694; 435/172.3; 435/252.35; 435/320.1; 435/10; 435/29; 435/47; 435/60; 435/75; 514/29; 536/23.2
[58] Field of Search .................. 435/69.1, 252.35, 435/172.3, 320.1, 76, 29; 536/23.2; 514/29

[56] References Cited

U.S. PATENT DOCUMENTS

| | | | |
|---|---|---|---|
| 4,874,748 | 10/1989 | Katz et al. | 514/29 |
| 4,935,340 | 6/1990 | Baltz et al. | 435/6 |
| 5,081,023 | 1/1992 | Yaginuma et al. | 435/76 |
| 5,087,563 | 2/1992 | Beremand et al. | 435/69.7 |
| 5,110,728 | 5/1992 | Kridl et al. | 435/64.1 |
| 5,141,926 | 8/1992 | Weber et al. | 514/29 |
| 5,252,474 | 10/1993 | Gewain et al. | 435/172.3 |

FOREIGN PATENT DOCUMENTS 238 323  3/1987  European Pat. Off. .

OTHER PUBLICATIONS

*Nature*, vol. 348(8), pp. 176–178 (1990), Cortes, et al.
*Gene*, vol. 90, pp. 21–29 (1990), Tuan, et al.
*Antimicrobial Agents and Chemotherapy* vol. 34 (8), pp. 1535–1541 (1990), Huber, et al.
*Molecular Genetics of Polyketides and its Comparison to Fatty Acid Biosynthesis*, vol. 24, pp. 37–66 (1990), Hopwood, et al.
*The EMBO Journal*, vol. 8(9), pp. 2727–2736 (1989), Bibb, et al.
*Journal of Bacteriology*, vol. 171(11), pp. 5872–5881 (1989), Vara et al.
*Molecular Microbiology*, vol. 3(10), pp. 1405–1414 (1989), Dhillon, et al.
*The EMBO Journal*, vol. 8(9), pp. 2717–2725 (1989), Sherman, et al.
*Antimicrobial Agents and Chemotherapy* vol. 33(9), pp. 1413–1418 1989, Kirst, et al.
*Genetics and Molecular Biology of Industrial Microorganism*, pp. 53–59 (1989), Donadio, et al.

(List continued on next page.)

*Primary Examiner*—Robert A. Wax
*Assistant Examiner*—William W. Moore
*Attorney, Agent, or Firm*—Andreas M. Danckers; Dianne Casuto

[57] ABSTRACT

A method to produce novel polyketide structures by designing and introducing specified changes in the DNA governing the synthesis of the polyketide is disclosed. The biosynthesis of specific polyketide analogs is accomplished by genetic manipulation of a polyketide-producing microorganism by isolating a polyketide biosynthetic gene-containing DNA sequence, identifying enzymatic activities associated within the DNA sequence, introducing one or more specified changes into the DNA sequence which codes for one of the enzymatic activities which results in an altered DNA sequence, introducing the altered DNA sequence into the polyketide-producing microorganism to replace the original sequence, growing a culture of the altered microorganism under conditions suitable for the formation of the specific polyketide analog, and isolating the specific polyketide analog from the culture. The method is most useful when the segment of the chromosome modified is involved in an enzymatic activity associated with polyketide biosynthesis, particularly for manipulating polyketide synthase genes from Saccarharopolyspora or Streptomyces.

28 Claims, 93 Drawing Sheets

OTHER PUBLICATIONS

*J. Chem. Soc. Chem. Commun.* 943–945 (1988), Kinoshita, et al.
*Antimicrobial Agents and Chemotherapy*, vol. 32(10), pp. 1472–1476 (1988), Tomich, P.K.
*Bio/technology*, vol. 4, pp. 229–232 (1986), Stanzak, et al.
D.A. Hopwood, et al., "Production of 'Hybrid' Antibiotics by Genetic Engineering", Nature, vol. 314, issued 18 Apr. 1985, pp. 642–644.

F. Malpartida, et al, "Homology Between Streptomyces Genes Coding for Synthesis of Different Polyketides Used to Clone Antibiotic Biosynthesis Genes", Nature, vol. 325, issued 26 Feb. 1987, pp. 818–821.
J.Mark Weber, et al, "Genetic Analysis of Erythromycin Production in Streptomyces Erythreus", Journal of Bacteriology, vol. 164, No. 1, issued Oct. 1985, pp. 425–433.
J.Mark Weber, et al, "Organization of a Cluster of Erythromycin Genes in Saccaropolyspora Erythraea", vol. 172, No. 5, issued May 1990, pp. 2372–2383.

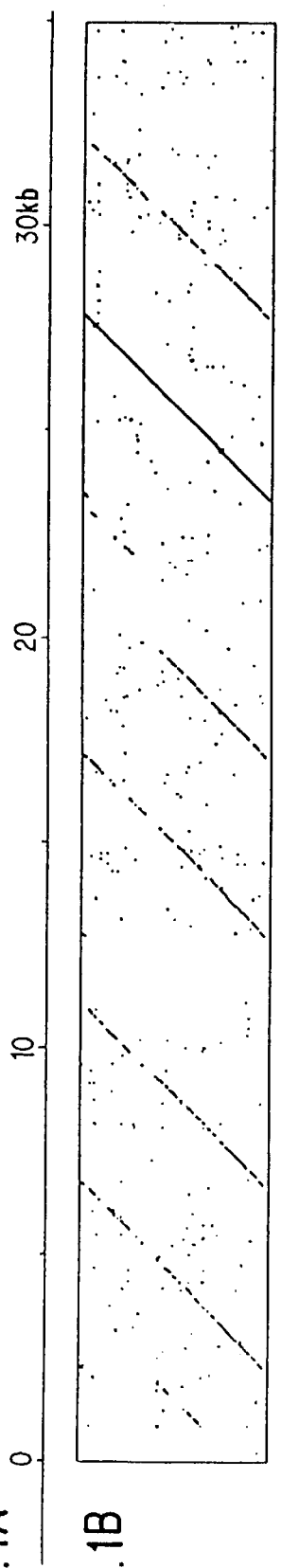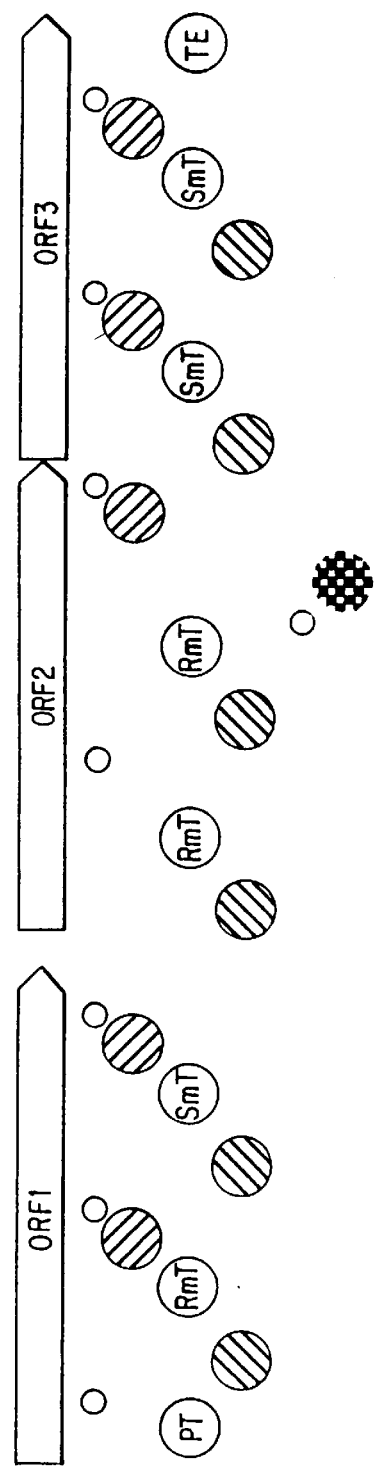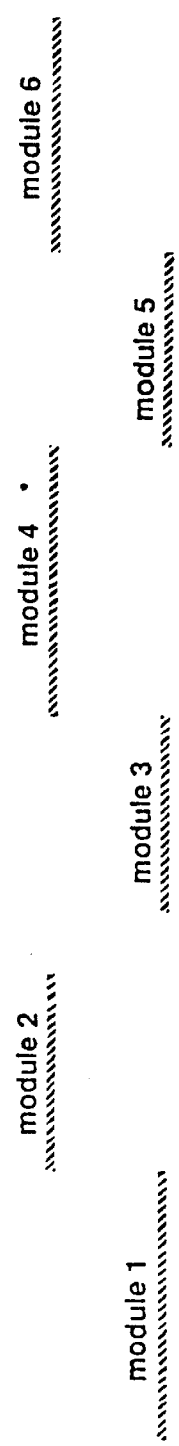
FIG.1A FIG.1B FIG.1C FIG.1D

FIG. 2-1

```
  1   GTCGACCTGCGGCGATCGTGCAGCGGCCGACGAGTCGTGCATCAGGCCGACGTTGACC    60
      ----------+---------+---------+---------+---------+---------+

61   CGCTCGGCTTCCGGGTCGGAGGTGCCGCTGCCCAGGTGGAACCCCGCTGCCTGCGTGCGCC   120
      ----------+---------+---------+---------+---------+---------+

121   ACCAGGTGCACGATCACGTCGGGCGTCCTCGACCTCGCGCGGCGGCCCCGGTTCCAGC    180
      ----------+---------+---------+---------+---------+---------+

181   AGGTCGGCGCGCAGGTCCTCGACCTCCCGCGGCGGCGGGACCGGGCGGGCGCTCCGCCG    240
      ----------+---------+---------+---------+---------+---------+

241   CGGGACACCGGCGCAGCCGGACCGGGTCGGCGCAGCTCGCGCAGAACCGCGCTCCCG    300
      ----------+---------+---------+---------+---------+---------+

301   ACGAAGCCGGAAGCGCCCAGAAGGGTGATCAATTGACGCGGGAATCACTGATCCCATTC    360
      ----------+---------+---------+---------+---------+---------+

361   ACCGGAGCATTGCTCGCTTTCCAGGTCGGTGCTACGGGGCGAAATTCAAAGAATCCCC    420
      ----------+---------+---------+---------+---------+---------+

421   AGCGCGATGTGCGGCAACCCGTCACTGGGCCACCACAGTAGCCGCGTTGATCTTG    480
      ----------+---------+---------+---------+---------+---------+

481   TCAACATGCAGATGTTCACAGGTTCGTTGGCTCGACGAGGCGATGTCAACCTCTTGATCC   540
      ----------+---------+---------+---------+---------+---------+

541   TTCCTATATTGTTCGCCCATTGCGTGGTCGTCGTGAGTAGGGGACGCGTGGCGGACCTGTC   600
      ----------+---------+---------+---------+---------+---------+
```

```
601  AAAGCTCTCCGACAGTCGGACTGCACAACCTGGGAGGATCGTTCGTCCGTGGCCCTGTC
     ---------+---------+---------+---------+---------+---------+ 660

661  GGGGTGCAATGAATCCGCCTTGCGGCCCGTGCGCGGCCAATTGCGTGCACACATCTCGATCG
     ---------+---------+---------+---------+---------+---------+ 720

721  ATTTCCCGATGCCGGGTGTGTCGAAGGTGTCGGGGCCGCTCGCGCACGAGCAGGCGGA
     ---------+---------+---------+---------+---------+---------+ 780
                          V  S  G  P  R  S  R  T  T  S  R  R  T  -

781  CGCCGGTCCGCATCGGGCGGTCGTCGTCGCCTCCTCCGACCTCCGAGCTGCTCGACGGCC
     ---------+---------+---------+---------+---------+---------+ 840
      P  V  R  I  G  A  V  V  V  A  S  S  T  S  E  L  L  D  G  L  -

841  TGGCCGCCGTCGCCGACGGCCGGCCACGCCTCGGTGGTCCGCGGTGTCCGGGCCGT
     ---------+---------+---------+---------+---------+---------+ 900
      A  A  V  A  D  G  R  P  H  A  S  V  V  R  G  V  A  R  P  S  -

901  CCGGCGCCGGTGGTGTTCGTCTTCCCGGGCCAGGGCGGCAATGGGCCGGGATGGCGGGGCG
     ---------+---------+---------+---------+---------+---------+ 960
      A  P  V  V  F  P  G  Q  G  A  Q  W  A  G  M  A  G  E  -

961  AACTCCTCGGCGAGTCAAGGGTTTCGCCGCGATGGACGCGTGCGCGGGCGTTCG
     ---------+---------+---------+---------+---------+---------+ 1020
```

```
        L  L  G  E  S  R  V  F  A  A  A  M  D  A  C  A  R  A  F  E  -
1021  AGCCCGTGACCGACTGGACGCTGGCGCAGGTCCTGGACTCTCCCGAGCAGTCGCGCCGCG  1080
        P  V  T  D  W  T  L  A  Q  V  L  D  S  P  E  Q  S  R  R  V  -
1081  TCGAGGTCGTCCAGCCCGCCCTGTTCGCGGTGCAGACGTCGCTGGCCGCGCTCTGGCGCT  1140
        E  V  V  Q  P  A  L  F  A  V  Q  T  S  L  A  A  L  W  R  S  -
1141  CCTTCGGGGTGACCCCCGACGCCGTGGTGGGCCACAGCATCGGCGAGCTGGCCGCCGCGC  1200
        F  G  V  T  P  D  A  V  V  G  H  S  I  G  E  L  A  A  A  H  -
1201  ACGTGTGCGGTGCGGCCGACGCCGCGCGCGCCGCGGTCGTGTGGAGCCGCG  1260
        V  C  G  A  A  G  A  A  D  A  A  R  A  A  A  L  W  S  R  E  -
1261  AGATGATTCCGTTGGTGGGCAACGGCGACATGGCAGCCGTCGCTCTCCGCCGACGAGA  1320
        M  I  P  L  V  G  N  G  D  M  A  A  V  A  L  S  A  D  E  I  -
1321  TCGAGCCGGCATCGCCCGGTGGGACGACGACGTGGTGCTGCCGGGTCAACGGTCCGC  1380
```

FIG. 2-4

```
1381  E  P  R  I  A  R  W  D  D  D  V  V  L  A  G  V  N  G  P  R  -
      GCTCGGTTCTGCTGACCGGGTCGGCCCGGAACCGGTCGGCGGGTCCAGGAGCTCTCGG
      ------+---------+---------+---------+---------+---------+  1440

1441  S  V  L  L  T  G  S  P  E  P  V  A  R  R  V  Q  E  L  S  A  -
      CCGAGGGGTCCGCGCACAGGTCATCAATGTGTCGATGGCGCACTCGGCGCAGGTCG
      ------+---------+---------+---------+---------+---------+  1500

1501  E  G  V  R  A  Q  V  I  N  V  S  M  A  A  H  S  A  Q  V  D  -
      ACGACATCGCCGAGGGGATGCGCTCGGCCCTGGCTGTTCGCCGTGGCTCGGAGG
      ------+---------+---------+---------+---------+---------+  1560

1561  D  I  A  E  G  M  R  S  A  L  A  W  E  A  P  G  G  S  E  V  -
      TGCCCTTCTACGCCAGCCTCACCGGAGGTGCGGTCGACACGCGGGAGCTGGTGGCCGACT
      ------+---------+---------+---------+---------+---------+  1620

1621  P  F  Y  A  S  L  T  G  G  A  V  D  T  R  E  L  V  A  D  Y  -
      ACTGGCGCCGCAGCTTCCGGCTGCCGGTTCGACGAGGCGATCCGGTCCGCCCTGG
      ------+---------+---------+---------+---------+---------+  1680

```
1681  AGGTCGGTCCCGGCACGTTCGTGAAGGAGCCCGCACCCGGTGTGGCCGGCGCTCC   1740
       V  G  P  G  T  F  V  E  A  S  P  H  P  V  L  A  A  A  L  Q

1741  AGCAGACGCTCGACGCCGAGGGCTCCTCGGCCGCGGTGGTCCCGGCCGTTCACCGGCCG   1800
       Q  T  L  D  A  E  G  S  S  A  A  V  V  P  T  L  Q  R  G  Q

1801  AGGGCGGCATGCGGCGGTTCCTGCTGGCCGCCGCCCAGGCCTTCACCGGCGGTGGCCG   1860
       G  G  M  R  R  F  L  L  A  A  A  Q  A  F  T  G  G  G  A  V

1861  TCGACTGGACCGCCGCCTACGACGACGTGGGGCCGAACCCGGCGCTCTGCCGGAGTTCGC   1920
       D  W  T  A  A  Y  D  D  V  G  P  N  P  A  L  C  R  S  S  R

1921  GCCGGCCGAGGAGGAAGACGAGCCGGCCGAGTCCGGTCGACTGGAACGCGCCACCGCA   1980
       R  P  R  R  K  T  S  R  P  S  P  A  S  T  G  T  R  H  R  T

1981  CGTGCTGCGAGCGGCTGCTCGCGGTCGTCAACGGCGAGACCGCCGTTGGCGGCCCGCG   2040
       C  C  E  R  L  L  A  V  V  N  G  E  T  A  A  L  A  G  R  E
```

FIG.2-6

```
2041 AAGCCGACGCCGAGGCCCACGTTCCGCGAGCTGGGGCTGGACTCGGTGCTGGCCGCGCAGC 2100
        A  D  A  E  A  T  F  R  E  L  G  L  D  S  V  L  A  A  Q  L

2101 TGCGCGCCAAGGTGAGCGCCGCGATCGGGCGCGAGGTCAACATCGCCCTGCTCTACGACC 2160
        R  A  K  V  S  A  A  I  G  R  E  V  N  I  A  L  L  Y  D  H

2161 ACCCGACTCCGCGCTCGCGGAAGCACTCGCCGCGGGAACCGAGGTCGCACAACGGG 2220
        P  T  P  R  A  L  A  E  A  L  A  A  G  T  E  V  A  Q  R  E

2221 AAACCCGGCGGCGGACCAACGAAGCGGCCCCGGCGAACCGTCGCGGTCGTCGCGATGG 2280
        T  R  A  R  T  N  E  A  A  P  G  E  P  V  A  V  V  A  M  A

2281 CCTGCCGGCTGCCCGGCGTGTGAGCACCCCGGAGGAGTTCTGGGAGCTGCTGTCGGAGG 2340
        C  R  L  P  G  G  V  S  T  P  E  E  F  W  E  L  L  S  E  G

2341 GCCGGCGACGGCGGTCGCGGACCTGCCGACCCGGACCGACTGGGACCTGGACTCGCTGTTCC 2400
```

FIG. 2-7

```
        R   D   A   V   A   G   L   P   T   D   R   G   W   D   L   D   S   L   F   H  -
2401  ACCCCGACCCCACGCGCTCGGGCACCGGCCACCAGCGCGGGCGCGGTTCCTGACCGAGG  2460
      ---------+---------+---------+---------+---------+---------+

P   D   P   T   R   S   G   T   A   H   Q   R   G   G   G   F   L   T   E   A  -
2461  CGACCGCGTTCGACCCGGCCTTCTTCGGCATGTCCCCGCGAGGCGCTGGCCGTCGACC  2520
      ---------+---------+---------+---------+---------+---------+

T   A   F   D   P   A   F   F   G   M   S   P   R   E   A   L   A   V   D   P  -
2521  CGCAGCAGCGGCTCATGCTCGAGCTCTCCTGGGAAGTGCTGGAACGGGCGGGAATCCCGC  2580
      ---------+---------+---------+---------+---------+---------+

Q   Q   R   L   M   L   E   L   S   W   E   V   L   E   R   A   G   I   P   P  -
2581  CGACCTCGTTGCAGGCCTCGCCCACTGGCCTGTTCGTCGGCCTGATCCCGCAGGAGTACG  2640
      ---------+---------+---------+---------+---------+---------+

T   S   L   Q   A   S   P   T   G   V   F   V   G   L   I   P   Q   E   Y   G  -
2641  GCCCGGCTGGCCGAGGGCGGCGAAGGCGTCGAGGGCTACCTGATGACCGGTACGACCA  2700
      ---------+---------+---------+---------+---------+---------+

P   R   L   A   E   G   G   E   G   V   E   G   Y   L   M   T   G   T   T   T  -
2701  CGAGCCGTCGCCTTCCGGCCGCATCGCTCGGCCTACACGCGCTCGGCCTGGAGGGCCCGGCGATCAGCG  2760
      ---------+---------+---------+---------+---------+---------+
```

FIG. 2-8

```
          S   V   A   S   G   R   I   A   Y   T   L   G   L   E   G   P   A   I   S   V   -
       TGGACACCGGCTGTCTCGCTCCTCCGCTCGGTGCACCTGCCGGTGCCAGTCGCTGCCGGC
2761   ------+---------+---------+---------+---------+---------+  2820

D   T   A   C   S   S   S   L   V   A   V   H   L   A   C   Q   S   L   R   R   -
       GCGGCGAGTCGTCGCTGGCGCTGGTCGCGGTGTCACGGTGTGATGCCGACGCCCGGCATGC
2821   ------+---------+---------+---------+---------+---------+  2880

G   E   S   S   L   A   M   A   G   G   V   T   V   M   P   T   P   G   M   L   -
       TGGTGGACTTCAGCCGGATGAACTCGCTGGCCCCGGACGGCCGGTGCAAGGCTTTCTCCG
2881   ------+---------+---------+---------+---------+---------+  2940

V   D   F   S   R   M   N   S   L   A   P   D   G   R   C   K   A   F   S   A   -
       CCGGCGCCAACGGTTTCGGCATGGCCGAGGGCGCCGGGATGCTCCTGCTGGAGCGGCTTT
2941   ------+---------+---------+---------+---------+---------+  3000

G   A   N   G   F   G   M   A   E   G   A   G   M   L   L   L   E   R   L   S   -
       CGGAACGCCCGGCCGCAACGGCCACCCGGTGCTCGCCGTGCTCAGGGGACGGGTCAACT
3001   ------+---------+---------+---------+---------+---------+  3060

D   A   R   R   N   G   H   P   V   L   A   V   L   R   G   T   A   V   N   S   -
       CCGACGGCGAGCAACGGGCTGTCGGCCCAACGGGCGGCCCAGGTGCGGGTCATCC
```

AGCAGGCGCTGGCAGAGTCCGGTCTCGGGCCCCGCCGACATCGACGCCGTCGAGGCGCACG
3121 ---------+---------+---------+---------+---------+---------+ 3180
           Q  A  L  A  E  S  G  L  G  P  A  D  I  D  A  V  E  A  H  G  -

GCACCGGTACCCCGACTCGGCCGGCGCTGTTCGAGGCGTACGGGC
3181 ---------+---------+---------+---------+---------+---------+ 3240
           T  G  T  R  L  G  D  P  I  E  A  R  A  L  F  E  A  Y  G  R  -

GCGACCGCGAGCAGCCGCTGCACCTGGGCTCGGTCAAGTCCAACCTCGGCCACACCCAGG
3241 ---------+---------+---------+---------+---------+---------+ 3300
           D  R  E  Q  P  L  H  L  G  S  V  K  S  N  L  G  H  T  Q  A  -

CGGCCCGCCGGGTGTTGCCGGCGTGATCAAGATGGTGCTGGCGATGCGCGGGCACCCTTC
3301 ---------+---------+---------+---------+---------+---------+ 3360
           A  A  G  V  A  G  V  I  K  M  V  L  A  M  R  A  G  T  L  P  -

CCCGCACTCTGCACGCATCGGAGCGGTCGAAGGAGATCGACTGGTCATCCGGTGCGATCA
3361 ---------+---------+---------+---------+---------+---------+ 3420
           R  T  L  H  A  S  E  R  S  K  E  I  D  W  S  S  G  A  I  S  -
```

FIG. 2-10

```
3421  GCCTGCTCGACGAGCCGGAGCCGTGGCCCGCCGGCGCCGACCGCGCCCGGGCGGGGGTCT
      ---------+---------+---------+---------+---------+---------+  3480
         L  L  D  E  P  E  P  W  P  A  G  A  R  P  R  R  A  G  V  S  -

3481  CGTCGTTCGGCATCAGCGGCACCAACGCGCACGCCATCATCGAGGAAGCTCCGCAGGTCG
      ---------+---------+---------+---------+---------+---------+  3540
         S  F  G  I  S  G  T  N  A  H  A  I  I  E  E  A  P  Q  V  V  -

3541  TCGAAGGCGAGCGGGTCGAGGCCGGCGACGTCGTGGCCCCTGGGTGCTTTCGGCGAGCA
      ---------+---------+---------+---------+---------+---------+  3600
         E  G  E  R  V  E  A  G  D  V  V  A  P  W  V  L  S  A  S  S  -

3601  GCGCGGAAGGTCTGCGCGCCCAGGCGGCCGCGCGACTGGCCGCGCACCTGCGCGAGCACCCCG
      ---------+---------+---------+---------+---------+---------+  3660
         A  E  G  L  R  A  Q  A  A  R  L  A  A  H  L  R  E  H  P  G  -

3661  GTCAGGACCCGCGCGACATCGCGTACTCGCTCGGCGACGGGCCGCGCTGCCCCACC
      ---------+---------+---------+---------+---------+---------+  3720
         Q  D  P  R  D  I  A  Y  S  L  A  T  G  R  A  A  L  P  H  R  -

3721  GCGCCGGCCTTCGCCCCGTCGACGAGTCCGCGGCGCTGCGCGTGCTCGACGGTCTCGGA
      ---------+---------+---------+---------+---------+---------+  3780
         A  A  F  A  P  V  D  E  S  A  A  L  R  V  L  D  G  L  A  T  -
```

FIG. 2-11

```
3781 CGGGAAACGCCGACGGTGCCGCCGTTGGAACGAGCCGGGCGCAGCAGCGCGCCCGTCTTCG 3840
      G  N  A  D  G  A  A  V  G  T  S  R  A  Q  Q  R  A  V  F  V  -

3841 TCTTCCCGGGCAGGGTTGGCAGTGGGCGGGCATGGCCGTCGACCTGCTCGACACCTCCC   3900
      F  P  G  Q  G  W  Q  W  A  G  M  A  V  D  L  L  D  T  S  P  -

3901 CGGTTTTCGCAGCCGCGTTGCGCGAGTGCGCCGACGCGCTCGAACCGCATCTGGACTTCG   3960
      V  F  A  A  A  L  R  E  C  A  D  A  L  E  P  H  L  D  F  E  -

3961 AGGTGATCCCCGTTCCTGCGCGCGGAAGCCGCCGGGAGCCAGGACGCGGCTGTCGA       4020
      V  I  P  F  L  R  A  E  A  A  R  R  E  Q  D  A  A  L  S  T  -

4021 CCGAGCGCGTGGACGTGGTGCAGCCCGTGATGTTCGCGGTCATGGTCTCGCTGGCGTCGA   4080
      E  R  V  D  V  V  Q  P  V  M  F  A  V  M  V  S  L  A  S  M  -

4081 TGTGGCGAGCCCACGGCGTCGAGCCGGCCGCGGTCATCGGGCACTCCCAGGGGCGAGATCG   4140
      W  R  A  H  G  V  E  P  A  A  V  I  G  H  S  Q  G  E  I  A  -
```

FIG. 2-12

```
       CCGCCGCTGCGTCGCGGGCGCGCTCTCGCTGGACGACGCCGCGGTCGCGCTGC
4141   ------------------------------------------------+  4200
       A  A  C  V  A  G  A  L  S  L  D  D  A  A  R  V  V  A  L  R  -

GCAGCCGCGTCATCGCCACCATGCCCGGAACAAGGGCATGGCCTCGATCGCCGCTCCGG
4201   ------------------------------------------------+  4260
       S  R  V  I  A  T  M  P  G  N  K  G  M  A  S  I  A  A  P  A  -

CCGGGCGAAGTCCGCGCGGCGAATCGGTGACCGCGTCGAGATCGCCGCGTCAACGGTCCGC
4261   ------------------------------------------------+  4320
       G  E  V  R  A  R  I  G  D  R  V  E  I  A  A  V  N  G  P  R  -

GCTCGGTGGTGGTCGCCGGCGACAGCGACGAACTGGACCGGCTGGTCGCTTCCTGCACCA
4321   ------------------------------------------------+  4380
       S  V  V  V  A  G  D  S  D  E  L  D  R  L  V  A  S  C  T  T  -

CCGAGTGCATCCGCGCCAAGCGCCTGGCCGTGGACTACGCGTCGCACTCCTCGCACGTCG
4381   ------------------------------------------------+  4440
       E  C  I  R  A  K  R  L  A  V  D  Y  A  S  H  S  S  H  V  E  -

AGACGATCCGAGACGCACTGCACGCCGAGCTGGGAGAGGACTTCCACCCGCTGCCGGGGT
4441   ------------------------------------------------+  4500
```

FIG. 2-13

```
         T  I  R  D  A  L  H  A  E  L  G  E  D  F  H  P  L  P  G  F  -
       TCGTGCCCTTCTCTCCACCGTCACCGGGCTGGACGCAGCCGGACGAGCTCGACGCCG
4501   ------+---------+---------+---------+---------+---------+  4560

V  P  F  S  T  V  T  G  R  W  T  Q  P  D  E  L  D  A  G  -
       GGTACTGGTACCGGAACCTGCGCCGCCACCGTGCGGTTCGCGGACGCCGTCCGTGCGCTCG
4561   ------+---------+---------+---------+---------+---------+  4620

Y  W  Y  R  N  L  R  R  T  V  R  F  A  D  A  V  R  A  L  A  -
       CCGAGCAGGGATATCGCGACGTTCCTGGAGGTCAGCGCGCACCCCGATCCTCACCGCCGCGA
4621   ------+---------+---------+---------+---------+---------+  4680

E  Q  G  Y  R  T  F  L  E  V  S  A  H  P  I  L  T  A  A  I  -
       TCGAGGAGATCGGGCGACGGATCGGGGCGCCGACCCTCTCCGCCATCCATTCGCTGCGCCGCG
4681   ------+---------+---------+---------+---------+---------+  4740

E  E  I  G  D  G  S  G  A  D  L  S  A  I  H  S  L  R  R  G  -
       GTGACGGGCCAGCCTCGGCGGACTTCGGCGAAGCGCTCTCCCGGCGTTCGCCGGTGTCG
4741   ------+---------+---------+---------+---------+---------+  4800

D  G  S  L  A  D  F  G  E  A  L  S  R  A  F  A  A  G  V  A  -
       CGGTGGACTGGGAGTCGGTGCACCTGGGCACCGGAGCACGCCGGGTGCCCTTGCCCACCT
4801   ------+---------+---------+---------+---------+---------+  4860
```

```
             V  D  W  E  S  V  H  L  G  T  G  A  R  R  V  P  L  P  T  Y  -
       ACCCGTTCCAGCGCGAGCGCGTCTGGCTCGAACCGAAGCCGGTGGCGCCGGTCCACCG
4861   ------+---------+---------+---------+---------+---------+ 4920

P  F  Q  R  E  R  V  W  L  E  P  K  P  V  A  R  R  S  T  E  -
       AGGTCGACGAGGTTCCGCGCTGCGCTACCGCATCGAGTGGCGCCCACCGGTGCCGGTG
4921   ------+---------+---------+---------+---------+---------+ 4980

V  D  E  V  S  A  L  R  Y  R  I  E  W  R  P  T  G  A  G  E  -
       AACCCGCCCGGCTCGACGGCCACCTGGTGGCCGAAGTACGCCGGAACCGCGACGAGA
4981   ------+---------+---------+---------+---------+---------+ 5040

P  A  R  L  D  G  T  W  L  V  A  K  Y  A  G  T  A  D  E  T  -
       CGAGCACCGGCGGCTCGGGGAGCCCCTGGAGTCGGCGCGGGGCCGGTCCGGAACTGGTCG
5041   ------+---------+---------+---------+---------+---------+ 5100

S  T  A  A  R  E  A  L  E  S  A  G  A  R  V  R  E  L  V  V  -
       TGGACGCCCGCTGCGCTCGGGACGGAGAACTCGCGGAGCGGCTTCGTTCGGCGAGGTGG
5101   ------+---------+---------+---------+---------+---------+ 5160

```
5161  CAGGAGTGCTGTCCCTGCTCGCGGTGGACGAAGCGGAGCCGGAGGAGGCGCCGCTCGCGC
      ------+---------+---------+---------+---------+---------+  5220
       G  V  L  S  L  L  A  V  D  E  A  E  P  E  E  A  P  L  A  L  -

5221  TGGCTTCGCTGGGGACACGCTCAGCCTCGTGCAGGCGATGGTGTCGGCCGAACTCGGAT
      ------+---------+---------+---------+---------+---------+  5280
       A  S  L  A  D  T  L  S  L  V  Q  A  M  V  S  A  E  L  G  C  -

5281  GTCCGCTGTGACGGTGACGGAAAGCCCGTCGGACGGGCCCGTTCGAACGCGTCCGCA
      ------+---------+---------+---------+---------+---------+  5340
       P  L  W  T  V  T  E  S  A  V  A  T  G  P  F  E  R  V  R  N  -

5341  ACGCCGCCCACGGCGCCCTGTGGGGCGTCGGGGTCATCGCGCTGGAGAACCCCGCCG
      ------+---------+---------+---------+---------+---------+  5400
       A  A  H  G  A  L  W  G  V  G  R  V  I  A  L  E  N  P  A  V  -

5401  TGTGGGGCGGCCTGGTCGACGTGCCCGCGGGGTCGGTCGCCGAGCTGGCCCGGCACCTCG
      ------+---------+---------+---------+---------+---------+  5460
       W  G  G  L  V  D  V  P  A  G  S  V  A  E  L  A  R  H  L  A  -

5461  CGGCCGGTCGTGTCCGGGGCGCCGGTGAGGACCAGCTCGCGCTGCGCCGACGGGGTGT
      ------+---------+---------+---------+---------+---------+  5520
       A  V  V  S  G  G  A  G  E  D  Q  L  A  L  R  A  D  G  V  Y  -
```

```
5521 ACGGACGCCGGTGGGTGCGCGGGCGGCCCCGGCGACCGATGACGAGTGGAAACCCACCG -------+---------+---------+---------+---------+---------+ 5580
        G  R  R  W  V  R  A  A  A  P  A  T  D  D  E  W  K  P  T  G

5581 GAACCGTGCTGGTCACCGGTGGCACGGGCGGTGTCGGGGCAGATCGCGCGCTGGCTCG -------+---------+---------+---------+---------+---------+ 5640
        T  V  L  V  T  G  G  T  G  G  V  G  G  Q  I  A  R  W  L  A

5641 CCCGGCGGGCGCGCCCCACCTGCTGCTGGTGAGCCGCAGCGGGCCGGACGCGGACGGCG -------+---------+---------+---------+---------+---------+ 5700
        R  R  G  A  P  H  L  L  L  V  S  R  S  G  P  D  A  D  G  A

5701 CCGGGCGAACTGGTCGCCGAGCTCGAGGCGCTGGGCGCCCGGACGACCGTCGCGGCCTGCG -------+---------+---------+---------+---------+---------+ 5760
        G  E  L  V  A  E  L  E  A  L  G  A  R  T  T  V  A  A  C  D

5761 ACGTGACCGACCGCGAGTCGGTTCGCGAGCTGCTCGGCGGCATCGGTGACGACGTCCCGC -------+---------+---------+---------+---------+---------+ 5820
        V  T  D  R  E  S  V  R  E  L  L  G  G  I  G  D  D  V  P  L

5821 TCTCGGCGTGTTCCAGCCGGCCACGCTCGACGACGGCACCGTGGACACCCTCACCG -------+---------+---------+---------+---------+---------+ 5880
```

```
        S  A  V  F  H  A  A  A  T  L  D  D  G  T  V  D  T  L  T  G
     GCGAGGGCATCGAGCGGGGCAAGTCGCGCCAAGGTGCTCGGCGCGCAACCTGCACGAGC
5881 ------+---------+---------+---------+---------+---------+ 5940
        E  R  I  E  R  A  S  R  A  K  V  L  G  A  R  N  L  H  E  L
     TGACGCGCGAGCTGGACCTGACCGCCTTCGTGCTGTTCTCGTCCTTCGCCTCGGCCTTCG
5941 ------+---------+---------+---------+---------+---------+ 6000
        T  R  E  L  D  L  T  A  F  V  L  F  S  S  F  A  S  A  F  G
     GCGCCCCCGGGCTCGGCGGCTACGCGCCCGGCAACGCCTACCTCGACGGCCTCGCCCAGC
6001 ------+---------+---------+---------+---------+---------+ 6060
        A  P  G  L  G  G  Y  A  P  G  N  A  Y  L  D  G  L  A  Q  Q
     AGCGGCGAGCGACGACTCCCCGCGGTGGCCGTGGGGACGTGGGCGGGCAGCG
6061 ------+---------+---------+---------+---------+---------+ 6120
        R  R  S  D  G  L  P  A  T  A  V  A  W  G  T  W  A  G  S  G
     GGATGGCCGAAGGCCGGTGGCCGCTTCCGGCACGGCGTCATCGAGATGCCTC
6121 ------+---------+---------+---------+---------+---------+ 6180
        M  A  E  G  A  V  A  D  R  F  R  R  H  G  V  I  E  M  P  P
     CCGAGACGGCCTGCGGGGCGTTGCAGAACGCGCTGGACCGGCGCTGCCCGATCG
6181 ------+---------+---------+---------+---------+---------+ 6240
```

FIG. 2-17

```
       E  T  A  C  R  A  L  Q  N  A  L  D  R  A  E  V  C  P  I  V  -
      TCATCGACGTCAGGTGGGACCGGTTCCTGCTCGCCTACACCGGCCCAGCGCCCGACCAGGC
6241  ------------+---------+---------+---------+---------+---------+  6300
      AGTAGCTGCAGTCCACCCTGGCCAAGGACGAGGCGGATGTGGCCGGGTCGCGGGCTGGTCCG

I  D  V  R  W  D  R  F  L  L  A  Y  T  A  Q  R  P  T  R  L  -
      TCTTCGACGAGATCGACGACGCGCGGCGCGCCGCTGCGCCGCAGGCGCCGGAACCGCGGGG
6301  ------------+---------+---------+---------+---------+---------+  6360
      AGAAGCTGCTCTAGCTGCTGCGCGCCGCGCGGCGACGCGGCGTCCGCGGCCTTGGCGCCCC

F  D  E  I  D  D  A  R  R  A  A  P  Q  A  P  A  E  P  R  V  -
      TGGGCGGCTGGCCGTCGGCCCGCCGGAGCGCGAGGAAGCGCTGTTCGAGCTCGTGC
6361  ------------+---------+---------+---------+---------+---------+  6420
      ACCCGCCGACCGGCAGCCGGGCGGCCTCGCGCTCCTTCGCGACAAGCTCGAGCACG

G  A  L  A  S  L  P  A  P  E  R  E  E  A  L  F  E  L  V  R  -
      GCTCGCACGCGGCCGCCGTCCTCGGCCACGCCTCGGCCGAGCGGGTGCCCGACCAGG
6421  ------------+---------+---------+---------+---------+---------+  6480
      CGAGCGTGCGCCGGCGGCAGGAGCCGGTGCGGAGCCGGCTCGCCCACGGGCTGGTCC

S  H  A  A  V  L  G  H  A  S  A  E  R  V  P  A  D  Q  A  -
      CCTTCGGGGAACTCGGCGTCGACTCGGCTGTCGGCGCTTGAGCTGCGCAACCGGCTCGGCG
6481  ------------+---------+---------+---------+---------+---------+  6540
      GGAAGCCCTTGAGCCGCAGCTGAGCCGACAGCCGCGAACTCGACGCGTTGGCCGAGCCGC

F  A  E  L  G  V  D  S  L  S  A  L  E  L  R  N  R  L  G  A  -
      CCGGCGACCGGTGTCCGCCGACGACGACCGTCTTCGACCACCCGACGTGCGGGACGC
```

```
6541 ---------+---------+---------+---------+---------+---------+ 6600
      A  T  G  V  R  L  P  T  T  V  F  D  H  P  D  V  R  T  L  -
     TGGGGCGGCGCACCTGGCCGCCGAACTCGGCGGTGCGACCGAGCAGGGCACCGG
6601 ---------+---------+---------+---------+---------+---------+ 6660
      A  A  H  L  A  A  E  L  G  G  A  T  G  A  E  Q  A  A  P  A  -
     CGACCACGGCCCCCGTCGACGAGCCGATCGCGTCGGGCATGGCGTGCCGGCTGCCCG
6661 ---------+---------+---------+---------+---------+---------+ 6720
      T  T  A  P  V  D  E  P  I  A  I  V  G  M  A  C  R  L  P  G  -
     GGGAGGTCGACTCCCCGGAGCGGCTGTGGGAGCTGATCACCTCGGGACGCGACTCCGCGG
6721 ---------+---------+---------+---------+---------+---------+ 6780
      E  V  D  S  P  E  R  L  W  E  L  I  T  S  G  R  D  S  A  A  -
     CGGAGGTCCCCGATGACCGGGGCTGGGTCCCCGACGAGCTGATGGCCTCCGACGCGGCGG
6781 ---------+---------+---------+---------+---------+---------+ 6840
      E  V  P  D  D  R  G  W  V  P  D  E  L  M  A  S  D  A  A  G  -
     GAACCCGCGCCACGGCAACTTCATGGCGGGCGGTGACTTCGACGCGGCGTTCTTCG
6841 ---------+---------+---------+---------+---------+---------+ 6900
      T  R  A  H  G  N  F  M  A  G  A  G  D  F  D  A  A  F  F  G  -
```

```
6901  GGATCTCGCCGCGGAGGCGCTGGCGATGGACCCGCAGCAGCGCCAGGCGCTGGAGACGA
      ---------+---------+---------+---------+---------+---------+  6960
       I  S  P  R  E  A  L  A  M  D  P  Q  Q  R  Q  A  L  E  T  T  -

6961  CGTGGGAGGCGCTGGAAAGCGCGGGCATCCCACCGGAGACGTTGCGCGGCAGCGACACCG
      ---------+---------+---------+---------+---------+---------+  7020
       W  E  A  L  E  S  A  G  I  P  P  E  T  L  R  G  S  D  T  G  -

7021  GCGTGTTCGTCGGCATGTCCCACCAGGGCTACGCGACCGGCCGTCCGCCCGAGGACG
      ---------+---------+---------+---------+---------+---------+  7080
       V  F  V  G  M  S  H  Q  G  Y  A  T  G  R  P  P  E  D  G  -

7081  GCGTCGACGGGTACCTGCTCACCGGCAACACCGCGAGCGTCGGGACGCATCGCCT
      ---------+---------+---------+---------+---------+---------+  7140
       V  D  G  Y  L  L  T  G  N  T  A  S  V  A  S  G  R  I  A  Y  -

7141  ACGTGCTGGGGCTGGAAGGTCCCGCGCTGACGGTGGACACGGCGTGTTCGTCGTCGTTGG
      ---------+---------+---------+---------+---------+---------+  7200
       V  L  G  L  E  G  P  A  L  T  V  D  T  A  C  S  S  S  L  V  -

7201  TGGCGTTGCACACGGCGTGTGGGTTCGTTGCCGTGACGGTGACTGCGGTCTTGCGGTGGCCG
      ---------+---------+---------+---------+---------+---------+  7260
       A  L  H  T  A  C  G  S  L  R  D  G  D  C  G  L  A  V  A  G  -
```

FIG. 2-20

```
7261 GTGGTGTGTCGGTGATGGCGGGTCCGGAGGTGTTCACCGAGTTCTCCCGCCAGGGCGCGC
     ----------+---------+---------+---------+---------+---------+ 7320
        G  V  S  V  M  A  G  P  E  V  F  T  E  F  S  R  Q  G  A  L  -

7321 TCTCGGCCCGGACGGGCCGGTGCAAGCCCTTCTCGGACGAGGCCGACGGATTCGGTCTCGGGG
     ----------+---------+---------+---------+---------+---------+ 7380
        S  P  D  G  R  C  K  P  F  S  D  E  A  D  G  F  G  L  G  E  -

7381 AGGGTTCGGCCGTTCGTCGTGCTCCAGCGGTTGTCCGACGCGGCCAGGGAGGGCCGCCGCG
     ----------+---------+---------+---------+---------+---------+ 7440
        G  S  A  F  V  V  L  Q  R  L  S  D  A  R  R  E  G  R  R  V  -

7441 TGCTCGGGCGTGGTCGCCGGGTCCGGGTGAACCAGGACGGCGAGCAACGGGCTCTCCG
     ----------+---------+---------+---------+---------+---------+ 7500
        L  G  V  V  A  G  S  A  V  N  Q  D  G  A  S  N  G  L  S  A  -

7501 CTCCGAGCGGCGTCGCCGCAGCAGGGTCATCCGCCCGGGCGTGGGCGCGTGCGGGGATCA
     ----------+---------+---------+---------+---------+---------+ 7560
        P  S  G  V  A  Q  Q  R  V  I  R  R  A  W  A  R  A  G  I  T  -

7561 CGGGCGCGGATGTGGCCGTGGTGGAGGCGCATGGGACCGGTACGCGGCTGGGCGATCCGG
     ----------+---------+---------+---------+---------+---------+ 7620
        G  A  D  V  A  V  V  E  A  H  G  T  G  T  R  L  G  D  P  V  -
```

FIG. 2-21

```
7621  TGGAGGGCGTCGGCGTTGCTGGCTACTTACGGCAAGTCCGCGGGTCGTCGGGCCCGGTGC
      ------+---------+---------+---------+---------+---------+ 7680
       E   A   S   A   L   L   A   T   Y   G   K   S   R   G   S   S   G   P   V   L

7681  TGCTGGGTTCGGTGAAGTCGAACATCGGTCACGCGCAGGCGGCCGCGGGTGTCGGGGCG
      ------+---------+---------+---------+---------+---------+ 7740
       L   G   S   V   K   S   N   I   G   H   A   Q   A   A   A   G   V   A   G

7741  TGATCAAGGTGCTGCTCGGCCTGGAACGCGGTGTGGTGCCCCCGATGCTGTGCCGGGGCG
      ------+---------+---------+---------+---------+---------+ 7800
       V   I   K   V   L   L   G   L   E   R   G   V   V   P   P   M   L   C   R   G

7801  AGAGGTCGGGGCCTCATCGACTGGTCCTCCGGCGAGATCGAGCTCGCAGACGGCGTGCGG
      ------+---------+---------+---------+---------+---------+ 7860
       E   R   S   G   L   I   D   W   S   S   G   E   I   E   L   A   D   G   V   R   E

7861  AGTGGTCGCCCGCCGACGGGGTGCGCCGCGCCGGTGTGTCGGCGTTCGGGGTGAGCG
      ------+---------+---------+---------+---------+---------+ 7920
       W   S   P   A   A   D   G   V   R   R   A   G   V   S   A   F   G   V   S   G

7921  GGACGAACGGCACGTGATCATCGCCGAGCCCGGAACCGGAGCCCGTGCCGCAACCGC
      ------+---------+---------+---------+---------+---------+ 7980
```

FIG. 2-22

```
       T  N  A  H  V  I  I  A  E  P  P  E  P  P  V  P  Q  P  R  -
       GACGCATGCTGCCCGGCGACCGGGGTGGTGCCGGTCGTGTCGGCCAGGACCGGGGCGG
7981   ------+---------+---------+---------+---------+---------+ 8040

R  M  L  P  A  T  G  V  V  P  V  V  L  S  A  R  T  G  A  A  -
       CGTTGCGCGGCCAGGCCGGCAGGCTCGCCGACCACTTCGCCGCCATCCCGGATCGCAC
8041   ------+---------+---------+---------+---------+---------+ 8100

L  R  A  Q  A  G  R  L  A  D  H  L  A  A  H  P  G  I  A  P  -
       CGGCCGACGTGAGCTGGACGATGGCGGGCCCCGCCAGCACTTCGAGGAGCGGGCCGCGG
8101   ------+---------+---------+---------+---------+---------+ 8160

A  D  V  S  W  T  M  A  R  A  R  Q  H  F  E  E  R  A  A  V  -
       TGCTCGCCGCCGACACCGCCGAGGCCGTGCACCGGTTGCGCCGTGGCCGACGGCGCGG
8161   ------+---------+---------+---------+---------+---------+ 8220

L  A  A  D  T  A  E  A  V  H  R  L  R  A  V  A  D  G  A  V  -
       TGGTTCCCGGTGTGTTGTCACCGGCAGTGCCTCCGACGGTGGTTCAGTGTTCGTCTTCCCTG
8221   ------+---------+---------+---------+---------+---------+ 8280

V  P  G  V  V  T  G  S  A  S  D  G  G  S  V  F  V  F  P  G  -
       GGCAGGGTGCCCAGTGGGAAGGCATGGCGCGGGAGTTGTTGCCGGTTCCCGTCTTCGCCG
8281   ------+---------+---------+---------+---------+---------+ 8340
```

```
      Q  G  A  Q  W  E  G  M  A  R  E  L  L  P  V  P  V  F  A  E  -
8341  AGTCGATCGCCGAGTGCGATGCGGAGGAGCTGTTGTCGGAGGTGCCGGATTCTCGGTGTCCGAGG  8400

S  I  A  E  C  D  A  V  L  S  E  V  A  G  F  S  V  S  E  V  -
8401  TGCTGGAGCCACGTCCGGACGCGCCGCTGGAGCCCGTCGACGTGGTGCAGCCGGTGC  8460

L  E  P  R  P  D  A  P  S  L  E  R  V  D  V  V  Q  P  V  L  -
8461  TGTTCGGGTGATGGTGTCGCTGGAGCGCTGGCGCTGCGGTGCCGTTCCTTCGG  8520

F  A  V  M  V  S  L  A  R  L  W  R  A  C  G  A  V  P  S  A  -
8521  CCGTCATAGGCACTCGCAGGGTGAGATCGCCGCGGTGGTGGCGGGAGCGTTGTCGC  8580

V  I  G  H  S  Q  G  E  I  A  A  A  V  V  A  G  A  L  S  L  -
8581  TGGAGGACGGCATGCGCGTCGTCGCCCGGTCGAGGGCGTGCGGTGCGGGGCC  8640

E  D  G  M  R  V  V  A  R  R  S  R  A  V  R  A  V  A  G  R  -
```

```
8641  GGGGAGCATGCTCTCGGTGCGCGGCCGCTCCGACGTCGAGAAGCTGCTCGCCGACG
      ---------+---------+---------+---------+---------+---------+  8700
       G  S  M  L  S  V  R  G  G  R  S  D  V  E  K  L  L  A  D  D  -

8701  ACAGCTGGACCGGCAGGCTGGAGGTCGCCGCCGGTCAACGGCCCCGACGCCGTGGTGG
      ---------+---------+---------+---------+---------+---------+  8760
       S  W  T  G  R  L  E  V  A  A  V  N  G  P  D  A  V  V  V  A  -

8761  CCGGTGACGCCCCAGGGCGCGCGAGTTCCTGGAGTACTGCGAGGGCGTGGGCATCCGCG
      ---------+---------+---------+---------+---------+---------+  8820
       G  D  A  Q  A  A  R  E  F  L  E  Y  C  E  G  V  G  I  R  A  -

8821  CCCGCGGCGATCCCGGTGGACTACGCCTCGCACACCGCGCACGTCGAGCCCGTGCGCGACG
      ---------+---------+---------+---------+---------+---------+  8880
       R  A  I  P  V  D  Y  A  S  H  T  A  H  V  E  P  V  R  D  E  -

8881  AACTGGTCCAGGCGCTGGCCGGGATCACCCCGCGACGGGCCGAGGTGCCGTTCTCTCCA
      ---------+---------+---------+---------+---------+---------+  8940
       L  V  Q  A  L  A  G  I  T  P  R  R  A  E  V  P  F  F  S  T  -

8941  CCCTGACCGGCGACTTCCTCGACGGCACCGAGCTGGACGCCGGCTACTGGTACCGCAACC
      ---------+---------+---------+---------+---------+---------+  9000
       L  T  G  D  F  L  D  G  T  E  L  D  A  G  Y  W  Y  R  N  L  -
```

```
9001 TGCGTCACCCGGTGGAGTTCCACTCCGCGGTGCAGGCGCTGACCGACCAGGGATACGCGA
     ------+---------+---------+---------+---------+---------+ 9060
      R   H   P   V   E   F   H   S   A   V   Q   A   L   T   D   Q   G   Y   A   T

9061 CGTTCATCGAGGTCAGCCCGCACCCGGTGCTGGCGTCGAGCGTCCAGGAGACCCTCGACG
     ------+---------+---------+---------+---------+---------+ 9120
      F   I   E   V   S   P   H   P   V   L   A   S   S   V   Q   E   T   L   D   D

9121 ACGCCGAGTCGGACGCGGCGGTGCTCGGGACGCTGGAACGCGACGCGGGCGACGCCGACC
     ------+---------+---------+---------+---------+---------+ 9180
      A   E   S   D   A   A   V   L   G   T   L   E   R   D   A   G   D   A   D   R

9181 GCTTCCTCACGGCCACTCGCCGACGCGCACACGCGGGGTCGGTCGACTGGGAAGCGG
     ------+---------+---------+---------+---------+---------+ 9240
      F   L   T   A   L   A   D   A   H   T   R   G   V   A   V   D   W   E   A   V

9241 TGCTCGGCCGGGCCGGACTGGTCGACCTGCCGGGTTATCCTTTCCAGGGCAAGCGGTTCT
     ------+---------+---------+---------+---------+---------+ 9300
      L   G   R   A   G   L   V   D   L   P   G   Y   P   F   Q   G   K   R   F   W

9301 GGCTGCTGCCGGACCGGACCCCGCACCACCCCGTGACGAGCTCGACGGCTGGTTCTACCGGGTCG
     ------+---------+---------+---------+---------+---------+ 9360
```

```
          L   L   P   D   R   T   T   P   R   D   E   L   D   G   W   F   Y   R   V   D   -
        ACTGGACCGAGGTGCCGGCTCCGAACCTGCCGCTGCGGGCCGTTGGCTCGTGGTGG
9361    -----+---------+---------+---------+---------+---------+   9420

W   T   E   V   P   R   S   E   P   A   A   L   R   G   R   W   L   V   V   V   -
        TGCCCGAGGGGCACGAGGAGGACGGCTGGACCGTCGAGGTGCGCTCGCCGAGG
9421    -----+---------+---------+---------+---------+---------+   9480

P   E   G   H   E   E   D   G   W   T   V   E   V   R   S   A   L   A   E   A   -
        CCGGCGCCGAACCGGAGGTCACGCGGGCTGGTCGGTGACTGCGCGGGCG
9481    -----+---------+---------+---------+---------+---------+   9540

G   A   E   P   E   V   T   R   G   V   G   G   L   V   G   D   C   A   G   V   -
        TGGTGTCGTTGCTCGCCCTCGAGGGCGATGGTGCGGTGCAAACCCTTGTGCTGGTGCGGG
9541    -----+---------+---------+---------+---------+---------+   9600

V   S   L   L   A   L   E   G   D   G   A   V   Q   T   L   V   L   V   R   E   -
        AACTCGACGCCGAGGGCATCGACGCCACTGTGGACGGTCACCTTCGGCGGTCGACG
9601    -----+---------+---------+---------+---------+---------+   9660

L   D   A   E   G   I   D   A   P   L   W   T   V   T   F   G   A   V   D   A   -
        CGGGCAGTCCGGTGCCCGACCCAGGCGAAGCTGTGGGCTGGCCAGGTCGCGT
9661    -----+---------+---------+---------+---------+---------+   9720
```

FIG. 2-27

```
                                                               G  S  P  V  A  R  P  D  Q  A  K  L  W  G  L  G  Q  V  A  S  -
                                                          CCCTGGAACGCGGGCCCCGCTGGACCTGCCGTCGACATGCCGGACCCGG
                                                   9721   ---------+---------+---------+---------+---------+---------+  9780

L  E  R  G  P  R  W  T  G  L  V  D  L  P  H  M  P  D  P  E  -
                                                          AACTGCGAGGCCCGTCTCACCGGTGCTGGCCGGGTGCTGGAGGACCAGGTCGCGGTGCGCG
                                                   9781   ---------+---------+---------+---------+---------+---------+  9840

L  R  G  R  L  T  A  V  L  A  G  S  E  D  Q  V  A  V  R  A  -
                                                          CCGACGCCGTGCGTGCCGGCTTTCCCCGCCCACGTCACCGCCACCTCGGAGTACG
                                                   9841   ---------+---------+---------+---------+---------+---------+  9900

D  A  V  R  A  R  R  L  S  P  A  H  V  T  A  T  S  E  Y  A  -
                                                          CGGTGCCGGGCGGCACAATCCTGGTCACCGGTGGCACCGCCGGGCCGCGAGGTGG
                                                   9901   ---------+---------+---------+---------+---------+---------+  9960

V  P  G  G  T  I  L  V  T  G  G  T  A  G  L  G  A  E  V  A  -
                                                          CCCGGTGGCTCCGCCGGTCGGGCCCGAACACCTCGCCGTCAGCAGGCGAGGCCCGG
                                                   9961   ---------+---------+---------+---------+---------+---------+  10020

R  W  L  A  G  R  G  A  E  H  L  A  L  V  S  R  R  G  P  D  -
                                                          ACACCGAGGGCGTCGG
```

TGCACGCGTGCGACGTCAGCAGCCGGCGAACTCGTGCACGGCCTGATCG
10081 ---------+---------+---------+---------+---------+---------+ 10140
           H  A  C  D  V  S  S  R  E  P  V  R  E  L  V  H  G  L  I  E  -

AGCAGGGCGACGTCGTCCGGTGTGGTGCACGCGGGACTGCCGCAGCAGGTCGCGA
10141 ---------+---------+---------+---------+---------+---------+ 10200
           Q  G  D  V  V  R  G  V  V  H  A  A  G  L  P  Q  Q  V  A  I  -

TCAACGACATGGACGAGGCCGCCTTCGACGAGGTGGTCGCGGCCAAGGCCGGGGCGGG
10201 ---------+---------+---------+---------+---------+---------+ 10260
           N  D  M  D  E  A  A  F  D  E  V  V  A  A  K  A  G  G  A  V  -

TGCACCTGGACGAGCTGTGCTCGGACGCCGAGCTGTTCCTGCTGTTCTCCTCCGGGCCG
10261 ---------+---------+---------+---------+---------+---------+ 10320
           H  L  D  E  L  C  S  D  A  E  L  F  L  L  F  S  S  G  A  G  -

GGGTGTGGGAAGCGCCCCGCCAGGGCGCCTACGCCGCGGCAACGCGTTCCTGGACGCCT
10321 ---------+---------+---------+---------+---------+---------+ 10380
           V  W  G  S  A  R  Q  G  A  Y  A  A  A  G  N  A  F  L  D  A  F  -
```

FIG. 2-29

```
10381  TCGCCCGGCACCGCGCGGGGCCGCGGGGCCCTGCCCGCCACGTCGGTGTGGGGCTGTGGG
       ------+---------+---------+---------+---------+---------+  10440
        A  R  H  R  R  G  R  G  L  P  A  T  S  V  A  W  G  L  W  A

10441  CGGCGGCGGCATGACCGGCGACGAGGAGGCCGTGTCGTTCCTGCGCGAGCGCGGTGTGC
       ------+---------+---------+---------+---------+---------+  10500
        A  G  G  M  T  G  D  E  E  A  V  S  F  L  R  E  R  G  V  R

10501  GGGCGATGCCCGTACCGCGGCGCTCGCCGCCCTGGACAGGGTGCTGGCCTCCGGGGAGA
       ------+---------+---------+---------+---------+---------+  10560
        A  M  P  V  P  R  A  L  A  A  A  L  D  R  V  L  A  S  G  E  T

10561  CGGCGGTGGTCGTGACGGTGGACGTGGACTGGCCCGCCTTCGCCGAGTCCTACACCGCCGCCC
       ------+---------+---------+---------+---------+---------+  10620
        A  V  V  V  T  D  V  D  W  P  A  F  A  E  S  Y  T  A  A  R

10621  GGCCCCGCCGTTGCTCGACCGCATCGTCACGACCGCGCCGAGCGGCCGAGAAC
       ------+---------+---------+---------+---------+---------+  10680
        P  R  P  L  L  D  R  I  V  T  T  A  P  S  E  R  A  G  E  P

10681  CGGAGACGGAGAGCCTGCGCGACCGGCTGCGCGCCGGTCTGCCGAGCGCCGACGGGCGG
       ------+---------+---------+---------+---------+---------+  10740
        E  T  E  S  L  R  D  R  L  A  G  L  P  R  A  E  R  T  A  E
```

FIG. 2-30

```
10741  AGCTGGTGCGCCTGGTCCGCCACCAGCACCGTGCTGGCCACGACGACCCGAAGG
       ----+----+----+----+----+----+----+----+----+----+----+  10800
          L  V  R  L  V  R  T  S  T  V  L  G  H  D  D  P  K  A  -

10801  CGGTGCGCGGACCACGCCGTTCAAGGAGCTCGGGTTCGACTCGCTGGCGGCCGC
       ----+----+----+----+----+----+----+----+----+----+----+  10860
          V  R  A  T  T  P  F  K  E  L  G  F  D  S  L  A  A  -

10861  TGCGCAACCTGCTCAACGCGGCCACCGGCCTCCGCCTGCCGTCGACGCTGGTCTTCGACC
       ----+----+----+----+----+----+----+----+----+----+----+  10920
          R  N  L  L  N  A  A  T  G  L  R  L  P  S  T  L  V  F  D  H  -

10921  ACCCGAACGCCTCCGGGTCGCCGGTTTCCTCGACGCCGAGCTCGGCACCGAGGTCCGGG
       ----+----+----+----+----+----+----+----+----+----+----+  10980
          P  N  A  S  A  V  A  G  F  L  D  A  E  L  G  T  E  V  R  G  -

10981  GGGAGGCGCCGTCGGCCCTCGCGGGCCTGGACGCGCTGGAAGGCGCCCTGCCCGAGGTGC
       ----+----+----+----+----+----+----+----+----+----+----+  11040
          E  A  P  S  A  L  A  G  L  D  A  L  E  G  A  L  P  E  V  P  -

11041  CCGCAACCGAGCGGGAAGAGCTGGTACAGCGGCTTGGAACGGATGCTCGCCGCTACGCC
       ----+----+----+----+----+----+----+----+----+----+----+  11100
          A  T  E  R  E  E  L  V  Q  R  L  E  R  M  L  A  A  L  R  P  -
```

FIG. 2-31

```
11101 CGGTCGCCCAGGCCCGGCCCTCCGGGCGCCAACCCGTCCGGCGACGACCTGG
      -----+---------+---------+---------+---------+---------+ 11160
        V  A  Q  A  A  D  A  S  G  T  G  A  N  P  S  G  D  D  L  G  -

11161 GCGAGGGCGTGGACGAACTGCTCGAAGCACTCGGGGAGCTCGACGGCGATTGA
      -----+---------+---------+---------+---------+---------+ 11219
        E  A  G  V  D  E  L  L  E  A  L  G  R  E  L  D  G  D  *

12643 CCGCCGATTGGAGAGAAAAGGTGACTGACAGCGAGAAGGTGGCGGAGTACCTCCGTCGGCG
      -----+---------+---------+---------+---------+---------+ 12702
                       V  T  D  S  E  K  V  A  E  Y  L  R  R  A  -

12703 ACGCTCGACCTGCGTGCCGCCCGGCAGCGCATCCGCGAGCTGGAATCCGACCCGATCGCC
      -----+---------+---------+---------+---------+---------+ 12762
        T  L  D  L  R  A  A  R  Q  R  I  R  E  L  E  S  D  P  I  A  -

12763 ATCGTCAGCATGGCCTGCCGCCTGCCCGGGGGTGAACACACCCCGCAGCGGCTGTGGGAG
      -----+---------+---------+---------+---------+---------+ 12822
        I  V  S  M  A  C  R  L  P  G  G  V  N  T  P  Q  R  L  W  E  -

CTGCTGCGCGAGGGCGGTGAGACGCTGTCGGGGCTTCCCCACCGACCGGGGCTGGACCTG
```

FIG. 2-32

```
12823 ------+---------+---------+---------+---------+---------+ 12882
            GCGGGGCTGCACCACCCCGACAACCCGGTACCAGTCTACGTCGACAAGGGCGGG
12883 ------+---------+---------+---------+---------+---------+ 12942
       L  L  R  E  G  G  E  T  L  S  G  F  P  T  D  R  G  W  D  L
            A  R  L  H  H  P  D  P  D  N  P  G  T  S  Y  V  D  K  G  G

12943 ------+---------+---------+---------+---------+---------+ 13002
            TTCCTGACGACGCGGCGGGCTTCGACGCGGAGTTCTTCGGCGTCTCGCCGCGAGGCC
13003 ------+---------+---------+---------+---------+---------+ 13062
       F  L  D  D  A  A  G  F  D  A  E  F  F  G  V  S  P  R  E  A
            A  A  M  D  P  Q  Q  R  L  L  L  E  T  S  W  E  L  V  E  N

13063 ------+---------+---------+---------+---------+---------+ 13122
            GCCGGCATGGACCCGCAGCAGCGGCTGCTGCTGGAGACGAGCTGGTGGAGAAC
            GCCGGCATCGACCCGCACTCGCTGCGCGGTACCGCGACCGGCGTCTTCCTCGGAGTGGCG
13123 ------+---------+---------+---------+---------+---------+ 13182
       A  G  I  D  P  H  S  L  R  G  T  A  T  G  V  F  L  G  V  A
            AAGTTCGGCTACGGCGAGGACACCGCGGCCGCGGAGGACGTCGAGGGCTACTCGGTCACC
       K  F  G  Y  G  E  D  T  A  A  A  E  D  V  E  G  Y  S  V  T
```

FIG. 2-33

```
13183  GGTGTGGGCGCCCCGCGGTCGCCCTCCGGCCGCATCTCCTACACCATGGGCCTGGAGGGCCG  13242
       ----------+---------+---------+---------+---------+---------+
        G  V  A  P  A  V  A  S  G  R  I  S  Y  T  M  G  L  E  G  P

13243  TCGATCAGCGTCGACACCGCGTGCTCGTCGCTGGTGGCGCTGCACCTGGCGGTCGAG       13302
       ----------+---------+---------+---------+---------+---------+
        S  I  S  V  D  T  A  C  S  S  L  V  A  L  H  L  A  V  E

13303  TCGCTGCGCAAGGGCGAGTCGTCGATGGCGGTCGTCGGCGGTGCCGCGGTGATGGCGACC  13362
       ----------+---------+---------+---------+---------+---------+
        S  L  R  K  G  E  S  S  M  A  V  V  G  G  A  A  V  M  A  T

13363  CCGGGGGTGTTCGTCGACTTCAGCCGGCAGCGGGCTCGCCGCCGACGGCGGTCGAAG    13422
       ----------+---------+---------+---------+---------+---------+
        P  G  V  F  V  D  F  S  R  Q  R  A  L  A  A  D  G  R  S  K

13423  GCGTTCGGTGCCGGTGCCGACGGGCGTTCGGCGTTCTCTCCGAAGGCGTCACCCTGGTCCTC  13482
       ----------+---------+---------+---------+---------+---------+
        A  F  G  A  G  A  D  G  F  G  F  S  E  G  V  T  L  V  L  L

13483  GAGCGGCTGTCGAGGCGGCGAAACGGGCACGAGGTGCTGGCGGTGGTTCGCGGCTCG     13542
       ----------+---------+---------+---------+---------+---------+
        E  R  L  S  E  A  R  R  N  G  H  E  V  L  A  V  V  R  G  S
```

FIG. 2-34

```
13543 GCGCTCAACCAGGACGGGGCCAGCAACGGGCTTTCCGCCGAGCGGGCCCGCGCAGCGC    13602
      ---+---------+---------+---------+---------+---------+----
      A  L  N  Q  D  G  A  S  N  G  L  S  A  P  S  G  P  A  Q  R

13603 AGGGTCATCCGGCAGGCCCTCGAGAGCTGCGGTCTGGAGCCCGGCGACGTCGACGCGGTG    13662
      ---+---------+---------+---------+---------+---------+----
      R  V  I  R  Q  A  L  E  S  C  G  L  E  P  G  D  V  D  A  V

13663 GAGGCGCACGGCACCGGTACGGCGCTCGGCGACCCGATCGAGGCGAACGCGCTGCTGGAC    13722
      ---+---------+---------+---------+---------+---------+----
      E  A  H  G  T  G  T  A  L  G  D  P  I  E  A  N  A  L  L  D

13723 ACCTACGGCCGCGACCGCGACGCCGACCGCCCGCTCTGGCTCGGTGAAGTCCAAC    13782
      ---+---------+---------+---------+---------+---------+----
      T  Y  G  R  D  R  D  A  D  R  P  L  W  L  G  S  V  K  S  N

13783 ATCGGCCACACCCAGGCCGCAGCCGGCGTCACCGGCCTGCTGAAGGTGGTCCTGGCGCTG    13842
      ---+---------+---------+---------+---------+---------+----
      I  G  H  T  Q  A  A  A  G  V  T  G  L  L  K  V  V  L  A  L

13843 CGCAACGGGGAACTGCCCGCGACCCTGCACGTCGAGGAGCCCACGCCCCACGTCGACTGG    13902
      ---+---------+---------+---------+---------+---------+----
      R  N  G  E  L  P  A  T  L  H  V  E  E  P  T  P  H  V  D  W
```

```
          TCGTCCGGCGCGTGGCGCTGCTGGCGGGCAACCAGCCCTGGCGGGGCGAGCGGACT
13903     ------+---------+---------+---------+---------+---------+   13962
          S   S   G   G   V   A   L   L   A   G   N   Q   P   W   R   R   G   E   R   T

CGGCGCGCCCGTGTTCCGCGTTCGGGATCAGCGGGACGAATGCGCACGTGATCGTCGAG
13963     ------+---------+---------+---------+---------+---------+   14022
          R   R   A   R   V   S   A   F   G   I   S   G   T   N   A   H   V   I   V   E

GAAGCTCCTGAGCGCGAGCACCGGGAGACCGCACGACGGCCGACCGGTTCCGCTG
14023     ------+---------+---------+---------+---------+---------+   14082
          E   A   P   E   R   E   H   R   E   T   T   A   H   D   G   R   P   V   P   L

GTGGTGTCCGCGCGCACGACGGCGGCGCTTGCGCGCCAGGCCCAGATCGCCGAGCTG
14083     ------+---------+---------+---------+---------+---------+   14142
          V   V   S   A   R   T   T   A   A   L   R   A   Q   A   A   Q   I   A   E   L

CTCGAACGCCCCGACGCCCTCGCCGGGGTCGGCCTGGGCCTGGCCACGACCCGGGCC
14143     ------+---------+---------+---------+---------+---------+   14202
          L   E   R   P   D   A   D   L   A   G   V   G   L   G   L   A   T   T   R   A

CGCCACGAGCACCGCGCCGTGGTGGCATCGACCCCGAGGAAGCGGTGCGCGGACTG
14203     ------+---------+---------+---------+---------+---------+   14262
```

FIG. 2-37

```
        R  H  E  H  R  A  A  V  V  A  S  T  R  E  E  A  V  R  G  L
14263   CGGGAGATCGCCGCCGGTGCCGCGACGGCCGTGTTCGAGGGCGTCACCGAGGTG   14322

R  E  I  A  A  G  A  A  T  A  D  A  V  V  E  G  V  T  E  V
14323   GACGGGGCGCAACGTCGTCTTCCCTGTTCCCGGGGCAGGGTTCGCAATGGGCCGGCATGGGT   14382

D  G  R  N  V  V  F  L  F  P  G  Q  G  S  Q  W  A  G  M  G
14383   GCCGAGCTGCTGTCGTCGCCGGTGTTCGCCGGGAAGATCCGGGCCTGCGACGAGTCG   14442

A  E  L  L  S  S  S  P  V  F  A  G  K  I  R  A  C  D  E  S
14443   ATGGCCCCGATGCAGGAGGACTGGAAGGTCTCCGACGTGCTGCGTCAGGCGCCGGGGGCCG   14502

M  A  P  M  Q  D  W  K  V  S  D  V  L  R  Q  A  P  G  A  P
14503   GGCCTGGACCGGGTCGACGTGGTGCAGCCGGTGTTGTTCGCGGTGATGGTGTCGCTGGCG   14562

G  L  D  R  V  D  V  V  Q  P  V  L  F  A  V  M  V  S  L  A
14563   GAGCTGTGGGCGCTCGTACGCGGGGTGGAGCCCGCGGTCGTGGGGCACTCGCAGGGCGAG   14622
```

FIG. 2-38

```
         E  L  W  R  S  Y  G  V  E  P  A  A  V  V  G  H  S  Q  G  E  -
       ATCGCGCCGGCGCACGTCGCCGGGCGCTCACGTTGGAGGACGCGGGCGAAGCTCGTG
14623  ------+---------+---------+---------+---------+---------+  14682
         I  A  A  H  V  A  G  A  L  T  L  E  D  A  A  K  L  V  V  -

GGCCGCAGCCGCTGATGCGGTCGCTCTCCGGGAGGGCATGGCCGCCGTCGCGCTG
14683  ------+---------+---------+---------+---------+---------+  14742
         G  R  S  R  L  M  R  S  L  S  G  E  G  G  M  A  A  V  A  L  -

GGCGAGGCCGCCGTGCGCGAGCGCCTGCGCCCGTGGCAGGACCGGCTCTCGGTGGCCGCG
14743  ------+---------+---------+---------+---------+---------+  14802
         G  E  A  A  V  R  E  R  L  R  P  W  Q  D  R  L  S  V  A  A  -

GTCAACGGTCCCCGGTCGGTCGTGGTCTCCGGGGAGCCCGGCGCTGCGGGCGTTTTCC
14803  ------+---------+---------+---------+---------+---------+  14862
         V  N  G  P  R  S  V  V  V  S  G  E  P  G  A  L  R  A  F  S  -

GAGGACTGCGCGGCCGCGGAGGGCATCCGCGTCCGCGACATCGACGTGGACTACGCCTGCAC
14863  ------+---------+---------+---------+---------+---------+  14922
         E  D  C  A  A  E  G  I  R  V  R  D  I  D  V  D  Y  A  S  H  -
```

FIG. 2-39

```
14923 TCGCCGCAGATCGAGCGGGTCCGCGAGGAACTCCTCGAAACGACCGGCGACATCGCGCCG 14982
       S  P  Q  I  E  R  V  R  E  E  L  L  E  T  T  G  D  I  A  P

14983 CGCCCGGCGCGGGTGACGTTCCACTCCACTGTGGAGTCGCGGTCTATGGACGGCACCGAG 15042
       R  P  A  R  V  T  F  H  S  T  V  E  S  R  S  M  D  G  T  E

15043 CTGGATGCCCGGTACTGGTACCGCAACCTGCGCGAGACGGTTGCGCTTCGCCGACGCCGTG 15102
       L  D  A  R  Y  W  Y  R  N  L  R  E  T  V  R  F  A  D  A  V

15103 ACGCGGCTGGCCGAGTCCGGATACGACGCCGTTCATCGAGGTCAGCCCGCATCCGGTCGTG 15162
       T  R  L  A  E  S  G  Y  D  A  F  I  E  V  S  P  H  P  V  V

15163 GTCCAGGCCGTCGAGGAGGCGGTCGAAGAGGCTGACGGTGCCGAAGACGCGGTCGTAGTC 15222
       V  Q  A  V  E  E  A  V  E  E  A  D  G  A  E  D  A  V  V  V

15223 GGCTCGCTGCACCGGCGACGGCGGTGACCTCTCGGCCTTCCTGCGGTCGATGGCCACCGCG 15282
       G  S  L  H  R  D  G  G  D  L  S  A  F  L  R  S  M  A  T  A
```

```
15283 CACGTGTCCGGTGTGGACATCAGGTGGGACGTCGCTCTGCCCGGGCCGGCCCCTTCGCG 15342
          ---------+---------+---------+---------+---------+---------+
            H  V  S  G  V  D  I  R  W  D  V  A  L  P  G  A  A  P  F  A

15343 CTGCCGACGTATCCGTTCCAGCGCAAGCGCTACTGGCTCCAGCCCGCCGCCCCGCC 15402
          ---------+---------+---------+---------+---------+---------+
            L  P  T  Y  P  F  Q  R  K  R  Y  W  L  Q  P  A  A  P  A  A

15403 GCCTCCGACGAGCTGGCCTACCGCGTTTCCTGGACTCCGATCGAAAAGCCGGAGTCGGGA 15462
          ---------+---------+---------+---------+---------+---------+
            A  S  D  E  L  A  Y  R  V  S  W  T  P  I  E  K  P  E  S  G

15463 AACCTGGACGGCGACTGGTTGGTTGTCACACCCCTCATCAGTCCGGAGTGGACGGAAATG 15522
          ---------+---------+---------+---------+---------+---------+
            N  L  D  G  D  W  L  V  V  T  P  L  I  S  P  E  W  T  E  M

15523 CTGTGCGAGGCCATCAACGCCAACGGTGGCAGGGCGTTGCGCTGCGAGGTGGACACGTCC 15582
          ---------+---------+---------+---------+---------+---------+
            L  C  E  A  I  N  A  N  G  G  R  A  L  R  C  E  V  D  T  S

15583 GCTTCGCGCACTGAGATGCCCAGGCCGTCGCACAGGCCGGAACGGGATTCCGGGGCGTG 15642
          ---------+---------+---------+---------+---------+---------+
```

```
         A   S   R   T   E   M   A   Q   A   V   A   Q   A   G   T   G   F   R   G   V
       CTCTCGTTGCTGTCGTCGGACGAATCCGCCTGCCGTCCGGGGGTTCCTGCCGTGCGGTC
15643  ------+---------+---------+---------+---------+---------+  15702

L   S   L   L   S   S   D   E   S   A   C   R   P   G   V   P   A   G   A   V
       GGCCTGCTCTCACCCTGGTCCAGGCCTGGGCGATGCCGGGGTCGACGCACCGGTGTGGTGC
15703  ------+---------+---------+---------+---------+---------+  15762

G   L   T   L   V   Q   A   L   G   D   A   G   V   D   A   P   V   W   C
       CTGACCCAGGGGTGCGGGTCCGCACTCCCGCCGACGACCTCGCCCGGCCTGCCAGACC
15763  ------+---------+---------+---------+---------+---------+  15822

L   T   Q   G   A   V   R   T   P   A   D   D   D   L   A   R   P   A   Q   T
       ACCGCGCACGGCTTCGCGCAGGTCGCAGGTCTGGAGCTGCCGGGCCGCTGGGGCGGTGTG
15823  ------+---------+---------+---------+---------+---------+  15882

T   A   H   G   F   A   Q   V   A   G   L   E   L   P   G   R   W   G   G   V
       GTCGACCTGCCCGAATCGGTCGACGACGCGGCGCTCTGCTCGTGCCAGTCCTGCGC
15883  ------+---------+---------+---------+---------+---------+  15942

V   D   L   P   E   S   V   D   D   A   A   L   R   L   L   V   A   V   L   R
       GGCGGGGCGGCCGTGCCGAGGACCACCTCGGCGTCCGGTCCGCCTCCACGGCCGTCGC
15943  ------+---------+---------+---------+---------+---------+  16002
```

```
                G  G  G  R  A  E  D  H  L  A  V  R  D  G  R  L  H  G  R  R
        16003   GTCGTCCGGCGCAAGCCTGCCGCAGTCCGGCTCGCGGAGCTGGACCCCGCACGGGACCGTG   16062

V  V  R  A  S  L  P  Q  S  G  S  R  S  W  T  P  H  G  T  V
        16063   CTGGTCACCGGCGCGGAGCCCCGTCGGCGACCAACTGTGGTGCGGTCTCGCCGACCGG     16122

L  V  T  G  A  A  S  P  V  G  D  Q  L  V  R  W  L  A  D  R
        16123   GGAGCCGAGCGGCTGGTGCTGGCCGGAGCCTGTCCGGGCGACGACCTGCTGGCCGCGGTC   16182

G  A  E  R  L  V  L  A  G  A  C  P  G  D  D  L  L  A  A  V
        16183   GAGGAAGCGGGCGCATCGGCCGTCGTGTGCGCCCAGGACGCGGCGGCTGCGCGAGGCG    16242

E  E  A  G  A  S  A  V  V  C  A  Q  D  A  A  A  L  R  E  A
        16243   CTCGGCGACGAGCCGGTGACCGCGCTCGTCCACGCCGGAACCCTGACGAACTTCGGCAGC   16302

L  G  D  E  P  V  T  A  L  V  H  A  G  T  L  T  N  F  G  S
                ATCAGCGGAAGTCGCACCGGAGGAGTTCGCCGGCCAAGACCGCGTTGCTC
```

```
16303 ------+---------+---------+---------+---------+---------+ 16362
            GCCGTGCTGGACGAAGTCCTCGGCGACCGGGCCGTCGAGCGGGAGGTCTACTGCTCGTCG
       I  S  E  V  A  P  E  E  F  A  E  T  I  A  A  K  T  A  L  L

16363 ------+---------+---------+---------+---------+---------+ 16422
            GTCGCCGGGATCTGGGGCGGCGCCGGGATGGCCGCCTACGCGGCCGGCAGCGCCTACCTC
       A  V  L  D  E  V  L  G  D  R  A  V  E  R  E  V  Y  C  S  S

16423 ------+---------+---------+---------+---------+---------+ 16482
            GACGCGCTGGCCGAGCACCACCGCGCGCGGGGCCGCTCGTGCACCTCGGTCGCCTGGACG
       V  A  G  I  W  G  G  A  G  M  A  A  Y  A  A  G  S  A  Y  L

16483 ------+---------+---------+---------+---------+---------+ 16542
            CCGTGGGCGCTGCCGGGGGCTGGGGCGGTGGACGACGGCTACCTGCGGGAACGCGGACTGCGC
       D  A  L  A  E  H  H  R  A  R  G  R  S  C  T  S  V  A  W  T

16543 ------+---------+---------+---------+---------+---------+ 16602
            AGCCTCTCCGCCGACAGGGCGATGCGCACCTGGGAGCGGGTGCTGGCCGCCGGGCCGGTG
       P  W  A  L  P  G  G  A  V  D  D  D  G  Y  L  R  E  R  G  L  R

```
16663  TCGGTCGCGGTGGCCGACGTGGGACTGGGCCGGTGCTCAGCGAAGGCTTCGCCGCCACCCGG  16722
        ---------+---------+---------+---------+---------+---------+
        S   V   A   V   A   D   V   D   W   P   V   L   S   E   G   F   A   A   T   R

16723  CCGACCGCGCTGTTCGCGGAACTCGCCGGCCGCGGCGGACAGGCGGAGGCGGAGCCGGAC   16782
        ---------+---------+---------+---------+---------+---------+
        P   T   A   L   F   A   E   L   A   G   R   G   G   Q   A   E   A   E   P   D

16783  AGCGGACCGACCGGAGCCGGCGCAGCGGCTCGCGGGGCTTTCCCCGGACGAGCAGCAG   16842
        ---------+---------+---------+---------+---------+---------+
        S   G   P   T   G   E   P   A   Q   R   L   A   G   L   S   P   D   E   Q   Q

16843  GAAAACCTGCTCGAACTCGTCGCGAACGCGGTTGCCGAGGTGCTTGGCCACGAGTCCGCC   16902
        ---------+---------+---------+---------+---------+---------+
        E   N   L   L   E   L   V   A   N   A   V   A   E   V   L   G   H   E   S   A

16903  GCCGAGATCAACGTGCGCCGCGCGTTCAGCGAGCTCGGACTCGACTCGCTCAACGCGATG   16962
        ---------+---------+---------+---------+---------+---------+
        A   E   I   N   V   R   R   A   F   S   E   L   G   L   D   S   L   N   A   M

16963  GCCCTGCGCAAGCGCCTGTCGGCGAGCACCGGCCTGCGCCTGCCCGCGTCGCTGGTGTTC   17022
        ---------+---------+---------+---------+---------+---------+
        A   L   R   K   R   L   S   A   S   T   G   L   R   L   P   A   S   L   V   F
```

FIG. 2-45

```
17023 GACCACCCCCACCGTCACCGCGCTCGGCGCAGCACCTGCGCGCCCGGCTCGTCGGTGACGCC
      ------+---------+---------+---------+---------+---------+ 17082
          D  H  P  T  V  T  A  L  A  Q  H  L  R  A  R  L  V  G  D  A  -

17083 GACCAGGCCGCGGTGCGCGTCGTGGGCGCCGACGAGTCCGAGCCCATCGCCATCGTC
      ------+---------+---------+---------+---------+---------+ 17142
          D  Q  A  A  V  R  V  V  G  A  A  D  E  S  E  P  I  A  I  V  -

17143 GGCATCGGCTGCCGTTCCCCGGCGGCATCGGCTCCCCGAGCAGTTGTGGCGGGTGCTG
      ------+---------+---------+---------+---------+---------+ 17202
          G  I  G  C  R  F  P  G  G  I  G  S  P  E  Q  L  W  R  V  L  -

17203 GCCGAGGGCGCGAACCTCACCACCGGCTTCCCCGGCCGACCGGCTGGGACATCGGGCGG
      ------+---------+---------+---------+---------+---------+ 17262
          A  E  G  A  N  L  T  T  G  F  P  A  D  R  G  W  D  I  G  R  -

17263 CTCTACCACCCGGACCCGGACAACCCCGGCACCAGCTACGTGGACAAGGGCGGGTTCCTC
      ------+---------+---------+---------+---------+---------+ 17322
          L  Y  H  P  D  P  D  N  P  G  T  S  Y  V  D  K  G  G  F  L  -

17323 ACCGACGCGGCGGATTTCGACCCGGGCTTCTTCGGCATCACGCCCCGGAAGGCTGGGCG
      ------+---------+---------+---------+---------+---------+ 17382
          T  D  A  A  D  F  D  P  G  F  F  G  I  T  P  R  E  A  L  A  -
```

```
17383  ATGGACCCGCAGCAGCGCCTCATGCTGGAGACGGCGTGGGAGGCAGTGGAACGCGCGGGC
       ----+---------+---------+---------+---------+---------+---  17442
        M  D  P  Q  Q  R  L  M  L  E  T  A  W  E  A  V  E  R  A  G  -

17443  ATCGACCCCGACGCCCTGCGAGGCACCGACACCGGGGTCTTCGTCGGCATGAACGGCCAG
       ----+---------+---------+---------+---------+---------+---  17502
        I  D  P  D  A  L  R  G  T  D  T  G  V  F  V  G  M  N  G  Q  -

17503  TCCTACATGCAGCTGCTGGCCGGTGAGGCCGAACGCGTCGACGGCTACCAGGGCCTCGGA
       ----+---------+---------+---------+---------+---------+---  17562
        S  Y  M  Q  L  L  A  G  E  A  E  R  V  D  G  Y  Q  G  L  G  -

17563  AACTCCGGAGCGTGCTCTCCGGGCCATCGCCTACACCTTCGGCTGGGAGGGCCCGGCG
       ----+---------+---------+---------+---------+---------+---  17622
        N  S  A  S  V  L  S  G  R  I  A  Y  T  F  G  W  E  G  P  A  -

17623  CTGACGGTGGACACCGCGTGCTCGTCCTCGCTGGTCGGCATCCACCTCGCGATGCAGGCG
       ----+---------+---------+---------+---------+---------+---  17682
        L  T  V  D  T  A  C  S  S  S  L  V  G  I  H  L  A  M  Q  A  -

17683  CTGCGGGCGGGTGAGTGCTCCCTGGCGCTGGCCGGGGTCACGGTCATGTCCGACCCG
       ----+---------+---------+---------+---------+---------+---  17742
```

FIG. 2-46

```
        L   R   R   G   E   C   S   L   A   L   A   G   G   V   T   V   M   S   D   P   —
       TACACCTTCGTCGACTTCAGCACGGCAGCGCGGGCTCGCCTCCGACGGTCGCTGCAAGGCG
17743  ------+---------+---------+---------+---------+---------+  17802
        Y   T   F   V   D   F   S   T   Q   R   G   L   A   S   D   G   R   C   K   A   —
       TTCTCCGGCGGCCGACGGTCGCTTCGCGCTGTCGGAAGGCGTCGCCGCGCTGGTGCTGGAG
17803  ------+---------+---------+---------+---------+---------+  17862
        F   S   A   R   A   D   G   F   A   L   S   E   G   V   A   A   L   V   L   E   —
       CCGCTTTCCCGGCGGCGGCCCAACGGGCACCAGGTGTGCTGGCCGTGCTGCGGCAGCGGCG
17863  ------+---------+---------+---------+---------+---------+  17922
        P   L   S   R   A   R   A   N   G   H   Q   V   L   A   V   L   R   G   S   A   —
       GTCAACCAGGACGGTGCCAGCAACGGTCTCGCCGCTCCCAACGGCCCGTCGCAGGAGCGG
17923  ------+---------+---------+---------+---------+---------+  17982
        V   N   Q   D   G   A   S   N   G   L   A   A   P   N   G   P   S   Q   E   R   —
       GTGATCCGGCAGGCGCTCGCCGCTTCGGCCGTGCCCGGCGCCGTCGACGTCGTGGAG
17983  ------+---------+---------+---------+---------+---------+  18042
        V   I   R   Q   A   L   A   A   A   S   G   V   P   A   A   D   V   D   V   V   E   —
```

FIG. 2-47

```
18043 GCGCACGGGACGGGCACCGAGCTCGGCGACCCGATCGAGGCCGGCGCGCTCATCGCGACC
          +---------+---------+---------+---------+---------+---------+ 18102
       A  H  G  T  G  T  E  L  G  D  P  I  E  A  G  A  L  I  A  T

18103 TACGGCCAGGACCGCCCGCTCCGGCTCGGTGAAGACCAACATCGGCCAC
          +---------+---------+---------+---------+---------+---------+ 18162
       Y  G  Q  D  R  D  R  P  L  R  L  G  S  V  K  T  N  I  G  H

18163 ACCCAGGCCGCCGCCGGGGCCGCGGGCGTGATCAAGGTCGTGCTGGCCGATGCGCACGGG
          +---------+---------+---------+---------+---------+---------+ 18222
       T  Q  A  A  A  G  A  A  G  V  I  K  V  V  L  A  M  R  H  G

18223 ATGCTGCCCCGGTCGCTTGCACGCCGACGAGCTGTCCCCGCACATCGACTGGGAGTCGGGG
          +---------+---------+---------+---------+---------+---------+ 18282
       M  L  P  R  S  L  H  A  D  E  L  S  P  H  I  D  W  E  S  G

18283 GCCGTGGAGGTGCTGCGCGAGGAGGTGCCGTGGCCGGCCGGGTGAGGCGCCCCGGCGGGGCG
          +---------+---------+---------+---------+---------+---------+ 18342
       A  V  E  V  L  R  E  E  V  P  W  P  A  G  E  R  P  R  R  A

18343 GGGGTGTCGTCCTTCGGCGTCAGCGGAACCAACGCGCACGTGATCGTCGAAGAGGCACCA
          +---------+---------+---------+---------+---------+---------+ 18402
       G  V  S  S  F  G  V  S  G  T  N  A  H  V  I  V  E  E  A  P
```

```
18403  GCAGAGCAGGAGGCCCGCCCCGAGGCGCACCGAGGCGGTCCGCTGCCGTTCGTGCTGTCCGGCCGC  18462
        A  E  Q  E  A  A  R  T  E  R  G  P  L  P  F  V  L  S  G  R

18463  AGCGAAGCCGTGGTCGCGGCCCAGGCCCGCGCGCTCGCCGAGCACCTGCGCGACACCCCG  18522
        S  E  A  V  V  A  A  Q  A  R  A  L  A  E  H  L  R  D  T  P

18523  GAGCTCGGCCTGACCGACGCGGCCTGGACGCTCGCGACCGGCCGCGCCAGGGGCGGTTCGACGTG  18582
        E  L  G  L  T  D  A  A  W  T  L  A  T  G  R  A  R  F  D  V

18583  CGAGCCGCCGTGCTCGGCGACGACCGCGCGGGCGTGTGCGCGGAGCTGGACGCGCTGGCC  18642
        R  A  A  V  L  G  D  D  R  A  G  V  C  A  E  L  D  A  L  A

18643  GAGGGCCGCCCGTCGGCCGACGCCGTCGCCGGTGACCTCCGCGCCAAGCCGGTC  18702
        E  G  R  P  S  A  D  A  V  A  P  V  T  S  A  P  R  K  P  V

18703  CTGGTCTTCCCCGGCCAGGGCGCGCAGTGGGTCGGCATGGCACGCGATCTGCTGGAATCC  18762
        L  V  F  P  G  Q  G  A  Q  W  V  G  M  A  R  D  L  L  E  S
```

FIG. 2-50

```
18763 TCCGAGGTGTTCGCCGAGTCGATGAGCCGGTGCGCCGAGGCGCTCTCGCCGCACACCGAC 18822
       ---------+---------+---------+---------+---------+---------+
       S  E  V  F  A  E  S  M  S  R  C  A  E  A  L  S  P  H  T  D

18823 TGGAAGTTGCTCGACGTCGTCCGGGGCGACGGCGGTCCCGACCCCGACGAGCGGCGTCGAC 18882
       ---------+---------+---------+---------+---------+---------+
       W  K  L  L  D  V  V  R  G  D  G  G  P  D  P  H  E  R  V  D

18883 GTGCTCCAGCCGGTGCTCTTCTCGATCATGGTCTCGCTGGCCGAGCTGTGGCGCGCAC 18942
       ---------+---------+---------+---------+---------+---------+
       V  L  Q  P  V  L  F  S  I  M  V  S  L  A  E  L  W  R  A  H

18943 GGCGTGACCCCGGCCGCCGTCGTCGGCCACTCGCAGGGCGAGATCGCCGCGGCCACGTG 19002
       ---------+---------+---------+---------+---------+---------+
       G  V  T  P  A  A  V  V  G  H  S  Q  G  E  I  A  A  A  H  V

19003 GCGGGGCGCGCTGTCGCTGGAAGCCGCCGGAAGGTGGTGGCCCTGCAGCCAGGTGTTG 19062
       ---------+---------+---------+---------+---------+---------+
       A  G  A  L  S  L  E  A  A  A  K  V  V  A  L  R  S  Q  V  L

19063 CGCGAGCTCGACGACCAGGGCGCATGGTGTCGGTCCCGGTCGGACGAGCTGGAG 19122
       ---------+---------+---------+---------+---------+---------+
```

FIG. 2-51

```
          R   E   L   D   D   Q   G   G   M   V   S   V   G   A   S   R   D   E   L   E
       ACCGTGCTCGGCGGCTGGGACGGCCGTGTCGGCGTGGGCGCCGTGAACGGGCCTGGCACC
19123  ------+---------+---------+---------+---------+---------+  19182

T   V   L   A   R   W   D   G   R   V   A   A   V   N   G   P   G   T
       AGCGTCGTTGCCGGGCCGACCGCGGAGCTGGACGAGTTCTTCGCCGAGGCCGAGGCGCGG
19183  ------+---------+---------+---------+---------+---------+  19242

S   V   V   A   G   P   T   A   E   L   D   E   F   F   A   E   A   E   A   R
       GAGATGAAGCCGCGGCGCATCGCCGTGCGCTACGCCTCCCACTCCCCGGAGGTGGCGCGC
19243  ------+---------+---------+---------+---------+---------+  19302

E   M   K   P   R   R   I   A   V   R   Y   A   S   H   S   P   E   V   A   R
       ATCGAGGACCGGCTCGCGGCCGAGCTGGGCACCATCACCGCCGTGCGGGGCTCGGTGCCG
19303  ------+---------+---------+---------+---------+---------+  19362

I   E   D   R   L   A   A   E   L   G   T   I   T   A   V   R   G   S   V   P
       CTGCACTCCACGGTGACCGGCGAGGTCATCGACACCTCCGCCATGGACGCCCTCCTACTGG
19363  ------+---------+---------+---------+---------+---------+  19422

L   H   S   T   V   T   G   E   V   I   D   T   S   A   M   D   A   S   Y   W
       TACCGCAACCTGCGCCGACTGCTCTTCGAGCAGGCGGTGCCGGTCTTGGTCGAGCAG
19423  ------+---------+---------+---------+---------+---------+  19482
```

FIG. 2-52

```
Y  GGCTTCGACACCTTCGTCGAGGTGAGCCCGGTGCTGCTGATGGCGGTCGAGGAG  19542
R
N
L
R
R
P
V
L
F
E
Q
A
V
R
G
L
V
E
Q
19483

G  ACCGCCGAGCACGCGGGGGCGGAAGTCACCTGCGTGCCGACGCTGCGCCGAGAGCAGAGC  19602
E
D
T
F
V
E
V
S
P
H
P
V
L
L
M
A
V
E
E
19543

T  GGACCGCACGAGTTCCTGCGCAACCTGCTGCGGGCTCACGTGCACGGCGTCGGCCCGAC  19662
A
E
H
A
G
A
E
V
T
C
V
P
T
L
R
R
E
Q
S
19603

G  CTGCGTCCGGCGGTGGCCGGGGACGCGGCCGAGCTGCCCACCTACCCGTTCGAACAC  19722
P
H
E
F
L
R
N
L
L
R
A
H
V
H
G
V
G
A
D
19663

L  CAGCGGCTTCTGGCCCGGCCACCGGCCCCGACGTCTCGGGCTGCGCCGGC  19782
R
P
A
V
A
G
G
R
P
A
E
L
P
T
Y
P
F
E
H
19723

Q  GCGGGAGCACCCGCTGCTCCGCGTCGACGTGCCGGCCACGGCGGGTGCGGGTGTTC
R
F
W
P
R
P
H
R
P
A
D
V
S
A
L
G
V
R
G
```

```
19783 ---------+---------+---------+---------+---------+---------+ 19842
         ACCGGAAGGCTTTCCACCGACGAGCAGCCGTGGCTGGCCGAACACGTCGTGGGCGGCCGG
          A  E  H  P  L  L  L  A  A  V  D  V  P  G  H  G  G  A  V  F

19843 ---------+---------+---------+---------+---------+---------+ 19902
         ACGCTGGTGCCGGGCAGCGTCCTGGTCGATCTCGCCCTCGCCGGGTGAGGACGTCGGG
          T  G  R  L  S  T  D  E  Q  P  W  L  A  E  H  V  V  G  G  R

19903 ---------+---------+---------+---------+---------+---------+ 19962
         CTGCCGGTCCTGGAGGAACTGGTCGTTGCAACGGCCGCTGGTGCCGGGGCGGGGGCG
          T  L  V  P  G  S  V  L  V  D  L  A  L  A  A  G  E  D  V  G

19963 ---------+---------+---------+---------+---------+---------+ 20022
         CTGCTGCGCATGTCGGTCGGCGCCCCGACGAGTCGGGCGGACGATCGACGTCCAC
          L  P  V  L  E  E  L  V  L  Q  R  P  L  V  L  A  G  A  G  A

20023 ---------+---------+---------+---------+---------+---------+ 20082
         GCCGCCGAAGACGTGGCCGACCTCGCCGACGCCAGTGGTCGCAGCACGCCACCGGGACG
          L  L  R  M  S  V  G  A  P  D  E  S  G  R  R  T  I  D  V  H

```
20143   CTCGCGCAGGGCGTCGCCGCGGGTCCGAGGATACCGAGCAGTGGCCGCCGGAGGACGCC
        ----------+---------+---------+---------+---------+---------+   20202
        L  A  Q  G  V  A  A  G  P  R  D  T  E  Q  W  P  P  E  D  A

20203   GTCCGCATCCCGCTCGACGACCACTACGACGGCCTCGCCGAGCAGGGCTACGAGTACGGA
        ----------+---------+---------+---------+---------+---------+   20262
        V  R  I  P  L  D  D  H  Y  D  G  L  A  E  Q  G  Y  E  Y  G

20263   CCGTCGTTCCAGGCCCTGCGAGCCGCCTGGCGCAAGGACGACTCGGTCTACGCCGAGGTG
        ----------+---------+---------+---------+---------+---------+   20322
        P  S  F  Q  A  L  R  A  A  W  R  K  D  D  S  V  Y  A  E  V

20323   TCCATCGCGGCGGACGAGGAAGGTTACGCGTTCCACCCGGTTGCTGCTCGACGCCGTGGCG
        ----------+---------+---------+---------+---------+---------+   20382
        S  I  A  A  D  E  E  G  Y  A  F  H  P  V  L  L  D  A  V  A

20383   CAGACGCTCAGCCTGGGCGCCCTCGGCGAGCCCGGGGGAAAGCTGCCGTTCGCGGTGG
        ----------+---------+---------+---------+---------+---------+   20442
        Q  T  L  S  L  G  A  L  G  E  P  G  G  G  K  L  P  F  A  W

20443   AACACCGTGACCCTGCACGCCTCCGGGGCGACCTCGGTGCGGGTCGTGGCGACGCCCGCC
        ----------+---------+---------+---------+---------+---------+   20502
        N  T  V  T  L  H  A  S  G  A  T  S  V  R  V  V  A  T  P  A
```

```
20503 GGGGCGGGACGCGATGGCCCTGCGGGTCACCGACCCGGCAGGCCACCTGGTCGCCACGGTC 20562
            G  A  D  A  M  A  L  R  V  T  D  P  A  G  H  L  V  A  T  V

20563 GACTCGCTGGTCGTCCGCAGCACCGGGGAGAAGTGGGAGCAGCCCGAACCCGGCGGTGGC 20622
            D  S  L  V  V  R  S  T  G  E  K  W  E  Q  P  E  P  R  G  G

20623 GAGGGCGAGCTGCACGCTCTGGACTGGGGACGGCTAGCCGAGCCCGGCTCGACCGGTCGT 20682
            E  G  E  L  H  A  L  D  W  G  R  L  A  E  P  G  S  T  G  R

20683 GTGGTCGCGGCCGATGCCTCGGACCTCGACGCCGTCCTGCGGTCCGGTGAACCCGAACCC 20742
            V  V  A  A  D  A  S  D  L  D  A  V  L  R  S  G  E  P  E  P

20743 GACGCGGGTCCTGGTCCGCTACGAACCCGAAGGCGACGACCCCCGCCGCGCCGCCCGCCAC 20802
            D  A  V  L  V  R  Y  E  P  E  G  D  D  P  R  A  A  A  R  H

20803 GGCGTCCTCTGGGCCCGCGCTCGTGCCGCTCGAACAGGAGGAGCTGCCGGGC 20862
```

FIG. 2-56

```
         G  V  L  W  A  A  A  L  V  R  R  W  L  E  Q  E  E  L  P  G
      GCGACGCTGGTCATCGCCACGTCCGGCGGGTCACCGTGTCCGACGACGACAGCGTTCCC
20863 ---------+---------+---------+---------+---------+---------+ 20922

A  T  L  V  I  A  T  S  G  A  V  T  V  S  D  D  D  S  V  P
      GAACCCGGCGACGCCCGCGATGTGGGGCGTGATCCGCTGTGCCAGGCCGAGTCGCCGGAC
20923 ---------+---------+---------+---------+---------+---------+ 20982

E  P  G  A  A  A  M  W  G  V  I  R  C  A  Q  A  E  S  P  D
      CGGTTCGTGCTCCTCGACACCGACGCGGAACCTGGGATGCTGCCTGCGGTTCCGGACAAC
20983 ---------+---------+---------+---------+---------+---------+ 21042

R  F  V  L  L  D  T  D  A  E  P  G  M  L  P  A  V  P  D  N
      CCGCAGCTCGCGTTGCGCGGCGACGACGTCTTCGTGCCGCGCCTCTCGCCGCTCGCACCT
21043 ---------+---------+---------+---------+---------+---------+ 21102

P  Q  L  A  L  R  G  D  D  V  F  V  P  R  L  S  P  L  A  P
      TCCGCGCTGACGCTTCCGGCACCCAACGTCTCGTGCCGGGTGACGGGGCGATCGAC
21103 ---------+---------+---------+---------+---------+---------+ 21162

S  A  L  T  L  P  A  G  T  Q  R  L  V  P  G  D  G  A  I  D
      TCCGTGGCCTTCGAGCCCGACGTCGAGCAGCCCGAGGTCCGG
21163 ---------+---------+---------+---------+---------+---------+ 21222
```

```
       S  V  A  F  E  P  A  P  D  V  E  Q  P  L  R  A  G  E  V  R
       GTGGACGTGGCGCGCCACCGGAGTCAACTTCCGCGACGTCCTCCTCGCACTCGGCATGTAT
21223  ------------+---------+---------+---------+---------+---------+  21282

V  D  V  R  A  T  G  V  N  F  R  D  V  L  L  A  L  G  M  Y
       CCGCAGAAGGCGGACATGGGCACCGAGGCCGCCGGTGTCGTCACGGCGGTCGGACCGGAC
21283  ------------+---------+---------+---------+---------+---------+  21342

P  Q  K  A  D  M  G  T  E  A  A  G  V  V  T  A  V  G  P  D
       GTGGACGCCTTCGCGCCGGGAGACCGGGTGCTCGGCCTGTTCCAGGGAGCCTTCGCGCCG
21343  ------------+---------+---------+---------+---------+---------+  21402

V  D  A  F  A  P  G  D  R  V  L  G  L  F  Q  G  A  F  A  P
       ATCGCGGTCACCGATCACCGGCTCCTCGCACGAGTGCCGGACGGCTGGAGCGACGCCGAC
21403  ------------+---------+---------+---------+---------+---------+  21462

I  A  V  T  D  H  R  L  L  A  R  V  P  D  G  W  S  D  A  D
       GCCGCGGCCGTGCCCATCGCCTACACCACGGGCCATTACGGCCTGCACGATCTCGGCGGGG
21463  ------------+---------+---------+---------+---------+---------+  21522

A  A  A  V  P  I  A  Y  T  T  A  H  Y  A  L  H  D  L  A  G
       CTGGCGGCGGGGTCAGTCGGTGCTCATCCACGCAGGCGGTGTCGGCATGGCGGCC
21523  ------------+---------+---------+---------+---------+---------+  21582
```

```
21583  GTCGCGCTGGCCCGCCGAGCGGGGCGGAGGTGTTGGCCACCGCCGGCCCGGCCAAGCAC  21642
        L  R  A  G  Q  S  V  L  I  H  A  A  A  G  G  V  G  M  A  A

21643  GGGACGCTGCGGGCGCTCGGTCTCGACGACGAGCACATCGCTTCCTCCCGGGAGACCGGT  21702
        V  A  L  A  R  R  A  G  A  E  V  L  A  T  A  G  P  A  K  H

21703  TTCGCCCGGAAGTTCCGGGAGCGCACCGGAGGCCGCGGTGGACGTGGTGCTCAACTCG  21762
        G  T  L  R  A  L  G  L  D  D  E  H  I  A  S  S  R  E  T  G

21763  CTCACCGGGGAACTGCTCGACGAGTCCGCGGATCTGCTCGCCGAGGACGGCGTCTTCGTC  21822
        F  A  R  K  F  R  E  R  T  G  G  R  G  V  D  V  V  L  N  S

21823  GAGATGGGCAAGACCGACCTGCGGGACGCCGGGGACTTCCGGGGCCGATACGCCCCGTTC  21882
        L  T  G  E  L  L  D  E  S  A  D  L  L  A  E  D  G  V  F  V

E  M  G  K  T  D  L  R  D  A  G  D  F  R  G  R  Y  A  P  F
```

```
21883  GACCTCGGCGAGGGGGTGACGACCGGCTCGGGGAGATCCTGCGCGAGGTCGTCGGCCTG  21942
       ----+---------+---------+---------+---------+---------+----
          D  L  G  E  A  G  D  D  D  R  L  G  E  I  L  R  E  V  V  G  L

21943  CTGGGCGCCGGGGAGCTCGACCGGCTCCCCGGTATCGGGGAGCTGGGATCCGCGCCC  22002
       ----+---------+---------+---------+---------+---------+----
          L  G  A  G  E  L  D  R  L  P  V  S  A  W  E  L  G  S  A  P

22003  GCGGCGTTGCAGCACATGAGCCGGGGCAGGCACGTCGGCAAGCTCGTGCTGACCCAGCCC  22062
       ----+---------+---------+---------+---------+---------+----
          A  A  L  Q  H  M  S  R  G  R  H  V  G  K  L  V  L  T  Q  P

22063  GCGCCGGTGGACCCGGACGGCACGGTGCTGATCACGGGTGGCACCGGCACGCTCGGACGG  22122
       ----+---------+---------+---------+---------+---------+----
          A  P  V  D  P  D  G  T  V  L  I  T  G  G  T  G  T  L  G  R

22123  CTGCTCGCGCGCCACCTCGTCACCGAGCACGGTGCGCGTGCACCTGCTGCTGGTCAGCAGG  22182
       ----+---------+---------+---------+---------+---------+----
          L  L  A  R  H  L  V  T  E  H  G  V  R  H  L  L  L  V  S  R

22183  CGCGGGCGGGACGGCGGGTTCCGGGTTCCGGACGAGCTGCGCGGAGATCGAGGACTTGGGGCG  22242
       ----+---------+---------+---------+---------+---------+----
```

FIG. 2-59

```
         R   G   A   D   A   P   G   S   D   E   L   R   A   E   I   E   D   L   G   A   -
         TCCGGGAGATCGCGGGCTTGCGACACCGCCGACCGCGACGGCGCTTTCGGCGCTGCTGGAC       22302
22243    ---------+---------+---------+---------+---------+---------+-
         S   A   E   I   A   A   C   D   T   A   D   R   D   A   L   S   A   L   L   D   -
         GGGCTGCCCCGGCGCTGACCGGTGTCGTGCACCGGTGTGCTGGCCGACGGGCTG              22362
22303    ---------+---------+---------+---------+---------+---------+-
         G   L   P   R   P   L   T   G   V   V   H   A   A   G   V   L   A   D   G   L   -
         GTCACCTCCATCGACGAGCCGGCTGTGGAGCAGGTGCTGCGCGCCAAGGTCGACGCGGGCG      22422
22363    ---------+---------+---------+---------+---------+---------+-
         V   T   S   I   D   E   P   A   V   E   Q   V   L   R   A   K   V   D   A   A   -
         TGGAACCTGCACGAGCTGACCGCGAACACCGGTCTCGAGCTTCTTCGTGCTGTTCTCGTCC      22482
22423    ---------+---------+---------+---------+---------+---------+-
         W   N   L   H   E   L   T   A   N   T   G   L   S   F   F   V   L   F   S   S   -
         GCGGGCGTCGGTGCTAGCCGGCCCCGGGCAGGGCGTGTACGCGGCCGAACGAGTCGCTC        22542
22483    ---------+---------+---------+---------+---------+---------+-
         A   A   S   V   L   A   G   P   G   Q   G   V   Y   A   A   A   N   E   S   L   -
         AACGCGCTGGCTGCCCTCCGGAGGACGCGGCCTTCCCGGAAGGCGCTCGGATGGGGA          22602
22543    ---------+---------+---------+---------+---------+---------+-
```

```
        N   A   L   A   A   L   R   R   T   R   G   L   P   A   K   A   L   G   W   G
        CTGTGGGGCAGGCCAGCGAGATGACCAGCGGACTCGGCGACCGCATCGCCCGGACCGGG      22662
22603   ---------------------------------------------------------

L   W   A   Q   A   S   E   M   T   S   G   L   G   D   R   I   A   R   T   G
        GTCGCCGCGCTGCCGACCGAGCGGGCGCTCGCACTGTTCGACAGCGCCCTGCGCCGCGGC      22722
22663   ---------------------------------------------------------

V   A   A   L   P   T   E   R   A   L   A   L   F   D   S   A   L   R   R   G
        GGTGAGGTCGTGTTCCCGCTGTCCATCAACCGTTCCGCTGCCAGGGCCGAGTTCGTG        22782
22723   ---------------------------------------------------------

G   E   V   V   F   P   L   S   I   N   R   S   A   L   R   R   A   E   F   V
        CCGGAGGTCCTGCGCGGCATGGTCAGGGCGAAGCTGCGCGGGCAGGCCCGGAGGCG          22842
22783   ---------------------------------------------------------

P   E   V   L   R   G   M   V   R   A   K   L   R   A   A   G   Q   A   E   A
        GCAGGGGCCGAACGTGGTCGACCGGCTCGCCGGTCCGAGTCCGACCAGTCGCCGGG          22902
22843   ---------------------------------------------------------

A   G   P   N   V   V   D   R   L   A   G   R   S   E   S   D   Q   V   A   G
        CTGGCCGAACTGGTCGCGTTCACACGCGGTCTCCGGTACGGCTCGGCCGACCAG            22962
22903   ---------------------------------------------------------
```

FIG. 2-62

```
         L  A  E  L  V  R  S  H  A  A  A  V  S  G  Y  Y  G  S  A  D  Q
22963  CTCCCCGAGCGGCAAGGCGTTCAAGGACCTCGGTTTCGACTCGCTGGCCGCGGTGGAGCTG  23022
         L  P  E  R  K  A  F  K  D  L  G  F  D  S  L  A  A  V  E  L
23023  CGCAACCGCCTCGTACCGGCGACCGGCGTGCGGCTGCCCAGCACGTTGGTGTTCGACCAC  23082
         R  N  R  L  G  T  A  T  G  V  R  L  P  S  T  L  V  F  D  H
23083  CCGACTCCGCTGGCCGTGGCCGAACACCTGCGGGACAGGCTGTTCGCGGCCTCACCGGCG  23142
         P  T  P  L  A  V  A  E  H  L  R  D  R  L  F  A  A  S  P  A
23143  GTGGACATCGGCGACCGGCTGGACGAGCTGGAGAAGGCGCTCGAAGCCCTGTCCGCCGAG  23202
         V  D  I  G  D  R  L  D  E  L  E  K  A  L  E  A  L  S  A  E
23203  GACGGGCACGACGACGTGGGCCAGCGCCTGGAGTCGCTGCTGCGGTGGAACAGCAGG     23262
         D  G  H  D  D  V  G  Q  R  L  E  S  L  L  R  R  W  N  S  R
       CGGGCGACGCCCCGAGCACGTCCGCGATCAGCGAGGACGCCAGTGACGACGAGCTGTTC
```

FIG. 2-63

```
23263 ---------+---------+---------+---------+---------+---------+ 23322
         R  A  D  A  P  S  T  S  A  I  S  E  D  A  S  D  D  E  L  F
      TCGATGCTCGACCAGCGGTTCGGCGGGGAGAGGACCTGTAGATGAGCGGTGACAACGGC
23323 ---------+---------+---------+---------+---------+---------+ 23382
         S  M  L  D  Q  R  F  G  G  G  E  D  L  *  M  S  G  D  N  G
      ATGACCGAGGAAAAGCTCCGGCGCTACCTCAAGCGCACCGTCACCGAGCTCGACTCGGTG
23383 ---------+---------+---------+---------+---------+---------+ 23442
         M  T  E  E  K  L  R  R  Y  L  K  R  T  V  T  E  L  D  S  V
      ACCGCGCGCCTGCGTGAAGTCGAGCACCGGGCCGGTGAGCCGATCGCGATCGTCGGCATG
23443 ---------+---------+---------+---------+---------+---------+ 23502
         T  A  R  L  R  E  V  E  H  R  A  G  E  P  I  A  I  V  G  M
      GCGTGCCGGTTCCCCGGCGACGTGGACTCGCCGGAGTCGTTCTGGGAGTTCGTGTCCGGC
23503 ---------+---------+---------+---------+---------+---------+ 23562
         A  C  R  F  P  G  D  V  D  S  P  E  S  F  W  E  F  V  S  G
      GGCGGGGACGCCATCGCGGAGGCCCCGGCCGACCGGGGCTGGGAGCCCGACCCCGACGCG
23563 ---------+---------+---------+---------+---------+---------+ 23622
         G  G  D  A  I  A  E  A  P  A  D  R  G  W  E  P  D  P  D  A
```

FIG.2-64

```
23623 CGGCTGGGCGGGATGCTCGCGGGCCGCGGGGCCGACTTCGACGCGGGCTTCTTCGGATCTCG 23682
       R  L  G  G  M  L  A  A  A  G  D  F  D  A  G  F  F  G  I  S

23683 CCGCGCGAGGCGCTGGCGATGGACCCGCAGCAGCGGATCATGCTGGAGATCTCGTGGGAG 23742
       P  R  E  A  L  A  M  D  P  Q  Q  R  I  M  L  E  I  S  W  E

23743 GCGCTGGAGCGCGCCGGCCACGATCCGGTGTCCCTGCGCGGCAGCGCGACCGGGGTGTTC 23802
       A  L  E  R  A  G  H  D  P  V  S  L  R  G  S  A  T  G  V  F

23803 ACCGGTGTCGGCACCGTGGACTACGGCCCCGACGAGGCCCCGGACGAGGTCCTG 23862
       T  G  V  G  T  V  D  Y  G  P  R  P  D  E  A  P  D  E  V  L

23863 GGCTACGTCGGCACCGGCGCCTCCAGCGTCGCCTCCGGCGTCGCCTACTGCCTG 23922
       G  Y  V  G  T  G  T  A  S  S  V  A  S  G  R  V  A  Y  C  L

23923 GGCCTGGAAGGCCCGGCGATGACCGTCGACACCGCCTGTTCCTCCGGGCTCACCGCCCTG 23982
       G  L  E  G  P  A  M  T  V  D  T  A  C  S  S  G  L  T  A  L
```

```
23983  CACCTGGCGATGGAGTCGCTGCGGCGCGACGAGTGCGGCCTGGCCCTGGCCGGCGGCGTG
       ------+---------+---------+---------+---------+---------+  24042
        H  L  A  M  E  S  L  R  R  D  E  C  G  L  A  L  A  G  G  V

24043  ACGGTGATGAGCAGTCCCGGGGCGGCGTTCACCGAGTTCCGCAGCCAGGGCGGCCTCGCCGCC
       ------+---------+---------+---------+---------+---------+  24102
        T  V  M  S  S  P  G  A  F  T  E  F  R  S  Q  G  G  L  A  A

24103  GACGGCCGCTGCAAGCCGTTCTCGAAGGCCGCCGACGGGTTCGGCCTGGCCGAGGGTGCC
       ------+---------+---------+---------+---------+---------+  24162
        D  G  R  C  K  P  F  S  K  A  A  D  G  F  G  L  A  E  G  A

24163  GGGGTCCTGGTGCTGCAACGGCTGTCGGCCGCGGAGGCAGACCGGTGCTGGCC
       ------+---------+---------+---------+---------+---------+  24222
        G  V  L  V  L  Q  R  L  S  A  A  R  R  E  G  R  P  V  L  A

24223  GTGCTGCGGGGCTCGGCGGTCAACCAGGACGGCGCCAGCAACGGGCTGACCGCCCCGAGC
       ------+---------+---------+---------+---------+---------+  24282
        V  L  R  G  S  A  V  N  Q  D  G  A  S  N  G  L  T  A  P  S

24283  GGACCCGCGCAGCAGGGTCATCCGCCCGGGCTGGAGAACGCCGGTGTCCGGGGGC
       ------+---------+---------+---------+---------+---------+  24342
```

```
       G  P  A  Q  Q  R  V  I  R  R  A  L  E  N  A  G  V  R  A  G  -
       GACGTCGACTACGTGGAGGCCCACGGCACCGGCTGGGCGACCCCATCGAGGTG
24343  ------+---------+---------+---------+---------+---------+-  24402

D  V  D  Y  V  E  A  H  G  T  G  T  R  L  G  D  P  I  E  V  -
       CACGGCGTGCTCTCGACCTACGGCGAACGCGACCCGGACGATCCACTGTGGATCGGT
24403  ------+---------+---------+---------+---------+---------+-  24462

H  A  L  L  S  T  Y  G  A  E  R  D  P  D  D  D  P  L  W  I  G  -
       TCGGTCAAGTCCAACATTGGCCACACCCAGGCCGCCGCCGGCGTCGCCGGGGTGATGAAG
24463  ------+---------+---------+---------+---------+---------+-  24522

S  V  K  S  N  I  G  H  T  Q  A  A  A  G  V  A  G  V  M  K  -
       GCGGTGCTGGCGCTGCGCCACGGCGAGATGCCGCGCACGCTGCACTTCGACGAGCCCTCG
24523  ------+---------+---------+---------+---------+---------+-  24582

A  V  L  A  L  R  H  G  E  M  P  R  T  L  H  F  D  E  P  S  -
       CCGCAGATCGAGTGGGACCTGGGCGCGGTGTCGGTGTCGCAGGCGCGTCGTGCCC
24583  ------+---------+---------+---------+---------+---------+-  24642

P  Q  I  E  W  D  L  G  A  V  S  V  V  S  Q  A  R  S  W  P  -
       GCCGGGGCGAGAGGCCCCAGGGCGTCTCCTCGTTCGGCATCAGCGGCACCAACGCG
24643  ------+---------+---------+---------+---------+---------+-  24702
```

```
           A  G  E  R  P  R  R  A  G  V  S  S  F  G  I  S  G  T  N  A
       CACGTCATCGTCGAAGAGGCGCCCGAGGCCCGACGAGCCGGCACCCGACTCGGGT       24762
24703  ---+----+----+----+----+----+----+----+----+----+----+---

H  V  I  V  E  E  A  P  E  A  D  E  P  E  P  A  P  D  S  G
       CCGGTCCCGCTGGTGTTGTCCGGCCGCGACGAGCAGGCGATGCGGGGCCAGGGGACGG     24822
24763  ---+----+----+----+----+----+----+----+----+----+----+---
           P  V  P  L  V  L  S  G  R  D  E  Q  A  M  R  A  Q  A  G  R

CTGGCAGACCACCTCGCCCGCGAGCCGGAACTCGTTGCGGACACCGGTtTCACGCTG      24882
24823  ---+----+----+----+----+----+----+----+----+----+----+---
           L  A  D  H  L  A  R  E  P  R  N  S  L  R  D  T  G  F  T  L

GCCACCCGCCGCCAGCGCGTGGGAGCACCGCCGGTGGTCGCCGACGCC               24942
24883  ---+----+----+----+----+----+----+----+----+----+----+---
           A  T  R  R  S  A  W  E  H  R  A  V  V  G  D  R  D  D  A

CTCGCCGGGCTGCGCGCGGTGGCCGACGGCCGCATCGCCGACGGCCACCGGGCAG        25002
24943  ---+----+----+----+----+----+----+----+----+----+----+---
           L  A  G  L  R  A  V  A  D  G  R  I  A  D  R  T  A  T  G  Q

GCCCGAACTCGCCCGGCGTCGGCGGCGATGGTGTTCCCGGCCAGGGGCGCAGTGGCAGGGG  25062
25003  ---+----+----+----+----+----+----+----+----+----+----+---
```

```
          A  R  T  R  R  G  V  A  M  V  F  P  G  Q  G  A  Q  W  Q  G
       ATGGCCCGCGACCTGCTGCGGGAGTCGCAGGTATTCGCCGACTCGATCCGCGACTGCGAG
25063  ------+---------+---------+---------+---------+---------+---  25122
          M  A  R  D  L  L  R  E  S  Q  V  F  A  D  S  I  R  D  C  E

R  A  L  A  P  H  V  D  W  S  L  T  D  L  L  S  G  A  R  P
       CGGGCGCTGGCCCCGCACGTCGACTGGTCGCTGACCGACCTGCTCAGCGGCGCGACCG
25123  ------+---------+---------+---------+---------+---------+---  25182

L  D  R  V  D  V  V  Q  P  A  L  F  A  V  M  V  S  L  A  A
       CTGGACCGGGTCGACGTCGTCCAGCCCGCGCTCTTCGCCGTCATGGTGTCGCTGGCGGCG
25183  ------+---------+---------+---------+---------+---------+---  25242

L  W  R  S  H  G  V  E  P  A  A  V  V  G  H  S  Q  G  E  I
       CTGTGGCGCTCCCACGGGGTCGAGCCCGCGGCCGTCGTCGGCCACTCGCAGGGCGAGATC
25243  ------+---------+---------+---------+---------+---------+---  25302

A  A  A  H  V  A  G  A  L  T  L  E  D  A  A  K  L  V  A  V
       GCCGCCGCGCACGTCGCCGGCGCGCTCACCCTGGAGGACGCCGCCAAGCTCGTCGCGGTC
25303  ------+---------+---------+---------+---------+---------+---  25362
```

```
25363  CGGAGCCGGGTCCTGGCCCGGCTCGGCGGCCAGGGCGCATGGCGTCGTTCGGGCTGGGC
       -----+---------+---------+---------+---------+---------+  25422
       R  S  R  V  L  A  R  L  G  G  Q  G  G  M  A  S  F  G  L  G

25423  ACCGAGCAGGCGGGCCGAACGGATCGGGCGCTTCGCGGGCGCTCTCCATCGCCTCGGTC
       -----+---------+---------+---------+---------+---------+  25482
       T  E  Q  A  A  E  R  I  G  R  F  A  G  A  L  S  I  A  S  V

25483  AACGGCCCCCGTCGGTCGTCGTCGCGGGAGAGCGGGCCGTGGACGAGCTGATCGCC
       -----+---------+---------+---------+---------+---------+  25542
       N  G  P  R  S  V  V  V  A  G  E  S  G  P  L  D  E  L  I  A

25543  GAGTGCGAGGCCGAAGGCATAACGGCGCGCCGCATCCCCGTCGACTACGCCCTCCCACTCA
       -----+---------+---------+---------+---------+---------+  25602
       E  C  E  A  E  G  I  T  A  R  R  I  P  V  D  Y  A  S  H  S

25603  CCGCAGGTGGAGTCGCTGCGCGAGGAGCTGCTGACCGAGCTGGCCGGGCATCTCCCCGGTG
       -----+---------+---------+---------+---------+---------+  25662
       P  Q  V  E  S  L  R  E  E  L  L  T  E  L  A  G  I  S  P  V

25663  TCGGGCGACGTGGCGCTCTACTCGACCACGAGCCCATCGACACCGCCACGATG
       -----+---------+---------+---------+---------+---------+  25722
```

```
        S  A  D  V  A  L  Y  S  T  T  T  G  Q  P  I  D  T  A  T  M
        GACACCGCCTACTGGTACGCGAACCTGCGCGAGCAGGTCCGCTTCCAGGACGCCGACGCCGG
25723   ------+---------+---------+---------+---------+---------+   25782

D  T  A  Y  W  Y  A  N  L  R  E  Q  V  R  F  Q  D  A  T  R
        CAGCTCGCCGAGGCCGGGGTTCGACGCCGTTCGTCGAGGTCAGCCCCGCATCCGGTGCTGACC
25783   ------+---------+---------+---------+---------+---------+   25842

Q  L  A  E  A  G  F  D  A  F  V  E  V  S  P  H  P  V  L  T
        GTCGGCATCGAGGCCACGCTGGACTCCGCGCTCCCCGGCCGACGCGCTGGCCTGCGTCGTG
25843   ------+---------+---------+---------+---------+---------+   25902

V  G  I  E  A  T  L  D  S  A  L  P  A  D  A  G  A  C  V  V
        GGCACCCTGCGCCGGGACCGCGGCGGGCTGGCCGACTTCCACACCGCTCGGGCGAGGCG
25903   ------+---------+---------+---------+---------+---------+   25962

G  T  L  R  R  D  R  G  G  L  A  D  F  H  T  A  L  G  E  A
        TACGCGCAGGGCGTGGAGGTCGACTGGAGCCCCGCCTTCGCCGACGCGCGGCCGGTCGAG
25963   ------+---------+---------+---------+---------+---------+   26022

Y  A  Q  G  V  E  V  D  W  S  P  A  F  A  D  A  R  P  V  E
        CTGCCCGTCTACCCGTTCCAGCGGCAGCGGTACTGGCTGCCCATCCCCACCGGGCCGGGCGC
26023   ------+---------+---------+---------+---------+---------+   26082
```

```
                L  P  V  Y  P  F  Q  R  Q  R  Y  W  L  P  I  P  T  G  G  R  -

GCACGGGACGAGGACGACGACTGGCGCTACCAGGTCGTATGGCGGGAAGCCGAGTGGGAG
26083      ------+---------+---------+---------+---------+---------+  26142

A  R  D  E  D  D  D  W  R  Y  Q  V  V  W  R  E  A  E  W  E  -

AGCGCTTCGCTGGCCGGACGCGCTGTGCTGTGGTGACCGGAACCGGGCCGTGCCGAGTTG
26143      ------+---------+---------+---------+---------+---------+  26202

S  A  S  L  A  G  R  V  L  L  V  T  G  P  G  V  P  S  E  L  -

TCGGACGCCATCCGAAGTGGACTGGAGCAGAGCGGTGCGACGGTCCTGACCTGCGACGTG
26203      ------+---------+---------+---------+---------+---------+  26262

S  D  A  I  R  S  G  L  E  Q  S  G  A  T  V  L  T  C  D  V  -

GAATCCCGTTCGACCATCGGCACCGCACTGGAGGCCGCCGACACCGACGCTCTGTCCACT
26263      ------+---------+---------+---------+---------+---------+  26322

E  S  R  S  T  I  G  T  A  L  E  A  A  D  T  D  A  L  S  T  -

GTGGTGTCGCTGCTGTCCCGGGACGGGGAGGCCGTCGATCCGTCGCTGGACGCGCTCGCC
26323      ------+---------+---------+---------+---------+---------+  26382

V  V  S  L  L  S  R  D  G  E  A  V  D  P  S  L  D  A  L  A  -

CTGGTCCAGGCCCTCGGAGCCCGGGGTCGAAGCACCGCGTCTGTGGGTGCTGACCCGCAAC
26383      ------+---------+---------+---------+---------+---------+  26442
```

```
                 L  V  Q  A  L  G  A  A  G  V  E  A  P  L  W  V  L  T  R  N     -
              GCCGTGCAGGTGGCCGACGGGCCGAACTGGTCGATCCGGGCCATGGTGGGCGGTCTC
26443         ------+---------+---------+---------+---------+---------+--  26502
                 A  V  Q  V  A  D  G  E  L  V  D  P  A  Q  A  M  V  G  G  L     -
              GGCCGCGTGGTCGGCATCGAGCAGCCGGGCCGGTCTCGGTGGACCTGGTCGAC
26503         ------+---------+---------+---------+---------+---------+--  26562
                 G  R  V  V  G  I  E  Q  P  G  R  W  G  G  L  V  D  L  V  D     -
              GCCGATGCCGCGGTCGATCCGGTCGCTGGGCGGTGCTGGGCGACCCGCGGCGAGGAG
26563         ------+---------+---------+---------+---------+---------+--  26622
                 A  D  A  A  S  I  R  S  L  A  A  V  L  A  D  P  R  G  E  E     -
              CAGGTCGCGGATCCGGGCGACGGGATCAAGGTGGCGGAGGCTCGTGCCCGCCCCGC
26623         ------+---------+---------+---------+---------+---------+--  26682
                 Q  V  A  I  R  A  D  G  I  K  V  A  R  L  V  P  A  P  A  R     -
              GCCGGCACGCACCCCGCTGAGCCCCTCGCGCACCGTGCTGGTCACCGGGCACCGGAGGG
26683         ------+---------+---------+---------+---------+---------+--  26742
                 A  A  R  T  R  W  S  P  R  G  T  V  L  V  T  G  G  T  G  G     -
              ATCGGCGGCACGTCGCCCGCTGGCCCGCTCGGCGCCGAGCACCTGGTGCTGCTG
```

```
26743 ------+---------+---------+---------+---------+---------+ 26802
       GGCAGGCGCGGTGCCGACGCACCCGGCGCGTCCGAGCTGAGGGAGGAGCTGACCGCGCTC
       I  G  A  H  V  A  R  W  L  A  R  S  G  A  E  H  L  V  L  L

26803 ------+---------+---------+---------+---------+---------+ 26862
       GGCACGGGCGTGACCATCGCCGCCTGCGACGTCGCCGACCGGGCGCGCTCGAAGCGGTG
       G  R  R  G  A  D  A  P  G  A  S  E  L  R  E  E  L  T  A  L

26863 ------+---------+---------+---------+---------+---------+ 26922
       CTCGCCGCGGAGCGCGCCGAGGGACGCACGGTCAGCGCCGTGATGCACGCGGCGGGGTT
       G  T  G  V  T  I  A  A  C  D  V  A  D  R  A  R  L  E  A  V

26923 ------+---------+---------+---------+---------+---------+ 26982
       TCCACGTCCACGCCCCTCGACGACCTCACCGAAGCCGAGTTCACCGAGATCGCCGACGTG
       L  A  A  E  R  A  E  G  R  T  V  S  A  V  M  H  A  A  G  V

26983 ------+---------+---------+---------+---------+---------+ 27042
       AAGGTGCGGGCACCGTCAACCTGGACGAGCTCTGCCCCGACCTCGACGCCGTTCGTGTTG
       S  T  S  T  P  L  D  D  L  T  E  A  E  F  T  E  I  A  D  V

```
27103  TTCTCCTCCAACGCGGGGCGTGTGGGGCAGTCCGGGCTGCGCCTCCTACGGCGGGCCAAC  27162
        F   S   S   N   A   G   V   W   G   S   P   G   L   A   S   Y   A   A   A   N

27163  GCCTTCCTCGACGGCTTCGCGGCGCGCCGGAGCGAGGGCGCGGTGACGTCCATC  27222
        A   F   L   D   G   F   A   R   R   R   R   S   E   G   A   P   V   T   S   I

27223  GCCTGGGGGCTCTGGGCCGGGCAGAACATGGCCGGGGACGAGGGCGGCGAGTACCTGCGC  27282
        A   W   G   L   W   A   G   Q   N   M   A   G   D   E   G   G   E   Y   L   R

27283  AGCCAGGGCCTGCGCGGCCATGGACCCCGGATCGGGCCGTCGAGGAACTGCACATCACCCTC  27342
        S   Q   G   L   R   A   M   D   P   D   R   A   V   E   E   L   H   I   T   L

27343  GACCACGGTCAGACGTCCGTGTCGGTGGACATGGATCGCAGGCGGTTCGTCGAGCTG  27402
        D   H   G   Q   T   S   V   S   V   V   D   M   D   R   R   R   F   V   E   L

27403  TTCACCGGGCCCGGCACCGGCTGTTCGACGAGATCGCCGGTGCCCGGGCGGAAGCC  27462
        F   T   A   A   R   H   R   P   L   F   D   E   I   A   G   A   R   A   E   A
```

FIG. 2-75

```
27463  CGGCAGAGCGAGGAGGGGCCCGGCGCTCGCCCAGCGGCTCGCGGGCGCTGTCGACGGCCGAG  27522
       R   Q   S   E   E   G   P   A   L   A   Q   R   L   A   A   L   S   T   A   E

27523  AGGCGCGAGCACTTCGCCCACCTGATCCGCGCCGAGGTCGCGGCCGTGCTCGGCCACGGC  27582
       R   R   E   H   L   A   H   L   I   R   A   E   V   A   A   V   L   G   H   G

27583  GACGACGCGGCGATCGACCGCGACCGCGCCTTCCGCGACCTCGGCTTCGACTCCATGACC  27642
       D   D   A   A   I   D   R   D   R   A   F   R   D   L   G   F   D   S   M   T

27643  GCCGTCGACCTGCGGAACCGGCTCGCCGCCGTGACCGGGGTGCGGGAAGCCGCGACGGTG  27702
       A   V   D   L   R   N   R   L   A   A   V   T   G   V   R   E   A   A   T   V

27703  GTCTTCGACCACCCGACCATCACCCGGCTCGCCGACCACTACCTGGAGCGGCTCGTCGGC  27762
       V   F   D   H   P   T   I   T   R   L   A   D   H   Y   L   E   R   L   V   G

27763  GCAGCAGAGGCGGAGCAAGCCCGCGCTCGTGCGCGAGGTGCCGAAGGATGCCGACGAC  27822
       A   A   E   A   E   Q   A   P   A   L   V   R   E   V   P   K   D   A   D   D
```

```
27823  CCGATCGCGATCGTCGGCATGGCCTGCGCTTCCCCGGCGTGCACAACCCCGGTGAG
       -----+---------+---------+---------+---------+---------+   27882
            P  I  A  I  V  G  M  A  C  R  F  P  G  G  V  H  N  P  G  E

27883  CTGTGGGAGTTCATCGTCGGCCGCGGCGAGACGCCGTGACGGAGATGCCACCGACGCGGC
       -----+---------+---------+---------+---------+---------+   27942
            L  W  E  F  I  V  G  R  G  D  A  V  T  E  M  P  T  D  R  G

27943  TGGGACCCTCGACGCGCTGTTCGACCCCGACCCGCCAGCGCCACGGAACCAGCTACTCGCGA
       -----+---------+---------+---------+---------+---------+   28002
            W  D  L  D  A  L  F  D  P  D  P  Q  R  H  G  T  S  Y  S  R

28003  CACGGCGCGTTCCTCGACGGGGCCGCCGACTTCGACGCCGCGTTCTTCGGGATCTCGCCG
       -----+---------+---------+---------+---------+---------+   28062
            H  G  A  F  L  D  G  A  A  D  F  D  A  A  F  F  G  I  S  P

28063  CGCGAGGCGCTGGCGATGGACCCGCAGCAGCGGCCAGGTCCTGGAAACGACGTGGAGCTG
       -----+---------+---------+---------+---------+---------+   28122
            R  E  A  L  A  M  D  P  Q  Q  R  Q  V  L  E  T  T  W  E  L

28123  TTCGAGAACGCCGGCATCGACCCGCACTCGCTGCGGGCAGCGGACACCGGCGTCTTCCTC
       -----+---------+---------+---------+---------+---------+   28182
```

FIG. 2-76

```
        F   E   N   A   G   I   D   P   H   S   L   R   G   S   D   T   G   V   F   L
        GGCGCCCGGCGTACCAGGGCTACGGGCCAGGACGCGGTGGTGCCCGAGGACAGCGAGGGCTAC
28183   ------+---------+---------+---------+---------+---------+   28242

G   A   A   Y   Q   G   Y   G   Q   D   A   V   V   P   E   D   S   E   G   Y
        CTGCTCACCGGCAACTCCTCCGCCGTGGTGTCCGGCGTCGCCTACGTGCTGGGCTG
28243   ------+---------+---------+---------+---------+---------+   28302

L   L   T   G   N   S   S   A   V   V   S   G   R   V   A   Y   V   L   G   L
        GAAGGCCCCGCGGTCACGGTGGACACGGTGTTCGTCGTTGGCCTTGCATTCG
28303   ------+---------+---------+---------+---------+---------+   28362

E   G   P   A   V   T   V   D   T   A   C   S   S   S   L   V   A   L   H   S
        GCGTGTGGGTCGTTGCGTTGACTGCGGTGACTGCGGTGCTCTTGCGGTCTTGCGGTGTGTCGGTG
28363   ------+---------+---------+---------+---------+---------+   28422

A   C   G   S   L   R   D   G   D   C   G   L   A   V   A   G   G   V   S   V
        ATGGCGGGCCCGGAGTTCTCCCCGCCAGGCCGCTTGGCCGTGGACGGG
28423   ------+---------+---------+---------+---------+---------+   28482

M   A   G   P   E   V   F   T   E   F   S   R   Q   G   G   L   A   V   D   G
        CGCTGCAAGGCCGTTCTCCCGGAGGCCGACGGCTTCGGTTTCGCCGAGGGCGTCGCGGTG
28483   ------+---------+---------+---------+---------+---------+   28542
```

```
        R   C   K   A   F   S   A   E   A   D   G   F   G   F   A   E   G   V   A   V
       GTCCTGCTCCAGCGGTTGTCCGACGCCCCGCAGGGCGGTCGCCAGGTGCTCGGCGTGGTC
28543  ---+---------+---------+---------+---------+---------+---------  28602

V   L   L   Q   R   L   S   D   A   R   R   A   G   R   Q   V   L   G   V   V
       GCGGGCTCGGCGATCAACCAGGACGGCGAGCAACGTCTCGGCGCCGAGCGGGCGTC
28603  ---+---------+---------+---------+---------+---------+---------  28662

A   G   S   A   I   N   Q   D   G   A   S   N   G   L   A   A   P   S   G   V
       GCCCAGCAGCCGCGTGATCCGCAAGGCGTGGGCGATCACCGGCGCGGATGTG
28663  ---+---------+---------+---------+---------+---------+---------  28722

A   Q   Q   R   V   I   R   K   A   W   A   R   A   G   I   T   G   A   D   V
       GCCGTGGTGGAGGCGCATGGCACCGGTACGCGGCTGGGCGATCCGGTGGAGGCGTCGGCG
28723  ---+---------+---------+---------+---------+---------+---------  28782

A   V   V   E   A   H   G   T   G   T   R   L   G   D   P   V   E   A   S   A
       TTGCTGGCTACTTACGGCAAGTCGCGCGGCTCGTCGGGCCCGGTGCTGCTGGGTTCGGTG
28783  ---+---------+---------+---------+---------+---------+---------  28842

L   L   A   T   Y   G   K   S   R   G   S   S   S   G   P   V   L   L   G   S  . V
```

```
28843  AAGTCGAACATCGGTCACGGCGCCAGGGCGGCCCGCGGGGCGTGTCGCGGGCGTGATCAAGGTGGTC  28902
       ---------+---------+---------+---------+---------+---------+
         K  S  N  I  G  H  A  Q  A  A  A  G  V  A  G  V  I  K  V  V

28903  CTGGGGTTGAACCGGGCCCTGGTGCCGCCGATGCTCTGCCGCGGCGAGCGGTCGCCGCTG  28962
       ---------+---------+---------+---------+---------+---------+
         L  G  L  N  R  G  L  V  P  P  M  L  C  R  G  E  R  S  P  L

28963  ATCGAATGGTCCTCGGGTGGTGTGGAACTTGCCGAGGCCGTGAGCCCGTGGCCTCCGGCC  29022
       ---------+---------+---------+---------+---------+---------+
         I  E  W  S  S  G  G  V  E  L  A  E  A  V  S  P  W  P  P  A

29023  GCGGACGGGGTGCGCCGGGCCGGTGTGTCGGCGTTCGGGGTGAGCGGACGAACGCGCAC  29082
       ---------+---------+---------+---------+---------+---------+
         A  D  G  V  R  R  A  G  V  S  A  F  G  V  S  G  T  N  A  H

29083  GTGATCATCGCCGAGCCCCCGGAGCCCGAGCCGCTGCCCGAACCCGGACCGGTGGGCGTG  29142
       ---------+---------+---------+---------+---------+---------+
         V  I  I  A  E  P  P  E  P  E  P  L  P  E  P  G  P  V  G  V

29143  CTGGCCGCTGCGAACTCGGTGCCCGTACTGCTGTGCGGCCAGGACCGAGACCGCGTTGGCA  29202
       ---------+---------+---------+---------+---------+---------+
```

```
       L   A   A   A   N   S   V   P   V   L   L   S   A   R   T   E   T   A   L   A   -
       GCGCAGGCGGGGGCTCCTGGAGTCCGCAGTGGACGACTCGGTTCCGTTGACGGCATTGGCT     29262
29203  ---------+---------+---------+---------+---------+---------+---

A   Q   A   R   L   L   E   S   A   V   D   D   D   S   V   P   L   T   A   L   A   -
       TCCGCGCTGGCCACCGGACGCCCCACCTGCCGCGTCGTGCCGCGTTGCTGGCAGGCGAC       29322
29263  ---------+---------+---------+---------+---------+---------+---

S   A   L   A   T   G   R   A   H   L   P   R   R   A   A   L   L   A   G   D   -
       CACGAACAGCTCCGGGCAGTTGCCGAGGGCTCGCCGCGTTGCGGCTCCCGTGCC            29382
29323  ---------+---------+---------+---------+---------+---------+---

H   E   Q   L   R   G   Q   L   R   A   V   A   E   G   V   A   A   P   G   A   -
       ACCACCGGAACCGCCTCCGCCGGGCCGTGGTTTCGTCTTCCCAGTCAGGGTGCTCAG         29442
29383  ---------+---------+---------+---------+---------+---------+---

T   T   G   T   A   S   A   G   G   V   V   F   V   F   P   G   Q   G   A   Q   -
       TGGGAGGGCATGGCCCGGGCCTTGCTCTCCGTCCCCGTCTTCGCCGAGTCGATCGCCGAG      29502
29443  ---------+---------+---------+---------+---------+---------+---

W   E   G   M   A   R   G   L   L   S   V   P   V   F   A   E   S   I   A   E   -
       TGCGATGCGGGTGTTGTCGGAGGTGGCCCGGTTCTCCGGAAGTGCTGGAGCAGGCGT         29562
29503  ---------+---------+---------+---------+---------+---------+---
```

```
         C   D   A   V   L   S   E   V   A   G   F   S   A   S   E   V   L   E   Q   R
         CCGGACGCGCCGTCGCTGGAGCGGGTCGACGTCGTACAGCCGGTGTTCTCCGTGATG
29563    ---------+---------+---------+---------+---------+---------+    29622

P   D   A   P   S   L   E   R   V   D   V   V   Q   P   V   L   F   S   V   M
         CCGGATGCGCCGTCGCTGGAGCGGGTCGACGTCGTACAGCCGGTGTTCTCCGTGATG
         GGCCTACGCGGCAGCGACCTCGCCCAGCTGCAGCATGTCGGCCACAAGAGGCACTAC
29623    ---------+---------+---------+---------+---------+---------+    29682
         GTGTCGCTGGCGCGGGCTGTGGGGCGCTTGCGGAGTCAGCCCCTCGGCCGTCATCGGCCAT

V   S   L   A   R   L   W   G   A   C   G   V   S   P   S   A   V   I   G   H
29683    ---------+---------+---------+---------+---------+---------+    29742
         TCGCAGGGCGAGATCGCGGCCGCCGTGGTGGCCGGGGTGTTGTCGCTGGAGGACGGGGTG

S   Q   G   E   I   A   A   A   V   V   A   G   V   L   S   L   E   D   G   V
29743    ---------+---------+---------+---------+---------+---------+    29802
         CGCGTCGTGGCCCTGCGCGCGAAGGCGTTGCGCTGGCCTGGCGCTGGCGCAAGGGCGCATGGTC

R   V   V   A   L   R   A   K   A   L   R   A   L   A   G   K   G   G   M   V
29803    ---------+---------+---------+---------+---------+---------+    29862
         TCGTTGGCGGCTCCCGGTGAACGCGCGGCGCTGATCGCACCGTGGGAGGACCGGATC

S   L   A   A   P   G   E   R   A   R   A   L   I   A   P   W   E   D   R   I
29863    ---------+---------+---------+---------+---------+---------+    29922
         TCCGTCGCGGGGGTCAACTCCCCGTCGTCCTCGGTCGTGGTCTCCGGCGATCCGGAGGCGCTG
```

FIG.2-81

```
         S  V  A  A  V  N  S  P  S  S  V  V  V  S  G  D  P  E  A  L
       GCCGAACTCGTCGCACGTTGCGAGGACGAGGGCGTGCGCCAAGACGCTCCCGGTGGAC
29923  ------------------------------+------------------------------  29982

A  E  L  V  A  R  C  E  D  E  G  V  R  A  K  T  L  P  V  D
       TACGCCTCGCACTCCCGCCACGTCGAGGAGATCCGCGAGACGATCCTCGCCGACCTCGAC
29983  ------------------------------+------------------------------  30042

Y  A  S  H  S  R  H  V  E  E  I  R  E  T  I  L  A  D  L  D
       GGCATCTCCGCGCGGGCTGCCGCCATCCCGCTCTACTCCACGCTGCACGGCGAACGGCGC
30043  ------------------------------+------------------------------  30102

G  I  S  A  R  R  A  A  I  P  L  Y  S  T  L  H  G  E  R  R
       GACGGGCGCCGACATGGGTCCGCGGTACTGGTACGACAACCTGCGCTCCCAGGTGCGCTTC
30103  ------------------------------+------------------------------  30162

D  G  A  D  M  G  P  R  Y  W  Y  D  N  L  R  S  Q  V  R  F
       GACGAGGCGGTCTCGGCGGCCGTCGCCGACGGTCACGCCACCTTCGTCGAGATGAGCCCG
30163  ------------------------------+------------------------------  30222

D  E  A  V  S  A  A  V  A  D  G  H  A  T  F  V  E  M  S  P
       CACCCGGTGCTCACCGGGTGCAGGAGATCGCCGGGACGCCGTGGCCATCGGTCG
```

```
30223 ---------+---------+---------+---------+---------+---------+ 30282
       CTGCACCGCGACACCGGCGAGGAGCACCTGATCGCCGAGCTCGCCCGGGCGCACGTGCAC
       H  P  V  L  T  A  A  V  Q  E  I  A  A  D  A  V  A  I  G  S

30283 ---------+---------+---------+---------+---------+---------+ 30342
       GGCGTGGCCGTGGACTGGCGGAACGTCTTCCCGGCGGCACCTCCGGTGGCTGCCCAAC
       L  H  R  D  T  A  E  E  H  L  I  A  E  L  A  R  A  H  V  H

30343 ---------+---------+---------+---------+---------+---------+ 30402
       TACCCGTTCGAGCCCCAGCGTACTGGCTCGCGGAGGTGTCCGACCAGCTCGCCGAC
       G  V  A  V  D  W  R  N  V  F  P  A  A  P  P  V  A  L  P  N

30403 ---------+---------+---------+---------+---------+---------+ 30462
       AGCCGCTACCGCGTCGACTGGCGACCGCTGGCCACCACGCCGGTGGACCTGGAAGGCGGC
       Y  P  F  E  P  Q  R  Y  W  L  A  P  E  V  S  D  Q  L  A  D

30463 ---------+---------+---------+---------+---------+---------+ 30522
       TTCCTGGTCCACGGGTCCGCACCGGAGTCGCTGACCAGCGCGGAGAAGGCCGGAGGC
       S  R  Y  R  V  D  W  R  P  L  A  T  T  P  V  D  L  E  G  G

```
30583  CGCGTCGTGCCGGTCGCCTCGGCCGACCGCGAAGCCTCGGCGCCCTGCGGGAGGTGCCG  30642
        R  V  V  P  V  A  S  A  D  R  E  A  S  A  A  L  R  E  V  P

30643  GGCGAGGTCGCGGCCGTGCTCTCGGTGCTCCACACCGGCGCCGCAACGCACCTCGCCCTGCAC  30702
        G  E  V  A  G  V  L  S  V  H  T  G  A  A  T  H  L  A  L  H

30703  CAGTCGCTGGGTGAGGCCGGGGTGCGGGCCCCGCTCTGGCTGGTCACCAGCCCGAGCGGGTC  30762
        Q  S  L  G  E  A  G  V  R  A  P  L  W  L  V  T  S  R  A  V

30763  GCGCTCGGGGAGTCCGAGCCGGTCGATCCCGAGCAGGCGATGGTGTGGGGTCTCGGGCGC  30822
        A  L  G  E  S  E  P  V  D  P  E  Q  A  M  V  W  G  L  G  R

30823  GTCATGGGCCTGGAGACCCCCGGAACGGTGGGGCCGGTTCGTGTTGGTGACCTGCCCGCCGAACCC  30882
        V  M  G  L  E  T  P  E  R  W  G  G  L  V  D  L  P  A  E  P

30883  GCGCCGGGGGACGGCGAGGCGGTTCGTCGCCTGCCTCGGCCGACGGCCACGAGGACCAG  30942
        A  P  G  D  G  E  A  F  V  A  C  L  G  A  D  G  H  E  D  Q
```

FIG. 2-85

```
30943 GTCGGCGATCCGTGACCACGCCCGCTACGGCCGCCGCCTCGTCCGCCCCGCTGGGCACC
      ----+----+----+----+----+----+----+----+----+----+----+---- 31002
       V  A  I  R  D  H  A  R  Y  G  R  R  L  V  R  A  P  L  G  T

31003 CGCGAGTCGAGCTGGGAGCCGGCGGGCACGGCGCTGGTCACCGGCGGCACCGGTGCGCTC
      ----+----+----+----+----+----+----+----+----+----+----+---- 31062
       R  E  S  S  W  E  P  A  G  T  A  L  V  T  G  G  T  G  A  L

31063 GGCGGCCACGTCGCCCGCCACCTCGCCCAGGTGCGGGGTGGAGGACCTGGTGCTGGTCAGC
      ----+----+----+----+----+----+----+----+----+----+----+---- 31122
       G  G  H  V  A  R  H  L  A  R  C  G  V  E  D  L  V  L  V  S

31123 AGGCGGCGGCGTCGACGCTCCCGGCGGCGGCCGAGCTGGAAGCCGAACTGGTCGCCCTCGGC
      ----+----+----+----+----+----+----+----+----+----+----+---- 31182
       R  R  G  V  D  A  P  G  A  A  E  L  E  A  E  L  V  A  L  G

31183 GCGAAGACGACCATCACCGCTGCGACTGGCCGAGCAGCTCTCCAAGCTGCTG
      ----+----+----+----+----+----+----+----+----+----+----+---- 31242
       A  K  T  T  I  T  A  C  D  V  A  D  R  E  Q  L  S  K  L  L

31243 GAAGAACTGGCGGGCAGGAGACGTCCGGTGCGGACCGTCGTGCACCGCCGGGGTGCCC
      ----+----+----+----+----+----+----+----+----+----+----+---- 31302
```

FIG. 2-86

```
       E   E   L   R   G   Q   G   R   P   V   R   T   V   V   H   T   A   G   V   P   -
       GAATCGAGGCCGCTGCACGAGATCGGGCGAGCTGGAGTCGGTCGTGCACACGGCGGGCGAAGGTGACC
31303  ------+---------+---------+---------+---------+---------+---------  31362

E   S   R   P   L   H   E   I   G   E   L   E   S   V   C   A   A   K   V   T   -
       GGGGCCCGGCTGCTCGACGAGCTGTGCCCGGACGCCGAGACCTTCGTCCTGTTCTCGTCC
31363  ------+---------+---------+---------+---------+---------+---------  31422

G   A   R   L   L   D   E   L   C   P   D   A   E   T   F   V   L   F   S   S   -
       GGAGCGGGGGTGTGGGGCAGTGCGGAACCTCGGCGCCTACTCCGGCCAACGCCTACCTC
31423  ------+---------+---------+---------+---------+---------+---------  31482

G   A   G   V   W   G   S   A   N   L   G   A   Y   S   A   A   N   A   Y   L   -
       GACGCGCTGGCCCACCGCCGCGCCGTGCGGAAGGCCGTGCGACGTCCGTCGCGTGGGGC
31483  ------+---------+---------+---------+---------+---------+---------  31542

D   A   L   A   H   R   R   R   A   E   G   R   A   A   T   S   V   A   W   G   -
       GCCTGGGCGGGCGAGGGCATGGCCACCGGCGACCTCGAGGGGCTCACCCGGCGGCCTG
31543  ------+---------+---------+---------+---------+---------+---------  31602

A   W   A   G   E   G   M   A   T   G   D   L   E   G   L   T   R   R   G   L   -
       CGCCCGATGGCGCCCGAGCGCGGCGATCCGGCGCGCTGGACAACGGCGAC
31603  ------+---------+---------+---------+---------+---------+---------  31662
```

```
           R  P  M  A  P  E  R  A  I  R  A  L  H  Q  A  L  D  N  G  D    -
         ACGTGCGTTTCGATCGCCGAGTGCCGACTGGGAGGCCTTCGCGGTCGGCTTCACCGCCGCC      - 31722
31663    ---------+---------+---------+---------+---------+---------+

T  C  V  S  I  A  D  V  D  W  E  A  F  A  V  G  F  T  A  A    -
         CGGCCGCGTCCGCTGCTGGACGAGAGCTCGTCACGCCGGGTGGGGGCCGTCCCCGGGTG        - 31782
31723    ---------+---------+---------+---------+---------+---------+

R  P  R  P  L  L  D  E  L  V  T  P  A  V  G  A  V  P  A  V    -
         CAGGCGGCCCCGCGCGGGAGATGACGTCGCAGGAGTTGCTGGAGTTCACGCACTCGCAC        - 31842
31783    ---------+---------+---------+---------+---------+---------+

Q  A  A  P  A  R  E  M  T  S  Q  E  L  L  E  F  T  H  S  H    -
         GTCGCGGCGATCCTCGGGCATTCCAGCCCGGACGCGGTCGGGCAGGACCAGCCGTTCACC       - 31902
31843    ---------+---------+---------+---------+---------+---------+

V  A  A  I  L  G  H  S  S  P  D  A  V  G  Q  D  Q  P  F  T    -
         GAGCTCGGCTTCGACTCGCTGACCGCTGTGGGCCTGCGCAACCAGCTCCAGCAGGCCACC       - 31962
31903    ---------+---------+---------+---------+---------+---------+

E  L  G  F  D  S  L  T  A  V  G  L  R  N  Q  L  Q  Q  A  T    -
         GGGCTCGCGCTGCCCGCGACCCTGGTGTTCGAGCACCCCAGCGTCCCGCAGGTTGGCCGAC      - 32022
31963    ---------+---------+---------+---------+---------+---------+
```

```
         G  L  A  L  P  A  T  L  V  F  E  H  P  T  V  R  R  L  A  D  -
32023    CACATAGGACAGCTCGACAGCGGGACTCCCGCCCGGGAAGCGAGCAGCGCTCTTCGC     32082
         ---------+---------+---------+---------+---------+---------+

H  I  G  Q  Q  L  D  S  G  T  P  A  R  E  A  S  S  A  L  R  -
32083    GACGGGCTACCGGGCCAGGGCGGAGCGTGTCGGGCAGGGTCCGGTCCTACCTCGACCTGCTGGCG  32142
         ---------+---------+---------+---------+---------+---------+

D  G  Y  R  Q  A  G  V  S  G  R  V  R  S  Y  L  D  L  L  A  -
32143    GGGCTGTGTCGGAGACTTCCGCGAGCACTTCGACGGTCTCCCTCGATCTCGTG           32202
         ---------+---------+---------+---------+---------+---------+

G  L  S  D  F  R  E  H  F  D  G  S  D  G  F  S  L  D  L  V  -
32203    GACATGGCCGACGGTCCCGGAGAGGTCACGGTGATCTGCTGCGGGAACGGGGCGGATC     32262
         ---------+---------+---------+---------+---------+---------+

D  M  A  D  G  P  G  E  V  T  V  I  C  C  A  G  T  A  A  I  -
32263    TCCGGTCCGCACGAGTTCACCCGGCTGGCTGCCGGGGCTCGCCGGGAATCGCTCCGGTTCGG  32322
         ---------+---------+---------+---------+---------+---------+

```
32323   GCCGTGCCCCAGCCCGGCTACGAGGAGGGCGAACCTCTGCCGTCGTCGATGGCGGCGGTG   32382
        A   V   P   Q   P   G   Y   E   E   G   E   P   L   P   S   S   M   A   A   V

32383   GCGGCGGTGCAGGCCGATGCGGTCATCAGGACACACAGGGGAGACAAGCCGTTCGTGGTGGCC   32442
        A   A   V   Q   A   D   A   V   I   R   T   Q   G   D   K   P   F   V   V   A

32443   GGTCACTCCGCGGGGGCACTGATGGCCTACGCGCTGGCGACCGAACTGCTCGATCGCGGG   32502
        G   H   S   A   G   A   L   M   A   Y   A   L   A   T   E   L   L   D   R   G

32503   CACCCGCCACGCGGCGTGGTCGTCCTGATCGACGTCTACCCGCCGGTCACCAGGACGCGATG   32562
        H   P   P   R   G   V   V   L   I   D   V   Y   P   P   G   H   Q   D   A   M

32563   AACGCCTGGCTGGAGGAGCTGACCGCCACGCTGTTCGACCGGGAGACGGTGCGGATGGAC   32622
        N   A   W   L   E   E   L   T   A   T   L   F   D   R   E   T   V   R   M   D

32623   GACACCAGGCTCACCGCCCTGGGCGCCTACGACCGCCTCACCGGTCAGTGGCGACCCCGG   32682
        D   T   R   L   T   A   L   G   A   Y   D   R   L   T   G   Q   W   R   P   R
```

```
32683  GAAACCGGGCTGCCGACGCTGCTGGTCAGCGCCGGCGAGCCGATGGGTCCGTGGCCCGAC  32742
       ----+----+----+----+----+----+----+----+----+----+----+----+
       E  T  G  L  P  T  L  L  V  S  A  G  E  P  M  G  P  W  P  D

32743  GACAGCTGGAAGCCGACGTGGCCCTTCGAGCACGACACCGTCGCCGTCCCCGGCGACCAC  32802
       ----+----+----+----+----+----+----+----+----+----+----+----+
       D  S  W  K  P  T  W  P  F  E  H  D  T  V  A  V  P  G  D  H

32803  TTCACGATGGTGCAGGAACACGCCGACGCGATCGCGCGGCACATCGACGCGCTGGCTGGGC  32862
       ----+----+----+----+----+----+----+----+----+----+----+----+
       F  T  M  V  Q  E  H  A  D  A  I  A  R  H  I  D  A  W  L  G

32863  GGAGGGAATTCATGA  32877
       ----+----+-----
       G  G  N  S  *
```

FIG. 2-90

| NUMBER | SITE | DISTANCE (Kb)[a] |
|--------|------|------------------|
| 1 | BamHI | −3.60 |
| 2 | PvuII | −3.50 |
| 3 | PvuII | −3.40 |
| 4 | PstI | −3.05 |
| 5 | BamHI | −2.95 |
| 6 | XhoI | −2.80 |
| 7 | PstI | −2.00 |
| 8 | HindII | −1.60 |
| 9 | SphI | −1.55 |
| 10 | EcoRI | −1.50 |
| 11 | KpnI | −1.35 |
| 12 | EcoRI | −1.05 |
| 13 | SmaI[b] | −0.90 |
| 14 | SphI | −0.75 |
| 15 | KpnI | −0.65 |
| 16 | SmaI | −0.20 |

FIG. 4

RECOMBINANT DNA METHOD FOR PRODUCING ERYTHROMYCIN ANALOGS

FIELD OF THE INVENTION

The present invention relates to a method for directing the biosynthesis of specific polyketide analogs by genetic manipulation. In particuar, polyketide biosynthetic genes are manipulated to produce precise, novel polyketides of predicted structure.

BACKGROUND OF THE INVENTION

Polyketides are a large class of natural products that includes many important antibiotics and immunosuppressants such as erythromycins, tetracyclines, and rapamycins. Their synthesis proceeds by an ordered condensation of acyl esters to generate carbon chains of varying length and substitution pattern that are later converted to mature polyketides. This process has long been recognized as resembling fatty acid biosynthesis, but with important differences. Unlike a fatty acid synthase, a typical polyketide synthase is programmed to make many choices during carbon chain assembly: For example, the choice of "starter" and "extender" units, which are often selected from acetate, propionate or butyrate residues in a defined sequence. The choice of using a full cycle of reduction-dehydration-reduction after some condensation steps, omitting it completely, or using one of two incomplete cycles (reduction alone or reduction followed by dehydration), which determines the pattern of keto or hydroxyl groups and the degree of saturation at different points in the chain is additionally programed. Finally the choice of stereochemistry for the substituents at many of the carbon atoms is programmed by the polyketide synthase.

Because of the commercial significance of Streptomyces, a great amount of effort has been expended in the study of Streptomyces genetics. Consequently much is known about Streptomyces and several cloning vectors exist for transformations of the organism.

Although many polyketides have been identified, there remains the need to obtain novel polyketide structures with enhanced properties. Current methods of obtaining such molecules include screening of natural isolates and chemical modification of existing polyketides, both of which are costly and time consuming. Current screening methods are based on gross properties of the molecule, i.e. antibacterial, antifungal activity, etc., and both a priori knowledge of the structure of the molecules obtained or predetermination of enhanced properties are virtually impossible. Chemical modification of preexisting structures has been successfully employed, but it still suffers from practical limitations to the type of compounds obtainable, largely connected to the poor yield of multistep syntheses and available chemistry to effect modifications. The following modifications are extremely difficult or inefficient at the present time: change of the stereochemistry of the side chains in the completed polyketide; change of the length of the polyketide by removal or addition of carbon units from the interior of the acyl chain; and dehydroxylation at unique positions in the acyl chain. Accordingly, there exists the need to obtain molecules wherein such changes can be specified and performed and would represent an improvement in the technology to produce altered polyketide molecules with predicted structure.

SUMMARY OF THE INVENTION

The present invention provides a method to produce novel structures from designing and introducing specified changes in the DNA governing the synthesis of the polyketide. According to the method of the present invention, the biosynthesis of specific polyketide analogs is accomplished by genetic manipulation of a polyketide-producing microorganism comprising the steps of:

(1) isolating a polyketide biosynthetic gene-containing DNA sequence;

(2) identifying enzymatic activities associated within said DNA sequence;

(3) introducing one or more specified changes into said DNA sequence which codes for one of said enzymatic activities which results in an altered DNA sequence;

(4) introducing said altered DNA sequence into the polyketide-producing microorganism to replace the original sequence;

(5) growing a culture of the altered microorganism under conditions suitable for the formation of the specific polyketide analog; and (6) isolating said specific polyketide analog from the culture.

The present method is most useful when the segment of the chromosome modified is involved in an enzymatic activity associated with polyketide biosynthesis. The present invention is especially useful in manipulating polyketide biosynthetic genes from Streptomyces, an organism which provides over one-half of the clinically useful antibiotics.

BRIEF DESCRIPTION OF THE DRAWINGS

FIG. 1 illustrates the organization of gene encoding polyketide synthase and designated eryA as follows: (a) Map coordinates of the DNA; (b) DOTPLOT of the output of COMPARE (window=50, stringency=32) program (Sequence Analysis Software Package of the Genetics Computer Group, University of Wisconsin, Biotechnology Center, 1710 University Avenue, Madison, Wis. 53705 of eryA segment (x-axis) vs. subsegment of eryA comprises between 23–27.5 sequence coordinates (y-axis) [see FIG. 2]; (c) Open reading frame organization of eryA and enzymatic activities encoded. PT=propionyltransferase; ACP=acyl carrier protein; KS=β-ketoacyl ACP synthase; RmT=(2R) methylmalonyl CoA transferase; KR=β-ketoreductase; SmT=(2S) methylmalonyl CoA transferase; DH=dehydratase; ER=enoylreductase; TE=thioesterase; and (d) Schematic diagram showing the extent of each of the six modules in eryA.

FIG. 2. illustrates the nucleotide sequence of eryA [SEQ ID NO:1] with corresponding translation of the three open reading frames. Standard one letter codes for the amino acids appear beneath their respective nucleic acid codons. The standard one letter codes for the amino acid sequences are as follows:

Figure 3:
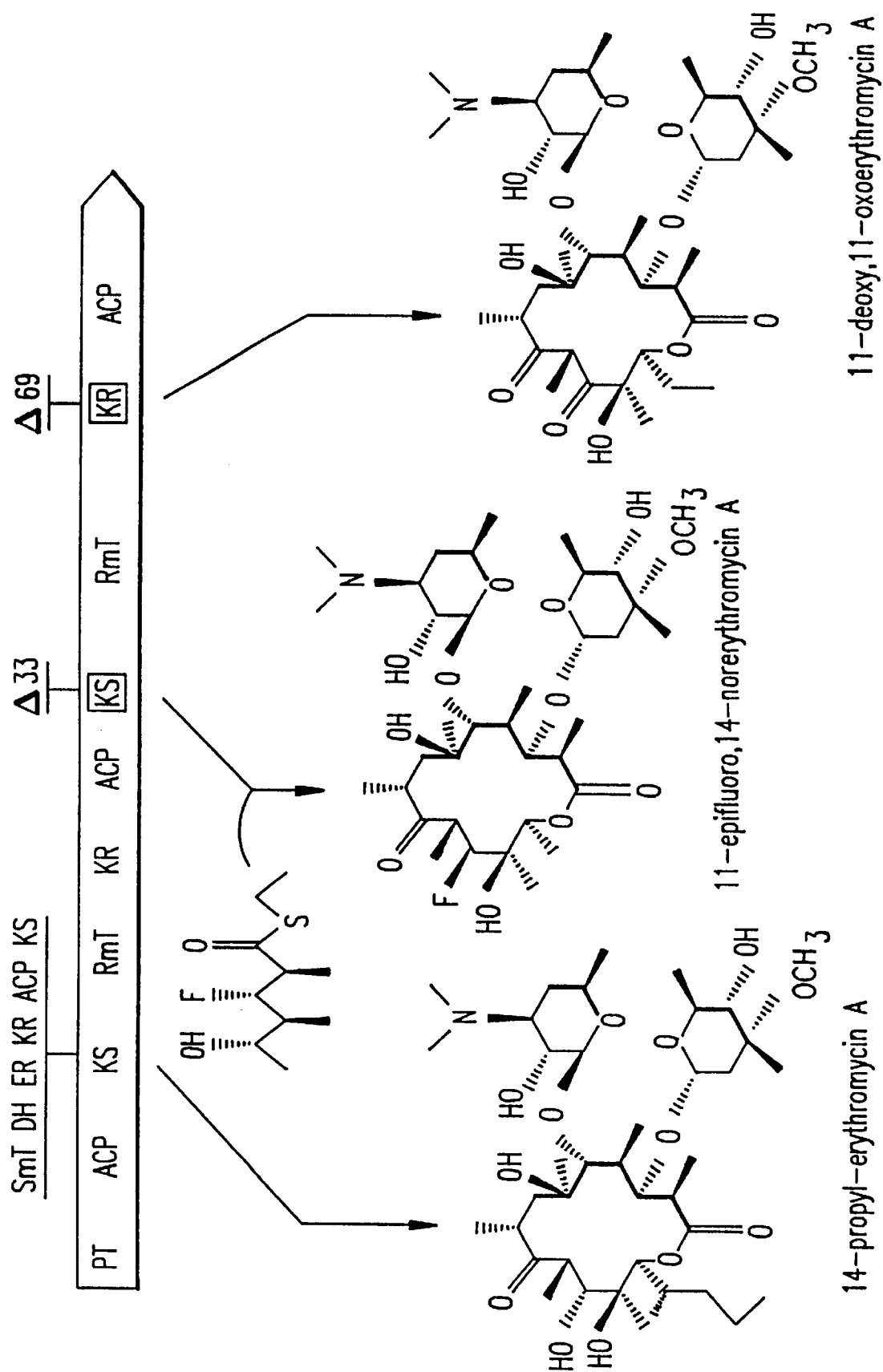

A—alanine
R—arginine
N—asparagine
D—aspartic acid
C—cysteine
Q—glutamine
E—glutamic acid
G—glycine
H—histidine
I—isoleucine
L—leucine
K—lysine
M—methionine (start)
F—phenylalanine
P—proline S—serine
T—threonine
W—tryptophan
Y—tyrosine
V—valine FIG. 3. is a schematic representation of Type I, Type II and Type III changes in eryA and structures of corresponding novel polyketides produced. Δ69 (Type I) and Δ33 (Type II) represent in-frame deletions of the base pairs in the DNA segments corresponding to the KR of module 2 and the β-ketoacyl ACP synthase of module 2, respectively. Insertion of a complete copy of module 4 within module 1 is also shown. Production of 11-epifluoro-15-norerythromycin in strain that carries Δ33 occurs when substrate analog (2S,3S,4S,5S)2,4-dimethyl-3-fluoro-5-hydroxyhexanoic acid-ethyl thioester is fed.

FIG. 4 illustrates the restriction site coordinates of cosmid pR1 5' to the sequence of eryA (FIG. 2).

DETAILED DESCRIPTION OF THE INVENTION

For the purposes of the present invention as disclosed and claimed herein, the following terms are defined.

The term "polyketide" as used refers to a large and diverse class of natural products, including antibiotics, pigments, and immunosuppressants. Antibiotics include, but are not limited to anthracyclines, tetracyclines, polyethers, ansamycins, macrolides of different types (polyenes and avermectins as well as classical macrolides such as erythromycins).

The term "polyketide-producing microorganism" as used herein includes any Actinomycetales which can produced a polyketide. Examples of Actinomycetes that produce polyketides include but are not limited to *Micromonospora rosaria, Micromonospora megalomicea, Sacharapolyspora erythraea, Streptomyces antibioticus, Streptomyces albireticuli, Streptomyces ambofasciens, Streptomyces avermitilis, Streptomyces fradiae, Streptomyces hygroscopicus, Streptomyces tsukubaensis, Streptomyces griseus, Streptomyces mycarofasciens, Streptomyces platensis, Streptomyces venezuelae, Streptomyces violaceoniger*, and various Actinomadura, Dactylosporangium and Nocardia strains that produce polyether type of polyketides.

The term "polyketide synthase" as used herein refers to the complex of enzymatic activities responsible for the biosynthesis of polyketides which include but are not limited to β-ketoreductase, dehydratase, acyl carrier protein, enoylreductase, β-ketoacyl ACP synthase, and acyltransferase.

The term "extender" as used herein refers to a coenzyme A thioester of a dicarboxylate which is incorporated into a polyketide by a polyketide synthase.

The term "starter" as used herein refers to a coenzyme A thioester of a carboxylic acid which is used by the polyketide synthase as the first building block of the polyketide.

The term "eryA" as used herein refers to the genes involved in the formation of the polyketide moiety of erythromycin.

The term "condensation" as used herein refers to the addition of an extender unit out to the nascent polyketide chain and requires the action of β-ketoacyl ACP synthase, acyltransferase, and acyl carrier protein.

The term "β-carbonyl processing" as used herein refers to changes effecting the carbonyl group of the growing polyketide via β-ketoreductase, dehydratase, and enoylreductase.

The term "module" as used herein refers to the genetic element encoding one condensation step, as defined above, and one β-carbonyl processing step, as defined herein.

The term "Type I change" as used herein refers to changes in DNA sequence which will result in the production of polyketide rings of length identical to that of 6-deoxyerythronolide A, but with altered functional groups at specific ring positions.

The term "Type II change" as used herein refers to alterations which will result in the production of macrolide rings only when fed exogenously with substrate analogs, e.g.thioesters of appropriate acyl compounds of various length. Thus Type II mutants are erythromycin non-producing (Ery⁻) mutants. The structure of the resulting macrolides will depend on the substrate employed.

The term "Type III change" as used herein refers to alterations which will result in the biosynthesis of macrolide rings of length reduced (deletion) or increased (insertion) by two carbon units, or macrolide rings altered in specific portions of the chain (replacement).

In its broadest sense, the present invention entails a general procedure for producing novel polyketide structures in vivo by selectively altering the genetic information of the organism that naturally produces a related polyketide. A set of examples described herein are a series of novel polyketides that make use of the genetic information for the biosynthesis of the polyketide portion of the macrolide antibiotic erythromycin. The organization of the segment of the *Saccharapolyspora erythraea* chromosome, designated eryA, and the corresponding polypeptides which it encodes that determine the biosynthesis of the polyketide segment of erythromycin, are shown in FIG. 1. It is seen that eryA is organized in modules, as shown, and that each module takes care of one condensation step, through the action of the β-ketoacyl ACP synthase specified within, wherein an extender unit, methylmalonyl CoA, is added first to the starter unit, propionyl CoA, and then to the successively growing acyl chain. The precise succession of elongation steps is dictated by the genetic order of the six modules: module 1 determines the first condensation; module 2, the second; module 3, the third, and so on until the sixth condensation step has occurred. Furthermore, the processing of the growing chain after each condensation is also determined by the information within each module. Thus β-ketoreduction of the β-carbonyl takes place after each step except for step 3, as determined by the presence of a functional β-ketoreductase in all modules except module 3, whereas dehydration and enoylreduction only take place after the fourth extender unit is added to the growing acyl chain, as determined by the presence of dehydratase and enoylreductase in module 4. Furthermore, the choice of the correct enantiomer (2R or 2S) of methylmalonyl-CoA as the extender unit employed at each condensation is specified by the acyltransferase function determined by each module (FIG. 1C).

In the present invention, novel polyketide molecules of desired structure are produced by the introduction of specific genetic alterations of the eryA sequence into the *Sac. erythraea* chromosome. The complete nucleotide sequence of the eryA segment of the *Sac. erythraea* chromosome and the sequence of the corresponding polypeptides are shown in FIG. 2. Three types of alterations to the eryA DNA sequence are described: (i) those inactivating a single function in a module which does not arrest acyl chain growth (β-ketoreductase, dehydratase, or enoylreductase); (ii) those inactivating a single function in a module which does arrest chain growth (β-ketoacyl ACP synthase, acyltransferase or acyl carrier protein); and (iii) those affecting an entire module (deletion, insertion, or replacement). The novel polyketides produced by strains carrying these types of mutations can be classified accordingly. Type I changes will result in the production of polyketide rings of length identical to that of 6-deoxyerythronolide A, but with altered functional groups at specific ring positions. Strains carrying type II alterations will result in the production of macrolide rings only when fed exogenously with substrate analogs, e.g.thioesters of appropriate acyl compounds of various length. Thus Type II mutants are erythromycin non-producing (Ery⁻) mutants. The structure of the resulting macrolides will depend on the substrate employed. Type III changes will result in the biosynthesis of macrolide rings of length reduced (deletion) or increased (insertion) by two carbon units, or macrolide rings altered in specific portions of the chain (replacement). A schematic representation of some examples of Type I, Type II and Type III alterations in eryA and the corresponding novel polyketides produced in hosts that carry such alterations is shown in FIG. 3.

In the examples described herein, specific mutations in the eryA region of the *Sac. erythraea* chromosome are introduced by a simple two-step approach: 1) introduction of a specified change in a cloned DNA segment; 2) exchange of the wild type allele with the mutated one. Step 1 requires standard recombinant DNA manipulations employing *E. coli* as the host. Step 2 requires one or more plasmids out of the several *E. coli-Sac. erythraea* shuttle vectors available and a simple screening procedure for the presence of the colony carrying the altered gene. Two methods are used to introduce the altered allele into the chromosome to replace the wild type allele. The first employs gene replacement, described in Examples 7, 11, 15, 19 and 24, wherein the gene to be altered, along with adjacent upstream and downstream DNA, is mutated and cloned into a *Sac. erythraea* non-replicating vector. The plasmid carrying the altered allele is then introduced into the host strain by transformation of protoplasts employing selection for a plasmid marker. Since the plasmid does not replicate, regenerated cells that carry the marker have undergone a single homologous recombination between one of the two segments flanking the mutation on the plasmid and its homologous counterpart in the chromosome. Some of the colonies that have subsequently lost the marker will have undergone a second recombination between the other plasmid borne adjacent DNA segment and its homologous chromosomal counterpart resulting in the retention of the mutation in the chromosome, replacing the normal allele with the mutant one. The second method to introduce an altered allele into the chromosome employs gene conversion, described in Examples 37 and 43. In this method, an Ery⁻ *Sac. erythraea* strain carrying a deletion of a specified region of the eryA segment of the chromosome is used as a host. Into a *Sac. erythraea* multicopy plasmid that carries a selectable marker is cloned the wild type counterpart (segment 1) of the eryA segment mutant in the host. Subsequently, the desired homologous or heterologous DNA segment to be introduced (segment 2) is cloned within the portion of segment 1 which is deleted in the mutant strain. The resulting plasmid is then introduced into the host employing selection for the marker. Among the transformants will be a population that have integrated segments 1 and 2 from the plasmid by the process of gene conversion which can be verified by examination of the DNA among the colonies that have recovered the ability to produce erythromycin.

Two examples each of Types I, II and III alterations to the eryA DNA sequence and the resultant novel polyketides produced are described in the examples described herein. Examples 1 through 8, 9 through 12 and 13 through 16 describe the construction and effect of three Type I mutants. Examples 17 through 22 and 23 through 27 describe the construction of two Type II mutants and the effects of feeding two different synthetic substrates to the mutant strains. Examples 28 through 38 and 39 through 44 outline the steps in constructing Type III changes and their respective effects on the structure of the novel polyketides produced. In Examples 1 through 7 a plasmid that contains a substantial deletion of the segment of the gene corresponding to the β-ketoreductase of module 5 is created, the altered gene is inserted into the *Sac. erythraea* chromosome to replace the wild type allele and the new strain carrying the altered gene is identified and isolated. In Example 8, the new strain is fermented and the novel polyketide 5-oxo-5,6-dideoxy-3α-mycarosyl erythronolide B that results from the introduction of the mutant allele is isolated. In Examples 9 through 11, a mutation is introduced into the β-ketoreductase of module 2 and the mutated allele is then used to replace the wild type allele in the chromosome. In Example 12, the strain carrying the altered allele is fermented and the novel compound 11-oxo-11-deoxyerythromycin A is isolated. Similarly, in Examples 13 through 16 a mutation is introduced into the dehydratase of module 4 and the mutated allele is then used to replace the wild type allele in the chromosome. The strain carrying this altered allele is then fermented and the novel products 7-hydroxyerythromycin A and 6-deoxy-7-hydroxyerythromycin A are isolated. In Examples 17 through 21, a mutation is made in the DNA corresponding to the β-ketoacyl-ACP synthase of module 1 and introduced into the chromosome to replace the wild type allele. This mutation has the effect of arresting the synthesis of the polyketide chain and results in the Ery⁻ phenotype. The synthetic substrate (2S,3R,4S,5S)3,5-dihydroxy-2,4-dimethylhexanoic acid-ethyl ester is then made and fed to the mutant resulting in the production of the novel compound (14S,15S)14(1-hydroxyethyl)erythromycin. Similarly, in Examples 22 through 24, a mutation is created in the β-ketoacyl-ACP synthase of module 2 and introduced into the chromosome to replace the wild type allele. In Example 25 and 26, the synthetic substrate (2S,3S,4S,5S)2,4-dimethyl-3-fluoro-5-hydroxyhexanoic acid-ethyl thioester is made and fed to the module 2 β-ketoacyl-ACP synthase mutant and the resulting novel compound 11-epifluoro-15-norerythromycin is isolated. In Examples 27 through 38, a copy of the DNA sequence corresponding to module 4 is introduced into the deleted segment of the β-ketoacyl-ACP synthase of module 1 resulting in the production of the novel compound 14(1-propyl)erythromycin. In Examples 40 through 44, a copy of the DNA sequence corresponding to module 5 is introduced into the deleted segment of the β-ketoacyl ACP synthase of module 1 resulting in the production of the novel compound 14[1(1-hydroxypropyl)]erythromycin.

GENERAL METHODS

Materials, Plasmids and Bacterial Strains

Restriction endonucleases, T4 DNA ligase, nick-translation kit, competent *E. coli* DH5α cells, X-gal, IPTG, and plasmids pUC19 and pUC12 are purchased from Bethesda Research Laboratories (BRL), Gaithersburg, Md. [α-$^{32}$P]dCTP and Hybond N are from Amersham Corp., Chicago, Ill. Seakem LE agarose and Seaplaque low gelling temperature agarose are from FMC Bioproducts, Rockland, Me. *E. coli* K12 strains carrying the *E. coli*-Sac. shuttle plasmids pWHM3 or pWHM4 (Vara et al., *J. Bacteriol.*

171:5872 (1989)) or the cosmids pS1 (Tuan et al., *Gene*, 90:21 (1990)) and *Sac. erythraea* strain NRRL2338 have been deposited in the culture collection of the Agricultural Research Laboratories, Peoria, Ill. and are available under the accession numbers NRRL XXXX, respectively. *Staphylococcus aureus* $Th^R$ (thiostrepton resistant) is obtained by plating $10^8$ cells of *S. aureus* on agar medium containing 10 mg/ml thiostrepton and picking a survivor after 48 hr growth at 37° C. Thiostrepton is obtained from Squibb-Bristol Myers, New Brunswick, N.J. All other chemical and reagents are from standard commercial sources unless specified otherwise.

DNA Manipulations

Standard conditions (Maniatis et al., *Molecular Cloning, A Laboratory Manual*, Cold Spring Harbor Laboratory, Cold Spring Harbor, N.Y., 1982) are employed for restriction endonuclease digestion, agarose gel-electrophoresis, nick translation of DNA to make $^{32}$P-labeled probes, DNA ligation, and transformation of *E. coli* employing selection for ampicillin resistance ($Ap^R$) on LB agar plates. Plasmid DNA is isolated from minipreps of *E. coli* transformants by the boiling method (Maniatis et al, 1982, supra). DNA fragments are recovered from low melting agarose gels using the method of Langridge et al., 1980. Total DNA from *Sac. erythraea* strains is prepared according to described procedures (Hopwood et al., *Genetic Manipulation of Streptomyces, A Laboratory Manual*, John Innes Foundation, Norwich, U.K., 1985). DNA is transferred from agarose gels onto Hybond N following the manufacturer's instructions. Hybridizations are performed in sealed bags containing 10–20 ml of [1×NET (20×NET=3M NaCl, 0.3M TrisHCl, 20 mM Na$_2$EDTA, pH 8.0), 5×Denhardt's solution (Maniatis et al., 1982, supra), 0.2 mg/ml denatured calf thymus DNA, 0.2% SDS, and 0.5–2×10$^7$ cpm of the nick-translated probe] for 16–20 hr at 65° C. Filters are washed three times in 1×NET/0.1% SDS for 20 min each at room temperature, and once in 0.05×NET/0.1% SDS for 20 min at 70° C. Filters are reused as described (Donadio et al., 1990).

Amplification of DNA fragments

Synthetic deoxyoligonucleotides are synthesized on an ABI Model 380A synthesizer (Applied Biosystems, Foster City, Calif.) following the manufacturer's recommendations. Amplification of DNA fragments is performed by the polymerase chain reaction (PCR) employing a Coy thermocycler. Reactions contain 100 pmol of each primer, 1 μg of template DNA (cosmid pS1 carrying the eryA segment from *Sac. erythraea* strain NRRL 2338), and 2.5 units of *Thermus aquaticus* DNA polymerase in a 100 ml volume of PCR buffer [50 mM KCl, 10 mM TrisHCl (pH 8.0) 2 mM MgCl$_2$, 0.01% gelatin) containing 200 mM of the 4 dNTPs. The above reagents are from Perkin Elmer Cetus, Norwalk, Conn. The reaction mixture is overlaid with a drop of paraffin oil and subjected to 30–50 cycles. Each cycle consists of one 94° C., one 55° C. and one 72° C. period, each of the duration of 3 min. The progress of the amplification is monitored by agarose gel-electrophoresis. The PCR primers described in the examples below are derived from the nucleotide sequence of eryA of FIG. 2.

Gene replacement and gene conversion

Protoplasts of *Sac. erythraea* strains are prepared and transformed with miniprep DNA isolated from *E. coli* according to published procedures (Yamamoto et al., 1986). Integrative transformants, in the case of pWHM3 derivatives, are selected after one round of non-selective growth of the primary $Th^R$ transformants as described by Weber et. al, *Gene*, 68:173 (1988). Loss of the $Th^R$ phenotype is monitored by plating serial dilutions of a $Th^R$ integrant on non-selective medium, followed by replica-plating on thiostrepton-containing medium. $Th^S$ (thiostrepton-sensitive) colonies arise at a frequency of $10^{-2}$ (Donadio et al., 1990). The retention of the mutant allele is established by Southern hybridization of a few $Th^S$ colonies.

A few hundred $Th^R$ colonies obtained by transformation of an eryA strain with pWHM4 derivatives are screened for antibiotic production by the agar-plug assay employing *Staphylococcus aureus* as $Th^R$ organism as described (Tuan et al., *Gene*, 90:21 (1990)). The frequency of gene conversion between a 5 kb segment of homologous sequence and a strain carrying a small deletion is >25% (Tuan et al., *Gene*, 90:21 (1990)). Colonies found to produce antibiotic activity are inoculated in SGGP (Yamamoto et al., 1986), protoplasts are prepared, and the regenerated protoplasts are scored for loss of the plasmid by replica-plating on non-selective medium. $Th^S$ colonies are then rechecked for antibiotic production, and six producers are analyzed on Southern blots.

Fermentation

*Sac. erythraea* cells are inoculated into 100 ml SCM medium (1.5% soluble starch, 2.0% Soytone [Difco], 0.15% Yeast Extract [Difco], 0.01% CaCl$_2$) and allowed to grow at 32° C. for 3 to 6 days. The entire culture is then inoculated into 10 liters of fresh SCM medium. The fermenter is operated for a period of 7 days at 32° C. maintaining constant aeration and pH at 7.0. After fermentation is complete, the cells are removed by centrifugation at 4° C. and the fermentation beer is kept in the cold until further use.

The present invention will now be illustrated, but is not intended to be limited, by the following examples:

EXAMPLE 1

Construction of plasmid pABX9

The 9.6 kb BamHI-XhoI segment comprised between sequence coordinates 21.96 and 31.52 was isolated from cosmid pS1 and ligated to SalI-digested pUC19 DNA. The resulting mixture contained the desired plasmid pABX9.

EXAMPLE 2

Construction of *E. coli* K12 DH5α/pABX9

Approximately 10 ng of plasmid pABX9, prepared as described in Example 1, were transformed into *E. coli* K12 DH5α and a few of the resulting white $Ap^R$ colonies that appeared on the LB-agar plates containing X-gal and ampicillin were analyzed for their plasmid content. One colony was found to carry pABX9, as verified by the observation of fragments of 3.93, 3.39, 2.01, 1.56, 0.87, and 0.48 kb in size upon agarose gel electrophoresis after SmaI digestion of the plasmid.

EXAMPLE 3

Construction of plasmid pABX9DN

Plasmid pABX9, isolated from *E. coli* K12 DH5α/pABX9, was digested with NcoI and then treated with T4 DNA ligase. The resulting mixture contained the desired plasmid pABX9DN.

EXAMPLE 4

Construction of *E. coli* K12 DH5α/pABX9DN

Approximately 10 ng of plasmid pABX9DN, prepared as described in Example 3, were transformed into *E. coli* K12

DH5α and a few of the resulting white Ap$^R$ colonies that appeared on the LB-agar plates containing X-gal and ampicillin were analyzed for their plasmid content. Colonies carrying pABX9DN exhibited a single NcoI fragment of 11.5 kb visible by agarose gel electrophoresis, confirming that the 813 bp NcoI—NcoI fragment from pABX9 has been deleted in pABX9DN.

EXAMPLE 5

Construction of plasmid pABX95DN

Plasmid pABX9DN was digested with EcoRI and HindIII and ligated to pWHM3 digested with the same two enzymes. The resulting mixture contained the desired plasmid pABX95DN.

EXAMPLE 6

Construction of *E. coli* K12 DH5α/pABX95DN

Approximately 10 ng of plasmid pABX95DN, prepared as described in Example 5, were transformed into *E. coli* K12 DH5a and a few of the resulting white Ap$^R$ colonies that appeared on the LB-agar plates containing X-gal and ampicillin were analyzed for their plasmid content. Colonies carrying pABX95DN exhibited fragments of 8.8 and 7.2 kb visible in agarose gels after EcoRI and HindIII digestion.

EXAMPLE 7

Construction of *Sac. erythraea* AKR5 carrying the eryAKR5 allele by gene replacement Approximately 1 mg of plasmid pABX95DN, isolated from *E. coli* K12 DH5α/pABX95DN, was transformed into *Sac. erythraea* NRRL 2338 and stable Th$^R$ colonies were isolated. Serial dilutions of one of these colonies were screened for the loss of the antibiotic resistance marker and total DNA from 5 Th$^S$ colonies as well as from untransformed *Sac. erythraea* NRRL 2338 was digested with SstI and analyzed by Southern hybridization employing the 0.8 kb SalI fragment between sequence coordinates 24.26 and 25.06 (from pABX9) as probe. Whereas NRRL 2338 showed one SstI band of 3.7 kb that hybridized to the probe, samples from four of the Th$^S$ strains exhibited a SstI-hybridizing band of 6.1 kb indicating the presence of the mutant allele. One of these colonies was kept and designated strain AKR5. It carries a deletion of 813 bp in the KR5 segment of eryA and is designated the eryAKR5 allele.

EXAMPLE 8

Isolation, purification and properties of 5-oxo-5,6-dideoxy-3-a-mycarosyl erythronolide B from *Sac. erythraea* AKR5

A 10-liter fermentation of *Sac. erythrea* AKR5 carrying the eryAKR5 allele in a Biolafitte fermentor using SNC Media. The fermentor was inoculated with 100 ml of a 3 day old seed. The pO$_2$ was initially 80 ppm and the temperature was maintained at 32° C. The pH was controlled to 7.0±0.2 by addition of propionic acid or potassium hydroxide as needed. At harvest (3 days), the whole broth was extracted three times with 4-liter portions of ethylacetate. The combined extracts were concentrated under reduced pressure and the residue was chromatographed on a column (50×5 cm) of silica gel packed and loaded in toluene and eluted with a stepwise gradient of increasing concentration of isopropanol in toluene. Fractions were analyzed by TLC and spots were detected by spraying with anisaldehyde sulfuric acid spray reagent and heating. A major component giving blue colored spots eluted with approximately 7% isopropanol. Fractions containing this material were combined and concentrated to a residue (800 mg). This was further chromatographed on a column (100×3 cm) of Sephadex LH-20 in chloroform-heptane-ethanol, 10:10:1, v/v/v. Fractions were analyzed as above, early fractions (9–13) yielded 5,6-dideoxy-3-a-mycarosyl-5-oxoerythronolide B (45 mg) which was crystallized from heptane/ethylacetate mixture to mp 163°–164° C.

| CMR spectrum in CDCl$_3$ (ppm downfield from TMS) | | |
|---|---|---|
| 8.6 | 37.9 | 70.0 |
| 9.9 | 38.7 | 76.2 |
| 9.9 | 40.4 | 76.4 |
| 10.4 | 40.7 | 80.4 |
| 14.5 | 43.3 | 100.4 |
| 15.2 | 45.8 | 175.8 |
| 17.1 | 46.8 | 210.8 |
| 17.7 | 48.9 | 217.7 |
| 25.3 | 66.5 | |
| 25.5 | 69.4 | |

Structure was determined by single crystal X-ray diffraction.

Later fractions (15–17) yielded 5,6-dideoxy-5-oxoerythronolide B (10 mg) and still later fractions yielded 5,6-dideoxy-6,6a-epoxy-5-oxoerythronolide B (2.8 mg).

EXAMPLE 9

Construction of plasmid pALeryAKR2

The 1.3 kb DNA segment comprised between coordinates 8.63–9.93 (fragment 1) is amplified by PCR employing two oligodeoxynucleotides, 1a (5'-GGGAGCATGCTCTCGGTGCGCGGCGGCCGC-3') [SEQ ID NO:6] and 1b (5'-GCCCTGCAGCGCGTACTCCGAGGTGGCGGT-3') [SEQ ID NO:7]. Similarly, the 1.3 kb DNA segment between coordinates 9.99–11.26 (fragment 2) is PCR-amplified employing primers 2a (5'-TGGTCTGCAGGCGAGGCCGGACACCGAGG-3') [SEQ ID NO:8] and 2b (5'-GGAAGAAGTCAAAGTTCCTCGGTCCCTTCT-3') [SEQ ID NO:9]. After digestion with SphI+PstI (fragment 1) and PstI+EcoRI (fragment 2), the two fragments are ligated to EcoRI+SphI-digested pWHM3. The resultant mixture contains the desired plasmid pALeryAKR2.

EXAMPLE 10

Construction of *E. coli* K12 DH5a/pALeryAKR2

Approximately 10 ng of plasmid pALeryAKR2, prepared as described in Example 9, are transformed into *E. coli* K12 DH5α, and a few of the resulting white Ap$^R$ colonies that appear on the LB-agar plates containing X-gal and ampicillin are analyzed for their plasmid content. The identity of plasmid pALeryA2KR2, 9.8 kb in size, and carrying a 2.6 kb EcoRI-SphI insert with an internal PstI site, is verified by SAlI digestion (fragments at 2.91, 2.21, 1.61, 1.42, 1.08, 0.29, 0.12 and 0.10 kb are released, visible by agarose gel electrophoresis). pALeryAKR2 contains an in-frame deletion of 102 base pairs of the corresponding segment of the wild type eryA chromosomal DNA. The cloned segment in pALeryAKR2 is designated the eryAKR2 allele.

EXAMPLE 11

Construction of *Sac. erythraea* AKR2 carrying the eryAKR2 allele by gene replacement Approximately 1 mg of plasmid pALeryAKR2, isolated from *E. coli* K12 DH5α/pALeryAKR2, is transformed into *Sac. erythraea* protoplasts and stable Th$^R$ colonies are isolated. Serial dilutions of one of these colonies are screened for loss of the antibiotic resistance marker, and six Th$^S$ colonies are analyzed for their genotype by Southern hybridization. Total DNA from the six Th$^S$ colonies and from untransformed *Sac. erythraea* NRRL2338 is digested with PstI and with SalI and is then examined by Southern hybridization using the 2.6 kb EcoRI-SphI insert from pALeryAKR2 as probe. Whereas NRRL2338 contains a 39 kb PstI hybridizing band, colonies in which the mutation in KR2 has been introduced (strain AKR2) exhibit two bands of approximately equal intensity, one at 27 kb and the other at 12 kb. The SalI digest, with bands at 1.04, 0.75, 0.29, 0.12 and 0.10 kb common to NRRL2338 and AKR2, but with the 1.16 kb band in NRRL2338 replaced by the 1.06 kb band in AKR2, confirms that the only change introduced into strain AKR2 is the deletion of the 102 bp segment from KR2, resulting in a strain carrying the eryAKR2 allele.

EXAMPLE 12

Isolation and purification of 11-deoxy-11-oxoerythromycin A

The fermentation beer of strain AKR2, cooled to 4° C. is adjusted to pH 8.0 and is extracted sequentially with three equal volumes of methylene chloride. The combined methylene extracts are concentrated to an oily residue and partitioned between heptane and methanol. The methanol layer is removed, washed once with heptane and concentrated to a residue. The residue is digested in methylene chloride and washed once with potassium phosphate buffer pH 7.8 and once with water. The methylene chloride layer is concentrated to a residue and digested in the lower phase (1:1:1, v/v/v) of a carbon tetrachloride; methanol; aqueous phosphate buffer (0.05M, pH 7.0) system and chromatographed on an Ito Coil Planet Centrifuge in the same system. Fractions containing the desired 11-oxo-11-deoxyerythromycin A were combined, concentrated, digested in methylene chloride, washed well with water and concentrated on rotary evaporator under reduced pressure to yield 11-deoxy-11-oxoerythromycin A as an off-white solid froth. Its identity is confirmed by comparison with antibiotic L53-18A. 11-Deoxy-11-oxoerythromycin A is dissolved in tetrahydrofuran and the solution is diluted with an equal volume of water. This is then acidified to pH 4.0 and allowed to stand at room temperature for 4 hours. The pH is adjusted to 9.0 and the solution is diluted with an equal volume of water and extracted with two volumes of methylene chloride. The combined methylene chloride extracts were evaporated to dryness under reduced pressure to yield antibiotic L53-18A as a white solid.

EXAMPLE 13

Construction of plasmid pALeryADH4

Primers 3a (GCGCGAGCTCGACGACCAGGGCGGCATGGT) [SEQ ID NO:10] and 3b (GGTGGCATGCTGCGACCACTGCGCGTCGGC) [SEQ ID NO:11] are used to PCR-amplify the 1.05 kb eryA segment of the *Sac. erythraea* chromosome between sequence coordinates 18.47–20.07 (fragment 3), and primers 4a (AGCTGCATGCTCTGGACTGGGGACGGCTAG) [SEQ ID NO:12] and 4b (CGCGGGATCCCAGCTCCCACGCCGATACCG) [SEQ ID NO:13] are used to amplify the 1.35 kb segment between sequence coordinates 20.58–21.96 (fragment 4) as described in Example 1. Fragment 3 and 4, after digestion with SstI+SphI and with SphI+BamHI, respectively, are ligated to SstI-, BamHI-digested pWHM3. The resulting ligation mixture contains the desired plasmid pALeryADH4.

EXAMPLE 14

Construction of *E. coli* K12 DH5a/pALeryADH4

Approximately 10 ng of pALeryADH4, prepared as described in Example 13, are transformed transformed into *E. coli* K12 DH5α, and a few of the resulting white Ap$^R$ colonies that appear on the LB-agar plates containing X-gal and ampicillin are analyzed for their plasmid content. The identity of plasmid pALeryADH4, 9.6 kb in size, is verified by SphI+EcoRI digestion (fragments at 7.2, 1.35 and 1.05 kb are released). pALeryADH4 carries a 498 base pair in-frame deletion of the corresponding segment of the wild type eryA DNA. The cloned segment in pALeryADH4 is designated the eryADH4 allele.

EXAMPLE 15

Construction of *Sac. erythraea* ADH4 carrying the eryADH4 allele by gene replacement Approximately 1 mg of plasmid pALeryADH4, isolated from *E. coli* K12 DH5α/pALeryADH4, is used for transformation into *Sac. erythraea* protoplasts and stable Th$^R$ colonies are isolated. Serial dilutions of one of these colonies are screened for loss of the antibiotic resistance marker, and six Th$^S$ colonies are analyzed for their genotype by Southern hybridization. Total DNA from the six Th$^S$ colonies and from untransformed *Sac. erythraea* NRRL2338 is digested with SphI and with SstI and examined by Southern hybridization using the 2.4 kb SstI-BamHI insert from pALeryADH4 as probe. Strains in which the wild type allele has been replaced by the mutated copy show two SphI bands, one at 13.5 kb and the other at 12.4 kb, whereas the wild type strain exhibits a single band at 26 kb. The SstI pattern, with the 2.9 kb band from NRRL2338 being replaced in ADH4 by a 2.5 kb band, confirms that the 487 bp deletion created in plasmid pALeryADH4 has been transferred into the chromosome of ADH4. Strains that carry the eryADH4 allele in place of the wild type sequence are designated *Sac. erythraea* ADH4.

EXAMPLE 16

Isolation and characterization of 7-hydroxyerythromycin A and 6-deoxy-7-hydroxyerythromycin A The fermentation beer of strain ADH4 is cooled to 4° C. and the pH is adjusted to 5.0. The mixture is extracted once with an equal volume of methylene chloride. The pH of the aqueous layer is readjusted to 9.0 and two further methylene chloride extracts are carried out. These two extracts are combined, washed with water and concentrated to a residue. This is digested in 10 ml of the upper phase of a (3:7:5, v/v/v) mixture of hexane, ethylacetate, aqueous phosphate buffer (0.05M, pH 7.5) and chromatographed on an Ito Coil Planet Centrifuge in the same system. Fractions containing the desired 7-hydroxyerythromycin were combined, concentrated, and partitioned between methylene chloride and dilute (pH 9.5) ammonium hydroxide solution. Fractions containing the desired 6-deoxy-7-hydroxyerythromycin were combined, concentrated, and partitioned between methylene chloride and dilute (pH 9.5) ammonium hydroxide solution. The methylene chloride layers are washed with water and then concentrated to yield the desired 7-hydroxyerythromycin A and 6-deoxy-7-hydroxyerythromycin A as white foams.

EXAMPLE 17

Construction of plasmid pALeryAKS1

The 1.4 kb segment of eryA, between sequence coordinates 1.11–2.54 (fragment 5) and the 1.5 kb segment between sequence coordinates 2.88–4.37 (fragment 6) are PCR-amplified using primers 5a (TGCAGAATTCGCTGGCCGCGCTCTGGCGCT) [SEQ ID NO:14] and 5b (GAGAGCTGCAGCATGAGCCGCTGCTGCGGG) [SEQ ID NO:15], and 6a (CATGCTGCAGGACTTCAGCCGGATGAACTC) [SEQ ID NO:16] and 6b (GAGGAAGCTTCCAGCCGGTCCAGTTCGTCC) [SEQ ID NO:17], respectively, as described in Example 9. After digestion with EcoRI+PstI (fragment 5) and PstI+HindIII (fragment 6), the two fragments are ligated to EcoRI+HindIII-digested pWHM3. The resulting mixture contains the desired plasmid pALeryAKS1.

EXAMPLE 18

Construction of E. coli K12 DH5a/pALeryAKS1

Approximately 10 ng of pALeryAKS1, prepared as described in Example 17, are transformed into E. coli K12 DH5α, and a few of the resulting white $Ap^R$ colonies that appear on the LB-agar plates containing X-gal and ampicillin are analyzed for their plasmid content. The identity of plasmid pALeryAKS1, 10.1 kb in size, is verified by digestion with PstI+HindIII (fragments of 8.6 and 1.5 kb are observed by agarose gel electrophoresis) and with SalI (fragments of 2.93, 2.21, 1.42, 1.37, 0.86, 0.54, 0.27, 0.14, 0.13, and 0.10 kb are observed). pALeryAKS1 carries an in-frame deletion of 282 base pairs of the corresponding wild type eryA DNA. The cloned insert in plasmid pALeryAKS1 is designated the eryAKS1 allele.

EXAMPLE 19

Construction of Sac. erythraea AKS1 carrying the eryAKS1 allele by gene replacement Approximately 1 mg of plasmid pALeryAKS1, isolated from E. coli K12 DH5α/pALeryAKS1, is used for transformation into Sac. erythraea protoplasts and stable $Th^R$ colonies are isolated. Serial dilutions of one of these colonies are screened for loss of the antibiotic resistance marker, and six $Th^S$ colonies are analyzed for their genotype by Southern hybridization. Total DNA from the six $Th^S$ colonies and from untransformed Sac. erythraea NRRL2338 is digested with PstI and with SmaI and examined in Southern hybridization employing the 2.9 kb EcoRI-HindIII insert from pALeryAKS1 as probe. Colonies in which the wild type allele has been replaced by the mutated copy (strain AKS1) show two PstI bands, one at 34.5 and the other at 4.4 kb, whereas the wild type strain exhibits a single band at 39 kb. The SmaI pattern, with the 2.9 kb band from NRRL2338 being replaced in AKS1 by a 2.6 kb band, confirms that the 282 bp created in plasmid pALeryAKS1 has been transferred into strain AKS1. Strains that carry the eryAKS1 allele are designated Sac. erythraea AKS1.

EXAMPLE 20

Synthesis of (2S,3R,4S,5S)3,5-dihydroxy-2,4-dimethylhexanoic acid n-butyl thioester A convenient source of this compound in chiral purity is the antibiotic oleandomycin. Oleandomycin (5 g) is dissolved in an aprotic solvent such as toluene and treated with diazabicydo[5.4.0]undecene-5 (1 g) and heated for one hour. The resulting solution is poured into iced water, agitated well and the organic layer is drawn off and concentrated to a residue. The residue is digested in methylene chloride and treated exhaustively with a solution of ozone. The resulting ozonide is oxidatively decomposed with dilute hydrogen peroxide in sufficient aqueous ethanol to yield a monophasic mixture. This is further diluted with water and made 0.1N with sodium hydroxide. The mixture is warmed for one hour at 70° C. and then cooled before being acidified to pH 2.5 with dilute sulfuric acid. The mixture is then exhaustively extracted with methylene chloride. The combined extracts are concentrated to an oily residue and the desired lactone is recovered by chromatography on silica gel eluted with a gradient of toluene-isopropanol.

The δ-lactone is converted to the butyl thioester before feeding to Sac. erythrea AKS1 by refluxing with n-butylthiol in the presence of a catalytic amount of triethylamine.

EXAMPLE 21

Isolation of (14S,15S)14(1-hydroxyethyl) erythromycin A

The fermentation broth of AKS1 is cooled to 4° C. and adjusted to pH 4.0 and extracted once with methylene chloride. The aqueous layer is readjusted to pH 9.0 and extracted twice with methylene chloride and the combined extracts are concentrated to a solid residue. This is digested in methanol and chromatographed over a column of Sephadex LH-20 in methanol. Fractions are tested for bioactivity against a sensitive organism, such as Staphylococcus aureus $Th^R$, and active fractions are combined. The combined fractions are concentrated and the residue is digested in 10 ml of the upper phase of a solvent system consisting of n-heptane, benzene, acetone, isopropanol, 0.05M, pH 7.0 aqueous phosphate buffer (5:10:3:2:5, v/v/v/v/v), and chromatographed on an Ito Coil Planet Centrifuge in the same system. Active fractions are combined, concentrated and partitioned between methylene chloride and dilute ammonium hydroxide (pH 9.0). The methylene chloride layer is separated and concentrated to yield the desired product as a white foam.

EXAMPLE 22

Construction of plasmid pALeryAKS2

Primers 7a (CGCCCGAATTCGAGGCGCTGGGCGCCCGGAC) [SEQ ID NO:18] and 7b (CCACCTGCAGCGCGGGACCTTCCAGCCCC) [SEQ ID NO:19], and primers 8a (GTGGGTCGCTGCAGACGGTGACTGCGG) [SEQ ID NO:20] and 8b (GGTCAAGCTTCGTCGGCGAGCAGCTTCTC) [SEQ ID NO:21] are used to PCR-amplify the 1.45 kb eryA segment between sequence coordinates 5.71–7.16 (fragment 7) and the 1.5 kb eryA segment between sequence coordinates 7.22–8.70 (fragment 8), respectively. After digestion with EcoRI+PstI (fragment 7) and with PstI+HindIII (fragment 8), the two fragments are ligated to pWHM3 cut with EcoRI+HindIII. The resulting mixture contains the desired plasmid pALeryAKS2.

EXAMPLE 23

Construction of *E. coli* K12 DH5a/pALeryAKS2

Approximately 10 ng of pALeryAKS2, prepared as described in Example 22, are transformed into *E. coli* K12 DH5α, and a few of the resulting white $Ap^R$ colonies that appear on the LB-agar plates containing X-gal and ampicillin are analyzed for their plasmid content. The identity of plasmid pALeryAKS2, 10.1 kb in size, is verified by digestion with PstI+HindIII (fragments of 8.6 and 1.5 kb are observed by agarose gel electrophoresis) and with SstII (fragments of 4.0, 2.3, 2.0, 0.72, 0.43, 0.40, 0.20, 0.18, 0.13 and 0.11 kb observed). Plasmid pALeryAKS2 carries an in-frame deletion of 60 base pairs of the corresponding wild type eryA DNA. This deletion removes the active site cysteine from KS2. The cloned insert in plasmid pALeryAKS2 is designated the eryAKS2 allele.

EXAMPLE 24

Construction of *Sac. erythraea* AKS2 carrying the eryAKS2 allele by gene replacement Approximately 1 mg of plasmid pALeryAKS2, isolated from *E. coli* K12 DH5α/pALeryAKS2, is used for transformation into *Sac. erythraea* protoplasts and stable $Th^R$ colonies are isolated. Serial dilutions of one of these colonies are screened for loss of the antibiotic resistance marker, and six $Th^S$ colonies are analyzed for their genotype by Southern hybridization. Total DNA from the six $Th^S$ colonies and from untransformed *Sac. erythraea* NRRL2338 is digested with PstI and with SstII and examined in Southern hybridization employing the 2.9 kb EcoRI-HindII insert from pALeryAKS2 as probe. Colonies in which the wild type allele has been replaced by the mutated copy (strain AKS2) show two PstI bands, one at 34.5 and the other at 4.4 kb, whereas the wild type strain exhibits a single band at 39 kb. The SstII pattern, with the 0.78 kb band from NRRL2338 being replaced in AKS2 by a 0.72 kb band, confirms that the 60 bp created in plasmid pALeryAKS2 has been transferred into strain AKS2. Strains that carry the eryAKS2 allele are designated *Sac. erythraea* AKS2.

EXAMPLE 25

Synthesis of (2R,3R,4S,5R)2,4-dimethyl-3-fluoro-5-hydroxyhexanoic acid n-butyl thioester (2R,3S,4S,5R)3,5-Dihydroxy-2,4-dimethylhexanoic acid-δ-lactone (1 g) from Example 20 is digested in 10 ml of pyridine and treated with p-toluenesulfonyl chloride (1.3 g) and allowed to stand at room temperature overnight. The mixture is poured into iced water and extracted with methylene chloride and the methylene chloride is concentrated to the crude sulfonate ester. This is digested in acetonitrile (100 ml) and heated under reflux after the addition of tetrabutylammonium fluoride (1.75 g). After 6 hours the mixture is cooled, poured over iced water (300 ml) and extracted three times with 200 ml portions of methylene chloride. The combined methylene chloride extracts were concentrated and the residue was chromatographed on a column of silica gel eluted with a stepwise gradient of isopropanol (0 to 50%) in toluene. Fractions containing (2R,3R,4S,5R)2,4-dimethyl-3-fluoro-5-hydroxyhexanoic acid_d-lactone were combined and concentrated to a white solid. The lactone is then converted to the n-butyl thiolester by refluxing in n-butyl thiol with a catalytic amount of triethylamine. Solvent is removed and the residue is digested in DMSO before feeding to fermentations of *Sac. erythraea* AKS2.

EXAMPLE 26

Isolation and purification of 11-epifluoro-15-norerythromycin A

The fermentation broth of strain AKS2 is cooled to 4° C. and adjusted to pH 4.0 and extracted once with ethylacetate. The aqueous layer is adjusted to pH 9.0 and extracted twice with methylene chloride and the combined extracts are concentrated to a white solid. This is chromatographed over a column of Sephadex LH-20 in a mixture of heptane, chloroform, ethanol (10:10:1, v/v/v) and fractions containing the desired product are combined and concentrated to a solid residue. This is further purified by countercurrent chromatography on an Ito Coil Planet Centrifuge on a system composed of carbon tetrachloride; methanol; 0.05M; pH 7.0 aqueous potassium phosphate buffer (1:1:1, v/v/v). Fractions containing the desired 11-epifluoro-15-norerythromycin were combined, and concentrated to a residue. This was digested in methylene chloride and dilute (pH 9.5) ammonium hydroxide and the methylene chloride layer was separated, washed with water and concentrated to yield the desired 11-epifluoro-15-norerythromycin A as white solid.

EXAMPLE 27

Construction of plasmid pALeryAM4.1

Primers 9a (GCGCCGAATTCTCGAGACGGCGTGGGAGGCA) [SEQ ID NO:22] and 9b (TTGCGGTACCAGTAGGAGGCGTCCATCGCG) [SEQ ID NO:23] are employed to PCR-amplify the 2.0 kb eryA segment between sequence coordinates 17.35–19.38 (fragment 9). After digestion with EcoRI+KpnI, fragment 9 is ligated to pUC19 cut with the same two enzymes The resulting mixture contains the desired plasmid pALeryAM4.1.

EXAMPLE 28

Construction of *E. coli* K12 DH5a/pALeryAM4.1

Approximately 10 ng of pALeryAM4.1, prepared as described in Example 27, are transformed into *E. coli* K12 DH5a, and a few of the resulting white $Ap^R$ colonies that appear on the LB-agar plates containing X-gal and ampicillin are analyzed for their plasmid content. The identity of plasmid pALeryAM4.1, 4.7 kb in size, is verified by digestion with SalI (fragments of 2.8, 0.85, 0.53, 0.27 and 0.22 kb are observed by agarose gel electrophoresis).

EXAMPLE 29

Construction of plasmid pALeryAM4.2

Primers 10a (GCTGGGATCCCGCGGCGCGGGTTGCAGCAC) [SEQ

ID NO:24] and 10b (CGGAACTCGGTGAGCATGCCGGGACTGCTC) [SEQ ID NO:25] are used to PCR-amplify the 2.1 kb eryA segment between sequence coordinates 21.94–24.00 (fragment 10). The 2.6 kb fragment KpnI(96)-BamHI(102) from cosmid clone pR1, and fragment 10 cut with BamHI+SphI, are ligated to pALeryAM4.1 cut with KpnI+SphI. The resulting mixture contains the desired plasmid pALeryAM4.2.

EXAMPLE 30

Construction of *E. coli* K12 DH5a/pALeryAM4.2

Approximately 10 ng of pALeryAM4.2, prepared as described in Example 29, are transformed into *E. coli* K12 DH5a, and a few of the resulting white Ap$^R$ colonies that appear on the LB-agar plates containing X-gal and ampicillin are analyzed for their plasmid content. The identity of plasmid pALeryAM4.2, 9.3 kb in size, is verified by digestion with XhoI+SphI (to ensure that the entire 6.65 kb insert is released) and with SalI, with fragments of 2.8, 1.82, 1.09, 0.94, 0.85, 0.75, 0.45, 0.27, 0.22 and 0.13 kb are observed by agarose gel electrophoresis).

EXAMPLE 31

Construction of plasmid pALeryAM1

The 2.9 kb SmaI(4)-SmaI(20) fragment from cosmid clone pR1 is ligated to pUC12 cut with SmaI. The resulting mixture contains plasmid pALeryAM1.

EXAMPLE 32

Construction of *E. coli* K12 DH5αa/pALeryAM1

Approximately 10 ng of pALeryAM1, prepared as described in Example 31, are transformed into *E. coli* K12 DH5α, and a few of the resulting white Ap$^R$ colonies that appear on the LB-agar plates containing X-gal and ampicillin are analyzed for their plasmid content. The identity of plasmid pALeryAM1, 5.6 kb in size, is verified by digestion with SmaI (the 2.9 kb insert is realeased) and with SphI, with release of one 4.4 and one 1.07 kb bands. Both orientations of the insert in plasmid pALeryAM1 are useful.

EXAMPLE 33

Construction of plasmid pALeryAM4.3

Plasmid pALeryAM1 is cut with XhoI to completion, partially with SphI, and the resulting 5.25 kb band, isolated from an agarose gel, is ligated to the 6.65 kb insert released from pALeryAM4.2 by XhoI+SphI digestion The resulting mixture contains the desired plasmid pALeryAM4.3.

EXAMPLE 34

Construction of *E. coli* K12 DH5a/pALeryAM4.3

Approximately 10 ng of pALeryAM4.3, prepared as described in Example 33, are transformed into *E. coli* K12 DH5α, and a few of the resulting white Ap$^R$ colonies that appear on the LB-agar plates containing X-gal and ampicillin are analyzed for their plasmid content. The identity of plasmid pALeryAM4.1, 11.9 kb in size, is verified by XhoI+SphI digestion (fragments of 6.65 and 5.25 kb are visible by agarose gel-electrophoresis). Plasmid pALeryAM4.3 carries the entire eryA module 4 inserted into the KS region of module 1. The cloned insert in pALeryAM4.3 is designated the eryAM412 allele.

EXAMPLE 35

Construction of plasmid pALeryAM4.4

Plasmid pALeryAM4.3 is cut with EcoRI+HindIII, and the resulting 9.2 kb band, recovered from an agarose gel, is ligated to pWHM4 cut with the same two enzymes. The resulting mixture contains the desired plasmid pALeryAM4.4.

EXAMPLE 36

Construction of *E. coli* K12 DH5α/pALeryAM4.4

Approximately 10 ng of pALeryAM4.4, prepared as described in Example 35, are transformed into *E. coli* K12 DH5α, and a few of the resulting white Ap$^R$ colonies that appear on the LB-agar plates containing X-gal and ampicillin are analyzed for their plasmid content. The identity of plasmid pALeryAM4.4, 16.5 kb in size, is verified by EcoRI+HindIII digestion, with fragments of 9.2 and 7.3 kb released. Plasmid pALeryAM4.4 carries the eryAM412 allele on the *Sac. erythraea* multicopy vector pWHM4.

EXAMPLE 37

Construction of *Sac. erythraea* AM412 carrying the eryAM412 allele by gene conversion Approximately 1 mg of plasmid pALeryAM4.4, isolated from *E. coli* K12 DH5α/pALeryAM4.4, is used for transformation into *Sac. erythraea* strain AKS1 protoplasts. A few hundred transformants are screened for antibiotic production by the agar-plug assay, and one of the colonies found to produce antimicrobial activity is cured of pALeryAM4.4 by protoplast formation and regeneration as described in General Methods. Total DNA from six antibiotic-producing, Th$^S$ colonies (strain AM412) and from strain AKS1 is digested with SphI and with XhoI and the resulting Southern blot is hybridized first to the 2.9 kb insert from pALeryAM1, and then to the 2.9 kb SstI(95)-SstI(101) fragment from plasmid pALeryAM4.2. With the first probe, the SphI band at 0.8 kb in strain AKS1 is seen to be replaced by a 7.5 kb band in strain AM412, whereas the other two bands at 2.4 kb and 5.2 kb are unaffected. In the XhoI digest, the AKS1 band at 2.9 kb is replaced by a 9.6 kb band in AM412, with the other band at 5.2 kb conserved in both strains. Using the SstI(95)-SstI(101) fragment as probe, strain AKS1 exhibits one band at 25.5 kb and one at 17.9 kb in the SphI and XhoI digests, respectively, whereas, in addition to these bands, strain AM412 shows one SphI band at 7.5 kb and one XhoI band at 9.6 kb. In this way, it is established that the eryAKS1 allele has been converted into the eryAM412 allele in strain AM412.

EXAMPLE 38

Isolation and purification of 14-(1-propyl) erythromycin A

At harvest the fermentation is adjusted to pH 9.5 and extracted twice with equal volumes of methylene chloride. The combined extracts are washed once with water and concentrated to an oily residue. This is partitioned in a heptane methanol water (5:5:1, v/v/v) system and the lower layer is washed once with heptane and then concentrated to a semisolid residue. This is digested in methanol and chromatographed over a column of Sephadex LH-20 in methanol. Fractions are tested for bioactivity in an agar diffusion assay on plates seeded with the macrolide-sensitive strain *Staphylococcus aureus* Th$^R$. Active fractions are combined and further purified by chromatography over silica gel a chloroform:methanol gradient containing 0.1% triethylamine. Fractions containing the desired 14-(1-propyl) erythromycin A are combined and concentrated to yield the product as a white solid.

EXAMPLE 39

Construction of plasmid pALeryAM5.1

The 4.7 kb eryA fragment between sequence coordinates 23.65–28.36 (fragment 11) is PCR-amplified employing primers 11a (ATGCTCGAGATCTCGTGGGAGGCGCTGGA) [SEQ ID NO:26] and 11b (AGAACTCGGTGAGCATGCCCGGGCCCGCCA) [SEQ ID NO:27]. Fragment 11, after digestion with XhoI+SphI, is ligated to the 5.25 kb fragment resulting from complete XhoI and partial SphI digestion of pALeryAM1, as in Example 33. The resulting mixture contains the desired plasmid pALeryAM5.1.

EXAMPLE 40

Construction of *E. coli* K12 DH5α/pALeryAM5.1

Approximately 10 ng of pALeryAM5.1, prepared as described in Example 39, are transformed into *E. coli* K12 DH5α, and a few of the resulting white Ap$^R$ colonies that appear on the LB-agar plates containing X-gal and ampicillin are analyzed for their plasmid content. The identity of plasmid pALeryAM5.1, 9.95 kb in size, is verified by SphI+XhoI digestion, with fragments of 5.25 and 4.7 kb released, and by SmaI digestion where fragments of 3.39, 2.68 and 1.94 (doublet) kb are observed. Plasmid pALeryAM5.1 carries the entire eryA module 5 inserted into the β-ketoacyl ACP synthase region of module 1. The cloned insert in plasmid pALeryAM5.1 is designated the eryA512 allele.

EXAMPLE 41

Construction of plasmid pALeryAM5.2

Plasmid pALeryAM5.1 is cut with EcoRI+HindIII and the resulting 6.3 kb fragment, recovered from an agarose gel, is ligated to pWHM4 cut with the same two enzymes. The resulting mixture contains the desired plasmid pALeryAM5.2.

EXAMPLE 42

Construction of *E. coli* K12 DH5α/pALeryAM5.2

Approximately 10 ng of pALeryAM5.2, prepared as described in Example 41, are transformed into *E. coli* K12 DH5α, and a few of the resulting white Ap$^R$ colonies that appear on the LB-agar plates containing X-gal and ampicillin are analyzed for their plasmid content. The identity of plasmid pALeryAM5.2, 13.6 kb in size, is verified by digestion with EcoRI+HindIII, with fragments of 7.3 and 6.3 kb released. Plasmid pALeryAM5.2 contains the eryAM512 allele on the *Sac. erythraea* multicopy vector pWHM4.

EXAMPLE 43

Construction of *Sac. erythraea* AM512 carrying the eryAM512 allele by gene conversion Approximately 1 mg of plasmid pALeryAM5.2, isolated from *E. coli* K12 DH5α/pALeryAM5.2, is used for transformation into *Sac. erythraea* strain AKS1 protoplasts. A few hundred transformants are screened for antibiotic production by the agar-plug assay, and one of the colonies found to produce antimicrobial activity is cured of pALeryAM5.2 by protoplast formation and regeneration as described in General Methods. Total DNA from six antibiotic-producing, Th$^S$ colonies (strain AM512) and from strain AKS1 is digested with SphI and with XhoI and the resulting Southern blot is hybridized first to the 2.9 kb insert from pALeryAM1, and then to the 0.8 kb NcoI(119)-NcoI(123) fragment from plasmid pALeryAM5.1. With the first probe, the SphI band at 0.8 kb in strain AKS1 is replaced by a 5.5 kb band in strain AM512, whereas the other two bands at 2.4 kb and 5.2 kb are unaffected. In the XhoI digest, the AKS1 band at 2.9 kb is replaced by a 7.6 kb band in AM512, with the other band at 5.2 kb conserved in both strains. Using the NcoI(119)-NcoI(123) fragment as probe, strain AKS1 exhibits one band at 25.5 kb and one at 17.9 kb in the SphI and XhoI digests, respectively, whereas, in addition to these bands, strain AM512 shows one SphI band at 5.5 kb and one XhoI band at 7.6 kb. In this way, it is established that the eryAKS1 allele has been converted into the eryAM512 allele in strain AM512.

EXAMPLE 44

Isolation and purification of 14[1(1-hydroxypropyl)] erythromycin A

At harvest the pH of the fermentation of AM512 is adjusted to 9.5 and the mixture is extracted twice with equal volumes of ethylacetate. The combined ethylacetate extracts are washed with water, dried and partitioned in a heptane, methanol, water (5:5:1, v/v/v) system. The lower (methanolic phase) is washed with an equal volume of heptane and is concentrated to a residue. This is chromatographed on a Sephadex LH-20 column in methanol and fractions containing the desired 14[1(1-hydroxypropyl)] erythromycin A are concentrated and further purified by chromatography on an Ito Coil Planet Centrifuge in a system consisting of n-heptane, benzene, acetone, isopropanol, 0.65M, pH 7.0 aqueous potassium phosphate buffer (5:10:2:3:5, v/v/v/v/v). Fractions containing the desired product are concentrated to a solid residue and partitioned between methylene chloride and dilute (pH 9.5) ammonium hydroxide. The organic layer is washed with water and concentrated to yield 14[1(1-hydroxypropyl)]erythromycin A as a white solid.

Although the present invention is described in the Examples listed above in terms of preferred embodiments, they are not to be regarded as limiting the scope of the invention. The above descriptions serve to illustrate the principles and methodologies involved in creating the three types of mutations that can be introduced into the eryA segment of the *Sac. erythraea* chromosome that result in the synthesis of novel polyketide products. Although single Type I alterations, leading to the production of 5-oxo-5,6,-dideoxy-3α-mycorosyl erythronolide B, 11-oxo-11-deoxyerythromycin A, 7-hydroxyerythromycin A, 7-oxo-7deoxyerythromycin A, 5-desosaminyl-3-oxo-3-deoxyerythronolide A, and Δ-6,7-anhydro-6-deoxyerythromycin A are specified herein, it is obvious that other Type I changes can be introduced into the eryA segment leading to novel polyketide structures. Among the additional Type I alterations that can be obtained are those in which two or more modules are affected leading to the synthesis of novel polyketides. Examples of combinations of two Type I alterations leading to useful compounds include but are not limited to: mutants of the the β-ketoreductase of module 2 (KR2) and the β-ketoreductase of module 4 (KR4) leading to the formation of 7,11-dioxo-7,11-dideoxyerythromycin A; mutants of KR2 and the β-ketoreductase of module 6 (KR6) leading to the formation of 3,11-dioxo-3,11-dideoxy-5-desosaminylerythronolide A; mutants of KR2 and the dehydratase of module 4 (DH4) leading to the synthesis of 7-hydroxy-11-oxo-11-deoxyerythromycin A; mutants of KR2 and the enoylreductase of module 4 (ER4) leading to the synthesis of Δ-6,7-anhydro-11-oxo-11-deoxyerythromycin A; mutants of KR4 and KR6 leading to the synthesis of 3,7-dioxo-3,7-dideoxy-5-desosaminylerythronolide A; mutants of KR6 and DH4 leading to the synthesis of 3-oxo-3-deoxy-5-desosaminyl-7-hydroxyerythronolide A; and mutants of KR6 and ER4 leading to the synthesis of 3-oxo-3-deoxy-5-desosaminyl-Δ-6,7-anhydroerythronolide A. Examples of combinations of three Type I alterations leading to the synthesis of novel polyketides include but are not limited to: mutants of KR2, KR4 and KR6 leading to the synthesis of 3,7,11-trioxo-3,7,11-trideoxy-5-desosaminylerythronolide A; mutants of KR2, KR6 and DH4 leading to the synthesis of 3,11-dioxo-3,11-dideoxy-5-desosaminyl-7-hydroxyerythronolide A; and mutants of KR2, KR6 and ER4 leading to the synthesis of 3,11-dioxo-3,11-dideoxy-5-desosaminyl-D-6,7-anhydroerythronolide A. All combinations of two or three Type I mutants, the *Sac. erythraea* strains that carry said combinations and the corresponding polyketides produced from said strains, therefore, are included within the scope of the present invention.

Although the Type II mutants specified herein have been constructed in the β-ketoacyl ACP synthase of module 1 (KS1) and the β-ketoacyl ACP synthase of module 2 (KS2), other Type II mutants can be constructed in other domains to result in the synthesis of novel polyketide structures upon feeding with appropriate substrate analogs. Other Type II mutants include but are not limited to: inactivation of the either of the acyltransferases or acyl carrier proteins of module 1, or the acyltransferase or acyl carrier protein of module 2, the β-ketoacyl ACP synthase, acyltransferase or acyl carrier protein of module 3, module 4 or module 5. Furthermore, compounds other than (2S,3R,4S,5S)3,5-dihydroxy-2,4-dimethylhexanoic acid-ethyl thioester and (2S,3S,4S,5S)2,4-dimethyl-3-fluoro-5-hydroxyhexanoic acid-ethyl thioester specified herein can be synthesized and fed to strains AKS1 or AKS2 specified herein or other strains that carry other Type II mutations to result in the creation of novel polyketides that are within the scope of the present invention.

Although two examples of Type III alterations are specified herein, it is apparent to those skilled in the art that many other examples of Type III changes are possible. Strains of *Sac. erythraea* carrying changes of this type offer the very high potential for the production of novel polyketides of specified structure, since they do not require synthetic substrates as do Type II mutants and they are not limited to the formation of derivatives of erythromycin, as in the case of Type I mutants. In the embodiments of Type III mutants specified herein, we have illustrated how a second copy of a complete module can be introduced at a desired position by gene conversion to result in the synthesis of 14-(1-propyl) erythromycin A or 14[1(1-hydroxypropyl])erythromycin A. These alterations make use of the high conservation and simultaneous lack of specificity of the β-ketoacyl ACP synthases of modules 1 and 2, thereby making possible the construction of hybrid β-ketoacyl ACP synthase functions consisting of portions of proteins derived from different modules. Those skilled in the art understand, therefore, that it is possible, as exemplified for KS1 and KS2, to delete a small portion of the β-ketoacyl ACP synthase of other modules and to construct strains carrying such alterations which can then be employed as hosts for introducing at the deleted β-ketoacyl ACP synthase location a second copy of any homologous module. Furthermore, as exemplified herein, it is also possible to delete any segment of eryA by ligation of two non-contiguous PCR-generated fragments and to subsequently construct strains, therefore, devoid of any or all portions of any module. Such strains deleted of a full module can be employed for reintroduction of either the same or a different module at a different location. It is possible, therefore, to determine the novel structures desired and then create a series of *Sac. erythraea* strains containing the corresponding arrangements of eryA modules that would produce said novel structures that are included within the scope of the present invention. Additional examples of novel compounds produced from the construction of Type III alterations include but are not limited to 11-deoxyerythromycin, resulting from the insertion of the eryA segment encoding DH4 and ER4 in module 2.

Moreover, it will also be apparent that two or more modules can be excised and introduced into various sites of the *Sac. erythraea* chromosome to produce novel polyketides of predicted structure such as the introduction of the eryA segment encoding DH4 and ER4 in both module 1 and module 2 to result in the production of 14(R)[1-hydroxypropyl]11-deoxyerythromycin A. All combinations, therefore, of Type III alterations and the strains of *Sac. erythraea* that carry said alterations as well as the polyketides produced from said strains are included within the scope of the present invention.

In addition, it is also possible to create combinations of Type I, Type II and Type II alterations and insert such alterations into *Sac. erythraea* to produce novel polyketides. Examples of such combinations include but are not limited to the following. The combination of a Type I alteration, such as an alteration in DH4 and a Type II alteration, such as a mutation in the KS1 to result in the formation of (14S,15S)14-[1-hydroxyethyl]-7-hydroxyerythromycin A when the strain of *Sac. erythraea* carrying such alterations is fed with the compound (2S,3R,4S,5S)3,5-dihydroxy-2,4-dimethylhexanoic acid ethyl ester. The combination of a Type I alteration, such as an alteration in DH4 and a Type III alteration, such as found in *Sac. erythraea* strain AM412, wherein a copy of the DNA segment of module 4 is introduced in module 1, such that the *Sac. erythraea* strain so constructed produces the compound 7-hydroxy-14-propylerythromycin A. All combinations of two or more alterations of Type I, Type II and Type III alterations, the *Sac. erythraea* strains that carry such alterations, and the polyketides produced from such strains are included within the scope of the present invention. It will also occur to those skilled in the art that novel structures can be produced by altering the specificity of the acyltransferase functions in any module. Examples include: replacement of the acyltransferase domains of modules 1, 2, 3, 4, 5, or 6 in eryA with those of modules 4, 4, 2, 2, 2, and 4, respectively, to result in the production of 12-epierythromycin A, 10-epierythromycin A, 8-epierythromycin A, 6-epierythromycin A, 4-epierythromycin A and 2-epierythromycin A, respectively, that are included within the scope of the present invention.

It should be emphasized that the introduction of an entire eryA module at a different location, as exemplified for the construction of *Sac. erythraea* strains AM412 and AM512 in Examples 29 and 35, respectively, does not rely on homologous recombination between the incoming eryA module and the host chromosome. Rather, gene conversion of the host allele with the eryA allele residing on the multicopy plasmid requires DNA sequences homologous to the host allele flanking the incoming module. Thus, any module carrying the desired specificities, either from homologous or heterologous sources, can be employed in gene conversion of the host allele, provided that is flanked by segments of homology. It will occur to those skilled in the art, therefore, that, given the large number of natural polyketide molecules existing, a wide variety of additional novel molecules of predicted structure can be produced in Type III mutants containing an additional module of desired specificities or where an endogenous module is replaced by an exogenous one. The length of the acyl chain can be easily controlled by suitably changing the number of modules involved in its synthesis. Similarly, the introduction of keto, hydroxy, enoyl, or methylene groups at specific points along the acyl chain can be easily achieved by introducing the proper $\beta$-carbon processing functions ($\beta$-ketoreductase, dehydratase and enoylreductase) in the required modules. Exogenous modules constitute the source of specificities for starter and extender units other than those employed by *Sac. erythraea* for erythromycin biosynthesis, making it thereby possible to employ, for example, malonylCoA or (2R)- or (2S)ethylmalonylCoA, etc. as extender units, and acetyl CoA, butyryl CoA, etc. as the starter unit. The result will be the formation of erythromycin analogs containing the desired functional groups and side chains with the desired stereochemistry. As an extension of the examples reported with eryA, the construction of a *Sac. erythraea* strain carrying a heterologous module inserted into eryA requires: (i) cloning of the genes from any other Actinomyces producing a polyketide with desired structural features; (ii) mapping of the modular organization of the cloned genes by low stringency hybridization and restriction analysis; (iii) locating the module carrying the desired specificities by partial sequencing; (iv) precise excision of the desired genetic element and cloning into a vector suitable for gene conversion; (v) construction and transformation of a *Sac. erythraea* strain suitable for gene conversion and screening for the novel compound. Any module, or portion thereof, can thus be precisely excised from the genome of a polyketide-producing microorganism and introduced into suitable *Sac. erythraea* strains to create a novel polyketide of predicted structure. Thus, replacement of the acyltransferase segments of modules 1, 2, 3, 4, 5, or 6 in eryA with the acyltransferase segment specific for malonyl CoA, such as can be found in the polyketide synthase genes for the synthesis of pikromycin in *Streptomyces venezuelae*, to result in the synthesis of 12-norerythromycin A, 10-norerythromycin A, 8-norerythromycin A, 6-norerythromycin A, 4-norerythromycin A and 2-norerythromycin A, respectively, that are included within the scope of the present invention. In addition, replacement of the acyltransferase segments of modules 1, 2, 3, 4, 5, or 6 in eryA with an acyltransferase specific for (2R)-ethylmalonyl CoA, such as can be found in the polyketide synthase genes for the synthesis of spiramycin in *Streptomyces ambofasciens*, will result in the formation of 12-homoerythromycin A, 10-homoerythromycin A, 8-epihomoerythromycin A, 6-epihomoerythromycin A, 4-epihomoerythromycin A and 2-homoerythromycin A, respectively, all of which are included within the scope of the present invention. Similarly, introduction of acyltransferase segments carrying desired specificities for the starter or extender unit into eryA DNA that results in the synthesis of novel compounds are included within the scope of the present invention. The erythromycin analogs produced by the method of this invention are structurally similar to known antibacterial and prokinetic agents.

It will also occur to those skilled in the art that genetic manipulations described herein need not be limited to *Sac. erythraea*. Suitable hosts are any other polyketide-producing Actinomyces where DNA can be precisely inserted into the chromosome. Hence, the choice of a convenient host is based solely on the relatedness of the novel polyketide to a natural counterpart so as to minimize the number of module rearrangements required for its biosynthesis. Therefore, Type I, Type II and Type III alterations can be constructed in other Actinomyces employing either endogenous or exogenous modules to produce novel polyketides employing strategies analogous to those described herein for *Sac. erythraea*. Thus all Type I, Type II or Type III mutations or various combinations thereof constructed in other actinomycetes according to the principles described herein, and the respective polyketides produced from such strains, are included within the scope of the present invention. Examples of polyketides that can be altered by creating Type I, Type II or Type III changes in the producing microorganisms include, but are not limited to macrolide antibiotics such as erythromycin, tylosin, spiramycin, etc.; ansamacrolides such as rifamycins, maytansines, etc.; polyketide antibiotics such as tetracycline; polyethers such as monesin, salinomycin, etc.; polyenes such as candicidin, amphothericins; immunosuppressants such as FK506, ascomycin, rapamycin, etc. and other complex polyketides such as avermectin.

Whereas the novel derivatives or modifications of erythromycin described herein have been specified as the A derivatives, such as 7-hydroxyerythromycin A, 11-oxo-11-deoxyerythromycin A, 14[1(1-hydroxypropyl)] erythromycin A, etc., those skilled in the art understand that the wild type strain of *Sac. erythraea* produces a family of erythromycin compounds, including erythromycin A, erythromycin B, erythromycin C and erythromycin D. Thus, modified strains of *Sac. erythraea*, such as strain AKR2, for example, would be expected to produce the corresponding members of the 11-oxo-11-deoxyerythromycin family, including 11-oxo-11-deoxyerythromycin A, 11-oxo-11-deoxyerythromycin B, 11-oxo-11-deoxyerythromycin C, and 11-oxo-11-deoxyerythromycin D. Similarly, strain AM412 would be expected to produce not only 14(1-propyl) erythromycin A but also the other members of the 14(1-propyl)erythromycin family including 14(1-propyl) erythromycin B, 14(1-propyl)erythromycin C and 14(1-propyl)erythromycin D. Similarly, all other modified strains of *Sac. erythraea* described herein that produce novel erythromycin derivatives would be expected to produce the A, B, C, and D forms of said derivatives. Therefore, all members of the family of each of the novel polyketides described herein are included within the scope of the present invention.

Variations and modifications of the methods for obtaining the desired plasmids, hosts for cloning and choices of vectors and segments of eryA DNA to clone and modify, other than those described herein that result in substantially the same strains and same products as those described herein will occur to those skilled in the art. For example, although we have described the use of the plasmids pWH3 and pWHM4 as *E. coli*-*Sac. erythraea* shuttle vectors, other vectors can be employed wherein all or part of pWHM3 or pWHM4 is replaced by other DNA segments that function in a similar manner, such as replacing the pUC19 component of pWHM3 and pWHM4 with pBR322, available from BRL, employing different segments of the pIJ101 or pJV1 replicons in pWHM3 and pWHM4, respectively, or employing selectable markers other than thiostrepton- and ampicillin-resistance. These are just few of a long list of possible examples all of which are included within the scope of the present invention. Similarly, the segments of the eryA locus subcloned into pWHM3 for generating strains AKS1, AKS2, etc. specified herein can readily be substituted for other segments of different length encoding the same functions, either produced by PCR-amplification of genomic DNA or of an isolated clone, or by isolating suitable restriction fragments from Sac. erythraea. In the same way, it is possible to create eryA strains carrying mutations functionally equivalent to those described herein by deleting different portions of the corresponding genes, by creating insertions into them, or by site-directed mutagenesis of specific nucleotide residues. Moreover, Sac. erythraea strains with mutant alleles other than the β-ketoacyl ACP synthase portions of eryA can be employed as hosts for gene conversion; Type III mutants can be constructed by double reciprocal crossover as exemplified for Type I and Type II mutants rather than by the gene conversion method described herein. Additional modifications include changes in the restriction sites used for cloning or in the general methodologies described above. All such changes are included in the scope of the invention. It will also occur to those skilled in the art that different methods are available to ferment Sac. erythraea, to extract the novel polyketides specified herein, and to synthesize substrate analogs, and that all such methods are also included within the scope of the present invention.

It will be apparent that many modifications and variations of the invention as set forth herein are possible without departing from the spirit and scope thereof, and that, accordingly, such limitations are imposed only as indicated by the appended claims.

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 11219 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Saccharopolyspora erythraea
        ( B ) STRAIN: NRRL 2338

( i x ) FEATURE:
        ( A ) NAME/KEY: misc_feature
        ( B ) LOCATION: 744..6659
        ( D ) OTHER INFORMATION: /function="APPROXIMATE SPAN OF
            MODULE 1"
        / label= FUNCTION ( i x ) FEATURE:
        ( A ) NAME/KEY: CDS
        ( B ) LOCATION: 744..11219
        ( D ) OTHER INFORMATION: /function="gene= "eryA""
        / product= ""ORF1 encoding modules 1 & 2 for
        6- deoxyerythronolide B""

( i x ) FEATURE:
        ( A ) NAME/KEY: misc_feature
        ( B ) LOCATION: 744..1868
        ( D ) OTHER INFORMATION: /function="approximate span of
            acyltransferase domain 1 of module 1"

( i x ) FEATURE:
        ( A ) NAME/KEY: misc_feature
        ( B ) LOCATION: 1998..2198
        ( D ) OTHER INFORMATION: /function="approximate span of
            acyl carrier domain 1 of module 1"

( i x ) FEATURE:
        ( A ) NAME/KEY: misc_feature
        ( B ) LOCATION: 2250..3626

-continued ( D ) OTHER INFORMATION: /function="approximate span of beta- ketoacylACP synthase domain/module1"

( i x ) FEATURE:
    ( A ) NAME/KEY: misc_feature
    ( B ) LOCATION: 3831..4811
    ( D ) OTHER INFORMATION: /function="approximate span of acyltransferase 2 domain of module 1"

( i x ) FEATURE:
    ( A ) NAME/KEY: misc_feature
    ( B ) LOCATION: 5574..6125
    ( D ) OTHER INFORMATION: /function="approximate span of beta- ketoreductase domain of module 1"

( i x ) FEATURE:
    ( A ) NAME/KEY: misc_feature
    ( B ) LOCATION: 6369..6626
    ( D ) OTHER INFORMATION: /function="approximate span of acyl carrier domain 2 of module 1"

( i x ) FEATURE:
    ( A ) NAME/KEY: misc_feature
    ( B ) LOCATION: 6678..11219
    ( D ) OTHER INFORMATION: /function="approximate span of module 2"

( i x ) FEATURE:
    ( A ) NAME/KEY: misc_feature
    ( B ) LOCATION: 6678..8066
    ( D ) OTHER INFORMATION: /function="approximate span of beta- ketoacyl ACPsynthase of module 2"

( i x ) FEATURE:
    ( A ) NAME/KEY: misc_feature
    ( B ) LOCATION: 8262..9305
    ( D ) OTHER INFORMATION: /function="approximate span of acyltransferase domain of module 2"

( i x ) FEATURE:
    ( A ) NAME/KEY: misc_feature
    ( B ) LOCATION: 9906..10454
    ( D ) OTHER INFORMATION: /function="approximate span of beta- ketoreductase domain of module 2"

( i x ) FEATURE:
    ( A ) NAME/KEY: misc_feature
    ( B ) LOCATION: 10707..10964
    ( D ) OTHER INFORMATION: /function="approximate span of acyl carrier domain of module 2"

( x i ) SEQUENCE DESCRIPTION: SEQ ID NO:1:

```
GTCGACCTGC  GGCGATCGTG  CAGCGCGCCG  ACGAGGTCGT  GCATCAGGCC  GACGTTGACC      60
CGCTCGGCTT  CCGGGTCGGA  GGTGGCGCTG  CGCCAGGTGG  AACCGCCCGC  TGCGTGCGCC     120
ACCAGGTGCA  CGATCACGTC  GGCGTCCTCG  ATCGCGGCGG  CGGCCCGGCC  CGGTTCCAGC     180
AGGTCGGCGC  GCAGGTCCTC  GACCTCCGCG  GCGCCGGGCG  GAACCGCGGG  CGCTCCGCCG     240
CGGGACACCG  CGCGCAGCCG  GACCGGGTGG  TCGCGCAGCT  CGCGCAGAAC  CGCGCTCCCG     300
ACGAAGCCGG  AAGCGCCCAG  AAGGGTGATC  AATTGACGCG  GGGAATCACT  GATCCCATTC     360
ACCGGAGCAT  TTGCTCGCTT  TCCAGGTCGG  TGCTACGGGC  GAAATTCAAA  GAATCTCCCC     420
AGCGCGATGT  GCGGCAACCC  GTCACTGGGC  CACCACAGTA  GGTAGCCGCC  GTTGATCTTG     480
TCAACATGCA  GATGTTCACA  GGTTCGTTGG  CTCGACGAGG  CGATGTCAAC  CTCTTGATCC     540
TTCCTATATT  GTTCGCCCAT  TGCGTGGTCG  TCGAGTAGGG  GGACGCGTGG  CGGACCTGTC     600
AAAGCTCTCC  GACAGTCGGA  CTGCACAACC  TGGGAGGATC  GTTCGTCCGT  GGCCCCTGTC     660
GGGGTGCAAT  GAATCCGCCT  TGCGGGCCCG  TGCGCGCCAA  TTGCGTGCAC  ATCTCGATCG     720
ATTTCCCGAT  GCCGGTGTCG  AAG GTG TCG GGG CCG CGC TCG CGC ACG ACG            770
                          Val Ser Gly Pro Arg Ser Arg Thr Thr
                           1                   5
```

| | | | | | | | | | | | | | | | | |
|---|---|---|---|---|---|---|---|---|---|---|---|---|---|---|---|---|
| AGC | AGG | CGG | ACG | CCG | GTC | CGC | ATC | GGC | GCG | GTC | GTC | GTC | GCC | TCC | TCG | 818 |
| Ser | Arg | Arg | Thr | Pro | Val | Arg | Ile | Gly | Ala | Val | Val | Val | Ala | Ser | Ser | |
| 10 | | | | 15 | | | | | 20 | | | | | | 25 | |
| ACC | TCC | GAG | CTG | CTC | GAC | GGC | CTG | GCC | GCC | GTC | GCC | GAC | GGC | CGG | CCG | 866 |
| Thr | Ser | Glu | Leu | Leu | Asp | Gly | Leu | Ala | Ala | Val | Ala | Asp | Gly | Arg | Pro | |
| | | | | 30 | | | | | 35 | | | | | | 40 | |
| CAC | GCC | TCG | GTG | GTC | CGC | GGC | GTG | GCC | CGG | CCG | TCC | GCG | CCG | GTG | GTG | 914 |
| His | Ala | Ser | Val | Val | Arg | Gly | Val | Ala | Arg | Pro | Ser | Ala | Pro | Val | Val | |
| | | | | 45 | | | | | 50 | | | | | | 55 | |
| TTC | GTC | TTC | CCG | GGC | CAG | GGC | GCG | CAA | TGG | GCC | GGG | ATG | GCG | GGC | GAA | 962 |
| Phe | Val | Phe | Pro | Gly | Gln | Gly | Ala | Gln | Trp | Ala | Gly | Met | Ala | Gly | Glu | |
| | | | 60 | | | | | 65 | | | | | 70 | | | |
| CTC | CTC | GGC | GAG | TCA | AGG | GTT | TTC | GCC | GCC | GCG | ATG | GAC | GCG | TGC | GCG | 1010 |
| Leu | Leu | Gly | Glu | Ser | Arg | Val | Phe | Ala | Ala | Ala | Met | Asp | Ala | Cys | Ala | |
| | 75 | | | | | 80 | | | | | 85 | | | | | |
| CGG | GCG | TTC | GAG | CCC | GTG | ACC | GAC | TGG | ACG | CTG | GCG | CAG | GTC | CTG | GAC | 1058 |
| Arg | Ala | Phe | Glu | Pro | Val | Thr | Asp | Trp | Thr | Leu | Ala | Gln | Val | Leu | Asp | |
| 90 | | | | | 95 | | | | | 100 | | | | | 105 | |
| TCT | CCC | GAG | CAG | TCG | CGC | CGC | GTC | GAG | GTC | GTC | CAG | CCC | GCC | CTG | TTC | 1106 |
| Ser | Pro | Glu | Gln | Ser | Arg | Arg | Val | Glu | Val | Val | Gln | Pro | Ala | Leu | Phe | |
| | | | | 110 | | | | | 115 | | | | | | 120 | |
| GCG | GTG | CAG | ACG | TCG | CTG | GCC | GCG | CTC | TGG | CGC | TCC | TTC | GGC | GTG | ACC | 1154 |
| Ala | Val | Gln | Thr | Ser | Leu | Ala | Ala | Leu | Trp | Arg | Ser | Phe | Gly | Val | Thr | |
| | | | 125 | | | | | 130 | | | | | 135 | | | |
| CCC | GAC | GCC | GTG | GTG | GGC | CAC | AGC | ATC | GGC | GAG | CTG | GCC | GCC | GCG | CAC | 1202 |
| Pro | Asp | Ala | Val | Val | Gly | His | Ser | Ile | Gly | Glu | Leu | Ala | Ala | Ala | His | |
| | | 140 | | | | | 145 | | | | | 150 | | | | |
| GTG | TGC | GGT | GCG | GCC | GGT | GCC | GCC | GAC | GCC | GCG | CGC | GCC | GCC | GCG | CTG | 1250 |
| Val | Cys | Gly | Ala | Ala | Gly | Ala | Ala | Asp | Ala | Ala | Arg | Ala | Ala | Ala | Leu | |
| | 155 | | | | | 160 | | | | | 165 | | | | | |
| TGG | AGC | CGC | GAG | ATG | ATT | CCG | TTG | GTG | GGC | AAC | GGC | GAC | ATG | GCA | GCC | 1298 |
| Trp | Ser | Arg | Glu | Met | Ile | Pro | Leu | Val | Gly | Asn | Gly | Asp | Met | Ala | Ala | |
| 170 | | | | | 175 | | | | | 180 | | | | | 185 | |
| GTC | GCG | CTC | TCC | GCC | GAC | GAG | ATC | GAG | CCG | CGC | ATC | GCC | CGG | TGG | GAC | 1346 |
| Val | Ala | Leu | Ser | Ala | Asp | Glu | Ile | Glu | Pro | Arg | Ile | Ala | Arg | Trp | Asp | |
| | | | | 190 | | | | | 195 | | | | | 200 | | |
| GAC | GAC | GTG | GTG | CTG | GCC | GGG | GTC | AAC | GGT | CCG | CGC | TCG | GTT | CTG | CTG | 1394 |
| Asp | Asp | Val | Val | Leu | Ala | Gly | Val | Asn | Gly | Pro | Arg | Ser | Val | Leu | Leu | |
| | | | 205 | | | | | 210 | | | | | 215 | | | |
| ACC | GGG | TCG | CCG | GAA | CCG | GTC | GCG | CGC | CGG | GTC | CAG | GAG | CTC | TCG | GCC | 1442 |
| Thr | Gly | Ser | Pro | Glu | Pro | Val | Ala | Arg | Arg | Val | Gln | Glu | Leu | Ser | Ala | |
| | | 220 | | | | | 225 | | | | | 230 | | | | |
| GAG | GGG | GTC | CGC | GCA | CAG | GTC | ATC | AAT | GTG | TCG | ATG | GCG | GCG | CAC | TCG | 1490 |
| Glu | Gly | Val | Arg | Ala | Gln | Val | Ile | Asn | Val | Ser | Met | Ala | Ala | His | Ser | |
| | 235 | | | | | 240 | | | | | 245 | | | | | |
| GCG | CAG | GTC | GAC | GAC | ATC | GCC | GAG | GGG | ATG | CGC | TCG | GCC | CTG | GCG | TGG | 1538 |
| Ala | Gln | Val | Asp | Asp | Ile | Ala | Glu | Gly | Met | Arg | Ser | Ala | Leu | Ala | Trp | |
| 250 | | | | | 255 | | | | | 260 | | | | | 265 | |
| TTC | GCG | CCC | GGT | GGC | TCG | GAG | GTG | CCC | TTC | TAC | GCC | AGC | CTC | ACC | GGA | 1586 |
| Phe | Ala | Pro | Gly | Gly | Ser | Glu | Val | Pro | Phe | Tyr | Ala | Ser | Leu | Thr | Gly | |
| | | | 270 | | | | | 275 | | | | | 280 | | | |
| GGT | GCG | GTC | GAC | ACG | CGG | GAG | CTG | GTG | GCC | GAC | TAC | TGG | CGC | CGC | AGC | 1634 |
| Gly | Ala | Val | Asp | Thr | Arg | Glu | Leu | Val | Ala | Asp | Tyr | Trp | Arg | Arg | Ser | |
| | | | 285 | | | | | 290 | | | | | 295 | | | |
| TTC | CGG | CTG | CCG | GTG | CGC | TTC | GAC | GAG | GCG | ATC | CGG | TCC | GCC | CTG | GAG | 1682 |
| Phe | Arg | Leu | Pro | Val | Arg | Phe | Asp | Glu | Ala | Ile | Arg | Ser | Ala | Leu | Glu | |
| | | 300 | | | | | 305 | | | | | 310 | | | | |
| GTC | GGT | CCC | GGC | ACG | TTC | GTC | GAA | GCG | AGC | CCG | CAC | CCG | GTG | CTG | GCC | 1730 |
| Val | Gly | Pro | Gly | Thr | Phe | Val | Glu | Ala | Ser | Pro | His | Pro | Val | Leu | Ala | |
| | 315 | | | | | 320 | | | | | 325 | | | | | |

```
GCC GCG CTC CAG CAG ACG CTC GAC GCC GAG GGC TCC TCG GCC GCG GTG      1778
Ala Ala Leu Gln Gln Thr Leu Asp Ala Glu Gly Ser Ser Ala Ala Val
330                 335                 340                 345

GTC CCG ACG CTG CAA CGC GGG CAG GGC GGC ATG CGG CGG TTC CTG CTG      1826
Val Pro Thr Leu Gln Arg Gly Gln Gly Gly Met Arg Arg Phe Leu Leu
                    350                 355                 360

GCC GCG GCC CAG GCG TTC ACC GGC GGC GTG GCC GTC GAC TGG ACC GCC      1874
Ala Ala Ala Gln Ala Phe Thr Gly Gly Val Ala Val Asp Trp Thr Ala
                365                 370                 375

GCC TAC GAC GAC GTG GGG CCG AAC CCG GCT CTC TGC CGG AGT TCG CGC      1922
Ala Tyr Asp Asp Val Gly Pro Asn Pro Ala Leu Cys Arg Ser Ser Arg
            380                 385                 390

CGG CCG AGG AGG AAG ACG AGC CGG CCG AGT CCG GCG TCG ACT GGA ACG      1970
Arg Pro Arg Arg Lys Thr Ser Arg Pro Ser Pro Ala Ser Thr Gly Thr
395                 400                 405

CGC CAC CGC ACG TGC TGC GAG CGG CTG CTC GCG GTC GTC AAC GGC GAG      2018
Arg His Arg Thr Cys Cys Glu Arg Leu Leu Ala Val Val Asn Gly Glu
410                 415                 420                 425

ACC GCC GCG TTG GCG GGC CGC GAA GCC GAC GCC GAG GCC ACG TTC CGC      2066
Thr Ala Ala Leu Ala Gly Arg Glu Ala Asp Ala Glu Ala Thr Phe Arg
                430                 435                 440

GAG CTG GGG CTG GAC TCG GTG CTG GCC GCG CAG CTG CGC GCC AAG GTG      2114
Glu Leu Gly Leu Asp Ser Val Leu Ala Ala Gln Leu Arg Ala Lys Val
                445                 450                 455

AGC GCC GCG ATC GGG CGC GAG GTC AAC ATC GCC CTG CTC TAC GAC CAC      2162
Ser Ala Ala Ile Gly Arg Glu Val Asn Ile Ala Leu Leu Tyr Asp His
            460                 465                 470

CCG ACT CCG CGT GCG CTC GCG GAA GCA CTC GCG GCG GGA ACC GAG GTC      2210
Pro Thr Pro Arg Ala Leu Ala Glu Ala Leu Ala Ala Gly Thr Glu Val
475                 480                 485

GCA CAA CGG GAA ACC CGC GCG CGG ACC AAC GAA GCG GCG CCC GGC GAA      2258
Ala Gln Arg Glu Thr Arg Ala Arg Thr Asn Glu Ala Ala Pro Gly Glu
490                 495                 500                 505

CCG GTC GCG GTC GTC GCG ATG GCC TGC CGG CTG CCC GGC GGT GTG AGC      2306
Pro Val Ala Val Val Ala Met Ala Cys Arg Leu Pro Gly Gly Val Ser
                510                 515                 520

ACC CCG GAG GAG TTC TGG GAG CTG CTG TCG GAG GGC CGC GAC GCG GTC      2354
Thr Pro Glu Glu Phe Trp Glu Leu Leu Ser Glu Gly Arg Asp Ala Val
                525                 530                 535

GCG GGA CTG CCG ACC GAC CGC GGC TGG GAC CTG GAC TCG CTG TTC CAC      2402
Ala Gly Leu Pro Thr Asp Arg Gly Trp Asp Leu Asp Ser Leu Phe His
                540                 545                 550

CCC GAC CCC ACG CGC TCG GGC ACC GCG CAC CAG CGC GGC GGC GGT TTC      2450
Pro Asp Pro Thr Arg Ser Gly Thr Ala His Gln Arg Gly Gly Gly Phe
555                 560                 565

CTG ACC GAG GCG ACC GCG TTC GAC CCG GCC TTC TTC GGC ATG TCC CCG      2498
Leu Thr Glu Ala Thr Ala Phe Asp Pro Ala Phe Phe Gly Met Ser Pro
570                 575                 580                 585

CGC GAG GCG CTG GCC GTC GAC CCG CAG CAG CGG CTC ATG CTC GAG CTC      2546
Arg Glu Ala Leu Ala Val Asp Pro Gln Gln Arg Leu Met Leu Glu Leu
                590                 595                 600

TCC TGG GAA GTG CTG GAA CGG GCG GGA ATC CCG CCG ACC TCG TTG CAG      2594
Ser Trp Glu Val Leu Glu Arg Ala Gly Ile Pro Pro Thr Ser Leu Gln
                605                 610                 615

GCC TCG CCC ACT GGC GTG TTC GTC GGC CTG ATC CCG CAG GAG TAC GGC      2642
Ala Ser Pro Thr Gly Val Phe Val Gly Leu Ile Pro Gln Glu Tyr Gly
                620                 625                 630

CCG CGG CTG GCC GAG GGC GGC GAA GGC GTC GAG GGC TAC CTG ATG ACC      2690
Pro Arg Leu Ala Glu Gly Gly Glu Gly Val Glu Gly Tyr Leu Met Thr
635                 640                 645
```

| | | | | | | | | | | | | | | | | |
|---|---|---|---|---|---|---|---|---|---|---|---|---|---|---|---|---|
| GGT | ACG | ACC | ACG | AGC | GTC | GCC | TCC | GGC | CGC | ATC | GCC | TAC | ACG | CTC | GGC | 2738 |
| Gly | Thr | Thr | Thr | Ser | Val | Ala | Ser | Gly | Arg | Ile | Ala | Tyr | Thr | Leu | Gly | |
| 650 | | | | | 655 | | | | | 660 | | | | | 665 | |
| CTG | GAG | GGC | CCG | GCG | ATC | AGC | GTG | GAC | ACC | GCG | TGC | TCG | TCC | TCG | CTG | 2786 |
| Leu | Glu | Gly | Pro | Ala | Ile | Ser | Val | Asp | Thr | Ala | Cys | Ser | Ser | Ser | Leu | |
| | | | | 670 | | | | | 675 | | | | | 680 | | |
| GTC | GCG | GTG | CAC | CTG | GCG | TGC | CAG | TCG | CTG | CGG | CGC | GGC | GAG | TCG | TCG | 2834 |
| Val | Ala | Val | His | Leu | Ala | Cys | Gln | Ser | Leu | Arg | Arg | Gly | Glu | Ser | Ser | |
| | | | 685 | | | | | 690 | | | | | 695 | | | |
| CTG | GCG | ATG | GCA | GGC | GGT | GTC | ACG | GTG | ATG | CCG | ACG | CCC | GGC | ATG | CTG | 2882 |
| Leu | Ala | Met | Ala | Gly | Gly | Val | Thr | Val | Met | Pro | Thr | Pro | Gly | Met | Leu | |
| | | 700 | | | | | 705 | | | | | 710 | | | | |
| GTG | GAC | TTC | AGC | CGG | ATG | AAC | TCG | CTG | GCG | CCG | GAC | GGC | CGG | TGC | AAG | 2930 |
| Val | Asp | Phe | Ser | Arg | Met | Asn | Ser | Leu | Ala | Pro | Asp | Gly | Arg | Cys | Lys | |
| | 715 | | | | | 720 | | | | | 725 | | | | | |
| GCT | TTC | TCC | GCC | GGC | GCC | AAC | GGT | TTC | GGC | ATG | GCC | GAG | GGC | GCC | GGG | 2978 |
| Ala | Phe | Ser | Ala | Gly | Ala | Asn | Gly | Phe | Gly | Met | Ala | Glu | Gly | Ala | Gly | |
| 730 | | | | | 735 | | | | | 740 | | | | | 745 | |
| ATG | CTC | CTG | CTG | GAG | CGG | CTT | TCG | GAC | GCC | CGC | CGC | AAC | GGC | CAC | CCG | 3026 |
| Met | Leu | Leu | Leu | Glu | Arg | Leu | Ser | Asp | Ala | Arg | Arg | Asn | Gly | His | Pro | |
| | | | | 750 | | | | | 755 | | | | | 760 | | |
| GTG | CTC | GCC | GTG | CTC | AGG | GGG | ACG | GCG | GTC | AAC | TCC | GAC | GGC | GCG | AGC | 3074 |
| Val | Leu | Ala | Val | Leu | Arg | Gly | Thr | Ala | Val | Asn | Ser | Asp | Gly | Ala | Ser | |
| | | | 765 | | | | | 770 | | | | | 775 | | | |
| AAC | GGG | CTG | TCG | GCG | CCC | AAC | GGG | CGG | GCG | CAG | GTG | CGG | GTC | ATC | CAG | 3122 |
| Asn | Gly | Leu | Ser | Ala | Pro | Asn | Gly | Arg | Ala | Gln | Val | Arg | Val | Ile | Gln | |
| | | 780 | | | | | 785 | | | | | 790 | | | | |
| CAG | GCG | CTG | GCA | GAG | TCC | GGT | CTC | GGG | CCC | GCC | GAC | ATC | GAC | GCC | GTC | 3170 |
| Gln | Ala | Leu | Ala | Glu | Ser | Gly | Leu | Gly | Pro | Ala | Asp | Ile | Asp | Ala | Val | |
| | 795 | | | | | 800 | | | | | 805 | | | | | |
| GAG | GCG | CAC | GGC | ACC | GGT | ACC | CGA | CTC | GGC | GAC | CCG | ATC | GAG | GCG | CGG | 3218 |
| Glu | Ala | His | Gly | Thr | Gly | Thr | Arg | Leu | Gly | Asp | Pro | Ile | Glu | Ala | Arg | |
| 810 | | | | | 815 | | | | | 820 | | | | | 825 | |
| GCG | CTG | TTC | GAG | GCG | TAC | GGG | CGC | GAC | CGC | GAG | CAG | CCG | CTG | CAC | CTG | 3266 |
| Ala | Leu | Phe | Glu | Ala | Tyr | Gly | Arg | Asp | Arg | Glu | Gln | Pro | Leu | His | Leu | |
| | | | | 830 | | | | | 835 | | | | | 840 | | |
| GGC | TCG | GTC | AAG | TCC | AAC | CTC | GGC | CAC | ACC | CAG | GCG | GCC | GCC | GGT | GTT | 3314 |
| Gly | Ser | Val | Lys | Ser | Asn | Leu | Gly | His | Thr | Gln | Ala | Ala | Ala | Gly | Val | |
| | | | 845 | | | | | 850 | | | | | 855 | | | |
| GCC | GGC | GTG | ATC | AAG | ATG | GTG | CTG | GCG | ATG | CGC | GCG | GGC | ACC | CTT | CCC | 3362 |
| Ala | Gly | Val | Ile | Lys | Met | Val | Leu | Ala | Met | Arg | Ala | Gly | Thr | Leu | Pro | |
| | | 860 | | | | | 865 | | | | | 870 | | | | |
| CGC | ACT | CTG | CAC | GCA | TCG | GAG | CGG | TCG | AAG | GAG | ATC | GAC | TGG | TCA | TCC | 3410 |
| Arg | Thr | Leu | His | Ala | Ser | Glu | Arg | Ser | Lys | Glu | Ile | Asp | Trp | Ser | Ser | |
| | 875 | | | | | 880 | | | | | 885 | | | | | |
| GGT | GCG | ATC | AGC | CTG | CTC | GAC | GAG | CCG | GAG | CCG | TGG | CCC | GCC | GGC | GCG | 3458 |
| Gly | Ala | Ile | Ser | Leu | Leu | Asp | Glu | Pro | Glu | Pro | Trp | Pro | Ala | Gly | Ala | |
| 890 | | | | | 895 | | | | | 900 | | | | | 905 | |
| CGA | CCG | CGC | CGG | GCG | GGG | GTC | TCG | TCG | TTC | GGC | ATC | AGC | GGC | ACC | AAC | 3506 |
| Arg | Pro | Arg | Arg | Ala | Gly | Val | Ser | Ser | Phe | Gly | Ile | Ser | Gly | Thr | Asn | |
| | | | | 910 | | | | | 915 | | | | | 920 | | |
| GCG | CAC | GCC | ATC | ATC | GAG | GAA | GCT | CCG | CAG | GTC | GTC | GAA | GGC | GAG | CGG | 3554 |
| Ala | His | Ala | Ile | Ile | Glu | Glu | Ala | Pro | Gln | Val | Val | Glu | Gly | Glu | Arg | |
| | | | 925 | | | | | 930 | | | | | 935 | | | |
| GTC | GAG | GCC | GGC | GAC | GTC | GTG | GCG | CCC | TGG | GTG | CTT | TCG | GCG | AGC | AGC | 3602 |
| Val | Glu | Ala | Gly | Asp | Val | Val | Ala | Pro | Trp | Val | Leu | Ser | Ala | Ser | Ser | |
| | | | 940 | | | | | 945 | | | | | 950 | | | |
| GCG | GAA | GGT | CTG | CGC | GCC | CAG | GCG | GCG | CGG | CTG | GCC | GCG | CAC | CTG | CGC | 3650 |
| Ala | Glu | Gly | Leu | Arg | Ala | Gln | Ala | Ala | Arg | Leu | Ala | Ala | His | Leu | Arg | |
| | | 955 | | | | | 960 | | | | | 965 | | | | |

```
GAG CAC CCC GGT CAG GAC CCG CGC GAC ATC GCG TAC TCG CTC GCG ACG      3698
Glu His Pro Gly Gln Asp Pro Arg Asp Ile Ala Tyr Ser Leu Ala Thr
970             975             980             985

GGA CGG GCC GCG CTG CCC CAC CGC GCC GCC TTC GCC CCC GTC GAC GAG      3746
Gly Arg Ala Ala Leu Pro His Arg Ala Ala Phe Ala Pro Val Asp Glu
    990             995             1000

TCC GCC GCG CTG CGC GTG CTC GAC GGT CTC GCG ACG GGA AAC GCC GAC      3794
Ser Ala Ala Leu Arg Val Leu Asp Gly Leu Ala Thr Gly Asn Ala Asp
1005            1010            1015

GGT GCC GCC GTT GGA ACG AGC CGG GCG CAG CAG CGC GCC GTC TTC GTC      3842
Gly Ala Ala Val Gly Thr Ser Arg Ala Gln Gln Arg Ala Val Phe Val
    1020            1025            1030

TTC CCC GGG CAG GGT TGG CAG TGG GCG GGC ATG GCC GTC GAC CTG CTC      3890
Phe Pro Gly Gln Gly Trp Gln Trp Ala Gly Met Ala Val Asp Leu Leu
1035            1040            1045

GAC ACC TCC CCG GTT TTC GCA GCC GCG TTG CGC GAG TGC GCC GAC GCG      3938
Asp Thr Ser Pro Val Phe Ala Ala Ala Leu Arg Glu Cys Ala Asp Ala
1050            1055            1060            1065

CTC GAA CCG CAT CTG GAC TTC GAG GTG ATC CCG TTC CTG CGC GCG AA      3986
Leu Glu Pro His Leu Asp Phe Glu Val Ile Pro Phe Leu Arg Ala Glu
    1070            1075            1080

GCC GCG AGG CGG GAG CAG GAC GCG GCG CTG TCG ACC GAG CGC GTG GAC      4034
Ala Ala Arg Arg Glu Gln Asp Ala Ala Leu Ser Thr Glu Arg Val Asp
    1085            1090            1095

GTG GTG CAG CCC GTG ATG TTC GCG GTC ATG GTC TCG CTG GCG TCG ATG      4082
Val Val Gln Pro Val Met Phe Ala Val Met Val Ser Leu Ala Ser Met
    1100            1105            1110

TGG CGA GCC CAC GGC GTC GAG CCG GCC GCG GTC ATC GGG CAC TCC CAG      4130
Trp Arg Ala His Gly Val Glu Pro Ala Ala Val Ile Gly His Ser Gln
    1115            1120            1125

GGC GAG ATC GCC GCC GCG TGC GTC GCG GGC GCG CTC TCG CTG GAC GAC      4178
Gly Glu Ile Ala Ala Ala Cys Val Ala Gly Ala Leu Ser Leu Asp Asp
1130            1135            1140            1145

GCC GCG CGC GTG GTC GCG CTG CGC AGC CGC GTC ATC GCC ACC ATG CCC      4226
Ala Ala Arg Val Val Ala Leu Arg Ser Arg Val Ile Ala Thr Met Pro
    1150            1155            1160

GGG AAC AAG GGC ATG GCC TCG ATC GCC GCT CCG GCC GGC GAA GTC CGC      4274
Gly Asn Lys Gly Met Ala Ser Ile Ala Ala Pro Ala Gly Glu Val Arg
    1165            1170            1175

GCG CGA ATC GGT GAC CGC GTC GAG ATC GCC GCC GTC AAC GGT CCG CGC      4322
Ala Arg Ile Gly Asp Arg Val Glu Ile Ala Ala Val Asn Gly Pro Arg
    1180            1185            1190

TCG GTG GTG GTC GCC GGC GAC AGC GAC GAA CTG GAC CGG CTG GTC GCT      4370
Ser Val Val Val Ala Gly Asp Ser Asp Glu Leu Asp Arg Leu Val Ala
    1195            1200            1205

TCC TGC ACC ACC GAG TGC ATC CGC GCC AAG CGG CTG GCC GTG GAC TAC      4418
Ser Cys Thr Thr Glu Cys Ile Arg Ala Lys Arg Leu Ala Val Asp Tyr
1210            1215            1220            1225

GCG TCG CAC TCC TCG CAC GTC GAG ACG ATC CGA GAC GCA CTG CAC GCC      4466
Ala Ser His Ser Ser His Val Glu Thr Ile Arg Asp Ala Leu His Ala
            1230            1235            1240

GAG CTG GGA GAG GAC TTC CAC CCG CTG CCG GGG TTC GTG CCC TTC TTC      4514
Glu Leu Gly Glu Asp Phe His Pro Leu Pro Gly Phe Val Pro Phe Phe
            1245            1250            1255

TCC ACC GTC ACC GGG CGC TGG ACG CAG CCG GAC GAG CTC GAC GCC GGG      4562
Ser Thr Val Thr Gly Arg Trp Thr Gln Pro Asp Glu Leu Asp Ala Gly
            1260            1265            1270

TAC TGG TAC CGG AAC CTG CGC CGC ACC GTG CGG TTC GCG GAC GCC GTC      4610
Tyr Trp Tyr Arg Asn Leu Arg Arg Thr Val Arg Phe Ala Asp Ala Val
1275            1280            1285
```

```
CGT GCG CTC GCC GAG CAG GGA TAT CGC ACG TTC CTG GAG GTC AGC GCG    4658
Arg Ala Leu Ala Glu Gln Gly Tyr Arg Thr Phe Leu Glu Val Ser Ala
1290                1295                1300                1305

CAC CCG ATC CTC ACC GCC GCG ATC GAG GAG ATC GGC GAC GGA TCG GGC    4706
His Pro Ile Leu Thr Ala Ala Ile Glu Glu Ile Gly Asp Gly Ser Gly
            1310                1315                1320

GCC GAC CTC TCC GCC ATC CAT TCG CTG CGC CGC GGT GAC GGC AGC CTC    4754
Ala Asp Leu Ser Ala Ile His Ser Leu Arg Arg Gly Asp Gly Ser Leu
1325                1330                1335

GCG GAC TTC GGC GAA GCG CTC TCC CGC GCG TTC GCC GCC GGT GTC GCG    4802
Ala Asp Phe Gly Glu Ala Leu Ser Arg Ala Phe Ala Ala Gly Val Ala
    1340                1345                1350

GTG GAC TGG GAG TCG GTG CAC CTG GGC ACC GGA GCA CGC CGG GTG CCC    4850
Val Asp Trp Glu Ser Val His Leu Gly Thr Gly Ala Arg Arg Val Pro
1355                1360                1365

TTG CCC ACC TAC CCG TTC CAG CGC GAG CGC GTC TGG CTC GAA CCG AAG    4898
Leu Pro Thr Tyr Pro Phe Gln Arg Glu Arg Val Trp Leu Glu Pro Lys
1370                1375                1380                1385

CCG GTG GCG CGC CGG TCC ACC GAG GTC GAC GAG GTT TCC GCG CTG CGC    4946
Pro Val Ala Arg Arg Ser Thr Glu Val Asp Glu Val Ser Ala Leu Arg
                1390                1395                1400

TAC CGC ATC GAG TGG CGG CCC ACC GGT GCC GGT GAA CCC GCC CGG CTC    4994
Tyr Arg Ile Glu Trp Arg Pro Thr Gly Ala Gly Glu Pro Ala Arg Leu
            1405                1410                1415

GAC GGC ACC TGG CTG GTG GCG AAG TAC GCC GGA ACC GCG GAC GAG ACG    5042
Asp Gly Thr Trp Leu Val Ala Lys Tyr Ala Gly Thr Ala Asp Glu Thr
1420                1425                1430

AGC ACC GCG GCT CGG GAG GCC CTG GAG TCG GCC GGG GCG CGG GTC CGC    5090
Ser Thr Ala Ala Arg Glu Ala Leu Glu Ser Ala Gly Ala Arg Val Arg
    1435                1440                1445

GAA CTG GTC GTG GAC GCC CGC TGC GGT CGC GAC GAA CTC GCG GAG CGG    5138
Glu Leu Val Val Asp Ala Arg Cys Gly Arg Asp Glu Leu Ala Glu Arg
1450                1455                1460                1465

CTT CGT TCG GTC GGC GAG GTG GCA GGA GTG CTG TCC CTG CTC GCG GTG    5186
Leu Arg Ser Val Gly Glu Val Ala Gly Val Leu Ser Leu Leu Ala Val
                1470                1475                1480

GAC GAA GCG GAG CCG GAG GAG GCG CCG CTC GCG CTG GCT TCG CTG GCG    5234
Asp Glu Ala Glu Pro Glu Glu Ala Pro Leu Ala Leu Ala Ser Leu Ala
            1485                1490                1495

GAC ACG CTC AGC CTC GTG CAG GCG ATG GTG TCG GCC GAA CTC GGA TGT    5282
Asp Thr Leu Ser Leu Val Gln Ala Met Val Ser Ala Glu Leu Gly Cys
1500                1505                1510

CCG CTG TGG ACG GTG ACG GAA AGC GCC GTC GCG ACG GGG CCG TTC GAA    5330
Pro Leu Trp Thr Val Thr Glu Ser Ala Val Ala Thr Gly Pro Phe Glu
    1515                1520                1525

CGC GTC CGC AAC GCC GCC CAC GGC GCC CTG TGG GGC GTC GGG CGG GTC    5378
Arg Val Arg Asn Ala Ala His Gly Ala Leu Trp Gly Val Gly Arg Val
1530                1535                1540                1545

ATC GCG CTG GAG AAC CCC GCC GTG TGG GGC GGC CTG GTC GAC GTG CCC    5426
Ile Ala Leu Glu Asn Pro Ala Val Trp Gly Gly Leu Val Asp Val Pro
                1550                1555                1560

GCG GGG TCG GTC GCC GAG CTG GCC CGG CAC CTC GCG GCG GTC GTG TCC    5474
Ala Gly Ser Val Ala Glu Leu Ala Arg His Leu Ala Ala Val Val Ser
            1565                1570                1575

GGC GGC GCC GGT GAG GAC CAG CTC GCG CTG CGC GCC GAC GGG GTG TAC    5522
Gly Gly Ala Gly Glu Asp Gln Leu Ala Leu Arg Ala Asp Gly Val Tyr
1580                1585                1590

GGA CGC CGG TGG GTG CGC GCG GCG GCC CCG GCG ACC GAT GAC GAG TGG    5570
Gly Arg Arg Trp Val Arg Ala Ala Ala Pro Ala Thr Asp Asp Glu Trp
    1595                1600                1605
```

```
AAA CCC ACC GGA ACC GTG CTG GTC ACC GGT GGC ACG GGC GGT GTC GGC     5618
Lys Pro Thr Gly Thr Val Leu Val Thr Gly Gly Thr Gly Gly Val Gly
1610            1615                1620                1625

GGG CAG ATC GCG CGC TGG CTC GCC CGG CGG GGC GCG CCC CAC CTG CTG     5666
Gly Gln Ile Ala Arg Trp Leu Ala Arg Arg Gly Ala Pro His Leu Leu
        1630                1635                1640

CTG GTG AGC CGC AGC GGG CCG GAC GCG GAC GGC GCC GGC GAA CTG GTC     5714
Leu Val Ser Arg Ser Gly Pro Asp Ala Asp Gly Ala Gly Glu Leu Val
            1645                1650                1655

GCC GAG CTC GAG GCG CTG GGC GCC CGG ACG ACC GTC GCG GCC TGC GAC     5762
Ala Glu Leu Glu Ala Leu Gly Ala Arg Thr Thr Val Ala Ala Cys Asp
                1660                1665                1670

GTG ACC GAC CGC GAG TCG GTT CGC GAG CTG CTC GGC GGC ATC GGT GAC     5810
Val Thr Asp Arg Glu Ser Val Arg Glu Leu Leu Gly Gly Ile Gly Asp
                    1675                1680                1685

GAC GTC CCG CTC TCG GCG GTG TTC CAC GCC GCC GCC ACG CTC GAC GAC     5858
Asp Val Pro Leu Ser Ala Val Phe His Ala Ala Ala Thr Leu Asp Asp
1690                1695                1700                1705

GGC ACC GTG GAC ACC CTC ACC GGC GAG CGC ATC GAG CGG GCA AGT CGC     5906
Gly Thr Val Asp Thr Leu Thr Gly Glu Arg Ile Glu Arg Ala Ser Arg
        1710                1715                1720

GCC AAG GTG CTC GGC GCG CGC AAC CTG CAC GAG CTG ACG CGC GAG CTG     5954
Ala Lys Val Leu Gly Ala Arg Asn Leu His Glu Leu Thr Arg Glu Leu
            1725                1730                1735

GAC CTG ACC GCC TTC GTG CTG TTC TCG TCC TTC GCC TCG GCC TTC GGC     6002
Asp Leu Thr Ala Phe Val Leu Phe Ser Ser Phe Ala Ser Ala Phe Gly
                1740                1745                1750

GCC CCC GGG CTC GGC GGC TAC GCG CCC GGC AAC GCC TAC CTC GAC GGC     6050
Ala Pro Gly Leu Gly Gly Tyr Ala Pro Gly Asn Ala Tyr Leu Asp Gly
                    1755                1760                1765

CTC GCC CAG CAG CGG CGG AGC GAC GGA CTC CCC GCG ACC GCC GTG GCG     6098
Leu Ala Gln Gln Arg Arg Ser Asp Gly Leu Pro Ala Thr Ala Val Ala
1770                1775                1780                1785

TGG GGG ACG TGG GCG GGC AGC GGG ATG GCC GAA GGC GCG GTG GCC GAC     6146
Trp Gly Thr Trp Ala Gly Ser Gly Met Ala Glu Gly Ala Val Ala Asp
        1790                1795                1800

CGC TTC CGC AGG CAC GGC GTC ATC GAG ATG CCT CCC GAG ACG GCC TGC     6194
Arg Phe Arg Arg His Gly Val Ile Glu Met Pro Pro Glu Thr Ala Cys
            1805                1810                1815

CGG GCG TTG CAG AAC GCG CTG GAC CGC GCC GAG GTC TGC CCG ATC GTC     6242
Arg Ala Leu Gln Asn Ala Leu Asp Arg Ala Glu Val Cys Pro Ile Val
                1820                1825                1830

ATC GAC GTC AGG TGG GAC CGG TTC CTG CTC GCC TAC ACC GCG CAG CGC     6290
Ile Asp Val Arg Trp Asp Arg Phe Leu Leu Ala Tyr Thr Ala Gln Arg
                    1835                1840                1845

CCG ACC AGG CTC TTC GAC GAG ATC GAC GAC GCG CGG CGG GCT GCG CCG     6338
Pro Thr Arg Leu Phe Asp Glu Ile Asp Asp Ala Arg Arg Ala Ala Pro
1850                1855                1860                1865

CAG GCG CCG GCC GAA CCG CGG GTG GGC GCG CTG GCG TCG CTG CCC GCG     6386
Gln Ala Pro Ala Glu Pro Arg Val Gly Ala Leu Ala Ser Leu Pro Ala
        1870                1875                1880

CCG GAG CGC GAG GAA GCG CTG TTC GAG CTC GTG CGC TCG CAC GCG GCC     6434
Pro Glu Arg Glu Glu Ala Leu Phe Glu Leu Val Arg Ser His Ala Ala
            1885                1890                1895

GCC GTC CTC GGC CAC GCC TCG GCC GAG CGG GTG CCC GCC GAC CAG GCC     6482
Ala Val Leu Gly His Ala Ser Ala Glu Arg Val Pro Ala Asp Gln Ala
                1900                1905                1910

TTC GCG GAA CTC GGC GTC GAC TCG CTG TCG GCG CTT GAG CTG CGC AAC     6530
Phe Ala Glu Leu Gly Val Asp Ser Leu Ser Ala Leu Glu Leu Arg Asn
                    1915                1920                1925
```

```
CGG CTC GGC GCC GCG ACC GGT GTC CGC CTG CCG ACG ACG ACC GTC TTC      6578
Arg Leu Gly Ala Ala Thr Gly Val Arg Leu Pro Thr Thr Thr Val Phe
1930                1935                1940                1945

GAC CAC CCC GAC GTG CGG ACG CTG GCG GCG CAC CTG GCC GCC GAA CTC      6626
Asp His Pro Asp Val Arg Thr Leu Ala Ala His Leu Ala Ala Glu Leu
        1950                1955                1960

GGC GGT GCG ACC GGA GCC GAG CAG GCG GCA CCG GCG ACC ACG GCC CCC      6674
Gly Gly Ala Thr Gly Ala Glu Gln Ala Ala Pro Ala Thr Thr Ala Pro
    1965                1970                1975

GTC GAC GAG CCG ATC GCG ATC GTC GGC ATG GCG TGC CGG CTG CCC GGG      6722
Val Asp Glu Pro Ile Ala Ile Val Gly Met Ala Cys Arg Leu Pro Gly
1980                1985                1990

GAG GTC GAC TCC CCG GAG CGG CTG TGG GAG CTG ATC ACC TCG GGA CGC      6770
Glu Val Asp Ser Pro Glu Arg Leu Trp Glu Leu Ile Thr Ser Gly Arg
    1995                2000                2005

GAC TCC GCG GCG GAG GTC CCC GAT GAC CGG GGC TGG GTC CCC GAC GAG      6818
Asp Ser Ala Ala Glu Val Pro Asp Asp Arg Gly Trp Val Pro Asp Glu
2010                2015                2020                2025

CTG ATG GCC TCC GAC GCG GCG GGA ACC CGC GCC CAC GGC AAC TTC ATG      6866
Leu Met Ala Ser Asp Ala Ala Gly Thr Arg Ala His Gly Asn Phe Met
        2030                2035                2040

GCG GGC GCC GGT GAC TTC GAC GCG GCG TTC TTC GGG ATC TCG CCG CGC      6914
Ala Gly Ala Gly Asp Phe Asp Ala Ala Phe Phe Gly Ile Ser Pro Arg
    2045                2050                2055

GAG GCG CTG GCG ATG GAC CCG CAG CAG CGC CAG GCG CTG GAG ACG ACG      6962
Glu Ala Leu Ala Met Asp Pro Gln Gln Arg Gln Ala Leu Glu Thr Thr
2060                2065                2070

TGG GAG GCG CTG GAA AGC GCG GGC ATC CCA CCG GAG ACG TTG CGC GGC      7010
Trp Glu Ala Leu Glu Ser Ala Gly Ile Pro Pro Glu Thr Leu Arg Gly
    2075                2080                2085

AGC GAC ACC GGC GTG TTC GTC GGC ATG TCC CAC CAG GGC TAC GCG ACC      7058
Ser Asp Thr Gly Val Phe Val Gly Met Ser His Gln Gly Tyr Ala Thr
2090                2095                2100                2105

GGG CGT CCG CGC CCG GAG GAC GGC GTC GAC GGG TAC CTG CTC ACC GGC      7106
Gly Arg Pro Arg Pro Glu Asp Gly Val Asp Gly Tyr Leu Leu Thr Gly
        2110                2115                2120

AAC ACC GCG AGC GTC GCG TCG GGA CGC ATC GCC TAC GTG CTG GGG CTG      7154
Asn Thr Ala Ser Val Ala Ser Gly Arg Ile Ala Tyr Val Leu Gly Leu
    2125                2130                2135

GAA GGT CCC GCG CTG ACG GTG GAC ACG GCG TGT TCG TCG TCG TTG GTG      7202
Glu Gly Pro Ala Leu Thr Val Asp Thr Ala Cys Ser Ser Ser Leu Val
2140                2145                2150

GCG TTG CAC ACG GCG TGT GGG TCG TTG CGT GAC GGT GAC TGC GGT CTT      7250
Ala Leu His Thr Ala Cys Gly Ser Leu Arg Asp Gly Asp Cys Gly Leu
        2155                2160                2165

GCG GTG GCC GGT GGT GTG TCG GTG ATG GCG GGT CCG GAG GTG TTC ACC      7298
Ala Val Ala Gly Gly Val Ser Val Met Ala Gly Pro Glu Val Phe Thr
2170                2175                2180                2185

GAG TTC TCC CGC CAG GGC GCG CTC TCG CCG GAC GGC CGG TGC AAG CCC      7346
Glu Phe Ser Arg Gln Gly Ala Leu Ser Pro Asp Gly Arg Cys Lys Pro
    2190                2195                2200

TTC TCG GAC GAG GCC GAC GGA TTC GGT CTC GGG GAG GGT TCG GCG TTC      7394
Phe Ser Asp Glu Ala Asp Gly Phe Gly Leu Gly Glu Gly Ser Ala Phe
        2205                2210                2215

GTC GTG CTC CAG CGG TTG TCC GAC GCC AGG CGG GAG GGC CGC CGC GTG      7442
Val Val Leu Gln Arg Leu Ser Asp Ala Arg Arg Glu Gly Arg Arg Val
    2220                2225                2230

CTC GGC GTG GTG GCC GGG TCC GCG GTG AAC CAG GAC GGC GCG AGC AAC      7490
Leu Gly Val Val Ala Gly Ser Ala Val Asn Gln Asp Gly Ala Ser Asn
    2235                2240                2245
```

```
GGG  CTC  TCC  GCT  CCG  AGC  GGC  GTC  GCG  CAG  CAG  CGG  GTC  ATC  CGC  CGG       7538
Gly  Leu  Ser  Ala  Pro  Ser  Gly  Val  Ala  Gln  Gln  Arg  Val  Ile  Arg  Arg
2250                     2255                     2260                     2265

GCG  TGG  GCG  CGT  GCG  GGG  ATC  ACG  GGC  GCG  GAT  GTG  GCC  GTG  GTG  GAG       7586
Ala  Trp  Ala  Arg  Ala  Gly  Ile  Thr  Gly  Ala  Asp  Val  Ala  Val  Val  Glu
                    2270                     2275                     2280

GCG  CAT  GGG  ACC  GGT  ACG  CGG  CTG  GGC  GAT  CCG  GTG  GAG  GCG  TCG  GCG       7634
Ala  His  Gly  Thr  Gly  Thr  Arg  Leu  Gly  Asp  Pro  Val  Glu  Ala  Ser  Ala
          2285                     2290                     2295

TTG  CTG  GCT  ACT  TAC  GGC  AAG  TCG  CGC  GGG  TCG  TCG  GGC  CCG  GTG  CTG       7682
Leu  Leu  Ala  Thr  Tyr  Gly  Lys  Ser  Arg  Gly  Ser  Ser  Gly  Pro  Val  Leu
               2300                     2305                     2310

CTG  GGT  TCG  GTG  AAG  TCG  AAC  ATC  GGT  CAC  GCG  CAG  GCG  GCC  GCG  GGT       7730
Leu  Gly  Ser  Val  Lys  Ser  Asn  Ile  Gly  His  Ala  Gln  Ala  Ala  Ala  Gly
          2315                     2320                     2325

GTC  GCG  GGC  GTG  ATC  AAG  GTG  CTG  CTC  GGC  CTG  GAA  CGC  GGT  GTG  GTG       7778
Val  Ala  Gly  Val  Ile  Lys  Val  Leu  Leu  Gly  Leu  Glu  Arg  Gly  Val  Val
2330                     2335                     2340                     2345

CCC  CCG  ATG  CTG  TGC  CGG  GGC  GAG  AGG  TCG  GGC  CTC  ATC  GAC  TGG  TCC       7826
Pro  Pro  Met  Leu  Cys  Arg  Gly  Glu  Arg  Ser  Gly  Leu  Ile  Asp  Trp  Ser
                    2350                     2355                     2360

TCC  GGC  GAG  ATC  GAG  CTC  GCA  GAC  GGC  GTG  CGG  GAG  TGG  TCG  CCC  GCC       7874
Ser  Gly  Glu  Ile  Glu  Leu  Ala  Asp  Gly  Val  Arg  Glu  Trp  Ser  Pro  Ala
               2365                     2370                     2375

GCG  GAC  GGG  GTG  CGC  CGG  GCA  GGT  GTG  TCG  GCG  TTC  GGG  GTG  AGC  GGG       7922
Ala  Asp  Gly  Val  Arg  Arg  Ala  Gly  Val  Ser  Ala  Phe  Gly  Val  Ser  Gly
          2380                     2385                     2390

ACG  AAC  GCG  CAC  GTG  ATC  ATC  GCC  GAG  CCG  CCG  GAA  CCG  GAG  CCC  GTG       7970
Thr  Asn  Ala  His  Val  Ile  Ile  Ala  Glu  Pro  Pro  Glu  Pro  Glu  Pro  Val
2395                     2400                     2405

CCG  CAA  CCG  CGA  CGC  ATG  CTG  CCC  GCG  ACC  GGG  GTG  GTG  CCG  GTC  GTG       8018
Pro  Gln  Pro  Arg  Arg  Met  Leu  Pro  Ala  Thr  Gly  Val  Val  Pro  Val  Val
2410                     2415                     2420                     2425

CTG  TCG  GCC  AGG  ACC  GGG  GCG  GCG  TTG  CGG  GCG  CAG  GCC  GGC  AGG  CTC       8066
Leu  Ser  Ala  Arg  Thr  Gly  Ala  Ala  Leu  Arg  Ala  Gln  Ala  Gly  Arg  Leu
                    2430                     2435                     2440

GCC  GAC  CAC  CTC  GCC  GCG  CAT  CCC  GGG  ATC  GCA  CCG  GCC  GAC  GTG  AGC       8114
Ala  Asp  His  Leu  Ala  Ala  His  Pro  Gly  Ile  Ala  Pro  Ala  Asp  Val  Ser
               2445                     2450                     2455

TGG  ACG  ATG  GCG  CGG  GCC  CGC  CAG  CAC  TTC  GAG  GAG  CGG  GCC  GCG  GTG       8162
Trp  Thr  Met  Ala  Arg  Ala  Arg  Gln  His  Phe  Glu  Glu  Arg  Ala  Ala  Val
          2460                     2465                     2470

CTC  GCC  GCC  GAC  ACC  GCC  GAG  GCC  GTG  CAC  CGG  TTG  CGG  GCG  GTG  GCC       8210
Leu  Ala  Ala  Asp  Thr  Ala  Glu  Ala  Val  His  Arg  Leu  Arg  Ala  Val  Ala
2475                     2480                     2485

GAC  GGC  GCG  GTG  GTT  CCC  GGT  GTT  GTC  ACC  GGC  AGT  GCC  TCC  GAC  GGT       8258
Asp  Gly  Ala  Val  Val  Pro  Gly  Val  Val  Thr  Gly  Ser  Ala  Ser  Asp  Gly
2490                     2495                     2500                     2505

GGT  TCA  GTG  TTC  GTC  TTC  CCT  GGG  CAG  GGT  GCC  CAG  TGG  GAA  GGC  ATG       8306
Gly  Ser  Val  Phe  Val  Phe  Pro  Gly  Gln  Gly  Ala  Gln  Trp  Glu  Gly  Met
                    2510                     2515                     2520

GCG  CGG  GAG  TTG  TTG  CCG  GTT  CCC  GTC  TTC  GCC  GAG  TCG  ATC  GCC  GAG       8354
Ala  Arg  Glu  Leu  Leu  Pro  Val  Pro  Val  Phe  Ala  Glu  Ser  Ile  Ala  Glu
          2525                     2530                     2535

TGC  GAT  GCG  GTG  TTG  TCG  GAG  GTG  GCC  GGA  TTC  TCG  GTG  TCC  GAG  GTG       8402
Cys  Asp  Ala  Val  Leu  Ser  Glu  Val  Ala  Gly  Phe  Ser  Val  Ser  Glu  Val
               2540                     2545                     2550

CTG  GAG  CCA  CGT  CCG  GAC  GCG  CCG  TCG  CTG  GAG  CGG  GTC  GAC  GTG  GTG       8450
Leu  Glu  Pro  Arg  Pro  Asp  Ala  Pro  Ser  Leu  Glu  Arg  Val  Asp  Val  Val
2555                     2560                     2565
```

```
CAG CCG GTG CTG TTC GCG GTG ATG GTG TCG CTG GCG CGG TTG TGG CGT    8498
Gln Pro Val Leu Phe Ala Val Met Val Ser Leu Ala Arg Leu Trp Arg
2570                2575                2580                2585

GCC TGC GGT GCC GTT CCT TCG GCC GTC ATA GGG CAC TCG CAG GGT GAG    8546
Ala Cys Gly Ala Val Pro Ser Ala Val Ile Gly His Ser Gln Gly Glu
            2590                2595                2600

ATC GCC GCC GCG GTG GTG GCG GGA GCG TTG TCG CTG GAG GAC GGC ATG    8594
Ile Ala Ala Ala Val Val Ala Gly Ala Leu Ser Leu Glu Asp Gly Met
        2605                2610                2615

CGC GTC GTC GCC CGC CGG TCG AGG GCG GTG CGT GCG GTC GCG GGC CGG    8642
Arg Val Val Ala Arg Arg Ser Arg Ala Val Arg Ala Val Ala Gly Arg
    2620                2625                2630

GGG AGC ATG CTC TCG GTG CGC GGC GGC CGC TCC GAC GTC GAG AAG CTG    8690
Gly Ser Met Leu Ser Val Arg Gly Gly Arg Ser Asp Val Glu Lys Leu
2635                2640                2645

CTC GCC GAC GAC AGC TGG ACC GGC AGG CTG GAG GTC GCC GCG GTC AAC    8738
Leu Ala Asp Asp Ser Trp Thr Gly Arg Leu Glu Val Ala Ala Val Asn
2650                2655                2660                2665

GGC CCC GAC GCC GTG GTG GTG GCC GGT GAC GCC CAG GCG GCG CGC GAG    8786
Gly Pro Asp Ala Val Val Val Ala Gly Asp Ala Gln Ala Ala Arg Glu
        2670                2675                2680

TTC CTG GAG TAC TGC GAG GGC GTG GGC ATC CGC GCC CGC GCG ATC CCG    8834
Phe Leu Glu Tyr Cys Glu Gly Val Gly Ile Arg Ala Arg Ala Ile Pro
            2685                2690                2695

GTG GAC TAC GCC TCG CAC ACC GCG CAC GTC GAG CCC GTG CGC GAC GAA    8882
Val Asp Tyr Ala Ser His Thr Ala His Val Glu Pro Val Arg Asp Glu
2700                2705                2710

CTG GTC CAG GCG CTG GCC GGG ATC ACC CCG CGA CGG GCC GAG GTG CCG    8930
Leu Val Gln Ala Leu Ala Gly Ile Thr Pro Arg Arg Ala Glu Val Pro
2715                2720                2725

TTC TTC TCC ACC CTG ACC GGC GAC TTC CTC GAC GGC ACC GAG CTG GAC    8978
Phe Phe Ser Thr Leu Thr Gly Asp Phe Leu Asp Gly Thr Glu Leu Asp
2730                2735                2740                2745

GCG GGC TAC TGG TAC CGC AAC CTG CGT CAC CCG GTG GAG TTC CAC TCC    9026
Ala Gly Tyr Trp Tyr Arg Asn Leu Arg His Pro Val Glu Phe His Ser
        2750                2755                2760

GCC GTG CAG GCG CTG ACC GAC CAG GGA TAC GCG ACG TTC ATC GAG GTC    9074
Ala Val Gln Ala Leu Thr Asp Gln Gly Tyr Ala Thr Phe Ile Glu Val
            2765                2770                2775

AGC CCG CAC CCG GTG CTG GCG TCG AGC GTC CAG GAG ACC CTC GAC GAC    9122
Ser Pro His Pro Val Leu Ala Ser Ser Val Gln Glu Thr Leu Asp Asp
        2780                2785                2790

GCC GAG TCG GAC GCG GCG GTG CTC GGG ACG CTG GAA CGC GAC GCG GGC    9170
Ala Glu Ser Asp Ala Ala Val Leu Gly Thr Leu Glu Arg Asp Ala Gly
    2795                2800                2805

GAC GCC GAC CGC TTC CTC ACG GCA CTC GCC GAC GCG CAC ACG CGC GGT    9218
Asp Ala Asp Arg Phe Leu Thr Ala Leu Ala Asp Ala His Thr Arg Gly
2810                2815                2820                2825

GTC GCG GTC GAC TGG GAA GCG GTG CTC GGC CGG GCC GGA CTG GTC GAC    9266
Val Ala Val Asp Trp Glu Ala Val Leu Gly Arg Ala Gly Leu Val Asp
                2830                2835                2840

CTG CCG GGT TAT CCT TTC CAG GGC AAG CGG TTC TGG CTG CTG CCG GAC    9314
Leu Pro Gly Tyr Pro Phe Gln Gly Lys Arg Phe Trp Leu Leu Pro Asp
            2845                2850                2855

CGC ACC ACC CCT CGT GAC GAG CTC GAC GGC TGG TTC TAC CGG GTC GAC    9362
Arg Thr Thr Pro Arg Asp Glu Leu Asp Gly Trp Phe Tyr Arg Val Asp
        2860                2865                2870

TGG ACC GAG GTG CCG CGC TCC GAA CCT GCC GCG CTG CGC GGC CGT TGG    9410
Trp Thr Glu Val Pro Arg Ser Glu Pro Ala Ala Leu Arg Gly Arg Trp
    2875                2880                2885
```

```
CTC GTG GTG GTG CCC GAG GGG CAC GAG GAG GAC GGC TGG ACC GTC GAG      9458
Leu Val Val Val Pro Glu Gly His Glu Glu Asp Gly Trp Thr Val Glu
2890                2895                2900                2905

GTG CGG TCC GCG CTC GCC GAG GCC GGC GCC GAA CCG GAG GTC ACG CGC      9506
Val Arg Ser Ala Leu Ala Glu Ala Gly Ala Glu Pro Glu Val Thr Arg
        2910                2915                2920

GGC GTC GGC GGG CTG GTC GGT GAC TGC GCG GGC GTG GTG TCG TTG CTC      9554
Gly Val Gly Gly Leu Val Gly Asp Cys Ala Gly Val Val Ser Leu Leu
    2925                2930                2935

GCC CTC GAG GGC GAT GGT GCG GTG CAA ACC CTT GTG CTG GTG CGG GAA      9602
Ala Leu Glu Gly Asp Gly Ala Val Gln Thr Leu Val Leu Val Arg Glu
            2940                2945                2950

CTC GAC GCC GAG GGC ATC GAC GCG CCA CTG TGG ACG GTC ACC TTC GGC      9650
Leu Asp Ala Glu Gly Ile Asp Ala Pro Leu Trp Thr Val Thr Phe Gly
                2955                2960                2965

GCG GTC GAC GCG GGC AGT CCG GTG GCC CGC CCG GAC CAG GCG AAG CTG      9698
Ala Val Asp Ala Gly Ser Pro Val Ala Arg Pro Asp Gln Ala Lys Leu
2970                2975                2980                2985

TGG GGG CTG GGC CAG GTC GCG TCC CTG GAA CGC GGG CCC CGC TGG ACC      9746
Trp Gly Leu Gly Gln Val Ala Ser Leu Glu Arg Gly Pro Arg Trp Thr
        2990                2995                3000

GGC CTC GTC GAC CTG CCG CAC ATG CCG GAC CCG GAA CTG CGA GGC CGT      9794
Gly Leu Val Asp Leu Pro His Met Pro Asp Pro Glu Leu Arg Gly Arg
    3005                3010                3015

CTC ACC GCG GTG CTG GCC GGC TCG GAG GAC CAG GTC GCG GTG CGC GCC      9842
Leu Thr Ala Val Leu Ala Gly Ser Glu Asp Gln Val Ala Val Arg Ala
            3020                3025                3030

GAC GCC GTG CGT GCG CGG CGG CTT TCC CCC GCC CAC GTC ACC GCC ACC      9890
Asp Ala Val Arg Ala Arg Arg Leu Ser Pro Ala His Val Thr Ala Thr
                3035                3040                3045

TCG GAG TAC GCG GTG CCG GGC GGC ACA ATC CTG GTC ACC GGT GGC ACC      9938
Ser Glu Tyr Ala Val Pro Gly Gly Thr Ile Leu Val Thr Gly Gly Thr
3050                3055                3060                3065

GCC GGC CTG GGC GCG GAG GTG GCC CGG TGG CTC GCC GGT CGC GGC GCC      9986
Ala Gly Leu Gly Ala Glu Val Ala Arg Trp Leu Ala Gly Arg Gly Ala
        3070                3075                3080

GAA CAC CTC GCG CTG GTC AGC AGG CGA GGC CCG GAC ACC GAG GGC GTC      10034
Glu His Leu Ala Leu Val Ser Arg Arg Gly Pro Asp Thr Glu Gly Val
    3085                3090                3095

GGC GAC CTG ACC GCC GAG CTG ACC CGG CTC GGC GCG CGG GTG TCG GTG      10082
Gly Asp Leu Thr Ala Glu Leu Thr Arg Leu Gly Ala Arg Val Ser Val
            3100                3105                3110

CAC GCG TGC GAC GTC AGC AGC CGC GAA CCG GTG AGG GAA CTC GTG CAC      10130
His Ala Cys Asp Val Ser Ser Arg Glu Pro Val Arg Glu Leu Val His
                3115                3120                3125

GGC CTG ATC GAG CAG GGC GAC GTC GTC CGC GGT GTG GTG CAC GCG GCG      10178
Gly Leu Ile Glu Gln Gly Asp Val Val Arg Gly Val Val His Ala Ala
3130                3135                3140                3145

GGA CTG CCG CAG CAG GTC GCG ATC AAC GAC ATG GAC GAG GCC GCC TTC      10226
Gly Leu Pro Gln Gln Val Ala Ile Asn Asp Met Asp Glu Ala Ala Phe
        3150                3155                3160

GAC GAG GTG GTC GCG GCC AAG GCC GGG GGC GCG GTG CAC CTG GAC GAG      10274
Asp Glu Val Val Ala Ala Lys Ala Gly Gly Ala Val His Leu Asp Glu
    3165                3170                3175

CTG TGC TCG GAC GCC GAG CTG TTC CTG CTG TTC TCC TCC GGG GCC GGG      10322
Leu Cys Ser Asp Ala Glu Leu Phe Leu Leu Phe Ser Ser Gly Ala Gly
            3180                3185                3190

GTG TGG GGA AGC GCC CGC CAG GGC GCC TAC GCC GCG GGC AAC GCG TTC      10370
Val Trp Gly Ser Ala Arg Gln Gly Ala Tyr Ala Ala Gly Asn Ala Phe
                3195                3200                3205
```

| | |
|---|---:|
| CTG GAC GCC TTC GCC CGG CAC CGC CGG GGC CGC GGC CTG CCC GCC ACG<br>Leu Asp Ala Phe Ala Arg His Arg Arg Gly Arg Gly Leu Pro Ala Thr<br>3210                        3215                          3220                          3225 | 10418 |
| TCG GTG GCG TGG GGG CTG TGG GCG GCG GGC GGC ATG ACC GGC GAC GAG<br>Ser Val Ala Trp Gly Leu Trp Ala Ala Gly Gly Met Thr Gly Asp Glu<br>                       3230                          3235                       3240 | 10466 |
| GAG GCC GTG TCG TTC CTG CGC GAG CGC GGT GTG CGG GCG ATG CCC GTA<br>Glu Ala Val Ser Phe Leu Arg Glu Arg Gly Val Arg Ala Met Pro Val<br>                3245                        3250                      3255 | 10514 |
| CCG CGC GCC CTC GCC GCC CTG GAC AGG GTG CTG GCC TCC GGG GAG ACG<br>Pro Arg Ala Leu Ala Ala Leu Asp Arg Val Leu Ala Ser Gly Glu Thr<br>3260                        3265                         3270 | 10562 |
| GCG GTG GTC GTG ACG GAC GTG GAC TGG CCC GCC TTC GCC GAG TCC TAC<br>Ala Val Val Val Thr Asp Val Asp Trp Pro Ala Phe Ala Glu Ser Tyr<br>3275                        3280                       3285 | 10610 |
| ACC GCC GCC CGG CCC CGG CCG TTG CTC GAC CGC ATC GTC ACG ACC GCG<br>Thr Ala Ala Arg Pro Arg Pro Leu Leu Asp Arg Ile Val Thr Thr Ala<br>3290                        3295                        3300                     3305 | 10658 |
| CCG AGC GAG CGG GCC GGA GAA CCG GAG ACG GAG AGC CTG CGC GAC CGG<br>Pro Ser Glu Arg Ala Gly Glu Pro Glu Thr Glu Ser Leu Arg Asp Arg<br>                       3310                          3315                       3320 | 10706 |
| CTG GCG GGT CTG CCG CGT GCC GAG CGG ACG GCG GAG CTG GTG CGC CTG<br>Leu Ala Gly Leu Pro Arg Ala Glu Arg Thr Ala Glu Leu Val Arg Leu<br>                3325                       3330                      3335 | 10754 |
| GTC CGC ACC AGC ACC GCG ACC GTG CTG GGC CAC GAC GAC CCG AAG GCG<br>Val Arg Thr Ser Thr Ala Thr Val Leu Gly His Asp Asp Pro Lys Ala<br>            3340                       3345                      3350 | 10802 |
| GTG CGC GCG ACC ACG CCG TTC AAG GAG CTC GGG TTC GAC TCG CTG GCG<br>Val Arg Ala Thr Thr Pro Phe Lys Glu Leu Gly Phe Asp Ser Leu Ala<br>3355                        3360                       3365 | 10850 |
| GCC GTC CGG CTG CGC AAC CTG CTC AAC GCG GCC ACC GGG CTC CGC CTG<br>Ala Val Arg Leu Arg Asn Leu Leu Asn Ala Ala Thr Gly Leu Arg Leu<br>3370                        3375                        3380                     3385 | 10898 |
| CCG TCG ACG CTG GTC TTC GAC CAC CCG AAC GCC TCC GCG GTC GCC GGT<br>Pro Ser Thr Leu Val Phe Asp His Pro Asn Ala Ser Ala Val Ala Gly<br>                3390                       3395                      3400 | 10946 |
| TTC CTC GAC GCC GAG CTC GGC ACC GAG GTC CGG GGG GAG GCG CCG TCG<br>Phe Leu Asp Ala Glu Leu Gly Thr Glu Val Arg Gly Glu Ala Pro Ser<br>            3405                       3410                      3415 | 10994 |
| GCC CTC GCC GGG CTG GAC GCG CTG GAA GGC GCC CTG CCC GAG GTG CCC<br>Ala Leu Ala Gly Leu Asp Ala Leu Glu Gly Ala Leu Pro Glu Val Pro<br>        3420                       3425                       3430 | 11042 |
| GCA ACC GAG CGG GAA GAG CTG GTA CAG CGC TTG GAA CGG ATG CTC GCC<br>Ala Thr Glu Arg Glu Glu Leu Val Gln Arg Leu Glu Arg Met Leu Ala<br>        3435                       3440                       3445 | 11090 |
| GCG CTA CGC CCG GTC GCC CAG GCC GCC GAC GCC TCC GGG ACC GGC GCC<br>Ala Leu Arg Pro Val Ala Gln Ala Ala Asp Ala Ser Gly Thr Gly Ala<br>3450                        3455                        3460                     3465 | 11138 |
| AAC CCG TCC GGC GAC GAC CTG GGC GAG GCG GGC GTG GAC GAA CTG CTC<br>Asn Pro Ser Gly Asp Asp Leu Gly Glu Ala Gly Val Asp Glu Leu Leu<br>                3470                       3475                      3480 | 11186 |
| GAA GCA CTC GGC CGG GAG CTC GAC GGC GAT TGA<br>Glu Ala Leu Gly Arg Glu Leu Asp Gly Asp<br>            3485                       3490 | 11219 |

( 2 ) INFORMATION FOR SEQ ID NO:2:

( i ) SEQUENCE CHARACTERISTICS:
        ( A ) LENGTH: 3491 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Val  Ser  Gly  Pro  Arg  Ser  Arg  Thr  Thr  Ser  Arg  Arg  Thr  Pro  Val  Arg
 1              5                        10                       15

Ile  Gly  Ala  Val  Val  Ala  Ser  Ser  Thr  Ser  Glu  Leu  Leu  Asp  Gly
              20                       25                       30

Leu  Ala  Ala  Val  Ala  Asp  Gly  Arg  Pro  His  Ala  Ser  Val  Arg  Gly
              35                       40                       45

Val  Ala  Arg  Pro  Ser  Ala  Pro  Val  Val  Phe  Val  Phe  Pro  Gly  Gln  Gly
         50                       55                       60

Ala  Gln  Trp  Ala  Gly  Met  Ala  Gly  Glu  Leu  Leu  Gly  Glu  Ser  Arg  Val
 65                       70                       75                       80

Phe  Ala  Ala  Ala  Met  Asp  Ala  Cys  Ala  Arg  Ala  Phe  Glu  Pro  Val  Thr
                   85                       90                       95

Asp  Trp  Thr  Leu  Ala  Gln  Val  Leu  Asp  Ser  Pro  Glu  Gln  Ser  Arg  Arg
              100                      105                      110

Val  Glu  Val  Val  Gln  Pro  Ala  Leu  Phe  Ala  Val  Gln  Thr  Ser  Leu  Ala
              115                      120                      125

Ala  Leu  Trp  Arg  Ser  Phe  Gly  Val  Thr  Pro  Asp  Ala  Val  Val  Gly  His
         130                      135                      140

Ser  Ile  Gly  Glu  Leu  Ala  Ala  His  Val  Cys  Gly  Ala  Ala  Gly  Ala
145                      150                      155                     160

Ala  Asp  Ala  Ala  Arg  Ala  Ala  Ala  Leu  Trp  Ser  Arg  Glu  Met  Ile  Pro
              165                      170                      175

Leu  Val  Gly  Asn  Gly  Asp  Met  Ala  Ala  Val  Ala  Leu  Ser  Ala  Asp  Glu
              180                      185                      190

Ile  Glu  Pro  Arg  Ile  Ala  Arg  Trp  Asp  Asp  Val  Val  Leu  Ala  Gly
              195                      200                      205

Val  Asn  Gly  Pro  Arg  Ser  Val  Leu  Leu  Thr  Gly  Ser  Pro  Glu  Pro  Val
         210                      215                      220

Ala  Arg  Arg  Val  Gln  Glu  Leu  Ser  Ala  Glu  Gly  Val  Arg  Ala  Gln  Val
225                      230                      235                     240

Ile  Asn  Val  Ser  Met  Ala  Ala  His  Ser  Ala  Gln  Val  Asp  Asp  Ile  Ala
                   245                      250                      255

Glu  Gly  Met  Arg  Ser  Ala  Leu  Ala  Trp  Phe  Ala  Pro  Gly  Gly  Ser  Glu
              260                      265                      270

Val  Pro  Phe  Tyr  Ala  Ser  Leu  Thr  Gly  Gly  Ala  Val  Asp  Thr  Arg  Glu
              275                      280                      285

Leu  Val  Ala  Asp  Tyr  Trp  Arg  Arg  Ser  Phe  Arg  Leu  Pro  Val  Arg  Phe
         290                      295                      300

Asp  Glu  Ala  Ile  Arg  Ser  Ala  Leu  Glu  Val  Gly  Pro  Gly  Thr  Phe  Val
305                      310                      315                     320

Glu  Ala  Ser  Pro  His  Pro  Val  Leu  Ala  Ala  Ala  Leu  Gln  Gln  Thr  Leu
                   325                      330                      335

Asp  Ala  Glu  Gly  Ser  Ser  Ala  Ala  Val  Val  Pro  Thr  Leu  Gln  Arg  Gly
              340                      345                      350

Gln  Gly  Gly  Met  Arg  Arg  Phe  Leu  Leu  Ala  Ala  Ala  Gln  Ala  Phe  Thr
              355                      360                      365

Gly  Gly  Val  Ala  Val  Asp  Trp  Thr  Ala  Ala  Tyr  Asp  Asp  Val  Gly  Pro
         370                      375                      380

Asn  Pro  Ala  Leu  Cys  Arg  Ser  Ser  Arg  Arg  Pro  Arg  Arg  Lys  Thr  Ser
385                      390                      395                     400
```

-continued

| | | | | | | | | | | | | | | |
|---|---|---|---|---|---|---|---|---|---|---|---|---|---|---|
| Arg | Pro | Ser | Pro | Ala | Ser | Thr | Gly | Thr | Arg | His | Arg | Thr | Cys | Cys | Glu |
| | | | | 405 | | | | 410 | | | | | | 415 |
| Arg | Leu | Leu | Ala | Val | Val | Asn | Gly | Glu | Thr | Ala | Ala | Leu | Ala | Gly | Arg |
| | | | 420 | | | | 425 | | | | | 430 | | | |
| Glu | Ala | Asp | Ala | Glu | Ala | Thr | Phe | Arg | Glu | Leu | Gly | Leu | Asp | Ser | Val |
| | | 435 | | | | | 440 | | | | | 445 | | | |
| Leu | Ala | Ala | Gln | Leu | Arg | Ala | Lys | Val | Ser | Ala | Ala | Ile | Gly | Arg | Glu |
| | | 450 | | | | 455 | | | | 460 | | | | | |
| Val | Asn | Ile | Ala | Leu | Leu | Tyr | Asp | His | Pro | Thr | Pro | Arg | Ala | Leu | Ala |
| 465 | | | | | 470 | | | | 475 | | | | | | 480 |
| Glu | Ala | Leu | Ala | Ala | Gly | Thr | Glu | Val | Ala | Gln | Arg | Glu | Thr | Arg | Ala |
| | | | | 485 | | | | 490 | | | | | 495 | | |
| Arg | Thr | Asn | Glu | Ala | Ala | Pro | Gly | Glu | Pro | Val | Ala | Val | Val | Ala | Met |
| | | | 500 | | | | 505 | | | | | 510 | | | |
| Ala | Cys | Arg | Leu | Pro | Gly | Gly | Val | Ser | Thr | Pro | Glu | Glu | Phe | Trp | Glu |
| | | 515 | | | | 520 | | | | | 525 | | | | |
| Leu | Leu | Ser | Glu | Gly | Arg | Asp | Ala | Val | Ala | Gly | Leu | Pro | Thr | Asp | Arg |
| | | 530 | | | | 535 | | | | | 540 | | | | |
| Gly | Trp | Asp | Leu | Asp | Ser | Leu | Phe | His | Pro | Asp | Pro | Thr | Arg | Ser | Gly |
| 545 | | | | | 550 | | | | 555 | | | | | | 560 |
| Thr | Ala | His | Gln | Arg | Gly | Gly | Gly | Phe | Leu | Thr | Glu | Ala | Thr | Ala | Phe |
| | | | | 565 | | | | | 570 | | | | | 575 | |
| Asp | Pro | Ala | Phe | Phe | Gly | Met | Ser | Pro | Arg | Glu | Ala | Leu | Ala | Val | Asp |
| | | | 580 | | | | | 585 | | | | | 590 | | |
| Pro | Gln | Gln | Arg | Leu | Met | Leu | Glu | Leu | Ser | Trp | Glu | Val | Leu | Glu | Arg |
| | | 595 | | | | | 600 | | | | | 605 | | | |
| Ala | Gly | Ile | Pro | Pro | Thr | Ser | Leu | Gln | Ala | Ser | Pro | Thr | Gly | Val | Phe |
| | 610 | | | | | 615 | | | | | 620 | | | | |
| Val | Gly | Leu | Ile | Pro | Gln | Glu | Tyr | Gly | Pro | Arg | Leu | Ala | Glu | Gly | Gly |
| 625 | | | | | 630 | | | | | 635 | | | | | 640 |
| Glu | Gly | Val | Glu | Gly | Tyr | Leu | Met | Thr | Gly | Thr | Thr | Thr | Ser | Val | Ala |
| | | | | 645 | | | | | 650 | | | | | 655 | |
| Ser | Gly | Arg | Ile | Ala | Tyr | Thr | Leu | Gly | Leu | Glu | Gly | Pro | Ala | Ile | Ser |
| | | | 660 | | | | | 665 | | | | | 670 | | |
| Val | Asp | Thr | Ala | Cys | Ser | Ser | Ser | Leu | Val | Ala | Val | His | Leu | Ala | Cys |
| | | 675 | | | | | 680 | | | | | 685 | | | |
| Gln | Ser | Leu | Arg | Arg | Gly | Glu | Ser | Ser | Leu | Ala | Met | Ala | Gly | Gly | Val |
| | 690 | | | | | 695 | | | | | 700 | | | | |
| Thr | Val | Met | Pro | Thr | Pro | Gly | Met | Leu | Val | Asp | Phe | Ser | Arg | Met | Asn |
| 705 | | | | | 710 | | | | | 715 | | | | | 720 |
| Ser | Leu | Ala | Pro | Asp | Gly | Arg | Cys | Lys | Ala | Phe | Ser | Ala | Gly | Ala | Asn |
| | | | | 725 | | | | | 730 | | | | | 735 | |
| Gly | Phe | Gly | Met | Ala | Glu | Gly | Ala | Gly | Met | Leu | Leu | Leu | Glu | Arg | Leu |
| | | | 740 | | | | | 745 | | | | | 750 | | |
| Ser | Asp | Ala | Arg | Arg | Asn | Gly | His | Pro | Val | Leu | Ala | Val | Leu | Arg | Gly |
| | | 755 | | | | | 760 | | | | | 765 | | | |
| Thr | Ala | Val | Asn | Ser | Asp | Gly | Ala | Ser | Asn | Gly | Leu | Ser | Ala | Pro | Asn |
| | 770 | | | | | 775 | | | | | 780 | | | | |
| Gly | Arg | Ala | Gln | Val | Arg | Val | Ile | Gln | Gln | Ala | Leu | Ala | Glu | Ser | Gly |
| 785 | | | | | 790 | | | | | 795 | | | | | 800 |
| Leu | Gly | Pro | Ala | Asp | Ile | Asp | Ala | Val | Glu | Ala | His | Gly | Thr | Gly | Thr |
| | | | | 805 | | | | | 810 | | | | | 815 | |
| Arg | Leu | Gly | Asp | Pro | Ile | Glu | Ala | Arg | Ala | Leu | Phe | Glu | Ala | Tyr | Gly |
| | | | 820 | | | | | 825 | | | | | 830 | | |

```
Arg Asp Arg Glu Gln Pro Leu His Leu Gly Ser Val Lys Ser Asn Leu
        835                 840                 845
Gly His Thr Gln Ala Ala Ala Gly Val Ala Gly Val Ile Lys Met Val
        850                 855                 860
Leu Ala Met Arg Ala Gly Thr Leu Pro Arg Thr Leu His Ala Ser Glu
865                 870                 875                 880
Arg Ser Lys Glu Ile Asp Trp Ser Ser Gly Ala Ile Ser Leu Leu Asp
                885                 890                 895
Glu Pro Glu Pro Trp Pro Ala Gly Ala Arg Pro Arg Arg Ala Gly Val
            900                 905                 910
Ser Ser Phe Gly Ile Ser Gly Thr Asn Ala His Ala Ile Ile Glu Glu
            915                 920                 925
Ala Pro Gln Val Val Glu Gly Glu Arg Val Glu Ala Gly Asp Val Val
        930                 935                 940
Ala Pro Trp Val Leu Ser Ala Ser Ser Ala Glu Gly Leu Arg Ala Gln
945                 950                 955                 960
Ala Ala Arg Leu Ala Ala His Leu Arg Glu His Pro Gly Gln Asp Pro
                965                 970                 975
Arg Asp Ile Ala Tyr Ser Leu Ala Thr Gly Arg Ala Ala Leu Pro His
            980                 985                 990
Arg Ala Ala Phe Ala Pro Val Asp Glu Ser Ala Ala Leu Arg Val Leu
        995                 1000                1005
Asp Gly Leu Ala Thr Gly Asn Ala Asp Gly Ala Ala Val Gly Thr Ser
1010                1015                1020
Arg Ala Gln Gln Arg Ala Val Phe Val Phe Pro Gly Gln Gly Trp Gln
1025                1030                1035                1040
Trp Ala Gly Met Ala Val Asp Leu Leu Asp Thr Ser Pro Val Phe Ala
                1045                1050                1055
Ala Ala Leu Arg Glu Cys Ala Asp Ala Leu Glu Pro His Leu Asp Phe
            1060                1065                1070
Glu Val Ile Pro Phe Leu Arg Ala Glu Ala Ala Arg Glu Gln Asp
            1075                1080                1085
Ala Ala Leu Ser Thr Glu Arg Val Asp Val Val Gln Pro Val Met Phe
        1090                1095                1100
Ala Val Met Val Ser Leu Ala Ser Met Trp Arg Ala His Gly Val Glu
1105                1110                1115                1120
Pro Ala Ala Val Ile Gly His Ser Gln Gly Glu Ile Ala Ala Ala Cys
                1125                1130                1135
Val Ala Gly Ala Leu Ser Leu Asp Asp Ala Ala Arg Val Val Ala Leu
            1140                1145                1150
Arg Ser Arg Val Ile Ala Thr Met Pro Gly Asn Lys Gly Met Ala Ser
        1155                1160                1165
Ile Ala Ala Pro Ala Gly Glu Val Arg Ala Arg Ile Gly Asp Arg Val
        1170                1175                1180
Glu Ile Ala Ala Val Asn Gly Pro Arg Ser Val Val Val Ala Gly Asp
1185                1190                1195                1200
Ser Asp Glu Leu Asp Arg Leu Val Ala Ser Cys Thr Thr Glu Cys Ile
                1205                1210                1215
Arg Ala Lys Arg Leu Ala Val Asp Tyr Ala Ser His Ser Ser His Val
            1220                1225                1230
Glu Thr Ile Arg Asp Ala Leu His Ala Glu Leu Gly Glu Asp Phe His
            1235                1240                1245
Pro Leu Pro Gly Phe Val Pro Phe Phe Ser Thr Val Thr Gly Arg Trp
```

-continued

```
                   1250                      1255                       1260
Thr  Gln  Pro  Asp  Glu  Leu  Asp  Ala  Gly  Tyr  Trp  Tyr  Arg  Asn  Leu  Arg
1265                      1270                      1275                      1280

Arg  Thr  Val  Arg  Phe  Ala  Asp  Ala  Val  Arg  Ala  Leu  Ala  Glu  Gln  Gly
                    1285                      1290                      1295

Tyr  Arg  Thr  Phe  Leu  Glu  Val  Ser  Ala  His  Pro  Ile  Leu  Thr  Ala  Ala
                    1300                      1305                      1310

Ile  Glu  Glu  Ile  Gly  Asp  Gly  Ser  Gly  Ala  Asp  Leu  Ser  Ala  Ile  His
                    1315                      1320                      1325

Ser  Leu  Arg  Arg  Gly  Asp  Gly  Ser  Leu  Ala  Asp  Phe  Gly  Glu  Ala  Leu
                    1330                      1335                      1340

Ser  Arg  Ala  Phe  Ala  Ala  Gly  Val  Ala  Val  Asp  Trp  Glu  Ser  Val  His
1345                      1350                      1355                      1360

Leu  Gly  Thr  Gly  Ala  Arg  Arg  Val  Pro  Leu  Pro  Thr  Tyr  Pro  Phe  Gln
                    1365                      1370                      1375

Arg  Glu  Arg  Val  Trp  Leu  Glu  Pro  Lys  Pro  Val  Ala  Arg  Arg  Ser  Thr
                    1380                      1385                      1390

Glu  Val  Asp  Glu  Val  Ser  Ala  Leu  Arg  Tyr  Arg  Ile  Glu  Trp  Arg  Pro
                    1395                      1400                      1405

Thr  Gly  Ala  Gly  Glu  Pro  Ala  Arg  Leu  Asp  Gly  Thr  Trp  Leu  Val  Ala
                    1410                      1415                      1420

Lys  Tyr  Ala  Gly  Thr  Ala  Asp  Glu  Thr  Ser  Thr  Ala  Ala  Arg  Glu  Ala
1425                      1430                      1435                      1440

Leu  Glu  Ser  Ala  Gly  Ala  Arg  Val  Arg  Glu  Leu  Val  Val  Asp  Ala  Arg
                    1445                      1450                      1455

Cys  Gly  Arg  Asp  Glu  Leu  Ala  Glu  Arg  Leu  Arg  Ser  Val  Gly  Glu  Val
                    1460                      1465                      1470

Ala  Gly  Val  Leu  Ser  Leu  Leu  Ala  Val  Asp  Glu  Ala  Glu  Pro  Glu  Glu
                    1475                      1480                      1485

Ala  Pro  Leu  Ala  Leu  Ala  Ser  Leu  Ala  Asp  Thr  Leu  Ser  Leu  Val  Gln
                    1490                      1495                      1500

Ala  Met  Val  Ser  Ala  Glu  Leu  Gly  Cys  Pro  Leu  Trp  Thr  Val  Thr  Glu
1505                      1510                      1515                      1520

Ser  Ala  Val  Ala  Thr  Gly  Pro  Phe  Glu  Arg  Val  Arg  Asn  Ala  Ala  His
                    1525                      1530                      1535

Gly  Ala  Leu  Trp  Gly  Val  Gly  Arg  Val  Ile  Ala  Leu  Glu  Asn  Pro  Ala
                    1540                      1545                      1550

Val  Trp  Gly  Gly  Leu  Val  Asp  Val  Pro  Ala  Gly  Ser  Val  Ala  Glu  Leu
                    1555                      1560                      1565

Ala  Arg  His  Leu  Ala  Ala  Val  Val  Ser  Gly  Gly  Ala  Gly  Glu  Asp  Gln
                    1570                      1575                      1580

Leu  Ala  Leu  Arg  Ala  Asp  Gly  Val  Tyr  Gly  Arg  Arg  Trp  Val  Arg  Ala
1585                      1590                      1595                      1600

Ala  Ala  Pro  Ala  Thr  Asp  Asp  Glu  Trp  Lys  Pro  Thr  Gly  Thr  Val  Leu
                    1605                      1610                      1615

Val  Thr  Gly  Gly  Thr  Gly  Gly  Val  Gly  Gly  Gln  Ile  Ala  Arg  Trp  Leu
                    1620                      1625                      1630

Ala  Arg  Arg  Gly  Ala  Pro  His  Leu  Leu  Leu  Val  Ser  Arg  Ser  Gly  Pro
                    1635                      1640                      1645

Asp  Ala  Asp  Gly  Ala  Gly  Glu  Leu  Val  Ala  Glu  Leu  Glu  Ala  Leu  Gly
                    1650                      1655                      1660

Ala  Arg  Thr  Thr  Val  Ala  Ala  Cys  Asp  Val  Thr  Asp  Arg  Glu  Ser  Val
1665                      1670                      1675                      1680
```

Arg Glu Leu Leu Gly Gly Ile Gly Asp Asp Val Pro Leu Ser Ala Val
            1685                    1690                1695

Phe His Ala Ala Ala Thr Leu Asp Asp Gly Thr Val Asp Thr Leu Thr
            1700                    1705                1710

Gly Glu Arg Ile Glu Arg Ala Ser Arg Ala Lys Val Leu Gly Ala Arg
            1715                    1720                1725

Asn Leu His Glu Leu Thr Arg Glu Leu Asp Leu Thr Ala Phe Val Leu
            1730                    1735                1740

Phe Ser Ser Phe Ala Ser Ala Phe Gly Ala Pro Gly Leu Gly Gly Tyr
1745                    1750                1755                1760

Ala Pro Gly Asn Ala Tyr Leu Asp Gly Leu Ala Gln Gln Arg Arg Ser
            1765                    1770                1775

Asp Gly Leu Pro Ala Thr Ala Val Ala Trp Gly Thr Trp Ala Gly Ser
            1780                    1785                1790

Gly Met Ala Glu Gly Ala Val Ala Asp Arg Phe Arg Arg His Gly Val
            1795                    1800                1805

Ile Glu Met Pro Pro Glu Thr Ala Cys Arg Ala Leu Gln Asn Ala Leu
            1810                    1815                1820

Asp Arg Ala Glu Val Cys Pro Ile Val Ile Asp Val Arg Trp Asp Arg
1825                    1830                    1835            1840

Phe Leu Leu Ala Tyr Thr Ala Gln Arg Pro Thr Arg Leu Phe Asp Glu
            1845                    1850                1855

Ile Asp Asp Ala Arg Arg Ala Ala Pro Gln Ala Pro Ala Glu Pro Arg
            1860                    1865                1870

Val Gly Ala Leu Ala Ser Leu Pro Ala Pro Glu Arg Glu Glu Ala Leu
            1875                    1880                1885

Phe Glu Leu Val Arg Ser His Ala Ala Ala Val Leu Gly His Ala Ser
            1890                    1895                1900

Ala Glu Arg Val Pro Ala Asp Gln Ala Phe Ala Glu Leu Gly Val Asp
1905                    1910                    1915            1920

Ser Leu Ser Ala Leu Glu Leu Arg Asn Arg Leu Gly Ala Ala Thr Gly
            1925                    1930                1935

Val Arg Leu Pro Thr Thr Thr Val Phe Asp His Pro Asp Val Arg Thr
            1940                    1945                1950

Leu Ala Ala His Leu Ala Ala Glu Leu Gly Gly Ala Thr Gly Ala Glu
            1955                    1960                1965

Gln Ala Ala Pro Ala Thr Thr Ala Pro Val Asp Glu Pro Ile Ala Ile
            1970                    1975                1980

Val Gly Met Ala Cys Arg Leu Pro Gly Glu Val Asp Ser Pro Glu Arg
1985                    1990                    1995            2000

Leu Trp Glu Leu Ile Thr Ser Gly Arg Asp Ser Ala Ala Glu Val Pro
            2005                    2010                2015

Asp Asp Arg Gly Trp Val Pro Asp Glu Leu Met Ala Ser Asp Ala Ala
            2020                    2025                2030

Gly Thr Arg Ala His Gly Asn Phe Met Ala Gly Ala Gly Asp Phe Asp
            2035                    2040                2045

Ala Ala Phe Phe Gly Ile Ser Pro Arg Glu Ala Leu Ala Met Asp Pro
            2050                    2055                2060

Gln Gln Arg Gln Ala Leu Glu Thr Thr Trp Glu Ala Leu Glu Ser Ala
2065                    2070                    2075            2080

Gly Ile Pro Pro Glu Thr Leu Arg Gly Ser Asp Thr Gly Val Phe Val
            2085                    2090                2095

Gly Met Ser His Gln Gly Tyr Ala Thr Gly Arg Pro Arg Pro Glu Asp
            2100                    2105                2110

```
Gly Val Asp Gly Tyr Leu Leu Thr Gly Asn Thr Ala Ser Val Ala Ser
              2115                2120                2125
Gly Arg Ile Ala Tyr Val Leu Gly Leu Glu Gly Pro Ala Leu Thr Val
              2130                2135                2140
Asp Thr Ala Cys Ser Ser Leu Val Ala Leu His Thr Ala Cys Gly
2145                2150                2155                2160
Ser Leu Arg Asp Gly Asp Cys Gly Leu Ala Val Ala Gly Gly Val Ser
              2165                2170                2175
Val Met Ala Gly Pro Glu Val Phe Thr Glu Phe Ser Arg Gln Gly Ala
              2180                2185                2190
Leu Ser Pro Asp Gly Arg Cys Lys Pro Phe Ser Asp Glu Ala Asp Gly
              2195                2200                2205
Phe Gly Leu Gly Glu Gly Ser Ala Phe Val Val Leu Gln Arg Leu Ser
              2210                2215                2220
Asp Ala Arg Arg Glu Gly Arg Arg Val Leu Gly Val Val Ala Gly Ser
2225                2230                2235                2240
Ala Val Asn Gln Asp Gly Ala Ser Asn Gly Leu Ser Ala Pro Ser Gly
              2245                2250                2255
Val Ala Gln Gln Arg Val Ile Arg Arg Ala Trp Ala Arg Ala Gly Ile
              2260                2265                2270
Thr Gly Ala Asp Val Ala Val Val Glu Ala His Gly Thr Gly Thr Arg
              2275                2280                2285
Leu Gly Asp Pro Val Glu Ala Ser Ala Leu Leu Ala Thr Tyr Gly Lys
              2290                2295                2300
Ser Arg Gly Ser Ser Gly Pro Val Leu Leu Gly Ser Val Lys Ser Asn
2305                2310                2315                2320
Ile Gly His Ala Gln Ala Ala Ala Gly Val Ala Gly Val Ile Lys Val
              2325                2330                2335
Leu Leu Gly Leu Glu Arg Gly Val Val Pro Pro Met Leu Cys Arg Gly
              2340                2345                2350
Glu Arg Ser Gly Leu Ile Asp Trp Ser Ser Gly Glu Ile Glu Leu Ala
              2355                2360                2365
Asp Gly Val Arg Glu Trp Ser Pro Ala Ala Asp Gly Val Arg Arg Ala
              2370                2375                2380
Gly Val Ser Ala Phe Gly Val Ser Gly Thr Asn Ala His Val Ile Ile
2385                2390                2395                2400
Ala Glu Pro Pro Glu Pro Glu Pro Val Pro Gln Pro Arg Arg Met Leu
              2405                2410                2415
Pro Ala Thr Gly Val Val Pro Val Val Leu Ser Ala Arg Thr Gly Ala
              2420                2425                2430
Ala Leu Arg Ala Gln Ala Gly Arg Leu Ala Asp His Leu Ala Ala His
              2435                2440                2445
Pro Gly Ile Ala Pro Ala Asp Val Ser Trp Thr Met Ala Arg Ala Arg
              2450                2455                2460
Gln His Phe Glu Glu Arg Ala Ala Val Leu Ala Ala Asp Thr Ala Glu
2465                2470                2475                2480
Ala Val His Arg Leu Arg Ala Val Ala Asp Gly Ala Val Val Pro Gly
              2485                2490                2495
Val Val Thr Gly Ser Ala Ser Asp Gly Gly Ser Val Phe Val Phe Pro
              2500                2505                2510
Gly Gln Gly Ala Gln Trp Glu Gly Met Ala Arg Glu Leu Leu Pro Val
              2515                2520                2525
Pro Val Phe Ala Glu Ser Ile Ala Glu Cys Asp Ala Val Leu Ser Glu
```

```
                   2530                      2535                           2540
Val  Ala  Gly  Phe  Ser  Val  Ser  Glu  Val  Leu  Glu  Pro  Arg  Pro  Asp  Ala
2545                     2550                          2555                     2560

Pro  Ser  Leu  Glu  Arg  Val  Asp  Val  Val  Gln  Pro  Val  Leu  Phe  Ala  Val
                    2565                     2570                    2575

Met  Val  Ser  Leu  Ala  Arg  Leu  Trp  Arg  Ala  Cys  Gly  Ala  Val  Pro  Ser
                         2580                    2585                     2590

Ala  Val  Ile  Gly  His  Ser  Gln  Gly  Glu  Ile  Ala  Ala  Ala  Val  Val  Ala
                    2595                     2600                      2605

Gly  Ala  Leu  Ser  Leu  Glu  Asp  Gly  Met  Arg  Val  Val  Ala  Arg  Arg  Ser
               2610                     2615                     2620

Arg  Ala  Val  Arg  Ala  Val  Ala  Gly  Arg  Gly  Ser  Met  Leu  Ser  Val  Arg
2625                     2630                     2635                          2640

Gly  Gly  Arg  Ser  Asp  Val  Glu  Lys  Leu  Leu  Ala  Asp  Asp  Ser  Trp  Thr
                    2645                     2650                     2655

Gly  Arg  Leu  Glu  Val  Ala  Ala  Val  Asn  Gly  Pro  Asp  Ala  Val  Val  Val
                    2660                     2665                     2670

Ala  Gly  Asp  Ala  Gln  Ala  Ala  Arg  Glu  Phe  Leu  Glu  Tyr  Cys  Glu  Gly
                    2675                     2680                     2685

Val  Gly  Ile  Arg  Ala  Arg  Ala  Ile  Pro  Val  Asp  Tyr  Ala  Ser  His  Thr
                    2690                     2695                     2700

Ala  His  Val  Glu  Pro  Val  Arg  Asp  Glu  Leu  Val  Gln  Ala  Leu  Ala  Gly
2705                     2710                     2715                          2720

Ile  Thr  Pro  Arg  Arg  Ala  Glu  Val  Pro  Phe  Phe  Ser  Thr  Leu  Thr  Gly
                         2725                    2730                     2735

Asp  Phe  Leu  Asp  Gly  Thr  Glu  Leu  Asp  Ala  Gly  Tyr  Trp  Tyr  Arg  Asn
                    2740                     2745                     2750

Leu  Arg  His  Pro  Val  Glu  Phe  His  Ser  Ala  Val  Gln  Ala  Leu  Thr  Asp
                    2755                     2760                     2765

Gln  Gly  Tyr  Ala  Thr  Phe  Ile  Glu  Val  Ser  Pro  His  Pro  Val  Leu  Ala
                    2770                     2775                     2780

Ser  Ser  Val  Gln  Glu  Thr  Leu  Asp  Asp  Ala  Glu  Ser  Asp  Ala  Ala  Val
2785                     2790                     2795                          2800

Leu  Gly  Thr  Leu  Glu  Arg  Asp  Ala  Gly  Asp  Ala  Asp  Arg  Phe  Leu  Thr
                         2805                    2810                     2815

Ala  Leu  Ala  Asp  Ala  His  Thr  Arg  Gly  Val  Ala  Val  Asp  Trp  Glu  Ala
                    2820                     2825                     2830

Val  Leu  Gly  Arg  Ala  Gly  Leu  Val  Asp  Leu  Pro  Gly  Tyr  Pro  Phe  Gln
                    2835                     2840                     2845

Gly  Lys  Arg  Phe  Trp  Leu  Leu  Pro  Asp  Arg  Thr  Thr  Pro  Arg  Asp  Glu
2850                     2855                     2860

Leu  Asp  Gly  Trp  Phe  Tyr  Arg  Val  Asp  Trp  Thr  Glu  Val  Pro  Arg  Ser
2865                     2870                     2875                          2880

Glu  Pro  Ala  Ala  Leu  Arg  Gly  Arg  Trp  Leu  Val  Val  Val  Pro  Glu  Gly
                         2885                    2890                     2895

His  Glu  Glu  Asp  Gly  Trp  Thr  Val  Glu  Val  Arg  Ser  Ala  Leu  Ala  Glu
                    2900                     2905                     2910

Ala  Gly  Ala  Glu  Pro  Glu  Val  Thr  Arg  Gly  Val  Gly  Gly  Leu  Val  Gly
                    2915                     2920                     2925

Asp  Cys  Ala  Gly  Val  Val  Ser  Leu  Leu  Ala  Leu  Glu  Gly  Asp  Gly  Ala
                    2930                     2935                     2940

Val  Gln  Thr  Leu  Val  Leu  Val  Arg  Glu  Leu  Asp  Ala  Glu  Gly  Ile  Asp
2945                     2950                     2955                          2960
```

```
Ala  Pro  Leu  Trp  Thr  Val  Thr  Phe  Gly  Ala  Val  Asp  Ala  Gly  Ser  Pro
               2965                2970                     2975

Val  Ala  Arg  Pro  Asp  Gln  Ala  Lys  Leu  Trp  Gly  Leu  Gly  Gln  Val  Ala
               2980                2985                     2990

Ser  Leu  Glu  Arg  Gly  Pro  Arg  Trp  Thr  Gly  Leu  Val  Asp  Leu  Pro  His
               2995                3000                     3005

Met  Pro  Asp  Pro  Glu  Leu  Arg  Gly  Arg  Leu  Thr  Ala  Val  Leu  Ala  Gly
               3010                3015                     3020

Ser  Glu  Asp  Gln  Val  Ala  Val  Arg  Ala  Asp  Ala  Val  Arg  Ala  Arg  Arg
3025                     3030                    3035                     3040

Leu  Ser  Pro  Ala  His  Val  Thr  Ala  Thr  Ser  Glu  Tyr  Ala  Val  Pro  Gly
               3045                3050                     3055

Gly  Thr  Ile  Leu  Val  Thr  Gly  Gly  Thr  Ala  Gly  Leu  Gly  Ala  Glu  Val
               3060                3065                     3070

Ala  Arg  Trp  Leu  Ala  Gly  Arg  Gly  Ala  Glu  His  Leu  Ala  Leu  Val  Ser
               3075                3080                     3085

Arg  Arg  Gly  Pro  Asp  Thr  Glu  Gly  Val  Gly  Asp  Leu  Thr  Ala  Glu  Leu
               3090                3095                     3100

Thr  Arg  Leu  Gly  Ala  Arg  Val  Ser  Val  His  Ala  Cys  Asp  Val  Ser  Ser
3105                     3110                    3115                     3120

Arg  Glu  Pro  Val  Arg  Glu  Leu  Val  His  Gly  Leu  Ile  Glu  Gln  Gly  Asp
               3125                3130                     3135

Val  Val  Arg  Gly  Val  Val  His  Ala  Ala  Gly  Leu  Pro  Gln  Gln  Val  Ala
               3140                3145                     3150

Ile  Asn  Asp  Met  Asp  Glu  Ala  Ala  Phe  Asp  Glu  Val  Val  Ala  Ala  Lys
               3155                3160                     3165

Ala  Gly  Gly  Ala  Val  His  Leu  Asp  Glu  Leu  Cys  Ser  Asp  Ala  Glu  Leu
               3170                3175                     3180

Phe  Leu  Leu  Phe  Ser  Ser  Gly  Ala  Gly  Val  Trp  Gly  Ser  Ala  Arg  Gln
3185                     3190                    3195                     3200

Gly  Ala  Tyr  Ala  Ala  Gly  Asn  Ala  Phe  Leu  Asp  Ala  Phe  Ala  Arg  His
               3205                3210                     3215

Arg  Arg  Gly  Arg  Gly  Leu  Pro  Ala  Thr  Ser  Val  Ala  Trp  Gly  Leu  Trp
               3220                3225                     3230

Ala  Ala  Gly  Gly  Met  Thr  Gly  Asp  Glu  Glu  Ala  Val  Ser  Phe  Leu  Arg
               3235                3240                     3245

Glu  Arg  Gly  Val  Arg  Ala  Met  Pro  Val  Pro  Arg  Ala  Leu  Ala  Ala  Leu
               3250                3255                     3260

Asp  Arg  Val  Leu  Ala  Ser  Gly  Glu  Thr  Ala  Val  Val  Val  Thr  Asp  Val
3265                     3270                    3275                     3280

Asp  Trp  Pro  Ala  Phe  Ala  Glu  Ser  Tyr  Thr  Ala  Ala  Arg  Pro  Arg  Pro
               3285                3290                     3295

Leu  Leu  Asp  Arg  Ile  Val  Thr  Thr  Ala  Pro  Ser  Glu  Arg  Ala  Gly  Glu
               3300                3305                     3310

Pro  Glu  Thr  Glu  Ser  Leu  Arg  Asp  Arg  Leu  Ala  Gly  Leu  Pro  Arg  Ala
               3315                3320                     3325

Glu  Arg  Thr  Ala  Glu  Leu  Val  Arg  Leu  Val  Arg  Thr  Ser  Thr  Ala  Thr
               3330                3335                     3340

Val  Leu  Gly  His  Asp  Asp  Pro  Lys  Ala  Val  Arg  Ala  Thr  Thr  Pro  Phe
3345                     3350                    3355                     3360

Lys  Glu  Leu  Gly  Phe  Asp  Ser  Leu  Ala  Ala  Val  Arg  Leu  Arg  Asn  Leu
               3365                3370                     3375

Leu  Asn  Ala  Ala  Thr  Gly  Leu  Arg  Leu  Pro  Ser  Thr  Leu  Val  Phe  Asp
               3380                3385                     3390
```

| | | | | | | | | | | | | | |
|---|---|---|---|---|---|---|---|---|---|---|---|---|---|
| His | Pro | Asn | Ala | Ser | Ala | Val | Ala | Gly | Phe | Leu | Asp | Ala | Glu | Leu | Gly |
| | | 3395 | | | | | 3400 | | | | | 3405 | | |
| Thr | Glu | Val | Arg | Gly | Glu | Ala | Pro | Ser | Ala | Leu | Ala | Gly | Leu | Asp | Ala |
| | | 3410 | | | | | 3415 | | | | | 3420 | | |
| Leu | Glu | Gly | Ala | Leu | Pro | Glu | Val | Pro | Ala | Thr | Glu | Arg | Glu | Glu | Leu |
| 3425 | | | | | 3430 | | | | | 3435 | | | | | 3440 |
| Val | Gln | Arg | Leu | Glu | Arg | Met | Leu | Ala | Ala | Leu | Arg | Pro | Val | Ala | Gln |
| | | | | 3445 | | | | | 3450 | | | | | 3455 | |
| Ala | Ala | Asp | Ala | Ser | Gly | Thr | Gly | Ala | Asn | Pro | Ser | Gly | Asp | Asp | Leu |
| | | | | 3460 | | | | | 3465 | | | | | 3470 | |
| Gly | Glu | Ala | Gly | Val | Asp | Glu | Leu | Leu | Glu | Ala | Leu | Gly | Arg | Glu | Leu |
| | | | | 3475 | | | | | 3480 | | | | | 3485 | |
| Asp | Gly | Asp | | | | | | | | | | | | | |
| | | 3490 | | | | | | | | | | | | | |

(2) INFORMATION FOR SEQ ID NO:3:

(i) SEQUENCE CHARACTERISTICS:
        (A) LENGTH: 20235 base pairs
        (B) TYPE: nucleic acid
        (C) STRANDEDNESS: double
        (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
        (A) ORGANISM: Saccharopolyspora erythraea
        (B) STRAIN: NRRL 238

(ix) FEATURE:
        (A) NAME/KEY: CDS
        (B) LOCATION: 19..10722
        (D) OTHER INFORMATION: /codon_start= 19
            / function= "gene eryA"
            / product= "eryA ORF2 encoding modules 3 & 4 for
            6- deoxyerythronolide B"

(ix) FEATURE:
        (A) NAME/KEY: misc_feature
        (B) LOCATION: 19..4470
        (D) OTHER INFORMATION: /function="approximate span of
            module 3"

(ix) FEATURE:
        (A) NAME/KEY: misc_feature
        (B) LOCATION: 97..1482
        (D) OTHER INFORMATION: /function="approximate span of
            beta- ketoacyl ACP synthase of module 3"

(ix) FEATURE:
        (A) NAME/KEY: misc_feature
        (B) LOCATION: 1693..2670
        (D) OTHER INFORMATION: /function="approximate span of
            acyltransferase domain module 3"

(ix) FEATURE:
        (A) NAME/KEY: misc_feature
        (B) LOCATION: 3406..3921
        (D) OTHER INFORMATION: /function="approximate span of
            beta- ketoreductase domain of module 3"

(ix) FEATURE:
        (A) NAME/KEY: misc_feature
        (B) LOCATION: 4171..4428
        (D) OTHER INFORMATION: /function="approximate span of
            acyl carrier domain of module 3"

(ix) FEATURE:

-continued ( A ) NAME/KEY: misc_feature
( B ) LOCATION: 4471..10722
( D ) OTHER INFORMATION: /function="approximate span of module 4"

( i x ) FEATURE:
( A ) NAME/KEY: misc_feature
( B ) LOCATION: 4471..5847
( D ) OTHER INFORMATION: /function="approximate span of beta- ketoacylACPsynhase domain of module"

( i x ) FEATURE:
( A ) NAME/KEY: misc_feature
( B ) LOCATION: 6054..7026
( D ) OTHER INFORMATION: /function="approximate span of acyltransferase domain of module 4"

( i x ) FEATURE:
( A ) NAME/KEY: misc_feature
( B ) LOCATION: 7165..9216
( D ) OTHER INFORMATION: /function="approximate span of dehydratase and enoylreductase domains m"

( i x ) FEATURE:
( A ) NAME/KEY: misc_feature
( B ) LOCATION: 9433..9984
( D ) OTHER INFORMATION: /function="approximate span beta- ketoreductase of module 4"

( i x ) FEATURE:
( A ) NAME/KEY: misc_feature
( B ) LOCATION: 10225..10483
( D ) OTHER INFORMATION: /function="approximate span of acyl carrier domain of module 4"

( i x ) FEATURE:
( A ) NAME/KEY: CDS
( B ) LOCATION: 10723..20235
( D ) OTHER INFORMATION: /codon_start= 10723
/ function= "gene =eryA"
/ product= "orf3 encoding modules 5 & 6
6- deoxyerythronolide B formatio"

( i x ) FEATURE:
( A ) NAME/KEY: misc_feature
( B ) LOCATION: 10723..15165
( D ) OTHER INFORMATION: /function="approximate span of module 5"

( i x ) FEATURE:
( A ) NAME/KEY: misc_feature
( B ) LOCATION: 10831..12174
( D ) OTHER INFORMATION: /function="approximate span of beta- ketoacylACPsynthase domain of modul"

( i x ) FEATURE:
( A ) NAME/KEY: misc_feature
( B ) LOCATION: 12379..13350
( D ) OTHER INFORMATION: /function="approximatr span of acyltransferase domain of module 5"

( i x ) FEATURE:
( A ) NAME/KEY: misc_feature
( B ) LOCATION: 14062..14610
( D ) OTHER INFORMATION: /function="approximate span of beta- ketoreductase of module 5"

( i x ) FEATURE:
( A ) NAME/KEY: misc_feature
( B ) LOCATION: 14857..15114
( D ) OTHER INFORMATION: /function="approximate span of acyl carrier domain of module 5"

( i x ) FEATURE:
( A ) NAME/KEY: misc_feature
( B ) LOCATION: 15166..20235
( D ) OTHER INFORMATION: /function="approximate span of module 6"

( i x ) FEATURE:

( A ) NAME/KEY: misc_feature
                ( B ) LOCATION: 15172..16569
                ( D ) OTHER INFORMATION: /function="approximate span of
                        beta- ketoacylACPsynthase domain of modul"

( i x ) FEATURE:
                ( A ) NAME/KEY: misc_feature
                ( B ) LOCATION: 16768..17721
                ( D ) OTHER INFORMATION: /function="approximate span of
                        acyltransferase domain of module 6"

( i x ) FEATURE:
                ( A ) NAME/KEY: misc_feature
                ( B ) LOCATION: 18379..18921
                ( D ) OTHER INFORMATION: /function="approximate span of
                        beta- ketoreductase domain of module 6"

( i x ) FEATURE:
                ( A ) NAME/KEY: misc_feature
                ( B ) LOCATION: 19149..19398
                ( D ) OTHER INFORMATION: /function="approximate span of
                        acyl carrier domain of module 6"

( i x ) FEATURE:
                ( A ) NAME/KEY: misc_feature
                ( B ) LOCATION: 19492..20235
                ( D ) OTHER INFORMATION: /function="approximate span of
                        thioesterase domain of module 6"

( x i ) SEQUENCE DESCRIPTION: SEQ ID NO:3:

```
CCGCCGATTG  GAGAAAAG  GTG  ACT  GAC  AGC  GAG  AAG  GTG  GCG  GAG  TAC  CTC         51
                      Val  Thr  Asp  Ser  Glu  Lys  Val  Ala  Glu  Tyr  Leu
                       1              5                             10

CGT  CGG  GCG  ACG  CTC  GAC  CTG  CGT  GCC  GCC  CGG  CAG  CGC  ATC  CGC  GAG      99
Arg  Arg  Ala  Thr  Leu  Asp  Leu  Arg  Ala  Ala  Arg  Gln  Arg  Ile  Arg  Glu
                15                       20                      25

CTG  GAA  TCC  GAC  CCG  ATC  GCC  ATC  GTC  AGC  ATG  GCC  TGC  CGC  CTG  CCG     147
Leu  Glu  Ser  Asp  Pro  Ile  Ala  Ile  Val  Ser  Met  Ala  Cys  Arg  Leu  Pro
          30                       35                      40

GGC  GGG  GTG  AAC  ACC  CCG  CAG  CGG  CTG  TGG  GAG  CTG  CTG  CGC  GAG  GGC     195
Gly  Gly  Val  Asn  Thr  Pro  Gln  Arg  Leu  Trp  Glu  Leu  Leu  Arg  Glu  Gly
     45                       50                      55

GGT  GAG  ACG  CTG  TCG  GGC  TTC  CCC  ACC  GAC  CGG  GGC  TGG  GAC  CTG  GCG     243
Gly  Glu  Thr  Leu  Ser  Gly  Phe  Pro  Thr  Asp  Arg  Gly  Trp  Asp  Leu  Ala
60                       65                      70                        75

CGG  CTG  CAC  CAC  CCC  GAC  CCG  GAC  AAC  CCC  GGT  ACC  AGC  TAC  GTC  GAC     291
Arg  Leu  His  His  Pro  Asp  Pro  Asp  Asn  Pro  Gly  Thr  Ser  Tyr  Val  Asp
                80                       85                      90

AAG  GGC  GGG  TTC  CTC  GAC  GAC  GCG  GCG  GGC  TTC  GAC  GCG  GAG  TTC  TTC     339
Lys  Gly  Gly  Phe  Leu  Asp  Asp  Ala  Ala  Gly  Phe  Asp  Ala  Glu  Phe  Phe
               95                       100                     105

GGC  GTC  TCG  CCG  CGC  GAG  GCC  GCG  GCC  ATG  GAC  CCG  CAG  CAG  CGG  CTG     387
Gly  Val  Ser  Pro  Arg  Glu  Ala  Ala  Ala  Met  Asp  Pro  Gln  Gln  Arg  Leu
              110                       115                     120

CTG  CTG  GAG  ACG  AGC  TGG  GAG  CTG  GTG  GAG  AAC  GCC  GGC  ATC  GAC  CCG     435
Leu  Leu  Glu  Thr  Ser  Trp  Glu  Leu  Val  Glu  Asn  Ala  Gly  Ile  Asp  Pro
     125                      130                     135

CAC  TCG  CTG  CGC  GGT  ACC  GCG  ACC  GGC  GTC  TTC  CTC  GGA  GTG  GCG  AAG     483
His  Ser  Leu  Arg  Gly  Thr  Ala  Thr  Gly  Val  Phe  Leu  Gly  Val  Ala  Lys
140                      145                     150                       155

TTC  GGC  TAC  GGC  GAG  GAC  ACC  GCC  GCG  GCG  GAG  GAC  GTC  GAG  GGC  TAC     531
Phe  Gly  Tyr  Gly  Glu  Asp  Thr  Ala  Ala  Ala  Glu  Asp  Val  Glu  Gly  Tyr
                         160                     165                       170

TCG  GTC  ACC  GGT  GTG  GCG  CCC  GCG  GTC  GCC  TCC  GGC  CGC  ATC  TCC  TAC     579
Ser  Val  Thr  Gly  Val  Ala  Pro  Ala  Val  Ala  Ser  Gly  Arg  Ile  Ser  Tyr
               175                      180                     185

ACC  ATG  GGC  CTG  GAG  GGG  CCG  TCG  ATC  AGC  GTC  GAC  ACC  GCG  TGC  TCG     627
```

```
Thr Met Gly Leu Glu Gly Pro Ser Ile Ser Val Asp Thr Ala Cys Ser
    190                 195                 200

TCG TCG CTG GTG GCG CTG CAC CTG GCG GTC GAG TCG CTG CGC AAG GGC      675
Ser Ser Leu Val Ala Leu His Leu Ala Val Glu Ser Leu Arg Lys Gly
    205                 210                 215

GAG TCG TCG ATG GCG GTC GTC GGC GGT GCC GCG GTG ATG GCG ACC CCG      723
Glu Ser Ser Met Ala Val Val Gly Gly Ala Ala Val Met Ala Thr Pro
220                 225                 230                 235

GGG GTG TTC GTC GAC TTC AGC CGG CAG CGC GCG CTC GCC GCC GAC GGG      771
Gly Val Phe Val Asp Phe Ser Arg Gln Arg Ala Leu Ala Ala Asp Gly
                240                 245                 250

CGG TCG AAG GCG TTC GGT GCC GGC GCC GAC GGG TTC GGC TTC TCC GAA      819
Arg Ser Lys Ala Phe Gly Ala Gly Ala Asp Gly Phe Gly Phe Ser Glu
            255                 260                 265

GGC GTC ACC CTG GTC CTG CTC GAG CGG CTG TCG GAG GCG CGG CGA AAC      867
Gly Val Thr Leu Val Leu Leu Glu Arg Leu Ser Glu Ala Arg Arg Asn
        270                 275                 280

GGG CAC GAG GTG CTG GCG GTG GTT CGC GGC TCG GCG CTC AAC CAG GAC      915
Gly His Glu Val Leu Ala Val Val Arg Gly Ser Ala Leu Asn Gln Asp
    285                 290                 295

GGG GCC AGC AAC GGG CTT TCC GCG CCG AGC GGG CCC GCG CAG CGC AGG      963
Gly Ala Ser Asn Gly Leu Ser Ala Pro Ser Gly Pro Ala Gln Arg Arg
300                 305                 310                 315

GTC ATC CGG CAG GCC CTC GAG AGC TGC GGT CTG GAG CCC GGC GAC GTC     1011
Val Ile Arg Gln Ala Leu Glu Ser Cys Gly Leu Glu Pro Gly Asp Val
                320                 325                 330

GAC GCG GTG GAG GCG CAC GGC ACC GGT ACG GCG CTC GGC GAC CCG ATC     1059
Asp Ala Val Glu Ala His Gly Thr Gly Thr Ala Leu Gly Asp Pro Ile
            335                 340                 345

GAG GCG AAC GCG CTG CTG GAC ACC TAC GGC CGC GAC CGC GAC GCC GAC     1107
Glu Ala Asn Ala Leu Leu Asp Thr Tyr Gly Arg Asp Arg Asp Ala Asp
        350                 355                 360

CGG CCG CTC TGG CTG GGC TCG GTG AAG TCC AAC ATC GGC CAC ACC CAG     1155
Arg Pro Leu Trp Leu Gly Ser Val Lys Ser Asn Ile Gly His Thr Gln
    365                 370                 375

GCG GCA GCG GGC GTC ACC GGC CTG CTG AAG GTG GTC CTG GCG CTG CGC     1203
Ala Ala Ala Gly Val Thr Gly Leu Leu Lys Val Val Leu Ala Leu Arg
380                 385                 390                 395

AAC GGG GAA CTG CCC GCG ACC CTG CAC GTC GAG GAG CCC ACG CCG CAC     1251
Asn Gly Glu Leu Pro Ala Thr Leu His Val Glu Glu Pro Thr Pro His
                400                 405                 410

GTC GAC TGG TCG TCC GGC GGT GTG GCG CTG CTG GCG GGC AAC CAG CCG     1299
Val Asp Trp Ser Ser Gly Gly Val Ala Leu Leu Ala Gly Asn Gln Pro
            415                 420                 425

TGG CGG CGC GGC GAG CGG ACT CGG CGC GCC CGT GTT TCC GCG TTC GGG     1347
Trp Arg Arg Gly Glu Arg Thr Arg Arg Ala Arg Val Ser Ala Phe Gly
        430                 435                 440

ATC AGC GGG ACG AAT GCG CAC GTG ATC GTC GAG GAA GCT CCT GAG CGC     1395
Ile Ser Gly Thr Asn Ala His Val Ile Val Glu Glu Ala Pro Glu Arg
    445                 450                 455

GAG CAC CGG GAG ACC ACC GCG CAC GAC GGC CGA CCG GTT CCG CTG GTG     1443
Glu His Arg Glu Thr Thr Ala His Asp Gly Arg Pro Val Pro Leu Val
460                 465                 470                 475

GTG TCC GCG CGC ACG ACG GCG GCG TTG CGG GCG CAG GCC GCC CAG ATC     1491
Val Ser Ala Arg Thr Thr Ala Ala Leu Arg Ala Gln Ala Ala Gln Ile
                480                 485                 490

GCC GAG CTG CTC GAA CGC CCG GAC GCC GAC CTC GCC GGG GTC GGG CTG     1539
Ala Glu Leu Leu Glu Arg Pro Asp Ala Asp Leu Ala Gly Val Gly Leu
            495                 500                 505

GGC CTG GCC ACG ACC CGC GCC CGC CAC GAG CAC CGC GCC GCC GTG GTG     1587
```

|     |     |     |     |     |     |     |     |     |     |     |     |     |     |     |      |
|-----|-----|-----|-----|-----|-----|-----|-----|-----|-----|-----|-----|-----|-----|-----|------|
| Gly | Leu | Ala | Thr | Thr | Arg | Ala | Arg | His | Glu | His | Arg | Ala | Ala | Val | Val  |
|     |     | 510 |     |     |     |     | 515 |     |     |     |     | 520 |     |     |      |
| GCA | TCG | ACC | CGC | GAG | GAA | GCG | GTG | CGC | GGA | CTG | CGG | GAG | ATC | GCC | GCC  | 1635 |
| Ala | Ser | Thr | Arg | Glu | Glu | Ala | Val | Arg | Gly | Leu | Arg | Glu | Ile | Ala | Ala  |
|     | 525 |     |     |     | 530 |     |     |     |     | 535 |     |     |     |     |      |
| GGT | GCC | GCG | ACG | GCC | GAC | GCC | GTG | GTC | GAG | GGC | GTC | ACC | GAG | GTG | GAC  | 1683 |
| Gly | Ala | Ala | Thr | Ala | Asp | Ala | Val | Val | Glu | Gly | Val | Thr | Glu | Val | Asp  |
| 540 |     |     |     |     | 545 |     |     |     |     | 550 |     |     |     |     | 555  |
| GGG | CGC | AAC | GTC | GTC | TTC | CTG | TTC | CCG | GGG | CAG | GGT | TCG | CAA | TGG | GCC  | 1731 |
| Gly | Arg | Asn | Val | Val | Phe | Leu | Phe | Pro | Gly | Gln | Gly | Ser | Gln | Trp | Ala  |
|     |     |     |     | 560 |     |     |     |     | 565 |     |     |     |     | 570 |      |
| GGC | ATG | GGT | GCC | GAG | CTG | CTG | TCG | TCG | TCG | CCG | GTG | TTC | GCC | GGG | AAG  | 1779 |
| Gly | Met | Gly | Ala | Glu | Leu | Leu | Ser | Ser | Ser | Pro | Val | Phe | Ala | Gly | Lys  |
|     |     |     | 575 |     |     |     |     | 580 |     |     |     |     | 585 |     |      |
| ATC | CGG | GCC | TGC | GAC | GAG | TCG | ATG | GCC | CCG | ATG | CAG | GAC | TGG | AAG | GTC  | 1827 |
| Ile | Arg | Ala | Cys | Asp | Glu | Ser | Met | Ala | Pro | Met | Gln | Asp | Trp | Lys | Val  |
|     |     | 590 |     |     |     |     | 595 |     |     |     |     | 600 |     |     |      |
| TCC | GAC | GTG | CTG | CGT | CAG | GCG | CCG | GGG | GCG | CCG | GGC | CTG | GAC | CGG | GTC  | 1875 |
| Ser | Asp | Val | Leu | Arg | Gln | Ala | Pro | Gly | Ala | Pro | Gly | Leu | Asp | Arg | Val  |
|     | 605 |     |     |     |     | 610 |     |     |     |     | 615 |     |     |     |      |
| GAC | GTG | GTG | CAG | CCG | GTG | TTG | TTC | GCG | GTG | ATG | GTG | TCG | CTG | GCG | GAG  | 1923 |
| Asp | Val | Val | Gln | Pro | Val | Leu | Phe | Ala | Val | Met | Val | Ser | Leu | Ala | Glu  |
| 620 |     |     |     | 625 |     |     |     |     | 630 |     |     |     |     |     | 635  |
| CTG | TGG | CGC | TCG | TAC | GGC | GTG | GAG | CCC | GCG | GCG | GTC | GTG | GGG | CAC | TCG  | 1971 |
| Leu | Trp | Arg | Ser | Tyr | Gly | Val | Glu | Pro | Ala | Ala | Val | Val | Gly | His | Ser  |
|     |     |     | 640 |     |     |     |     | 645 |     |     |     |     | 650 |     |      |
| CAG | GGC | GAG | ATC | GCC | GCC | GCG | CAC | GTC | GCC | GGG | GCG | CTC | ACG | TTG | GAG  | 2019 |
| Gln | Gly | Glu | Ile | Ala | Ala | Ala | His | Val | Ala | Gly | Ala | Leu | Thr | Leu | Glu  |
|     |     |     | 655 |     |     |     |     | 660 |     |     |     |     | 665 |     |      |
| GAC | GCG | GCG | AAG | CTC | GTC | GTG | GGC | CGC | AGC | CGC | CTG | ATG | CGG | TCG | CTC  | 2067 |
| Asp | Ala | Ala | Lys | Leu | Val | Val | Gly | Arg | Ser | Arg | Leu | Met | Arg | Ser | Leu  |
|     |     | 670 |     |     |     |     | 675 |     |     |     |     | 680 |     |     |      |
| TCC | GGG | GAG | GGC | GGC | ATG | GCC | GCC | GTC | GCG | CTG | GGC | GAG | GCC | GCG | GTG  | 2115 |
| Ser | Gly | Glu | Gly | Gly | Met | Ala | Ala | Val | Ala | Leu | Gly | Glu | Ala | Ala | Val  |
|     |     | 685 |     |     |     | 690 |     |     |     |     | 695 |     |     |     |      |
| CGC | GAG | CGC | CTG | CGG | CCG | TGG | CAG | GAC | CGG | CTC | TCG | GTG | GCC | GCG | GTC  | 2163 |
| Arg | Glu | Arg | Leu | Arg | Pro | Trp | Gln | Asp | Arg | Leu | Ser | Val | Ala | Ala | Val  |
| 700 |     |     |     |     | 705 |     |     |     |     | 710 |     |     |     |     | 715  |
| AAC | GGT | CCC | CGG | TCG | GTC | GTG | GTC | TCC | GGC | GAG | CCC | GGC | GCG | CTG | CGG  | 2211 |
| Asn | Gly | Pro | Arg | Ser | Val | Val | Val | Ser | Gly | Glu | Pro | Gly | Ala | Leu | Arg  |
|     |     |     |     | 720 |     |     |     |     | 725 |     |     |     |     | 730 |      |
| GCG | TTT | TCC | GAG | GAC | TGC | GCG | GCC | GAG | GGC | ATC | CGC | GTC | CGC | GAC | ATC  | 2259 |
| Ala | Phe | Ser | Glu | Asp | Cys | Ala | Ala | Glu | Gly | Ile | Arg | Val | Arg | Asp | Ile  |
|     |     |     | 735 |     |     |     |     | 740 |     |     |     |     | 745 |     |      |
| GAC | GTG | GAC | TAC | GCC | TCG | CAC | TCG | CCG | CAG | ATC | GAG | CGG | GTC | CGC | GAG  | 2307 |
| Asp | Val | Asp | Tyr | Ala | Ser | His | Ser | Pro | Gln | Ile | Glu | Arg | Val | Arg | Glu  |
|     |     | 750 |     |     |     |     | 755 |     |     |     |     | 760 |     |     |      |
| GAA | CTC | CTC | GAA | ACG | ACC | GGC | GAC | ATC | GCG | CCG | CGC | CCG | GCG | CGG | GTG  | 2355 |
| Glu | Leu | Leu | Glu | Thr | Thr | Gly | Asp | Ile | Ala | Pro | Arg | Pro | Ala | Arg | Val  |
|     | 765 |     |     |     |     | 770 |     |     |     |     | 775 |     |     |     |      |
| ACG | TTC | CAC | TCC | ACT | GTG | GAG | TCG | CGG | TCT | ATG | GAC | GGC | ACC | GAG | CTG  | 2403 |
| Thr | Phe | His | Ser | Thr | Val | Glu | Ser | Arg | Ser | Met | Asp | Gly | Thr | Glu | Leu  |
| 780 |     |     |     |     | 785 |     |     |     |     | 790 |     |     |     |     | 795  |
| GAT | GCC | CGG | TAC | TGG | TAC | CGC | AAC | CTG | CGC | GAG | ACG | GTG | CGC | TTC | GCC  | 2451 |
| Asp | Ala | Arg | Tyr | Trp | Tyr | Arg | Asn | Leu | Arg | Glu | Thr | Val | Arg | Phe | Ala  |
|     |     |     |     | 800 |     |     |     |     | 805 |     |     |     |     | 810 |      |
| GAC | GCC | GTG | ACG | CGG | CTG | GCG | GAG | TCG | GGA | TAC | GAC | GCG | TTC | ATC | GAG  | 2499 |
| Asp | Ala | Val | Thr | Arg | Leu | Ala | Glu | Ser | Gly | Tyr | Asp | Ala | Phe | Ile | Glu  |
|     |     |     | 815 |     |     |     | 820 |     |     |     |     | 825 |     |     |      |
| GTC | AGC | CCG | CAT | CCG | GTC | GTG | GTC | CAG | GCC | GTC | GAG | GAG | GCG | GTC | GAA  | 2547 |

```
Val  Ser  Pro  His  Pro  Val  Val  Val  Gln  Ala  Val  Glu  Glu  Ala  Val  Glu
          830                      835                     840

GAG  GCT  GAC  GGT  GCC  GAA  GAC  GCG  GTC  GTA  GTC  GGC  TCG  CTG  CAC  CGC       2595
Glu  Ala  Asp  Gly  Ala  Glu  Asp  Ala  Val  Val  Val  Gly  Ser  Leu  His  Arg
     845                      850                     855

GAC  GGC  GGT  GAC  CTC  TCG  GCC  TTC  CTG  CGG  TCG  ATG  GCC  ACC  GCG  CAC       2643
Asp  Gly  Gly  Asp  Leu  Ser  Ala  Phe  Leu  Arg  Ser  Met  Ala  Thr  Ala  His
860                      865                     870                     875

GTG  TCC  GGT  GTG  GAC  ATC  AGG  TGG  GAC  GTC  GCT  CTG  CCC  GGC  GCC  GCG       2691
Val  Ser  Gly  Val  Asp  Ile  Arg  Trp  Asp  Val  Ala  Leu  Pro  Gly  Ala  Ala
                    880                      885                     890

CCC  TTC  GCG  CTG  CCG  ACG  TAT  CCG  TTC  CAG  CGC  AAG  CGC  TAC  TGG  CTC       2739
Pro  Phe  Ala  Leu  Pro  Thr  Tyr  Pro  Phe  Gln  Arg  Lys  Arg  Tyr  Trp  Leu
               895                      900                     905

CAG  CCC  GCC  GCA  CCC  GCC  GCC  GCC  TCC  GAC  GAG  CTG  GCC  TAC  CGC  GTT       2787
Gln  Pro  Ala  Ala  Pro  Ala  Ala  Ala  Ser  Asp  Glu  Leu  Ala  Tyr  Arg  Val
          910                      915                     920

TCC  TGG  ACT  CCG  ATC  GAA  AAG  CCG  GAG  TCG  GGA  AAC  CTG  GAC  GGC  GAC       2835
Ser  Trp  Thr  Pro  Ile  Glu  Lys  Pro  Glu  Ser  Gly  Asn  Leu  Asp  Gly  Asp
     925                      930                     935

TGG  TTG  GTT  GTC  ACA  CCC  CTC  ATC  AGT  CCG  GAG  TGG  ACG  GAA  ATG  CTG       2883
Trp  Leu  Val  Val  Thr  Pro  Leu  Ile  Ser  Pro  Glu  Trp  Thr  Glu  Met  Leu
940                      945                     950                     955

TGC  GAG  GCC  ATC  AAC  GCC  AAC  GGT  GGC  AGG  GCG  TTG  CGC  TGC  GAG  GTG       2931
Cys  Glu  Ala  Ile  Asn  Ala  Asn  Gly  Gly  Arg  Ala  Leu  Arg  Cys  Glu  Val
                    960                      965                     970

GAC  ACG  TCC  GCT  TCG  CGC  ACT  GAG  ATG  GCC  CAG  GCC  GTC  GCA  CAG  GCC       2979
Asp  Thr  Ser  Ala  Ser  Arg  Thr  Glu  Met  Ala  Gln  Ala  Val  Ala  Gln  Ala
               975                      980                     985

GGA  ACG  GGA  TTC  CGG  GGC  GTG  CTC  TCG  TTG  CTG  TCG  TCG  GAC  GAA  TCC       3027
Gly  Thr  Gly  Phe  Arg  Gly  Val  Leu  Ser  Leu  Leu  Ser  Ser  Asp  Glu  Ser
          990                      995                     1000

GCC  TGC  CGT  CCG  GGG  GTT  CCT  GCC  GGT  GCG  GTC  GGC  CTG  CTC  ACC  CTG       3075
Ala  Cys  Arg  Pro  Gly  Val  Pro  Ala  Gly  Ala  Val  Gly  Leu  Leu  Thr  Leu
     1005                     1010                    1015

GTC  CAG  GCG  CTG  GGC  GAT  GCC  GGG  GTC  GAC  GCA  CCG  GTG  TGG  TGC  CTG       3123
Val  Gln  Ala  Leu  Gly  Asp  Ala  Gly  Val  Asp  Ala  Pro  Val  Trp  Cys  Leu
1020                     1025                    1030                    1035

ACC  CAG  GGT  GCG  GTC  CGC  ACT  CCC  GCC  GAC  GAC  GAC  CTC  GCC  CGG  CCT       3171
Thr  Gln  Gly  Ala  Val  Arg  Thr  Pro  Ala  Asp  Asp  Asp  Leu  Ala  Arg  Pro
                    1040                     1045                    1050

GCG  CAG  ACC  ACC  GCG  CAC  GGC  TTC  GCG  CAG  GTC  GCC  GGG  CTG  GAG  CTG       3219
Ala  Gln  Thr  Thr  Ala  His  Gly  Phe  Ala  Gln  Val  Ala  Gly  Leu  Glu  Leu
               1055                     1060                    1065

CCG  GGC  CGC  TGG  GGC  GGT  GTG  GTC  GAC  CTG  CCC  GAA  TCG  GTC  GAC  GAC       3267
Pro  Gly  Arg  Trp  Gly  Gly  Val  Val  Asp  Leu  Pro  Glu  Ser  Val  Asp  Asp
          1070                     1075                    1080

GCG  GCG  CTG  CGT  CTG  CTC  GTG  GCA  GTC  CTG  CGC  GGC  GGC  GGC  CGT  GCC       3315
Ala  Ala  Leu  Arg  Leu  Leu  Val  Ala  Val  Leu  Arg  Gly  Gly  Gly  Arg  Ala
     1085                     1090                    1095

GAG  GAC  CAC  CTC  GCG  GTC  CGG  GAC  GGC  CGC  CTC  CAC  GGC  CGT  CGC  GTC       3363
Glu  Asp  His  Leu  Ala  Val  Arg  Asp  Gly  Arg  Leu  His  Gly  Arg  Arg  Val
1100                     1105                    1110                    1115

GTC  CGC  GCA  AGC  CTG  CCG  CAG  TCC  GGC  TCG  CGG  AGC  TGG  ACC  CCG  CAC       3411
Val  Arg  Ala  Ser  Leu  Pro  Gln  Ser  Gly  Ser  Arg  Ser  Trp  Thr  Pro  His
                    1120                     1125                    1130

GGG  ACC  GTG  CTG  GTC  ACC  GGC  GCG  GCG  AGC  CCC  GTC  GGC  GAC  CAA  CTG       3459
Gly  Thr  Val  Leu  Val  Thr  Gly  Ala  Ala  Ser  Pro  Val  Gly  Asp  Gln  Leu
               1135                     1140                    1145

GTG  CGG  TGG  CTC  GCC  GAC  CGG  GGA  GCC  GAG  CGG  CTG  GTG  CTG  GCC  GGA       3507
```

-continued

| | | | | | | | | | | | | | | | |
|---|---|---|---|---|---|---|---|---|---|---|---|---|---|---|---|
| Val | Arg | Trp | Leu | Ala | Asp | Arg | Gly | Ala | Glu | Arg | Leu | Val | Leu | Ala | Gly |
| | | | 1150 | | | | 1155 | | | | 1160 | | | | |

```
GCC  TGT  CCG  GGC  GAC  GAC  CTG  CTG  GCC  GCG  GTC  GAG  GAA  GCG  GGC  GCA        3555
Ala  Cys  Pro  Gly  Asp  Asp  Leu  Leu  Ala  Ala  Val  Glu  Glu  Ala  Gly  Ala
     1165                1170                     1175

TCG  GCC  GTC  GTG  TGC  GCC  CAG  GAC  GCG  GCG  GCG  CTG  CGC  GAG  GCG  CTC        3603
Ser  Ala  Val  Val  Cys  Ala  Gln  Asp  Ala  Ala  Ala  Leu  Arg  Glu  Ala  Leu
1180                1185                     1190                     1195

GGC  GAC  GAG  CCG  GTG  ACC  GCG  CTC  GTG  CAC  GCC  GGA  ACC  CTG  ACG  AAC        3651
Gly  Asp  Glu  Pro  Val  Thr  Ala  Leu  Val  His  Ala  Gly  Thr  Leu  Thr  Asn
                     1200                     1205                     1210

TTC  GGC  AGC  ATC  AGC  GAA  GTC  GCA  CCG  GAG  GAG  TTC  GCC  GAG  ACG  ATC        3699
Phe  Gly  Ser  Ile  Ser  Glu  Val  Ala  Pro  Glu  Glu  Phe  Ala  Glu  Thr  Ile
                1215                     1220                     1225

GCG  GCC  AAG  ACC  GCG  TTG  CTC  GCC  GTG  CTG  GAC  GAA  GTC  CTC  GGC  GAC        3747
Ala  Ala  Lys  Thr  Ala  Leu  Leu  Ala  Val  Leu  Asp  Glu  Val  Leu  Gly  Asp
           1230                     1235                     1240

CGG  GCC  GTC  GAG  CGG  GAG  GTC  TAC  TGC  TCG  TCG  GTC  GCC  GGG  ATC  TGG        3795
Arg  Ala  Val  Glu  Arg  Glu  Val  Tyr  Cys  Ser  Ser  Val  Ala  Gly  Ile  Trp
      1245                     1250                     1255

GGC  GGC  GCC  GGG  ATG  GCC  GCC  TAC  GCG  GCA  GGC  AGC  GCC  TAC  CTC  GAC        3843
Gly  Gly  Ala  Gly  Met  Ala  Ala  Tyr  Ala  Ala  Gly  Ser  Ala  Tyr  Leu  Asp
1260                1265                     1270                     1275

GCG  CTG  GCC  GAG  CAC  CAC  CGC  GCG  CGG  GGC  CGC  TCG  TGC  ACC  TCG  GTC        3891
Ala  Leu  Ala  Glu  His  His  Arg  Ala  Arg  Gly  Arg  Ser  Cys  Thr  Ser  Val
                1280                     1285                     1290

GCC  TGG  ACG  CCG  TGG  GCG  CTG  CCG  GGC  GGG  GCG  GTG  GAC  GAC  GGC  TAC        3939
Ala  Trp  Thr  Pro  Trp  Ala  Leu  Pro  Gly  Gly  Ala  Val  Asp  Asp  Gly  Tyr
           1295                     1300                     1305

CTG  CGG  GAA  CGC  GGA  CTG  CGC  AGC  CTC  TCC  GCC  GAC  AGG  GCG  ATG  CGC        3987
Leu  Arg  Glu  Arg  Gly  Leu  Arg  Ser  Leu  Ser  Ala  Asp  Arg  Ala  Met  Arg
      1310                     1315                     1320

ACC  TGG  GAG  CGG  GTG  CTG  GCC  GCC  GGG  CCG  GTG  TCG  GTC  GCG  GTG  GCC        4035
Thr  Trp  Glu  Arg  Val  Leu  Ala  Ala  Gly  Pro  Val  Ser  Val  Ala  Val  Ala
1325                     1330                     1335

GAC  GTG  GAC  TGG  CCG  GTG  CTC  AGC  GAA  GGC  TTC  GCC  GCC  ACC  CGG  CCG        4083
Asp  Val  Asp  Trp  Pro  Val  Leu  Ser  Glu  Gly  Phe  Ala  Ala  Thr  Arg  Pro
1340                     1345                     1350                     1355

ACC  GCG  CTG  TTC  GCC  GAA  CTC  GCC  GGC  CGC  GGC  GGA  CAG  GCG  GAG  GCC        4131
Thr  Ala  Leu  Phe  Ala  Glu  Leu  Ala  Gly  Arg  Gly  Gly  Gln  Ala  Glu  Ala
                1360                     1365                     1370

GAG  CCG  GAC  AGC  GGA  CCG  ACC  GGC  GAG  CCG  GCA  CAA  CGG  CTC  GCG  GGG        4179
Glu  Pro  Asp  Ser  Gly  Pro  Thr  Gly  Glu  Pro  Ala  Gln  Arg  Leu  Ala  Gly
           1375                     1380                     1385

CTT  TCC  CCG  GAC  GAG  CAG  CAG  GAA  AAC  CTG  CTC  GAA  CTC  GTC  GCG  AAC        4227
Leu  Ser  Pro  Asp  Glu  Gln  Gln  Glu  Asn  Leu  Leu  Glu  Leu  Val  Ala  Asn
      1390                     1395                     1400

GCG  GTT  GCC  GAG  GTG  CTT  GGC  CAC  GAG  TCC  GCC  GCC  GAG  ATC  AAC  GTG        4275
Ala  Val  Ala  Glu  Val  Leu  Gly  His  Glu  Ser  Ala  Ala  Glu  Ile  Asn  Val
1405                     1410                     1415

CGC  CGC  GCG  TTC  AGC  GAG  CTC  GGA  CTC  GAC  TCG  CTC  AAC  GCG  ATG  GCC        4323
Arg  Arg  Ala  Phe  Ser  Glu  Leu  Gly  Leu  Asp  Ser  Leu  Asn  Ala  Met  Ala
1420                     1425                     1430                     1435

CTG  CGC  AAG  CGC  CTG  TCG  GCG  AGC  ACC  GGC  CTG  CGG  CTG  CCC  GCG  TCG        4371
Leu  Arg  Lys  Arg  Leu  Ser  Ala  Ser  Thr  Gly  Leu  Arg  Leu  Pro  Ala  Ser
                1440                     1445                     1450

CTG  GTG  TTC  GAC  CAC  CCC  ACC  GTC  ACC  GCG  CTC  GCG  CAG  CAC  CTG  CGC        4419
Leu  Val  Phe  Asp  His  Pro  Thr  Val  Thr  Ala  Leu  Ala  Gln  His  Leu  Arg
           1455                     1460                     1465

GCC  CGG  CTC  GTC  GGT  GAC  GCC  GAC  CAG  GCC  GCG  GTG  CGC  GTC  GTC  GGC        4467
```

```
                                     -continued

Ala Arg Leu Val Gly Asp Ala Asp Gln Ala Ala Val Arg Val Val Gly
        1470                    1475                    1480

GCG GCC GAC GAG TCC GAG CCC ATC GCC ATC GTC GGC ATC GGC TGC CGT       4515
Ala Ala Asp Glu Ser Glu Pro Ile Ala Ile Val Gly Ile Gly Cys Arg
1485                    1490                    1495

TTC CCC GGC GGC ATC GGC TCG CCC GAG CAG TTG TGG CGG GTG CTG GCC       4563
Phe Pro Gly Gly Ile Gly Ser Pro Glu Gln Leu Trp Arg Val Leu Ala
1500                    1505                    1510                1515

GAG GGC GCG AAC CTC ACC ACC GGC TTC CCG GCC GAC CGG GGC TGG GAC       4611
Glu Gly Ala Asn Leu Thr Thr Gly Phe Pro Ala Asp Arg Gly Trp Asp
                1520                    1525                    1530

ATC GGG CGG CTC TAC CAC CCG GAC CCG GAC AAC CCC GGC ACC AGC TAC       4659
Ile Gly Arg Leu Tyr His Pro Asp Pro Asp Asn Pro Gly Thr Ser Tyr
                    1535                    1540                    1545

GTG GAC AAG GGC GGG TTC CTC ACC GAC GCG GCG GAT TTC GAC CCG GGC       4707
Val Asp Lys Gly Gly Phe Leu Thr Asp Ala Ala Asp Phe Asp Pro Gly
            1550                    1555                    1560

TTC TTC GGC ATC ACG CCC CGC GAA GCG CTG GCG ATG GAC CCG CAG CAG       4755
Phe Phe Gly Ile Thr Pro Arg Glu Ala Leu Ala Met Asp Pro Gln Gln
        1565                    1570                    1575

CGC CTC ATG CTG GAG ACG GCG TGG GAG GCA GTG GAA CGC GCG GGC ATC       4803
Arg Leu Met Leu Glu Thr Ala Trp Glu Ala Val Glu Arg Ala Gly Ile
1580                    1585                    1590                1595

GAC CCC GAC GCC CTG CGA GGC ACC GAC ACC GTC TTC GTC GGC ATG           4851
Asp Pro Asp Ala Leu Arg Gly Thr Asp Thr Val Phe Val Gly Met
                1600                    1605                    1610

AAC GGC CAG TCC TAC ATG CAG CTG CTG GCC GGT GAG GCC GAA CGC GTC       4899
Asn Gly Gln Ser Tyr Met Gln Leu Leu Ala Gly Glu Ala Glu Arg Val
                    1615                    1620                    1625

GAC GGC TAC CAG GGC CTC GGA AAC TCC GCG AGC GTG CTC TCC GGG CGC       4947
Asp Gly Tyr Gln Gly Leu Gly Asn Ser Ala Ser Val Leu Ser Gly Arg
            1630                    1635                    1640

ATC GCC TAC ACC TTC GGC TGG GAG GGC CCG GCG CTG ACG GTG GAC ACC       4995
Ile Ala Tyr Thr Phe Gly Trp Glu Gly Pro Ala Leu Thr Val Asp Thr
        1645                    1650                    1655

GCG TGC TCG TCC TCG CTG GTC GGC ATC CAC CTC GCG ATG CAG GCG CTG       5043
Ala Cys Ser Ser Ser Leu Val Gly Ile His Leu Ala Met Gln Ala Leu
1660                    1665                    1670                1675

CGG CGC GGT GAG TGC TCC CTG GCG CTG GCC GGC GGC GTC ACG GTC ATG       5091
Arg Arg Gly Glu Cys Ser Leu Ala Leu Ala Gly Gly Val Thr Val Met
                1680                    1685                    1690

TCC GAC CCG TAC ACC TTC GTC GAC TTC AGC ACG CAG CGC GGG CTC GCC       5139
Ser Asp Pro Tyr Thr Phe Val Asp Phe Ser Thr Gln Arg Gly Leu Ala
                    1695                    1700                    1705

TCC GAC GGT CGC TGC AAG GCG TTC TCC GCG CGG GCC GAC GGC TTC GCG       5187
Ser Asp Gly Arg Cys Lys Ala Phe Ser Ala Arg Ala Asp Gly Phe Ala
            1710                    1715                    1720

CTG TCG GAA GGC GTC GCC GCG CTG GTG CTG GAG CCG CTT TCC CGG GCG       5235
Leu Ser Glu Gly Val Ala Ala Leu Val Leu Glu Pro Leu Ser Arg Ala
        1725                    1730                    1735

CGC GCC AAC GGG CAC CAG GTG CTG GCC GTG CTG CGC GGC AGC GCG GTC       5283
Arg Ala Asn Gly His Gln Val Leu Ala Val Leu Arg Gly Ser Ala Val
1740                    1745                    1750                1755

AAC CAG GAC GGT GCC AGC AAC GGT CTC GCC GCT CCC AAC GGC CCG TCG       5331
Asn Gln Asp Gly Ala Ser Asn Gly Leu Ala Ala Pro Asn Gly Pro Ser
                1760                    1765                    1770

CAG GAG CGG GTG ATC CGG CAG GCG CTC GCC GCT TCG GGC GTG CCG GCC       5379
Gln Glu Arg Val Ile Arg Gln Ala Leu Ala Ala Ser Gly Val Pro Ala
                    1775                    1780                    1785

GCG GAC GTC GAC GTC GTG GAG GCG CAC GGG ACG GGC ACC GAG CTC GGC       5427
```

```
Ala Asp Val Asp Val Val Glu Ala His Gly Thr Gly Thr Glu Leu Gly
        1790                1795                1800

GAC CCG ATC GAG GCC GGC GCG CTC ATC GCG ACC TAC GGC CAG GAC CGC      5475
Asp Pro Ile Glu Ala Gly Ala Leu Ile Ala Thr Tyr Gly Gln Asp Arg
        1805                1810                1815

GAC CGG CCG CTG CGG CTC GGC TCG GTG AAG ACC AAC ATC GGC CAC ACC      5523
Asp Arg Pro Leu Arg Leu Gly Ser Val Lys Thr Asn Ile Gly His Thr
1820                1825                1830                1835

CAG GCC GCG GCG GGC GCC GCG GGC GTG ATC AAG GTC GTG CTG GCG ATG      5571
Gln Ala Ala Ala Gly Ala Ala Gly Val Ile Lys Val Val Leu Ala Met
                1840                1845                1850

CGG CAC GGG ATG CTG CCC CGG TCG TTG CAC GCC GAC GAG CTG TCC CCG      5619
Arg His Gly Met Leu Pro Arg Ser Leu His Ala Asp Glu Leu Ser Pro
                    1855                1860                1865

CAC ATC GAC TGG GAG TCG GGG GCC GTG GAG GTG CTG CGC GAG GAG GTG      5667
His Ile Asp Trp Glu Ser Gly Ala Val Glu Val Leu Arg Glu Glu Val
        1870                1875                1880

CCG TGG CCG GCG GGT GAG CGC CCC CGG CGG GCG GGG GTG TCG TCC TTC      5715
Pro Trp Pro Ala Gly Glu Arg Pro Arg Arg Ala Gly Val Ser Ser Phe
            1885                1890                1895

GGC GTC AGC GGA ACC AAC GCG CAC GTG ATC GTC GAA GAG GCA CCA GCA      5763
Gly Val Ser Gly Thr Asn Ala His Val Ile Val Glu Glu Ala Pro Ala
1900                1905                1910                1915

GAG CAG GAG GCC GCC CGC ACC GAG CGC GGT CCG CTG CCG TTC GTG CTG      5811
Glu Gln Glu Ala Ala Arg Thr Glu Arg Gly Pro Leu Pro Phe Val Leu
                1920                1925                1930

TCC GGC CGC AGC GAA GCC GTG GTC GCG GCC CAG GCC GCG CTC GCC          5859
Ser Gly Arg Ser Glu Ala Val Val Ala Ala Gln Ala Arg Ala Leu Ala
            1935                1940                1945

GAG CAC CTG CGC GAC ACC CCG GAG CTC GGC CTG ACC GAC GCG GCG TGG      5907
Glu His Leu Arg Asp Thr Pro Glu Leu Gly Leu Thr Asp Ala Ala Trp
        1950                1955                1960

ACG CTC GCG ACC GGC AGG GCG CGG TTC GAC GTG CGA GCC GCC GTG CTC      5955
Thr Leu Ala Thr Gly Arg Ala Arg Phe Asp Val Arg Ala Ala Val Leu
        1965                1970                1975

GGC GAC GAC CGC GCG GGC GTG TGC GCG GAG CTG GAC GCG CTG GCC GAG      6003
Gly Asp Asp Arg Ala Gly Val Cys Ala Glu Leu Asp Ala Leu Ala Glu
1980                1985                1990                1995

GGC CGC CCG TCG GCC GAC GCC GTC GCG CCG GTG ACC TCC GCG CCG CGC      6051
Gly Arg Pro Ser Ala Asp Ala Val Ala Pro Val Thr Ser Ala Pro Arg
                2000                2005                2010

AAG CCG GTC CTG GTC TTC CCC GGC CAG GGC GCG CAG TGG GTC GGC ATG      6099
Lys Pro Val Leu Val Phe Pro Gly Gln Gly Ala Gln Trp Val Gly Met
                2015                2020                2025

GCA CGC GAT CTG CTG GAA TCC TCC GAG GTG TTC GCC GAG TCG ATG AGC      6147
Ala Arg Asp Leu Leu Glu Ser Ser Glu Val Phe Ala Glu Ser Met Ser
                2030                2035                2040

CGG TGC GCC GAG GCG CTC TCG CCG CAC ACC GAC TGG AAG TTG CTC GAC      6195
Arg Cys Ala Glu Ala Leu Ser Pro His Thr Asp Trp Lys Leu Leu Asp
        2045                2050                2055

GTC GTC CGC GGC GAC GGC GGT CCC GAC CCG CAC GAG CGC GTC GAC GTG      6243
Val Val Arg Gly Asp Gly Gly Pro Asp Pro His Glu Arg Val Asp Val
        2060                2065                2070                2075

CTC CAG CCG GTG CTC TTC TCG ATC ATG GTC TCG CTG GCC GAG CTG TGG      6291
Leu Gln Pro Val Leu Phe Ser Ile Met Val Ser Leu Ala Glu Leu Trp
                2080                2085                2090

CGC GCG CAC GGC GTG ACC CCG GCC GCC GTC GTC GGC CAC TCG CAG GGC      6339
Arg Ala His Gly Val Thr Pro Ala Ala Val Val Gly His Ser Gln Gly
                2095                2100                2105

GAG ATC GCC GCG GCG CAC GTG GCG GGC GCG CTG TCG CTG GAA GCC GCC      6387
```

-continued

| | | | | | | | | | | | | | | | | |
|---|---|---|---|---|---|---|---|---|---|---|---|---|---|---|---|---|
| | Glu | Ile | Ala | Ala | Ala | His | Val | Ala | Gly | Ala | Leu | Ser | Leu | Glu | Ala | Ala |
| | | | 2110 | | | | 2115 | | | | | 2120 | | | | |

```
GCG  AAG  GTG  GTG  GCC  CTG  CGC  AGC  CAG  GTG  TTG  CGC  GAG  CTC  GAC  GAC    6435
Ala  Lys  Val  Val  Ala  Leu  Arg  Ser  Gln  Val  Leu  Arg  Glu  Leu  Asp  Asp
     2125                     2130                         2135

CAG  GGC  GGC  ATG  GTG  TCG  GTC  GGC  GCG  TCC  CGC  GAC  GAG  CTG  GAG  ACC    6483
Gln  Gly  Gly  Met  Val  Ser  Val  Gly  Ala  Ser  Arg  Asp  Glu  Leu  Glu  Thr
2140                          2145                         2150                 2155

GTG  CTC  GCG  CGC  TGG  GAC  GGC  CGT  GTC  GCG  GTG  GCC  GCC  GTG  AAC  GGG    6531
Val  Leu  Ala  Arg  Trp  Asp  Gly  Arg  Val  Ala  Val  Ala  Ala  Val  Asn  Gly
                    2160                     2165                     2170

CCT  GGC  ACC  AGC  GTC  GTT  GCC  GGG  CCG  ACC  GCG  GAG  CTG  GAC  GAG  TTC    6579
Pro  Gly  Thr  Ser  Val  Val  Ala  Gly  Pro  Thr  Ala  Glu  Leu  Asp  Glu  Phe
               2175                     2180                     2185

TTC  GCC  GAG  GCC  GAG  GCG  CGG  GAG  ATG  AAG  CCG  CGC  CGG  ATC  GCC  GTG    6627
Phe  Ala  Glu  Ala  Glu  Ala  Arg  Glu  Met  Lys  Pro  Arg  Arg  Ile  Ala  Val
          2190                     2195                     2200

CGC  TAC  GCC  TCC  CAC  TCC  CCG  GAG  GTG  GCG  CGC  ATC  GAG  GAC  CGG  CTC    6675
Arg  Tyr  Ala  Ser  His  Ser  Pro  Glu  Val  Ala  Arg  Ile  Glu  Asp  Arg  Leu
     2205                     2210                     2215

GCG  GCC  GAG  CTG  GGC  ACC  ATC  ACC  GCC  GTG  CGG  GGC  TCG  GTG  CCG  CTG    6723
Ala  Ala  Glu  Leu  Gly  Thr  Ile  Thr  Ala  Val  Arg  Gly  Ser  Val  Pro  Leu
2220                          2225                     2230                     2235

CAC  TCC  ACG  GTG  ACC  GGC  GAG  GTC  ATC  GAC  ACC  TCC  GCG  ATG  GAC  GCC    6771
His  Ser  Thr  Val  Thr  Gly  Glu  Val  Ile  Asp  Thr  Ser  Ala  Met  Asp  Ala
                    2240                     2245                     2250

TCC  TAC  TGG  TAC  CGC  AAC  CTG  CGC  CGA  CCA  GTG  CTC  TTC  GAG  CAG  GCG    6819
Ser  Tyr  Trp  Tyr  Arg  Asn  Leu  Arg  Arg  Pro  Val  Leu  Phe  Glu  Gln  Ala
               2255                     2260                     2265

GTG  CGC  GGT  CTG  GTC  GAG  CAG  GGC  TTC  GAC  ACC  TTC  GTC  GAG  GTG  AGC    6867
Val  Arg  Gly  Leu  Val  Glu  Gln  Gly  Phe  Asp  Thr  Phe  Val  Glu  Val  Ser
          2270                     2275                     2280

CCG  CAC  CCG  GTG  CTG  CTG  ATG  GCG  GTC  GAG  GAG  ACC  GCC  GAG  CAC  GCG    6915
Pro  His  Pro  Val  Leu  Leu  Met  Ala  Val  Glu  Glu  Thr  Ala  Glu  His  Ala
     2285                     2290                     2295

GGC  GCG  GAA  GTC  ACC  TGC  GTG  CCG  ACG  CTG  CGC  CGC  GAG  CAG  AGC  GGA    6963
Gly  Ala  Glu  Val  Thr  Cys  Val  Pro  Thr  Leu  Arg  Arg  Glu  Gln  Ser  Gly
2300                          2305                     2310                     2315

CCG  CAC  GAG  TTC  CTG  CGC  AAC  CTG  CTG  CGG  GCT  CAC  GTG  CAC  GGC  GTC    7011
Pro  His  Glu  Phe  Leu  Arg  Asn  Leu  Leu  Arg  Ala  His  Val  His  Gly  Val
               2320                     2325                     2330

GGC  GCC  GAC  CTG  CGT  CCG  GCG  GTG  GCC  GGG  GGA  CGG  CCG  GCC  GAG  CTG    7059
Gly  Ala  Asp  Leu  Arg  Pro  Ala  Val  Ala  Gly  Gly  Arg  Pro  Ala  Glu  Leu
                    2335                     2340                     2345

CCC  ACC  TAC  CCG  TTC  GAA  CAC  CAG  CGC  TTC  TGG  CCG  CGG  CCG  CAC  CGG    7107
Pro  Thr  Tyr  Pro  Phe  Glu  His  Gln  Arg  Phe  Trp  Pro  Arg  Pro  His  Arg
          2350                     2355                     2360

CCC  GCC  GAC  GTC  TCG  GCG  CTG  GGC  GTG  CGC  GGC  GCG  GAG  CAC  CCG  CTG    7155
Pro  Ala  Asp  Val  Ser  Ala  Leu  Gly  Val  Arg  Gly  Ala  Glu  His  Pro  Leu
     2365                     2370                     2375

CTG  CTC  GCC  GCG  GTC  GAC  GTG  CCG  GGC  CAC  GGC  GGT  GCG  GTG  TTC  ACC    7203
Leu  Leu  Ala  Ala  Val  Asp  Val  Pro  Gly  His  Gly  Gly  Ala  Val  Phe  Thr
2380                          2385                     2390                     2395

GGA  AGG  CTT  TCC  ACC  GAC  GAG  CAG  CCG  TGG  CTG  GCC  GAA  CAC  GTC  GTG    7251
Gly  Arg  Leu  Ser  Thr  Asp  Glu  Gln  Pro  Trp  Leu  Ala  Glu  His  Val  Val
               2400                     2405                     2410

GGC  GGC  CGG  ACG  CTG  GTG  CCG  GGC  AGC  GTC  CTG  GTC  GAT  CTC  GCG  CTC    7299
Gly  Gly  Arg  Thr  Leu  Val  Pro  Gly  Ser  Val  Leu  Val  Asp  Leu  Ala  Leu
                    2415                     2420                     2425

GCC  GCG  GGT  GAG  GAC  GTC  GGG  CTG  CCG  GTC  CTG  GAG  GAA  CTG  GTG  TTG    7347
```

```
Ala  Ala  Gly  Glu  Asp  Val  Gly  Leu  Pro  Val  Leu  Glu  Glu  Leu  Val  Leu
          2430                2435                2440

CAA  CGG  CCG  CTG  GTG  CTG  GCC  GGG  GCG  GGG  GCG  CTG  CTG  CGC  ATG  TCG     7395
Gln  Arg  Pro  Leu  Val  Leu  Ala  Gly  Ala  Gly  Ala  Leu  Leu  Arg  Met  Ser
     2445                2450                2455

GTC  GGC  GCG  CCC  GAC  GAG  TCG  GGG  CGG  CGG  ACG  ATC  GAC  GTC  CAC  GCC     7443
Val  Gly  Ala  Pro  Asp  Glu  Ser  Gly  Arg  Arg  Thr  Ile  Asp  Val  His  Ala
2460                2465                2470                               2475

GCC  GAA  GAC  GTG  GCC  GAC  CTC  GCC  GAC  GCG  CAG  TGG  TCG  CAG  CAC  GCC     7491
Ala  Glu  Asp  Val  Ala  Asp  Leu  Ala  Asp  Ala  Gln  Trp  Ser  Gln  His  Ala
               2480                2485                2490

ACC  GGG  ACG  CTC  GCG  CAG  GGC  GTC  GCC  GCG  GGT  CCG  AGG  GAT  ACC  GAG     7539
Thr  Gly  Thr  Leu  Ala  Gln  Gly  Val  Ala  Ala  Gly  Pro  Arg  Asp  Thr  Glu
                    2495                2500                2505

CAG  TGG  CCG  CCG  GAG  GAC  GCC  GTC  CGC  ATC  CCG  CTC  GAC  GAC  CAC  TAC     7587
Gln  Trp  Pro  Pro  Glu  Asp  Ala  Val  Arg  Ile  Pro  Leu  Asp  Asp  His  Tyr
               2510                2515                2520

GAC  GGC  CTC  GCC  GAG  CAG  GGC  TAC  GAG  TAC  GGA  CCG  TCG  TTC  CAG  GCC     7635
Asp  Gly  Leu  Ala  Glu  Gln  Gly  Tyr  Glu  Tyr  Gly  Pro  Ser  Phe  Gln  Ala
          2525                2530                2535

CTG  CGA  GCC  GCG  TGG  CGC  AAG  GAC  GAC  TCG  GTC  TAC  GCC  GAG  GTG  TCC     7683
Leu  Arg  Ala  Ala  Trp  Arg  Lys  Asp  Asp  Ser  Val  Tyr  Ala  Glu  Val  Ser
2540                2545                2550                               2555

ATC  GCG  GCG  GAC  GAG  GAA  GGT  TAC  GCG  TTC  CAC  CCG  GTG  CTG  CTC  GAC     7731
Ile  Ala  Ala  Asp  Glu  Glu  Gly  Tyr  Ala  Phe  His  Pro  Val  Leu  Leu  Asp
               2560                2565                2570

GCC  GTG  GCG  CAG  ACG  CTC  AGC  CTG  GGC  GCC  CTC  GGC  GAG  CCG  GGC  GGG     7779
Ala  Val  Ala  Gln  Thr  Leu  Ser  Leu  Gly  Ala  Leu  Gly  Glu  Pro  Gly  Gly
                    2575                2580                2585

GGA  AAG  CTG  CCG  TTC  GCG  TGG  AAC  ACC  GTG  ACC  CTG  CAC  GCC  TCC  GGG     7827
Gly  Lys  Leu  Pro  Phe  Ala  Trp  Asn  Thr  Val  Thr  Leu  His  Ala  Ser  Gly
          2590                2595                2600

GCG  ACC  TCG  GTG  CGG  GTC  GTG  GCG  ACG  CCC  GCC  GGG  GCG  GAC  GCG  ATG     7875
Ala  Thr  Ser  Val  Arg  Val  Val  Ala  Thr  Pro  Ala  Gly  Ala  Asp  Ala  Met
     2605                2610                2615

GCC  CTG  CGG  GTC  ACC  GAC  CCG  GCA  GGC  CAC  CTG  GTC  GCC  ACG  GTC  GAC     7923
Ala  Leu  Arg  Val  Thr  Asp  Pro  Ala  Gly  His  Leu  Val  Ala  Thr  Val  Asp
2620                2625                2630                               2635

TCG  CTG  GTC  GTC  CGC  AGC  ACC  GGG  GAG  AAG  TGG  GAG  CAG  CCC  GAA  CCG     7971
Ser  Leu  Val  Val  Arg  Ser  Thr  Gly  Glu  Lys  Trp  Glu  Gln  Pro  Glu  Pro
               2640                2645                2650

CGC  GGT  GGC  GAG  GGC  GAG  CTG  CAC  GCT  CTG  GAC  TGG  GGA  CGG  CTA  GCC     8019
Arg  Gly  Gly  Glu  Gly  Glu  Leu  His  Ala  Leu  Asp  Trp  Gly  Arg  Leu  Ala
          2655                2660                2665

GAG  CCC  GGC  TCG  ACC  GGT  CGT  GTG  GTC  GCG  GCC  GAT  GCC  TCG  GAC  CTC     8067
Glu  Pro  Gly  Ser  Thr  Gly  Arg  Val  Val  Ala  Ala  Asp  Ala  Ser  Asp  Leu
     2670                2675                2680

GAC  GCC  GTC  CTG  CGG  TCC  GGT  GAA  CCC  GAA  CCC  GAC  GCG  GTC  CTG  GTC     8115
Asp  Ala  Val  Leu  Arg  Ser  Gly  Glu  Pro  Glu  Pro  Asp  Ala  Val  Leu  Val
2685                2690                2695

CGC  TAC  GAA  CCC  GAA  GGC  GAC  GAC  CCC  CGC  GCC  GCG  GCC  CGC  CAC  GGC     8163
Arg  Tyr  Glu  Pro  Glu  Gly  Asp  Asp  Pro  Arg  Ala  Ala  Ala  Arg  His  Gly
2700                2705                2710                               2715

GTC  CTC  TGG  GCC  GCC  GCG  CTC  GTG  CGC  CGC  TGG  CTC  GAA  CAG  GAG  GAG     8211
Val  Leu  Trp  Ala  Ala  Ala  Leu  Val  Arg  Arg  Trp  Leu  Glu  Gln  Glu  Glu
          2720                2725                2730

CTG  CCG  GGC  GCG  ACG  CTG  GTC  ATC  GCC  ACG  TCC  GGC  GCG  GTC  ACC  GTG     8259
Leu  Pro  Gly  Ala  Thr  Leu  Val  Ile  Ala  Thr  Ser  Gly  Ala  Val  Thr  Val
               2735                2740                2745

TCC  GAC  GAC  GAC  AGC  GTT  CCC  GAA  CCC  GGC  GCC  GCC  GCG  ATG  TGG  GGC     8307
```

```
Ser Asp Asp Asp Ser Val Pro Glu Pro Gly Ala Ala Ala Met Trp Gly
        2750            2755            2760

GTG ATC CGC TGT GCG CAG GCC GAG TCG CCG GAC CGG TTC GTG CTC CTC    8355
Val Ile Arg Cys Ala Gln Ala Glu Ser Pro Asp Arg Phe Val Leu Leu
    2765            2770            2775

GAC ACC GAC GCG GAA CCT GGG ATG CTG CCT GCG GTT CCG GAC AAC CCG    8403
Asp Thr Asp Ala Glu Pro Gly Met Leu Pro Ala Val Pro Asp Asn Pro
2780            2785            2790            2795

CAG CTC GCG TTG CGC GGC GAC GAC GTC TTC GTG CCG CGC CTC TCG CCG    8451
Gln Leu Ala Leu Arg Gly Asp Asp Val Phe Val Pro Arg Leu Ser Pro
            2800            2805            2810

CTC GCA CCT TCC GCG CTG ACG CTT CCG GCA GGC ACC CAA CGT CTC GTG    8499
Leu Ala Pro Ser Ala Leu Thr Leu Pro Ala Gly Thr Gln Arg Leu Val
        2815            2820            2825

CCG GGT GAC GGG GCG ATC GAC TCC GTG GCC TTC GAG CCC GCA CCC GAC    8547
Pro Gly Asp Gly Ala Ile Asp Ser Val Ala Phe Glu Pro Ala Pro Asp
    2830            2835            2840

GTC GAG CAG CCG CTC CGG GCG GGC GAG GTC CGG GTG GAC GTG CGC GCC    8595
Val Glu Gln Pro Leu Arg Ala Gly Glu Val Arg Val Asp Val Arg Ala
    2845            2850            2855

ACC GGA GTC AAC TTC CGC GAC GTC CTC CTC GCA CTC GGC ATG TAT CCG    8643
Thr Gly Val Asn Phe Arg Asp Val Leu Leu Ala Leu Gly Met Tyr Pro
2860            2865            2870            2875

CAG AAG GCG GAC ATG GGC ACC GAG GCC GCC GGT GTC GTC ACG GCG GTC    8691
Gln Lys Ala Asp Met Gly Thr Glu Ala Ala Gly Val Val Thr Ala Val
            2880            2885            2890

GGA CCG GAC GTG GAC GCC TTC GCG CCG GGA GAC CGG GTG CTC GGC CTG    8739
Gly Pro Asp Val Asp Ala Phe Ala Pro Gly Asp Arg Val Leu Gly Leu
        2895            2900            2905

TTC CAG GGA GCC TTC GCG CCG ATC GCG GTC ACC GAT CAC CGG CTC CTC    8787
Phe Gln Gly Ala Phe Ala Pro Ile Ala Val Thr Asp His Arg Leu Leu
    2910            2915            2920

GCA CGA GTG CCG GAC GGC TGG AGC GAC GCC GAC GCC GCG GCC GTG CCC    8835
Ala Arg Val Pro Asp Gly Trp Ser Asp Ala Asp Ala Ala Ala Val Pro
2925            2930            2935

ATC GCC TAC ACC ACG GCG CAT TAC GCG CTG CAC GAT CTC GCG GGG CTG    8883
Ile Ala Tyr Thr Thr Ala His Tyr Ala Leu His Asp Leu Ala Gly Leu
2940            2945            2950            2955

CGC GCG GGT CAG TCG GTG CTC ATC CAC GCA GCG GCA GGC GGT GTC GGC    8931
Arg Ala Gly Gln Ser Val Leu Ile His Ala Ala Ala Gly Gly Val Gly
            2960            2965            2970

ATG GCG GCC GTC GCG CTG GCC CGC CGA GCG GGG GCG GAG GTG TTG GCC    8979
Met Ala Ala Val Ala Leu Ala Arg Arg Ala Gly Ala Glu Val Leu Ala
        2975            2980            2985

ACC GCC GGC CCG GCC AAG CAC GGG ACG CTG CGG GCG CTC GGT CTC GAC    9027
Thr Ala Gly Pro Ala Lys His Gly Thr Leu Arg Ala Leu Gly Leu Asp
            2990            2995            3000

GAC GAG CAC ATC GCT TCC TCC CGG GAG ACC GGT TTC GCC CGG AAG TTC    9075
Asp Glu His Ile Ala Ser Ser Arg Glu Thr Gly Phe Ala Arg Lys Phe
        3005            3010            3015

CGG GAG CGC ACC GGA GGC CGC GGC GTG GAC GTG GTG CTC AAC TCG CTC    9123
Arg Glu Arg Thr Gly Gly Arg Gly Val Asp Val Val Leu Asn Ser Leu
3020            3025            3030            3035

ACC GGG GAA CTG CTC GAC GAG TCC GCG GAT CTG CTC GCC GAG GAC GGC    9171
Thr Gly Glu Leu Leu Asp Glu Ser Ala Asp Leu Leu Ala Glu Asp Gly
            3040            3045            3050

GTC TTC GTC GAG ATG GGC AAG ACC GAC CTG CGG GAC GCC GGG GAC TTC    9219
Val Phe Val Glu Met Gly Lys Thr Asp Leu Arg Asp Ala Gly Asp Phe
    3055            3060            3065

CGG GGC CGA TAC GCC CCG TTC GAC CTC GGC GAG GCG GGT GAC GAC CGG    9267
```

```
Arg  Gly  Arg  Tyr  Ala  Pro  Phe  Asp  Leu  Gly  Glu  Ala  Gly  Asp  Asp  Arg
          3070                3075                3080

CTC  GGG  GAG  ATC  CTG  CGC  GAG  GTC  GTC  GGC  CTG  CTG  GGC  GCC  GGG  GAG        9315
Leu  Gly  Glu  Ile  Leu  Arg  Glu  Val  Val  Gly  Leu  Leu  Gly  Ala  Gly  Glu
     3085                3090                3095

CTC  GAC  CGG  CTC  CCG  GTA  TCG  GCG  TGG  GAG  CTG  GGA  TCC  GCG  CCC  GCG        9363
Leu  Asp  Arg  Leu  Pro  Val  Ser  Ala  Trp  Glu  Leu  Gly  Ser  Ala  Pro  Ala
3100                3105                3110                3115

GCG  TTG  CAG  CAC  ATG  AGC  CGG  GGC  AGG  CAC  GTC  GGC  AAG  CTC  GTG  CTG        9411
Ala  Leu  Gln  His  Met  Ser  Arg  Gly  Arg  His  Val  Gly  Lys  Leu  Val  Leu
3120                3125                3130

ACC  CAG  CCC  GCG  CCG  GTG  GAC  CCG  GAC  GGC  ACG  GTG  CTG  ATC  ACG  GGT        9459
Thr  Gln  Pro  Ala  Pro  Val  Asp  Pro  Asp  Gly  Thr  Val  Leu  Ile  Thr  Gly
               3135                3140                3145

GGC  ACC  GGC  ACG  CTC  GGA  CGG  CTG  CTC  GCG  CGC  CAC  CTC  GTC  ACC  GAG        9507
Gly  Thr  Gly  Thr  Leu  Gly  Arg  Leu  Leu  Ala  Arg  His  Leu  Val  Thr  Glu
     3150                3155                3160

CAC  GGC  GTG  CGG  CAC  CTG  CTG  CTG  GTC  AGC  AGG  CGC  GGC  GCG  GAC  GCG        9555
His  Gly  Val  Arg  His  Leu  Leu  Leu  Val  Ser  Arg  Arg  Gly  Ala  Asp  Ala
          3165                3170                3175

CCG  GGT  TCC  GAC  GAG  CTG  CGC  GCG  GAG  ATC  GAG  GAC  TTG  GGC  GCG  TCC        9603
Pro  Gly  Ser  Asp  Glu  Leu  Arg  Ala  Glu  Ile  Glu  Asp  Leu  Gly  Ala  Ser
3180                3185                3190                3195

GCG  GAG  ATC  GCG  GCT  TGC  GAC  ACC  GCC  GAC  CGC  GAC  GCG  CTT  TCG  GCG        9651
Ala  Glu  Ile  Ala  Ala  Cys  Asp  Thr  Ala  Asp  Arg  Asp  Ala  Leu  Ser  Ala
               3200                3205                3210

CTG  CTG  GAC  GGG  CTG  CCC  CGG  CCG  CTG  ACC  GGT  GTC  GTG  CAC  GCG  GCG        9699
Leu  Leu  Asp  Gly  Leu  Pro  Arg  Pro  Leu  Thr  Gly  Val  Val  His  Ala  Ala
     3215                3220                3225

GGT  GTG  CTG  GCC  GAC  GGG  CTG  GTC  ACC  TCC  ATC  GAC  GAG  CCG  GCG  GTG        9747
Gly  Val  Leu  Ala  Asp  Gly  Leu  Val  Thr  Ser  Ile  Asp  Glu  Pro  Ala  Val
3230                3235                3240

GAG  CAG  GTG  CTG  CGC  GCC  AAG  GTC  GAC  GCG  GCG  TGG  AAC  CTG  CAC  GAG        9795
Glu  Gln  Val  Leu  Arg  Ala  Lys  Val  Asp  Ala  Ala  Trp  Asn  Leu  His  Glu
          3245                3250                3255

CTG  ACC  GCG  AAC  ACC  GGT  CTG  AGC  TTC  TTC  GTG  CTG  TTC  TCG  TCC  GCG        9843
Leu  Thr  Ala  Asn  Thr  Gly  Leu  Ser  Phe  Phe  Val  Leu  Phe  Ser  Ser  Ala
3260                3265                3270                3275

GCG  TCG  GTG  CTA  GCC  GGC  CCG  GGG  CAG  GGC  GTG  TAC  GCG  GCC  GCG  AAC        9891
Ala  Ser  Val  Leu  Ala  Gly  Pro  Gly  Gln  Gly  Val  Tyr  Ala  Ala  Ala  Asn
     3280                3285                3290

GAG  TCG  CTC  AAC  GCG  CTG  GCT  GCC  CTC  CGG  AGG  ACG  CGC  GGC  CTT  CCC        9939
Glu  Ser  Leu  Asn  Ala  Leu  Ala  Ala  Leu  Arg  Arg  Thr  Arg  Gly  Leu  Pro
               3295                3300                3305

GCG  AAG  GCG  CTC  GGA  TGG  GGA  CTG  TGG  GCG  CAG  GCC  AGC  GAG  ATG  ACC        9987
Ala  Lys  Ala  Leu  Gly  Trp  Gly  Leu  Trp  Ala  Gln  Ala  Ser  Glu  Met  Thr
     3310                3315                3320

AGC  GGA  CTC  GGC  GAC  CGC  ATC  GCC  CGG  ACC  GGG  GTC  GCC  GCG  CTG  CCG       10035
Ser  Gly  Leu  Gly  Asp  Arg  Ile  Ala  Arg  Thr  Gly  Val  Ala  Ala  Leu  Pro
3325                3330                3335

ACC  GAG  CGG  GCG  CTC  GCA  CTG  TTC  GAC  AGC  GCC  CTG  CGC  CGC  GGC  GGT       10083
Thr  Glu  Arg  Ala  Leu  Ala  Leu  Phe  Asp  Ser  Ala  Leu  Arg  Arg  Gly  Gly
3340                3345                3350                3355

GAG  GTC  GTG  TTC  CCG  CTG  TCC  ATC  AAC  CGT  TCC  GCG  CTG  CGC  AGG  GCC       10131
Glu  Val  Val  Phe  Pro  Leu  Ser  Ile  Asn  Arg  Ser  Ala  Leu  Arg  Arg  Ala
          3360                3365                3370

GAG  TTC  GTG  CCG  GAG  GTC  CTG  CGC  GGC  ATG  GTC  AGG  GCG  AAG  CTG  CGC       10179
Glu  Phe  Val  Pro  Glu  Val  Leu  Arg  Gly  Met  Val  Arg  Ala  Lys  Leu  Arg
               3375                3380                3385

GCC  GCC  GGG  CAG  GCC  GAG  GCG  GCA  GGG  CCG  AAC  GTG  GTC  GAC  CGG  CTC       10227
```

```
                Ala  Ala  Gly  Gln  Ala  Glu  Ala  Ala  Gly  Pro  Asn  Val  Val  Asp  Arg  Leu
                          3390                3395                     3400

GCC  GGT  CGG  TCC  GAG  TCC  GAC  CAG  GTC  GCC  GGG  CTG  GCC  GAA  CTG  GTG           10275
Ala  Gly  Arg  Ser  Glu  Ser  Asp  Gln  Val  Ala  Gly  Leu  Ala  Glu  Leu  Val
3405                     3410                     3415

CGT  TCA  CAC  GCG  GCG  GCG  GTC  TCC  GGG  TAC  GGC  TCG  GCC  GAC  CAG  CTC           10323
Arg  Ser  His  Ala  Ala  Ala  Val  Ser  Gly  Tyr  Gly  Ser  Ala  Asp  Gln  Leu
3420                     3425                     3430                     3435

CCC  GAG  CGC  AAG  GCG  TTC  AAG  GAC  CTC  GGT  TTC  GAC  TCG  CTG  GCC  GCG           10371
Pro  Glu  Arg  Lys  Ala  Phe  Lys  Asp  Leu  Gly  Phe  Asp  Ser  Leu  Ala  Ala
                    3440                3445                     3450

GTG  GAG  CTG  CGC  AAC  CGC  CTC  GGT  ACC  GCG  ACC  GGC  GTG  CGG  CTG  CCC           10419
Val  Glu  Leu  Arg  Asn  Arg  Leu  Gly  Thr  Ala  Thr  Gly  Val  Arg  Leu  Pro
                    3455                3460                     3465

AGC  ACG  TTG  GTG  TTC  GAC  CAC  CCG  ACT  CCG  CTG  GCG  GTG  GCC  GAA  CAC           10467
Ser  Thr  Leu  Val  Phe  Asp  His  Pro  Thr  Pro  Leu  Ala  Val  Ala  Glu  His
                    3470                3475                     3480

CTG  CGG  GAC  AGG  CTG  TTC  GCG  GCC  TCA  CCG  GCG  GTG  GAC  ATC  GGC  GAC           10515
Leu  Arg  Asp  Arg  Leu  Phe  Ala  Ala  Ser  Pro  Ala  Val  Asp  Ile  Gly  Asp
                    3485                3490                     3495

CGG  CTG  GAC  GAG  CTG  GAG  AAG  GCG  CTC  GAA  GCC  CTG  TCC  GCC  GAG  GAC           10563
Arg  Leu  Asp  Glu  Leu  Glu  Lys  Ala  Leu  Glu  Ala  Leu  Ser  Ala  Glu  Asp
3500                     3505                     3510                     3515

GGG  CAC  GAC  GAC  GTG  GGC  CAG  CGC  CTG  GAG  TCG  CTG  CTG  CGC  CGG  TGG           10611
Gly  His  Asp  Asp  Val  Gly  Gln  Arg  Leu  Glu  Ser  Leu  Leu  Arg  Arg  Trp
                    3520                3525                     3530

AAC  AGC  AGG  CGG  GCG  GAC  GCC  CCG  AGC  ACG  TCC  GCG  ATC  AGC  GAG  GAC           10659
Asn  Ser  Arg  Arg  Ala  Asp  Ala  Pro  Ser  Thr  Ser  Ala  Ile  Ser  Glu  Asp
                    3535                3540                     3545

GCC  AGT  GAC  GAC  GAG  CTG  TTC  TCG  ATG  CTC  GAC  CAG  CGG  TTC  GGC  GGG           10707
Ala  Ser  Asp  Asp  Glu  Leu  Phe  Ser  Met  Leu  Asp  Gln  Arg  Phe  Gly  Gly
                    3550                3555                     3560

GGA  GAG  GAC  CTG  TAGATG  AGC  GGT  GAC  AAC  GGC  ATG  ACC  GAG  GAA  AAG            10755
Gly  Glu  Asp  Leu          Met  Ser  Gly  Asp  Asn  Gly  Met  Thr  Glu  Glu  Lys
                    3565    1                5                              10

CTC  CGG  CGC  TAC  CTC  AAG  CGC  ACC  GTC  ACC  GAG  CTC  GAC  TCG  GTG  ACC           10803
Leu  Arg  Arg  Tyr  Leu  Lys  Arg  Thr  Val  Thr  Glu  Leu  Asp  Ser  Val  Thr
                    15                  20                       25

GCG  CGC  CTG  CGT  GAA  GTC  GAG  CAC  CGG  GCC  GGT  GAG  CCG  ATC  GCG  ATC           10851
Ala  Arg  Leu  Arg  Glu  Val  Glu  His  Arg  Ala  Gly  Glu  Pro  Ile  Ala  Ile
               30                   35                       40

GTC  GGC  ATG  GCG  TGC  CGG  TTC  CCC  GGC  GAC  GTG  GAC  TCG  CCG  GAG  TCG           10899
Val  Gly  Met  Ala  Cys  Arg  Phe  Pro  Gly  Asp  Val  Asp  Ser  Pro  Glu  Ser
               45                   50                       55

TTC  TGG  GAG  TTC  GTG  TCC  GGC  GGC  GGG  GAC  GCC  ATC  GCG  GAG  GCC  CCC           10947
Phe  Trp  Glu  Phe  Val  Ser  Gly  Gly  Gly  Asp  Ala  Ile  Ala  Glu  Ala  Pro
60                       65                       70                       75

GCC  GAC  CGC  GGC  TGG  GAG  CCG  GAC  CCC  GAC  GCG  CGG  CTG  GGC  GGG  ATG           10995
Ala  Asp  Arg  Gly  Trp  Glu  Pro  Asp  Pro  Asp  Ala  Arg  Leu  Gly  Gly  Met
                         80                       85                       90

CTC  GCG  GCC  GCG  GGC  GAC  TTC  GAC  GCG  GGC  TTC  TTC  GGG  ATC  TCG  CCG           11043
Leu  Ala  Ala  Ala  Gly  Asp  Phe  Asp  Ala  Gly  Phe  Phe  Gly  Ile  Ser  Pro
                    95                  100                      105

CGC  GAG  GCG  CTG  GCG  ATG  GAC  CCG  CAG  CAG  CGG  ATC  ATG  CTG  GAG  ATC           11091
Arg  Glu  Ala  Leu  Ala  Met  Asp  Pro  Gln  Gln  Arg  Ile  Met  Leu  Glu  Ile
                    110                 115                      120

TCG  TGG  GAG  GCG  CTG  GAG  CGC  GCC  GGC  CAC  GAT  CCG  GTG  TCC  CTG  CGC           11139
Ser  Trp  Glu  Ala  Leu  Glu  Arg  Ala  Gly  His  Asp  Pro  Val  Ser  Leu  Arg
125                      130                      135

GGC  AGC  GCG  ACC  GGG  GTG  TTC  ACC  GGT  GTC  GGC  ACC  GTG  GAC  TAC  GGC           11187
```

```
Gly Ser Ala Thr Gly Val Phe Thr Gly Val Gly Thr Val Asp Tyr Gly
140                 145                 150                 155

CCG CGA CCC GAC GAG GCC CCG GAC GAG GTC CTG GGC TAC GTC GGC ACC    11235
Pro Arg Pro Asp Glu Ala Pro Asp Glu Val Leu Gly Tyr Val Gly Thr
                        160                 165                 170

GGC ACC GCC TCC AGC GTC GCC TCC GGC CGG GTC GCC TAC TGC CTG GGC    11283
Gly Thr Ala Ser Ser Val Ala Ser Gly Arg Val Ala Tyr Cys Leu Gly
            175                 180                 185

CTG GAA GGC CCG GCG ATG ACC GTC GAC ACC GCC TGT TCC TCC GGG CTC    11331
Leu Glu Gly Pro Ala Met Thr Val Asp Thr Ala Cys Ser Ser Gly Leu
        190                 195                 200

ACC GCC CTG CAC CTG GCG ATG GAG TCG CTG CGC GGG GAC GAG TGC GGC    11379
Thr Ala Leu His Leu Ala Met Glu Ser Leu Arg Arg Asp Glu Cys Gly
    205                 210                 215

CTG GCG CTG GCC GGC GGC GTG ACG GTG ATG AGC AGT CCC GGG GCG TTC    11427
Leu Ala Leu Ala Gly Gly Val Thr Val Met Ser Ser Pro Gly Ala Phe
220                 225                 230                 235

ACC GAG TTC CGC AGC CAG GGC GGG CTC GCC GCC GAC GGC CGC TGC AAG    11475
Thr Glu Phe Arg Ser Gln Gly Gly Leu Ala Ala Asp Gly Arg Cys Lys
                240                 245                 250

CCG TTC TCG AAG GCC GCC GAC GGG TTC GGC CTG GCC GAG GGT GCC GGG    11523
Pro Phe Ser Lys Ala Ala Asp Gly Phe Gly Leu Ala Glu Gly Ala Gly
            255                 260                 265

GTC CTG GTG CTG CAA CGG CTG TCG GCC GCG CGG CGG GAG GGC AGA CCG    11571
Val Leu Val Leu Gln Arg Leu Ser Ala Ala Arg Arg Glu Gly Arg Pro
        270                 275                 280

GTG CTG GCC GTG CTG CGG GGC TCG GCG GTC AAC CAG GAC GGC GCC AGC    11619
Val Leu Ala Val Leu Arg Gly Ser Ala Val Asn Gln Asp Gly Ala Ser
    285                 290                 295

AAC GGG CTG ACC GCG CCG AGC GGA CCC GCG CAG CAG CGG GTC ATC CGC    11667
Asn Gly Leu Thr Ala Pro Ser Gly Pro Ala Gln Gln Arg Val Ile Arg
300                 305                 310                 315

CGG GCG CTG GAG AAC GCC GGT GTC CGG GCG GGC GAC GTC GAC TAC GTG    11715
Arg Ala Leu Glu Asn Ala Gly Val Arg Ala Gly Asp Val Asp Tyr Val
                320                 325                 330

GAG GCC CAC GGC ACC GGC ACC AGG CTG GGC GAC CCC ATC GAG GTG CAC    11763
Glu Ala His Gly Thr Gly Thr Arg Leu Gly Asp Pro Ile Glu Val His
            335                 340                 345

GCG CTG CTC TCG ACC TAC GGC GCG GAA CGC GAC CCG GAC GAT CCA CTG    11811
Ala Leu Leu Ser Thr Tyr Gly Ala Glu Arg Asp Pro Asp Asp Pro Leu
        350                 355                 360

TGG ATC GGT TCG GTC AAG TCC AAC ATT GGC CAC ACC CAG GCC GCC GCC    11859
Trp Ile Gly Ser Val Lys Ser Asn Ile Gly His Thr Gln Ala Ala Ala
    365                 370                 375

GGC GTC GCC GGG GTG ATG AAG GCG GTG CTG GCG CTG CGG CAC GGC GAG    11907
Gly Val Ala Gly Val Met Lys Ala Val Leu Ala Leu Arg His Gly Glu
380                 385                 390                 395

ATG CCG CGC ACG CTG CAC TTC GAC GAG CCC TCG CCG CAG ATC GAG TGG    11955
Met Pro Arg Thr Leu His Phe Asp Glu Pro Ser Pro Gln Ile Glu Trp
                400                 405                 410

GAC CTG GGC GCG GTG TCG GTG GTG TCG CAG GCG CGG TCG TGG CCC GCC    12003
Asp Leu Gly Ala Val Ser Val Val Ser Gln Ala Arg Ser Trp Pro Ala
            415                 420                 425

GGC GAG AGG CCC CGC AGG GCG GGC GTC TCC TCG TTC GGC ATC AGC GGC    12051
Gly Glu Arg Pro Arg Arg Ala Gly Val Ser Ser Phe Gly Ile Ser Gly
        430                 435                 440

ACC AAC GCG CAC GTC ATC GTC GAA GAG GCG CCC GAG GCC GAC GAG CCC    12099
Thr Asn Ala His Val Ile Val Glu Glu Ala Pro Glu Ala Asp Glu Pro
    445                 450                 455

GAG CCG GCA CCC GAC TCG GGT CCG GTC CCG CTG GTG TTG TCC GGC CGC    12147
```

```
Glu  Pro  Ala  Pro  Asp  Ser  Gly  Pro  Val  Pro  Leu  Val  Leu  Ser  Gly  Arg
460            465                 470                 475

GAC  GAG  CAG  GCG  ATG  CGG  GCG  CAG  GCG  GGA  CGG  CTG  GCA  GAC  CAC  CTC   12195
Asp  Glu  Gln  Ala  Met  Arg  Ala  Gln  Ala  Gly  Arg  Leu  Ala  Asp  His  Leu
               480                 485                 490

GCC  CGC  GAG  CCG  CGG  AAC  TCG  TTG  CGC  GAC  ACC  GGT  TTC  ACG  CTG  GCC   12243
Ala  Arg  Glu  Pro  Arg  Asn  Ser  Leu  Arg  Asp  Thr  Gly  Phe  Thr  Leu  Ala
               495                 500                 505

ACC  CGC  CGC  AGC  GCG  TGG  GAG  CAC  CGC  GCG  GTG  GTG  GTC  GGC  GAC  CGC   12291
Thr  Arg  Arg  Ser  Ala  Trp  Glu  His  Arg  Ala  Val  Val  Val  Gly  Asp  Arg
               510                 515                 520

GAC  GAC  GCC  CTC  GCC  GGG  CTG  CGC  GCG  GTG  GCC  GAC  GGC  CGC  ATC  GCC   12339
Asp  Asp  Ala  Leu  Ala  Gly  Leu  Arg  Ala  Val  Ala  Asp  Gly  Arg  Ile  Ala
          525                 530                 535

GAC  CGG  ACG  GCC  ACC  GGG  CAG  GCC  CGA  ACT  CGC  CGC  GGC  GTC  GCG  ATG   12387
Asp  Arg  Thr  Ala  Thr  Gly  Gln  Ala  Arg  Thr  Arg  Arg  Gly  Val  Ala  Met
540                 545                 550                 555

GTG  TTC  CCC  GGC  CAG  GGC  GCG  CAG  TGG  CAG  GGG  ATG  GCC  CGC  GAC  CTG   12435
Val  Phe  Pro  Gly  Gln  Gly  Ala  Gln  Trp  Gln  Gly  Met  Ala  Arg  Asp  Leu
               560                 565                 570

CTG  CGG  GAG  TCG  CAG  GTA  TTC  GCC  GAC  TCG  ATC  CGC  GAC  TGC  GAG  CGG   12483
Leu  Arg  Glu  Ser  Gln  Val  Phe  Ala  Asp  Ser  Ile  Arg  Asp  Cys  Glu  Arg
               575                 580                 585

GCG  CTG  GCC  CCG  CAC  GTC  GAC  TGG  TCG  CTG  ACC  GAC  CTG  CTC  AGC  GGC   12531
Ala  Leu  Ala  Pro  His  Val  Asp  Trp  Ser  Leu  Thr  Asp  Leu  Leu  Ser  Gly
               590                 595                 600

GCG  CGA  CCG  CTG  GAC  CGG  GTC  GAC  GTC  GTC  CAG  CCC  GCG  CTC  TTC  GCC   12579
Ala  Arg  Pro  Leu  Asp  Arg  Val  Asp  Val  Val  Gln  Pro  Ala  Leu  Phe  Ala
          605                 610                 615

GTC  ATG  GTG  TCG  CTG  GCG  GCG  CTG  TGG  CGC  TCC  CAC  GGC  GTC  GAG  CCC   12627
Val  Met  Val  Ser  Leu  Ala  Ala  Leu  Trp  Arg  Ser  His  Gly  Val  Glu  Pro
620                 625                 630                 635

GCC  GCG  GTC  GTC  GGC  CAC  TCG  CAG  GGC  GAG  ATC  GCC  GCC  GCG  CAC  GTC   12675
Ala  Ala  Val  Val  Gly  His  Ser  Gln  Gly  Glu  Ile  Ala  Ala  Ala  His  Val
               640                 645                 650

GCC  GGC  GCG  CTC  ACC  CTG  GAG  GAC  GCC  GCC  AAG  CTC  GTC  GCG  GTC  CGG   12723
Ala  Gly  Ala  Leu  Thr  Leu  Glu  Asp  Ala  Ala  Lys  Leu  Val  Ala  Val  Arg
               655                 660                 665

AGC  CGG  GTC  CTG  GCC  CGG  CTC  GGC  GGC  CAG  GGC  GGC  ATG  GCG  TCG  TTC   12771
Ser  Arg  Val  Leu  Ala  Arg  Leu  Gly  Gly  Gln  Gly  Gly  Met  Ala  Ser  Phe
          670                 675                 680

GGG  CTG  GGC  ACC  GAG  CAG  GCG  GCC  GAA  CGG  ATC  GGG  CGC  TTC  GCG  GGC   12819
Gly  Leu  Gly  Thr  Glu  Gln  Ala  Ala  Glu  Arg  Ile  Gly  Arg  Phe  Ala  Gly
          685                 690                 695

GCG  CTC  TCC  ATC  GCC  TCG  GTC  AAC  GGC  CCC  CGG  TCG  GTC  GTC  GTC  GCG   12867
Ala  Leu  Ser  Ile  Ala  Ser  Val  Asn  Gly  Pro  Arg  Ser  Val  Val  Val  Ala
700                 705                 710                 715

GGG  GAG  AGC  GGG  CCG  CTG  GAC  GAG  CTG  ATC  GCC  GAG  TGC  GAG  GCC  GAA   12915
Gly  Glu  Ser  Gly  Pro  Leu  Asp  Glu  Leu  Ile  Ala  Glu  Cys  Glu  Ala  Glu
               720                 725                 730

GGC  ATA  ACG  GCG  CGC  CGC  ATC  CCC  GTC  GAC  TAC  GCC  TCC  CAC  TCA  CCG   12963
Gly  Ile  Thr  Ala  Arg  Arg  Ile  Pro  Val  Asp  Tyr  Ala  Ser  His  Ser  Pro
               735                 740                 745

CAG  GTG  GAG  TCG  CTG  CGC  GAG  GAG  CTG  CTG  ACC  GAG  CTG  GCG  GGC  ATC   13011
Gln  Val  Glu  Ser  Leu  Arg  Glu  Glu  Leu  Leu  Thr  Glu  Leu  Ala  Gly  Ile
          750                 755                 760

TCC  CCG  GTG  TCG  GCG  GAC  GTG  GCG  CTC  TAC  TCG  ACC  ACG  ACC  GGG  CAG   13059
Ser  Pro  Val  Ser  Ala  Asp  Val  Ala  Leu  Tyr  Ser  Thr  Thr  Thr  Gly  Gln
765                 770                 775

CCC  ATC  GAC  ACC  GCC  ACG  ATG  GAC  ACC  GCC  TAC  TGG  TAC  GCG  AAC  CTG   13107
```

```
        Pro  Ile  Asp  Thr  Ala  Thr  Met  Asp  Thr  Ala  Tyr  Trp  Tyr  Ala  Asn  Leu
        780            785                      790                      795

CGC GAG CAG GTC CGC TTC CAG GAC GCG ACG CGG CAG CTC GCC GAG GCG            13155
Arg Glu Gln Val Arg Phe Gln Asp Ala Thr Arg Gln Leu Ala Glu Ala
            800                      805                      810

GGG TTC GAC GCG TTC GTC GAG GTC AGC CCG CAT CCG GTG CTG ACC GTC            13203
Gly Phe Asp Ala Phe Val Glu Val Ser Pro His Pro Val Leu Thr Val
                815                      820                      825

GGC ATC GAG GCC ACG CTG GAC TCC GCG CTC CCG GCC GAC GCC GGC GCC            13251
Gly Ile Glu Ala Thr Leu Asp Ser Ala Leu Pro Ala Asp Ala Gly Ala
            830                      835                      840

TGC GTC GTG GGC ACC CTG CGG CGG GAC CGC GGC GGC CTG GCC GAC TTC            13299
Cys Val Val Gly Thr Leu Arg Arg Asp Arg Gly Gly Leu Ala Asp Phe
    845                      850                      855

CAC ACC GCG CTC GGC GAG GCG TAC GCG CAG GGC GTG GAG GTC GAC TGG            13347
His Thr Ala Leu Gly Glu Ala Tyr Ala Gln Gly Val Glu Val Asp Trp
860                      865                      870                      875

AGC CCC GCC TTC GCC GAC GCG CGG CCG GTC GAG CTG CCC GTC TAC CCG            13395
Ser Pro Ala Phe Ala Asp Ala Arg Pro Val Glu Leu Pro Val Tyr Pro
            880                      885                      890

TTC CAG CGG CAG CGG TAC TGG CTG CCC ATC CCC ACC GGC GGG CGC GCA            13443
Phe Gln Arg Gln Arg Tyr Trp Leu Pro Ile Pro Thr Gly Gly Arg Ala
                895                      900                      905

CGG GAC GAG GAC GAC GAC TGG CGC TAC CAG GTC GTA TGG CGG GAA GCC            13491
Arg Asp Glu Asp Asp Asp Trp Arg Tyr Gln Val Val Trp Arg Glu Ala
            910                      915                      920

GAG TGG GAG AGC GCT TCG CTG GCC GGA CGC GTG CTG CTG GTG ACC GGA            13539
Glu Trp Glu Ser Ala Ser Leu Ala Gly Arg Val Leu Leu Val Thr Gly
    925                      930                      935

CCG GGC GTG CCG TCC GAG TTG TCG GAC GCC ATC GAA AGT GGA CTG GAG            13587
Pro Gly Val Pro Ser Glu Leu Ser Asp Ala Ile Arg Ser Gly Leu Glu
940                      945                      950                      955

CAG AGC GGT GCG ACG GTC CTG ACC TGC GAC GTG GAA TCC CGT TCG ACC            13635
Gln Ser Gly Ala Thr Val Leu Thr Cys Asp Val Glu Ser Arg Ser Thr
            960                      965                      970

ATC GGC ACC GCA CTG GAG GCC GCC GAC ACC GAC GCT CTG TCC ACT GTG            13683
Ile Gly Thr Ala Leu Glu Ala Ala Asp Thr Asp Ala Leu Ser Thr Val
                975                      980                      985

GTG TCG CTG CTG TCC CGC GAC GGC GAG GCC GTC GAT CCG TCG CTG GAC            13731
Val Ser Leu Leu Ser Arg Asp Gly Glu Ala Val Asp Pro Ser Leu Asp
        990                      995                      1000

GCG CTC GCC CTG GTC CAG GCC CTC GGA GCG GCC GGG GTC GAA GCA CCG            13779
Ala Leu Ala Leu Val Gln Ala Leu Gly Ala Ala Gly Val Glu Ala Pro
        1005                     1010                     1015

CTG TGG GTG CTG ACC CGC AAC GCC GTG CAG GTG GCC GAC GGC GAA CTG            13827
Leu Trp Val Leu Thr Arg Asn Ala Val Gln Val Ala Asp Gly Glu Leu
1020                     1025                     1030                     1035

GTC GAT CCG GCG CAG GCC ATG GTG GGC GGT CTC GGC CGC GTG GTC GGC            13875
Val Asp Pro Ala Gln Ala Met Val Gly Gly Leu Gly Arg Val Val Gly
                1040                     1045                     1050

ATC GAG CAG CCG GGG CGC TGG GGC GGT CTG GTG GAC CTG GTC GAC GCC            13923
Ile Glu Gln Pro Gly Arg Trp Gly Gly Leu Val Asp Leu Val Asp Ala
            1055                     1060                     1065

GAT GCC GCG TCG ATC CGG TCG CTG GCC GCG GTG CTG GCG GAC CCG CGC            13971
Asp Ala Ala Ser Ile Arg Ser Leu Ala Ala Val Leu Ala Asp Pro Arg
        1070                     1075                     1080

GGC GAG GAG CAG GTC GCG ATC CGG GCG GAC GGG ATC AAG GTG GCG AGG            14019
Gly Glu Glu Gln Val Ala Ile Arg Ala Asp Gly Ile Lys Val Ala Arg
        1085                     1090                     1095

CTC GTG CCC GCC CCC GCC CGC GCC GCA CGC ACC CGC TGG AGC CCT CGC            14067
```

```
Leu  Val  Pro  Ala  Pro  Ala  Arg  Ala  Ala  Arg  Thr  Arg  Trp  Ser  Pro  Arg
1100                1105                      1110                     1115

GGC  ACC  GTG  CTG  GTC  ACC  GGC  GGC  ACC  GGA  GGG  ATC  GGC  GCG  CAC  GTC    14115
Gly  Thr  Val  Leu  Val  Thr  Gly  Gly  Thr  Gly  Gly  Ile  Gly  Ala  His  Val
               1120                     1125                          1130

GCC  CGC  TGG  CTG  GCC  CGC  TCG  GGC  GCC  GAG  CAC  CTG  GTG  CTG  CTG  GGC    14163
Ala  Arg  Trp  Leu  Ala  Arg  Ser  Gly  Ala  Glu  His  Leu  Val  Leu  Leu  Gly
               1135                     1140                          1145

AGG  CGC  GGT  GCC  GAC  GCA  CCC  GGC  GCG  TCC  GAG  CTG  AGG  GAG  GAG  CTG    14211
Arg  Arg  Gly  Ala  Asp  Ala  Pro  Gly  Ala  Ser  Glu  Leu  Arg  Glu  Glu  Leu
1150                1155                      1160

ACC  GCG  CTC  GGC  ACG  GGC  GTG  ACC  ATC  GCC  GCC  TGC  GAC  GTC  GCC  GAC    14259
Thr  Ala  Leu  Gly  Thr  Gly  Val  Thr  Ile  Ala  Ala  Cys  Asp  Val  Ala  Asp
               1165                     1170                          1175

CGG  GCG  CGG  CTC  GAA  GCG  GTG  CTC  GCC  GCG  GAG  CGC  GCC  GAG  GGA  CGC    14307
Arg  Ala  Arg  Leu  Glu  Ala  Val  Leu  Ala  Ala  Glu  Arg  Ala  Glu  Gly  Arg
1180                1185                      1190                     1195

ACG  GTC  AGC  GCC  GTG  ATG  CAC  GCG  GCG  GGG  GTT  TCC  ACG  TCC  ACG  CCC    14355
Thr  Val  Ser  Ala  Val  Met  His  Ala  Ala  Gly  Val  Ser  Thr  Ser  Thr  Pro
               1200                     1205                          1210

CTC  GAC  GAC  CTC  ACC  GAA  GCC  GAG  TTC  ACC  GAG  ATC  GCC  GAC  GTG  AAG    14403
Leu  Asp  Asp  Leu  Thr  Glu  Ala  Glu  Phe  Thr  Glu  Ile  Ala  Asp  Val  Lys
               1215                     1220                          1225

GTG  CGC  GGC  ACC  GTC  AAC  CTG  GAC  GAG  CTC  TGC  CCG  GAC  CTC  GAC  GCG    14451
Val  Arg  Gly  Thr  Val  Asn  Leu  Asp  Glu  Leu  Cys  Pro  Asp  Leu  Asp  Ala
               1230                     1235                          1240

TTC  GTG  TTG  TTC  TCC  TCC  AAC  GCG  GGC  GTG  TGG  GGC  AGT  CCG  GGG  CTC    14499
Phe  Val  Leu  Phe  Ser  Ser  Asn  Ala  Gly  Val  Trp  Gly  Ser  Pro  Gly  Leu
               1245                     1250                          1255

GCC  TCC  TAC  GCG  GCG  GCC  AAC  GCC  TTC  CTC  GAC  GGC  TTC  GCG  CGG  CGG    14547
Ala  Ser  Tyr  Ala  Ala  Ala  Asn  Ala  Phe  Leu  Asp  Gly  Phe  Ala  Arg  Arg
1260                1265                      1270                     1275

CGC  CGG  AGC  GAG  GGC  GCG  CCG  GTG  ACG  TCC  ATC  GCC  TGG  GGG  CTC  TGG    14595
Arg  Arg  Ser  Glu  Gly  Ala  Pro  Val  Thr  Ser  Ile  Ala  Trp  Gly  Leu  Trp
               1280                     1285                          1290

GCC  GGG  CAG  AAC  ATG  GCC  GGG  GAC  GAG  GGC  GGC  GAG  TAC  CTG  CGC  AGC    14643
Ala  Gly  Gln  Asn  Met  Ala  Gly  Asp  Glu  Gly  Gly  Glu  Tyr  Leu  Arg  Ser
               1295                     1300                          1305

CAG  GGC  CTG  CGG  GCC  ATG  GAC  CCG  GAT  CGG  GCC  GTC  GAG  GAA  CTG  CAC    14691
Gln  Gly  Leu  Arg  Ala  Met  Asp  Pro  Asp  Arg  Ala  Val  Glu  Glu  Leu  His
               1310                     1315                          1320

ATC  ACC  CTC  GAC  CAC  GGT  CAG  ACG  TCC  GTG  TCG  GTC  GTG  GAC  ATG  GAT    14739
Ile  Thr  Leu  Asp  His  Gly  Gln  Thr  Ser  Val  Ser  Val  Val  Asp  Met  Asp
               1325                     1330                          1335

CGC  AGG  CGG  TTC  GTC  GAG  CTG  TTC  ACC  GCG  GCC  CGG  CAC  CGG  CCG  CTG    14787
Arg  Arg  Arg  Phe  Val  Glu  Leu  Phe  Thr  Ala  Ala  Arg  His  Arg  Pro  Leu
1340                1345                      1350                     1355

TTC  GAC  GAG  ATC  GCC  GGT  GCC  CGG  GCG  GAA  GCC  CGG  CAG  AGC  GAG  GAG    14835
Phe  Asp  Glu  Ile  Ala  Gly  Ala  Arg  Ala  Glu  Ala  Arg  Gln  Ser  Glu  Glu
               1360                     1365                          1370

GGC  CCG  GCG  CTC  GCC  CAG  CGG  CTC  GCG  GCG  CTG  TCG  ACG  GCC  GAG  AGG    14883
Gly  Pro  Ala  Leu  Ala  Gln  Arg  Leu  Ala  Ala  Leu  Ser  Thr  Ala  Glu  Arg
               1375                     1380                          1385

CGC  GAG  CAC  CTC  GCC  CAC  CTG  ATC  CGC  GCC  GAG  GTC  GCC  GCG  GTG  CTC    14931
Arg  Glu  His  Leu  Ala  His  Leu  Ile  Arg  Ala  Glu  Val  Ala  Ala  Val  Leu
               1390                     1395                          1400

GGC  CAC  GGC  GAC  GAC  GCG  GCG  ATC  GAC  CGC  GAC  CGC  GCC  TTC  CGC  GAC    14979
Gly  His  Gly  Asp  Asp  Ala  Ala  Ile  Asp  Arg  Asp  Arg  Ala  Phe  Arg  Asp
               1405                     1410                          1415

CTC  GGC  TTC  GAC  TCC  ATG  ACC  GCC  GTC  GAC  CTG  CGG  AAC  CGG  CTC  GCC    15027
```

```
Leu Gly Phe Asp Ser Met Thr Ala Val Asp Leu Arg Asn Arg Leu Ala
1420                1425                1430                1435

GCG GTG ACC GGG GTG CGG GAA GCC GCG ACG GTG GTC TTC GAC CAC CCG    15075
Ala Val Thr Gly Val Arg Glu Ala Ala Thr Val Val Phe Asp His Pro
            1440                1445                1450

ACC ATC ACC CGG CTC GCC GAC CAC TAC CTG GAG CGG CTC GTC GGC GCA    15123
Thr Ile Thr Arg Leu Ala Asp His Tyr Leu Glu Arg Leu Val Gly Ala
            1455                1460                1465

GCA GAG GCG GAG CAA GCC CCG GCG CTC GTG CGC GAG GTG CCG AAG GAT    15171
Ala Glu Ala Glu Gln Ala Pro Ala Leu Val Arg Glu Val Pro Lys Asp
        1470                1475                1480

GCC GAC GAC CCG ATC GCG ATC GTC GGC ATG GCC TGC CGC TTC CCC GGC    15219
Ala Asp Asp Pro Ile Ala Ile Val Gly Met Ala Cys Arg Phe Pro Gly
        1485                1490                1495

GGC GTG CAC AAC CCC GGT GAG CTG TGG GAG TTC ATC GTC GGC CGC GGA    15267
Gly Val His Asn Pro Gly Glu Leu Trp Glu Phe Ile Val Gly Arg Gly
1500                1505                1510                1515

GAC GCC GTG ACG GAG ATG CCC ACC GAC CGC GGC TGG GAC CTC GAC GCG    15315
Asp Ala Val Thr Glu Met Pro Thr Asp Arg Gly Trp Asp Leu Asp Ala
                1520                1525                1530

CTG TTC GAC CCC GAC CCG CAG CGC CAC GGA ACC AGC TAC TCG CGA CAC    15363
Leu Phe Asp Pro Asp Pro Gln Arg His Gly Thr Ser Tyr Ser Arg His
            1535                1540                1545

GGC GCG TTC CTC GAC GGG GCC GCC GAC TTC GAC GCG GCG TTC TTC GGG    15411
Gly Ala Phe Leu Asp Gly Ala Ala Asp Phe Asp Ala Ala Phe Phe Gly
            1550                1555                1560

ATC TCG CCG CGC GAG GCG CTG GCG ATG GAC CCG CAG CAG CGC CAG GTC    15459
Ile Ser Pro Arg Glu Ala Leu Ala Met Asp Pro Gln Gln Arg Gln Val
        1565                1570                1575

CTG GAA ACG ACG TGG GAG CTG TTC GAG AAC GCC GGC ATC GAC CCG CAC    15507
Leu Glu Thr Thr Trp Glu Leu Phe Glu Asn Ala Gly Ile Asp Pro His
1580                1585                1590                1595

TCG CTG CGG GGC AGC GAC ACC GGC GTC TTC CTC GGC GCC GCG TAC CAG    15555
Ser Leu Arg Gly Ser Asp Thr Gly Val Phe Leu Gly Ala Ala Tyr Gln
                1600                1605                1610

GGC TAC GGC CAG GAC GCG GTG GTG CCC GAG GAC AGC GAG GGC TAC CTG    15603
Gly Tyr Gly Gln Asp Ala Val Val Pro Glu Asp Ser Glu Gly Tyr Leu
            1615                1620                1625

CTC ACC GGC AAC TCC TCC GCC GTG GTG TCC GGC CGG GTC GCC TAC GTG    15651
Leu Thr Gly Asn Ser Ser Ala Val Val Ser Gly Arg Val Ala Tyr Val
        1630                1635                1640

CTG GGG CTG GAA GGC CCC GCG GTC ACG GTG GAC ACG GCG TGT TCG TCG    15699
Leu Gly Leu Glu Gly Pro Ala Val Thr Val Asp Thr Ala Cys Ser Ser
    1645                1650                1655

TCG TTG GTG GCC TTG CAT TCG GCG TGT GGG TCG TTG CGT GAC GGT GAC    15747
Ser Leu Val Ala Leu His Ser Ala Cys Gly Ser Leu Arg Asp Gly Asp
1660                1665                1670                1675

TGC GGT CTT GCG GTG GCC GGT GGT GTG TCG GTG ATG GCG GGC CCG GAG    15795
Cys Gly Leu Ala Val Ala Gly Gly Val Ser Val Met Ala Gly Pro Glu
                1680                1685                1690

GTG TTC ACC GAG TTC TCC CGC CAG GGC GGC TTG GCC GTG GAC GGG CGC    15843
Val Phe Thr Glu Phe Ser Arg Gln Gly Gly Leu Ala Val Asp Gly Arg
            1695                1700                1705

TGC AAG GCG TTC TCC GCG GAG GCC GAC GGC TTC GGT TTC GCC GAG GGC    15891
Cys Lys Ala Phe Ser Ala Glu Ala Asp Gly Phe Gly Phe Ala Glu Gly
        1710                1715                1720

GTC GCG GTG GTC CTG CTC CAG CGG TTG TCC GAC GCC CGC AGG GCG GGT    15939
Val Ala Val Val Leu Leu Gln Arg Leu Ser Asp Ala Arg Arg Ala Gly
        1725                1730                1735

CGC CAG GTG CTC GGC GTG GTC GCG GGC TCG GCG ATC AAC CAG GAC GGC    15987
```

-continued

| | | | | | | | | | | | | | | | |
|---|---|---|---|---|---|---|---|---|---|---|---|---|---|---|---|
|Arg|Gln|Val|Leu|Gly|Val|Val|Ala|Gly|Ser|Ala|Ile|Asn|Gln|Asp|Gly|
|1740| | | |1745| | | |1750| | | | |1755| | |

```
GCG  AGC  AAC  GGT  CTC  GCG  GCG  CCG  AGC  GGC  GTC  GCC  CAG  CAG  CGC  GTG    16035
Ala  Ser  Asn  Gly  Leu  Ala  Ala  Pro  Ser  Gly  Val  Ala  Gln  Gln  Arg  Val
               1760                     1765                    1770

ATC  CGC  AAG  GCG  TGG  GCG  CGT  GCG  GGG  ATC  ACC  GGC  GCG  GAT  GTG  GCC    16083
Ile  Arg  Lys  Ala  Trp  Ala  Arg  Ala  Gly  Ile  Thr  Gly  Ala  Asp  Val  Ala
               1775                     1780                    1785

GTG  GTG  GAG  GCG  CAT  GGG  ACC  GGT  ACG  CGG  CTG  GGC  GAT  CCG  GTG  GAG    16131
Val  Val  Glu  Ala  His  Gly  Thr  Gly  Thr  Arg  Leu  Gly  Asp  Pro  Val  Glu
               1790                     1795                    1800

GCG  TCG  GCG  TTG  CTG  GCT  ACT  TAC  GGC  AAG  TCG  CGC  GGG  TCG  TCG  GGC    16179
Ala  Ser  Ala  Leu  Leu  Ala  Thr  Tyr  Gly  Lys  Ser  Arg  Gly  Ser  Ser  Gly
               1805                     1810                    1815

CCG  GTG  CTG  CTG  GGT  TCG  GTG  AAG  TCG  AAC  ATC  GGT  CAC  GCG  CAG  GCG    16227
Pro  Val  Leu  Leu  Gly  Ser  Val  Lys  Ser  Asn  Ile  Gly  His  Ala  Gln  Ala
1820                1825                    1830                     1835

GCC  GCG  GGT  GTC  GCG  GGC  GTG  ATC  AAG  GTG  GTC  CTG  GGG  TTG  AAC  CGC    16275
Ala  Ala  Gly  Val  Ala  Gly  Val  Ile  Lys  Val  Val  Leu  Gly  Leu  Asn  Arg
               1840                     1845                    1850

GGC  CTG  GTG  CCG  CCG  ATG  CTC  TGC  CGC  GGC  GAG  CGG  TCG  CCG  CTG  ATC    16323
Gly  Leu  Val  Pro  Pro  Met  Leu  Cys  Arg  Gly  Glu  Arg  Ser  Pro  Leu  Ile
               1855                     1860                    1865

GAA  TGG  TCC  TCG  GGT  GGT  GTG  GAA  CTT  GCC  GAG  GCC  GTG  AGC  CCG  TGG    16371
Glu  Trp  Ser  Ser  Gly  Gly  Val  Glu  Leu  Ala  Glu  Ala  Val  Ser  Pro  Trp
               1870                     1875                    1880

CCT  CCG  GCC  GCG  GAC  GGG  GTG  CGC  CGG  GCC  GGT  GTG  TCG  GCG  TTC  GGG    16419
Pro  Pro  Ala  Ala  Asp  Gly  Val  Arg  Arg  Ala  Gly  Val  Ser  Ala  Phe  Gly
               1885                     1890                    1895

GTG  AGC  GGG  ACG  AAC  GCG  CAC  GTG  ATC  ATC  GCC  GAG  CCC  CCG  GAG  CCC    16467
Val  Ser  Gly  Thr  Asn  Ala  His  Val  Ile  Ile  Ala  Glu  Pro  Pro  Glu  Pro
1900                1905                    1910                     1915

GAG  CCG  CTG  CCG  GAA  CCC  GGA  CCG  GTG  GGC  GTG  CTG  GCC  GCT  GCG  AAC    16515
Glu  Pro  Leu  Pro  Glu  Pro  Gly  Pro  Val  Gly  Val  Leu  Ala  Ala  Ala  Asn
               1920                     1925                    1930

TCG  GTG  CCC  GTA  CTG  CTG  TCG  GCC  AGG  ACC  GAG  ACC  GCG  TTG  GCA  GCG    16563
Ser  Val  Pro  Val  Leu  Leu  Ser  Ala  Arg  Thr  Glu  Thr  Ala  Leu  Ala  Ala
               1935                     1940                    1945

CAG  GCG  CGG  CTC  CTG  GAG  TCC  GCA  GTG  GAC  GAC  TCG  GTT  CCG  TTG  ACG    16611
Gln  Ala  Arg  Leu  Leu  Glu  Ser  Ala  Val  Asp  Asp  Ser  Val  Pro  Leu  Thr
               1950                     1955                    1960

GCA  TTG  GCT  TCC  GCG  CTG  GCC  ACC  GGA  CGC  GCC  CAC  CTG  CCG  CGT  CGT    16659
Ala  Leu  Ala  Ser  Ala  Leu  Ala  Thr  Gly  Arg  Ala  His  Leu  Pro  Arg  Arg
               1965                     1970                    1975

GCG  GCG  TTG  CTG  GCA  GGC  GAC  CAC  GAA  CAG  CTC  CGC  GGG  CAG  TTG  CGA    16707
Ala  Ala  Leu  Leu  Ala  Gly  Asp  His  Glu  Gln  Leu  Arg  Gly  Gln  Leu  Arg
1980                1985                    1990                     1995

GCG  GTC  GCC  GAG  GGC  GTT  GCG  GCT  CCC  GGT  GCC  ACC  ACC  GGA  ACC  GCC    16755
Ala  Val  Ala  Glu  Gly  Val  Ala  Ala  Pro  Gly  Ala  Thr  Thr  Gly  Thr  Ala
               2000                     2005                    2010

TCC  GCC  GGC  GGC  GTG  GTT  TTC  GTC  TTC  CCA  GGT  CAG  GGT  GCT  CAG  TGG    16803
Ser  Ala  Gly  Gly  Val  Val  Phe  Val  Phe  Pro  Gly  Gln  Gly  Ala  Gln  Trp
               2015                     2020                    2025

GAG  GGC  ATG  GCC  CGG  GGC  TTG  CTC  TCG  GTC  CCC  GTC  TTC  GCC  GAG  TCG    16851
Glu  Gly  Met  Ala  Arg  Gly  Leu  Leu  Ser  Val  Pro  Val  Phe  Ala  Glu  Ser
               2030                     2035                    2040

ATC  GCC  GAG  TGC  GAT  GCG  GTG  TTG  TCG  GAG  GTG  GCC  GGG  TTC  TCG  GCC    16899
Ile  Ala  Glu  Cys  Asp  Ala  Val  Leu  Ser  Glu  Val  Ala  Gly  Phe  Ser  Ala
               2045                     2050                    2055

TCC  GAA  GTG  CTG  GAG  CAG  CGT  CCG  GAC  GCG  CCG  TCG  CTG  GAG  CGG  GTC    16947
```

-continued

| | | | | | | | | | | | | | | | |
|---|---|---|---|---|---|---|---|---|---|---|---|---|---|---|---|
| Ser | Glu | Val | Leu | Glu | Gln | Arg | Pro | Asp | Ala | Pro | Ser | Leu | Glu | Arg | Val |
| 2060 | | | | 2065 | | | | 2070 | | | | | 2075 | | |

| GAC | GTC | GTA | CAG | CCG | GTG | TTG | TTC | TCC | GTG | ATG | GTG | TCG | CTG | GCG | CGG | 16995 |
|---|---|---|---|---|---|---|---|---|---|---|---|---|---|---|---|---|
| Asp | Val | Val | Gln | Pro | Val | Leu | Phe | Ser | Val | Met | Val | Ser | Leu | Ala | Arg | |
| | | | 2080 | | | | | 2085 | | | | | 2090 | | | |

| CTG | TGG | GGC | GCT | TGC | GGA | GTC | AGC | CCC | TCG | GCC | GTC | ATC | GGC | CAT | TCG | 17043 |
|---|---|---|---|---|---|---|---|---|---|---|---|---|---|---|---|---|
| Leu | Trp | Gly | Ala | Cys | Gly | Val | Ser | Pro | Ser | Ala | Val | Ile | Gly | His | Ser | |
| | | | 2095 | | | | | 2100 | | | | | 2105 | | | |

| CAG | GGC | GAG | ATC | GCC | GCC | GCG | GTG | GTG | GCC | GGG | GTG | TTG | TCG | CTG | GAG | 17091 |
|---|---|---|---|---|---|---|---|---|---|---|---|---|---|---|---|---|
| Gln | Gly | Glu | Ile | Ala | Ala | Ala | Val | Val | Ala | Gly | Val | Leu | Ser | Leu | Glu | |
| | | | 2110 | | | | | 2115 | | | | | 2120 | | | |

| GAC | GGC | GTG | CGC | GTC | GTG | GCC | CTG | CGC | GCG | AAG | GCG | TTG | CGT | GCG | CTG | 17139 |
|---|---|---|---|---|---|---|---|---|---|---|---|---|---|---|---|---|
| Asp | Gly | Val | Arg | Val | Val | Ala | Leu | Arg | Ala | Lys | Ala | Leu | Arg | Ala | Leu | |
| | | | 2125 | | | | | 2130 | | | | | 2135 | | | |

| GCG | GGC | AAG | GGC | GGC | ATG | GTC | TCG | TTG | GCG | GCT | CCC | GGT | GAA | CGC | GCC | 17187 |
|---|---|---|---|---|---|---|---|---|---|---|---|---|---|---|---|---|
| Ala | Gly | Lys | Gly | Gly | Met | Val | Ser | Leu | Ala | Ala | Pro | Gly | Glu | Arg | Ala | |
| 2140 | | | | 2145 | | | | 2150 | | | | | 2155 | | | |

| CGC | GCG | CTG | ATC | GCA | CCG | TGG | GAG | GAC | CGG | ATC | TCC | GTC | GCG | GCG | GTC | 17235 |
|---|---|---|---|---|---|---|---|---|---|---|---|---|---|---|---|---|
| Arg | Ala | Leu | Ile | Ala | Pro | Trp | Glu | Asp | Arg | Ile | Ser | Val | Ala | Ala | Val | |
| | | | 2160 | | | | | 2165 | | | | | 2170 | | | |

| AAC | TCC | CCG | TCC | TCG | GTC | GTG | GTC | TCC | GGC | GAT | CCG | GAG | GCG | CTG | GCC | 17283 |
|---|---|---|---|---|---|---|---|---|---|---|---|---|---|---|---|---|
| Asn | Ser | Pro | Ser | Ser | Val | Val | Val | Ser | Gly | Asp | Pro | Glu | Ala | Leu | Ala | |
| | | | 2175 | | | | | 2180 | | | | | 2185 | | | |

| GAA | CTC | GTC | GCA | CGT | TGC | GAG | GAC | GAG | GGC | GTG | CGC | GCC | AAG | ACG | CTC | 17331 |
|---|---|---|---|---|---|---|---|---|---|---|---|---|---|---|---|---|
| Glu | Leu | Val | Ala | Arg | Cys | Glu | Asp | Glu | Gly | Val | Arg | Ala | Lys | Thr | Leu | |
| | | | 2190 | | | | | 2195 | | | | | 2200 | | | |

| CCG | GTG | GAC | TAC | GCC | TCG | CAC | TCC | CGC | CAC | GTC | GAG | GAG | ATC | CGC | GAG | 17379 |
|---|---|---|---|---|---|---|---|---|---|---|---|---|---|---|---|---|
| Pro | Val | Asp | Tyr | Ala | Ser | His | Ser | Arg | His | Val | Glu | Glu | Ile | Arg | Glu | |
| | | | 2205 | | | | | 2210 | | | | | 2215 | | | |

| ACG | ATC | CTC | GCC | GAC | CTC | GAC | GGC | ATC | TCC | GCG | CGG | CGT | GCC | GCC | ATC | 17427 |
|---|---|---|---|---|---|---|---|---|---|---|---|---|---|---|---|---|
| Thr | Ile | Leu | Ala | Asp | Leu | Asp | Gly | Ile | Ser | Ala | Arg | Arg | Ala | Ala | Ile | |
| 2220 | | | | 2225 | | | | | 2230 | | | | | 2235 | | |

| CCG | CTC | TAC | TCC | ACG | CTG | CAC | GGC | GAA | CGG | CGC | GAC | GGC | GCC | GAC | ATG | 17475 |
|---|---|---|---|---|---|---|---|---|---|---|---|---|---|---|---|---|
| Pro | Leu | Tyr | Ser | Thr | Leu | His | Gly | Glu | Arg | Arg | Asp | Gly | Ala | Asp | Met | |
| | | | 2240 | | | | | 2245 | | | | | 2250 | | | |

| GGT | CCG | CGG | TAC | TGG | TAC | GAC | AAC | CTG | CGC | TCC | CAG | GTG | CGC | TTC | GAC | 17523 |
|---|---|---|---|---|---|---|---|---|---|---|---|---|---|---|---|---|
| Gly | Pro | Arg | Tyr | Trp | Tyr | Asp | Asn | Leu | Arg | Ser | Gln | Val | Arg | Phe | Asp | |
| | | | 2255 | | | | | 2260 | | | | | 2265 | | | |

| GAG | GCG | GTC | TCG | GCC | GCC | GTC | GCC | GAC | GGT | CAC | GCC | ACC | TTC | GTC | GAG | 17571 |
|---|---|---|---|---|---|---|---|---|---|---|---|---|---|---|---|---|
| Glu | Ala | Val | Ser | Ala | Ala | Val | Ala | Asp | Gly | His | Ala | Thr | Phe | Val | Glu | |
| | | | 2270 | | | | | 2275 | | | | | 2280 | | | |

| ATG | AGC | CCG | CAC | CCG | GTG | CTC | ACC | GCG | GCG | GTG | CAG | GAG | ATC | GCC | GCG | 17619 |
|---|---|---|---|---|---|---|---|---|---|---|---|---|---|---|---|---|
| Met | Ser | Pro | His | Pro | Val | Leu | Thr | Ala | Ala | Val | Gln | Glu | Ile | Ala | Ala | |
| | | | 2285 | | | | | 2290 | | | | | 2295 | | | |

| GAC | GCC | GTG | GCC | ATC | GGG | TCG | CTG | CAC | CGC | GAC | ACC | GCG | GAG | GAG | CAC | 17667 |
|---|---|---|---|---|---|---|---|---|---|---|---|---|---|---|---|---|
| Asp | Ala | Val | Ala | Ile | Gly | Ser | Leu | His | Arg | Asp | Thr | Ala | Glu | Glu | His | |
| 2300 | | | | 2305 | | | | | 2310 | | | | | 2315 | | |

| CTG | ATC | GCC | GAG | CTC | GCC | CGG | GCG | CAC | GTG | CAC | GGC | GTG | GCC | GTG | GAC | 17715 |
|---|---|---|---|---|---|---|---|---|---|---|---|---|---|---|---|---|
| Leu | Ile | Ala | Glu | Leu | Ala | Arg | Ala | His | Val | His | Gly | Val | Ala | Val | Asp | |
| | | | 2320 | | | | | 2325 | | | | | 2330 | | | |

| TGG | CGG | AAC | GTC | TTC | CCG | GCG | GCA | CCT | CCG | GTG | GCG | CTG | CCC | AAC | TAC | 17763 |
|---|---|---|---|---|---|---|---|---|---|---|---|---|---|---|---|---|
| Trp | Arg | Asn | Val | Phe | Pro | Ala | Ala | Pro | Pro | Val | Ala | Leu | Pro | Asn | Tyr | |
| | | | 2335 | | | | | 2340 | | | | | 2345 | | | |

| CCG | TTC | GAG | CCC | CAG | CGG | TAC | TGG | CTC | GCC | CCG | GAG | GTG | TCC | GAC | CAG | 17811 |
|---|---|---|---|---|---|---|---|---|---|---|---|---|---|---|---|---|
| Pro | Phe | Glu | Pro | Gln | Arg | Tyr | Trp | Leu | Ala | Pro | Glu | Val | Ser | Asp | Gln | |
| | | | 2350 | | | | | 2355 | | | | | 2360 | | | |

| CTC | GCC | GAC | AGC | CGC | TAC | CGC | GTC | GAC | TGG | CGA | CCG | CTG | GCC | ACC | ACG | 17859 |
|---|---|---|---|---|---|---|---|---|---|---|---|---|---|---|---|---|
| Leu | Ala | Asp | Ser | Arg | Tyr | Arg | Val | Asp | Trp | Arg | Pro | Leu | Ala | Thr | Thr | |
| | | | 2365 | | | | | 2370 | | | | | 2375 | | | |

| CCG | GTG | GAC | CTG | GAA | GGC | GGC | TTC | CTG | GTC | CAC | GGG | TCC | GCA | CCG | GAG | 17907 |

```
Pro Val Asp Leu Glu Gly Gly Phe Leu Val His Gly Ser Ala Pro Glu
2380                2385                2390                2395

TCG CTG ACC AGC GCA GTC GAG AAG GCC GGA GGC CGC GTC GTG CCG GTC    17955
Ser Leu Thr Ser Ala Val Glu Lys Ala Gly Gly Arg Val Val Pro Val
            2400                2405                2410

GCC TCG GCC GAC CGC GAA GCC TCG GCG GCC CTG CGG GAG GTG CCG GGC    18003
Ala Ser Ala Asp Arg Glu Ala Ser Ala Ala Leu Arg Glu Val Pro Gly
            2415                2420                2425

GAG GTC GCC GGC GTG CTC TCG GTC CAC ACC GGC GCC GCA ACG CAC CTC    18051
Glu Val Ala Gly Val Leu Ser Val His Thr Gly Ala Ala Thr His Leu
            2430                2435                2440

GCC CTG CAC CAG TCG CTG GGT GAG GCC GGC GTG CGG GCC CCG CTC TGG    18099
Ala Leu His Gln Ser Leu Gly Glu Ala Gly Val Arg Ala Pro Leu Trp
            2445                2450                2455

CTG GTC ACC AGC CGA GCG GTC GCG CTC GGG GAG TCC GAG CCG GTC GAT    18147
Leu Val Thr Ser Arg Ala Val Ala Leu Gly Glu Ser Glu Pro Val Asp
2460                2465                2470                2475

CCC GAG CAG GCG ATG GTG TGG GGT CTC GGG CGC GTC ATG GGC CTG GAG    18195
Pro Glu Gln Ala Met Val Trp Gly Leu Gly Arg Val Met Gly Leu Glu
            2480                2485                2490

ACC CCG GAA CGG TGG GGC GGT CTG GTG GAC CTG CCC GCC GAA CCC GCG    18243
Thr Pro Glu Arg Trp Gly Gly Leu Val Asp Leu Pro Ala Glu Pro Ala
            2495                2500                2505

CCG GGG GAC GGC GAG GCG TTC GTC GCC TGC CTC GGC GCG GAC GGC CAC    18291
Pro Gly Asp Gly Glu Ala Phe Val Ala Cys Leu Gly Ala Asp Gly His
            2510                2515                2520

GAG GAC CAG GTC GCG ATC CGT GAC CAC GCC CGC TAC GGC CGC CGC CTC    18339
Glu Asp Gln Val Ala Ile Arg Asp His Ala Arg Tyr Gly Arg Arg Leu
            2525                2530                2535

GTC CGC GCC CCG CTG GGC ACC CGC GAG TCG AGC TGG GAG CCG GCG GGC    18387
Val Arg Ala Pro Leu Gly Thr Arg Glu Ser Ser Trp Glu Pro Ala Gly
2540                2545                2550                2555

ACG GCG CTG GTC ACC GGC GGC ACC GGT GCG CTC GGC GGC CAC GTC GCC    18435
Thr Ala Leu Val Thr Gly Gly Thr Gly Ala Leu Gly Gly His Val Ala
            2560                2565                2570

CGC CAC CTC GCC AGG TGC GGG GTG GAG GAC CTG GTG CTG GTC AGC AGG    18483
Arg His Leu Ala Arg Cys Gly Val Glu Asp Leu Val Leu Val Ser Arg
            2575                2580                2585

CGC GGC GTC GAC GCT CCC GGC GCG GCC GAG CTG GAA GCC GAA CTG GTC    18531
Arg Gly Val Asp Ala Pro Gly Ala Ala Glu Leu Glu Ala Glu Leu Val
            2590                2595                2600

GCC CTC GGC GCG AAG ACG ACC ATC ACC GCC TGC GAC GTG GCC GAC CGC    18579
Ala Leu Gly Ala Lys Thr Thr Ile Thr Ala Cys Asp Val Ala Asp Arg
            2605                2610                2615

GAG CAG CTC TCC AAG CTG CTG GAA GAA CTG CGC GGG CAG GGA CGT CCG    18627
Glu Gln Leu Ser Lys Leu Leu Glu Glu Leu Arg Gly Gln Gly Arg Pro
2620                2625                2630                2635

GTG CGG ACC GTC GTG CAC ACC GCC GGG GTG CCC GAA TCG AGG CCG CTG    18675
Val Arg Thr Val Val His Thr Ala Gly Val Pro Glu Ser Arg Pro Leu
            2640                2645                2650

CAC GAG ATC GGC GAG CTG GAG TCG GTC TGC GCG GCG AAG GTG ACC GGG    18723
His Glu Ile Gly Glu Leu Glu Ser Val Cys Ala Ala Lys Val Thr Gly
            2655                2660                2665

GCC CGG CTG CTC GAC GAG CTG TGC CCG GAC GCC GAG ACC TTC GTC CTG    18771
Ala Arg Leu Leu Asp Glu Leu Cys Pro Asp Ala Glu Thr Phe Val Leu
            2670                2675                2680

TTC TCG TCC GGA GCG GGG GTG TGG GGC AGT GCG AAC CTC GGC GCC TAC    18819
Phe Ser Ser Gly Ala Gly Val Trp Gly Ser Ala Asn Leu Gly Ala Tyr
            2685                2690                2695

TCC GCG GCC AAC GCC TAC CTC GAC GCG CTG GCC CAC CGC CGC CGT GCG    18867
```

```
              Ser  Ala  Ala  Asn  Ala  Tyr  Leu  Asp  Ala  Leu  Ala  His  Arg  Arg  Arg  Ala
              2700                2705                2710                2715

GAA  GGC  CGT  GCG  GCG  ACG  TCC  GTC  GCG  TGG  GGC  GCC  TGG  GCG  GGC  GAG              18915
Glu  Gly  Arg  Ala  Ala  Thr  Ser  Val  Ala  Trp  Gly  Ala  Trp  Ala  Gly  Glu
              2720                2725                2730

GGC  ATG  GCC  ACC  GGC  GAC  CTC  GAG  GGG  CTC  ACC  CGG  CGC  GGC  CTG  CGC              18963
Gly  Met  Ala  Thr  Gly  Asp  Leu  Glu  Gly  Leu  Thr  Arg  Arg  Gly  Leu  Arg
              2735                2740                2745

CCG  ATG  GCG  CCC  GAG  CGC  GCG  ATC  CGC  GCG  CTG  CAC  CAG  GCG  CTG  GAC              19011
Pro  Met  Ala  Pro  Glu  Arg  Ala  Ile  Arg  Ala  Leu  His  Gln  Ala  Leu  Asp
              2750                2755                2760

AAC  GGC  GAC  ACG  TGC  GTT  TCG  ATC  GCC  GAC  GTC  GAC  TGG  GAG  GCC  TTC              19059
Asn  Gly  Asp  Thr  Cys  Val  Ser  Ile  Ala  Asp  Val  Asp  Trp  Glu  Ala  Phe
              2765                2770                2775

GCG  GTC  GGC  TTC  ACC  GCC  GCC  CGG  CCG  CGT  CCG  CTG  CTG  GAC  GAG  CTC              19107
Ala  Val  Gly  Phe  Thr  Ala  Ala  Arg  Pro  Arg  Pro  Leu  Leu  Asp  Glu  Leu
2780                2785                2790                2795

GTC  ACG  CCG  GCG  GTG  GGG  GCC  GTC  CCC  GCG  GTG  CAG  GCG  GCC  CCG  GCG              19155
Val  Thr  Pro  Ala  Val  Gly  Ala  Val  Pro  Ala  Val  Gln  Ala  Ala  Pro  Ala
              2800                2805                2810

CGG  GAG  ATG  ACG  TCG  CAG  GAG  TTG  CTG  GAG  TTC  ACG  CAC  TCG  CAC  GTC              19203
Arg  Glu  Met  Thr  Ser  Gln  Glu  Leu  Leu  Glu  Phe  Thr  His  Ser  His  Val
              2815                2820                2825

GCG  GCG  ATC  CTC  GGG  CAT  TCC  AGC  CCG  GAC  GCG  GTC  GGG  CAG  GAC  CAG              19251
Ala  Ala  Ile  Leu  Gly  His  Ser  Ser  Pro  Asp  Ala  Val  Gly  Gln  Asp  Gln
              2830                2835                2840

CCG  TTC  ACC  GAG  CTC  GGC  TTC  GAC  TCG  CTG  ACC  GCG  GTC  GGG  CTG  CGC              19299
Pro  Phe  Thr  Glu  Leu  Gly  Phe  Asp  Ser  Leu  Thr  Ala  Val  Gly  Leu  Arg
              2845                2850                2855

AAC  CAG  CTC  CAG  CAG  GCC  ACC  GGG  CTC  GCG  CTG  CCC  GCG  ACC  CTG  GTG              19347
Asn  Gln  Leu  Gln  Gln  Ala  Thr  Gly  Leu  Ala  Leu  Pro  Ala  Thr  Leu  Val
2860                2865                2870                2875

TTC  GAG  CAC  CCC  ACG  GTC  CGC  AGG  TTG  GCC  GAC  CAC  ATA  GGA  CAG  CAG              19395
Phe  Glu  His  Pro  Thr  Val  Arg  Arg  Leu  Ala  Asp  His  Ile  Gly  Gln  Gln
              2880                2885                2890

CTC  GAC  AGC  GGG  ACT  CCC  GCC  CGG  GAA  GCG  AGC  AGC  GCT  CTT  CGC  GAC              19443
Leu  Asp  Ser  Gly  Thr  Pro  Ala  Arg  Glu  Ala  Ser  Ser  Ala  Leu  Arg  Asp
              2895                2900                2905

GGC  TAC  CGG  CAG  GCG  GGC  GTG  TCG  GGC  AGG  GTC  CGG  TCC  TAC  CTC  GAC              19491
Gly  Tyr  Arg  Gln  Ala  Gly  Val  Ser  Gly  Arg  Val  Arg  Ser  Tyr  Leu  Asp
              2910                2915                2920

CTG  CTG  GCG  GGG  CTG  TCG  GAC  TTC  CGC  GAG  CAC  TTC  GAC  GGC  TCC  GAC              19539
Leu  Leu  Ala  Gly  Leu  Ser  Asp  Phe  Arg  Glu  His  Phe  Asp  Gly  Ser  Asp
              2925                2930                2935

GGG  TTC  TCC  CTC  GAT  CTC  GTG  GAC  ATG  GCC  GAC  GGT  CCC  GGA  GAG  GTC              19587
Gly  Phe  Ser  Leu  Asp  Leu  Val  Asp  Met  Ala  Asp  Gly  Pro  Gly  Glu  Val
2940                2945                2950                2955

ACG  GTG  ATC  TGC  TGC  GCG  GGA  ACG  GCG  GCG  ATC  TCC  GGT  CCG  CAC  GAG              19635
Thr  Val  Ile  Cys  Cys  Ala  Gly  Thr  Ala  Ala  Ile  Ser  Gly  Pro  His  Glu
              2960                2965                2970

TTC  ACC  CGG  CTC  GCC  GGG  GCG  CTG  CGC  GGA  ATC  GCT  CCG  GTT  CGG  GCC              19683
Phe  Thr  Arg  Leu  Ala  Gly  Ala  Leu  Arg  Gly  Ile  Ala  Pro  Val  Arg  Ala
              2975                2980                2985

GTG  CCC  CAG  CCC  GGC  TAC  GAG  GAG  GGC  GAA  CCT  CTG  CCG  TCG  TCG  ATG              19731
Val  Pro  Gln  Pro  Gly  Tyr  Glu  Glu  Gly  Glu  Pro  Leu  Pro  Ser  Ser  Met
              2990                2995                3000

GCG  GCG  GTG  GCG  GCG  GTG  CAG  GCC  GAT  GCG  GTC  ATC  AGG  ACA  CAG  GGG              19779
Ala  Ala  Val  Ala  Ala  Val  Gln  Ala  Asp  Ala  Val  Ile  Arg  Thr  Gln  Gly
              3005                3010                3015

GAC  AAG  CCG  TTC  GTG  GTG  GCC  GGT  CAC  TCC  GCG  GGG  GCA  CTG  ATG  GCC              19827
```

| | | | | | | | | | | | | | | | | |
|---|---|---|---|---|---|---|---|---|---|---|---|---|---|---|---|---|
| Asp | Lys | Pro | Phe | Val | Val | Ala | Gly | His | Ser | Ala | Gly | Ala | Leu | Met | Ala | |
| 3020 | | | | 3025 | | | | | 3030 | | | | | | 3035 | |

| TAC | GCG | CTG | GCG | ACC | GAA | CTG | CTC | GAT | CGC | GGG | CAC | CCG | CCA | CGC | GGT | 19875 |
|---|---|---|---|---|---|---|---|---|---|---|---|---|---|---|---|---|
| Tyr | Ala | Leu | Ala | Thr | Glu | Leu | Leu | Asp | Arg | Gly | His | Pro | Pro | Arg | Gly | |
| | | | | 3040 | | | | | 3045 | | | | | | 3050 | |

| GTC | GTC | CTG | ATC | GAC | GTC | TAC | CCG | CCC | GGT | CAC | CAG | GAC | GCG | ATG | AAC | 19923 |
|---|---|---|---|---|---|---|---|---|---|---|---|---|---|---|---|---|
| Val | Val | Leu | Ile | Asp | Val | Tyr | Pro | Pro | Gly | His | Gln | Asp | Ala | Met | Asn | |
| | | | | 3055 | | | | | 3060 | | | | | | 3065 | |

| GCC | TGG | CTG | GAG | GAG | CTG | ACC | GCC | ACG | CTG | TTC | GAC | CGC | GAG | ACG | GTG | 19971 |
|---|---|---|---|---|---|---|---|---|---|---|---|---|---|---|---|---|
| Ala | Trp | Leu | Glu | Glu | Leu | Thr | Ala | Thr | Leu | Phe | Asp | Arg | Glu | Thr | Val | |
| | | | | 3070 | | | | | 3075 | | | | | | 3080 | |

| CGG | ATG | GAC | GAC | ACC | AGG | CTC | ACC | GCC | CTG | GGC | GCC | TAC | GAC | CGC | CTC | 20019 |
|---|---|---|---|---|---|---|---|---|---|---|---|---|---|---|---|---|
| Arg | Met | Asp | Asp | Thr | Arg | Leu | Thr | Ala | Leu | Gly | Ala | Tyr | Asp | Arg | Leu | |
| | | | | 3085 | | | | | 3090 | | | | | | 3095 | |

| ACC | GGT | CAG | TGG | CGA | CCC | CGG | GAA | ACC | GGG | CTG | CCG | ACG | CTG | CTG | GTC | 20067 |
|---|---|---|---|---|---|---|---|---|---|---|---|---|---|---|---|---|
| Thr | Gly | Gln | Trp | Arg | Pro | Arg | Glu | Thr | Gly | Leu | Pro | Thr | Leu | Leu | Val | |
| 3100 | | | | | 3105 | | | | | 3110 | | | | | 3115 | |

| AGC | GCC | GGC | GAG | CCG | ATG | GGT | CCG | TGG | CCC | GAC | GAC | AGC | TGG | AAG | CCG | 20115 |
|---|---|---|---|---|---|---|---|---|---|---|---|---|---|---|---|---|
| Ser | Ala | Gly | Glu | Pro | Met | Gly | Pro | Trp | Pro | Asp | Asp | Ser | Trp | Lys | Pro | |
| | | | | 3120 | | | | | 3125 | | | | | | 3130 | |

| ACG | TGG | CCC | TTC | GAG | CAC | GAC | ACC | GTC | GCC | GTC | CCC | GGC | GAC | CAC | TTC | 20163 |
|---|---|---|---|---|---|---|---|---|---|---|---|---|---|---|---|---|
| Thr | Trp | Pro | Phe | Glu | His | Asp | Thr | Val | Ala | Val | Pro | Gly | Asp | His | Phe | |
| | | | | 3135 | | | | | 3140 | | | | | | 3145 | |

| ACG | ATG | GTG | CAG | GAA | CAC | GCC | GAC | GCG | ATC | GCG | CGG | CAC | ATC | GAC | GCC | 20211 |
|---|---|---|---|---|---|---|---|---|---|---|---|---|---|---|---|---|
| Thr | Met | Val | Gln | Glu | His | Ala | Asp | Ala | Ile | Ala | Arg | His | Ile | Asp | Ala | |
| | | | | 3150 | | | | | 3155 | | | | | | 3160 | |

| TGG | CTG | GGC | GGA | GGG | AAT | TCA | TGA | | | | | | | | | 20235 |
|---|---|---|---|---|---|---|---|---|---|---|---|---|---|---|---|---|
| Trp | Leu | Gly | Gly | Gly | Asn | Ser | | | | | | | | | | |
| 3165 | | | | | | 3170 | | | | | | | | | | |

( 2 ) INFORMATION FOR SEQ ID NO:4:

( i ) SEQUENCE CHARACTERISTICS:
        ( A ) LENGTH: 3567 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Val | Thr | Asp | Ser | Glu | Lys | Val | Ala | Glu | Tyr | Leu | Arg | Arg | Ala | Thr | Leu |
|---|---|---|---|---|---|---|---|---|---|---|---|---|---|---|---|
| 1 | | | | 5 | | | | | 10 | | | | | | 15 |

| Asp | Leu | Arg | Ala | Ala | Arg | Gln | Arg | Ile | Arg | Glu | Leu | Glu | Ser | Asp | Pro |
|---|---|---|---|---|---|---|---|---|---|---|---|---|---|---|---|
| | | | | 20 | | | | | 25 | | | | | 30 | |

| Ile | Ala | Ile | Val | Ser | Met | Ala | Cys | Arg | Leu | Pro | Gly | Gly | Val | Asn | Thr |
|---|---|---|---|---|---|---|---|---|---|---|---|---|---|---|---|
| | | | 35 | | | | | 40 | | | | | 45 | | |

| Pro | Gln | Arg | Leu | Trp | Glu | Leu | Leu | Arg | Glu | Gly | Gly | Glu | Thr | Leu | Ser |
|---|---|---|---|---|---|---|---|---|---|---|---|---|---|---|---|
| | 50 | | | | | 55 | | | | | 60 | | | | |

| Gly | Phe | Pro | Thr | Asp | Arg | Gly | Trp | Asp | Leu | Ala | Arg | Leu | His | His | Pro |
|---|---|---|---|---|---|---|---|---|---|---|---|---|---|---|---|
| 65 | | | | | 70 | | | | | 75 | | | | | 80 |

| Asp | Pro | Asp | Asn | Pro | Gly | Thr | Ser | Tyr | Val | Asp | Lys | Gly | Gly | Phe | Leu |
|---|---|---|---|---|---|---|---|---|---|---|---|---|---|---|---|
| | | | | 85 | | | | | 90 | | | | | 95 | |

| Asp | Asp | Ala | Ala | Gly | Phe | Asp | Ala | Glu | Phe | Phe | Gly | Val | Ser | Pro | Arg |
|---|---|---|---|---|---|---|---|---|---|---|---|---|---|---|---|
| | | | 100 | | | | | 105 | | | | | 110 | | |

| Glu | Ala | Ala | Ala | Met | Asp | Pro | Gln | Gln | Arg | Leu | Leu | Leu | Glu | Thr | Ser |
|---|---|---|---|---|---|---|---|---|---|---|---|---|---|---|---|
| | | | 115 | | | | | 120 | | | | | 125 | | |

| Trp | Glu | Leu | Val | Glu | Asn | Ala | Gly | Ile | Asp | Pro | His | Ser | Leu | Arg | Gly |
|---|---|---|---|---|---|---|---|---|---|---|---|---|---|---|---|
| | 130 | | | | | 135 | | | | | 140 | | | | |

| Thr | Ala | Thr | Gly | Val | Phe | Leu | Gly | Val | Ala | Lys | Phe | Gly | Tyr | Gly | Glu |
|---|---|---|---|---|---|---|---|---|---|---|---|---|---|---|---|
| 145 | | | | | 150 | | | | | 155 | | | | | 160 |

```
Asp Thr Ala Ala Ala Glu Asp Val Glu Gly Tyr Ser Val Thr Gly Val
                165             170             175
Ala Pro Ala Val Ala Ser Gly Arg Ile Ser Tyr Thr Met Gly Leu Glu
            180             185             190
Gly Pro Ser Ile Ser Val Asp Thr Ala Cys Ser Ser Ser Leu Val Ala
            195             200             205
Leu His Leu Ala Val Glu Ser Leu Arg Lys Gly Glu Ser Ser Met Ala
        210             215             220
Val Val Gly Gly Ala Ala Val Met Ala Thr Pro Gly Val Phe Val Asp
225             230             235                     240
Phe Ser Arg Gln Arg Ala Leu Ala Ala Asp Gly Arg Ser Lys Ala Phe
                245             250             255
Gly Ala Gly Ala Asp Gly Phe Gly Phe Ser Glu Gly Val Thr Leu Val
            260             265             270
Leu Leu Glu Arg Leu Ser Glu Ala Arg Arg Asn Gly His Glu Val Leu
            275             280             285
Ala Val Val Arg Gly Ser Ala Leu Asn Gln Asp Gly Ala Ser Asn Gly
            290             295             300
Leu Ser Ala Pro Ser Gly Pro Ala Gln Arg Arg Val Ile Arg Gln Ala
305             310             315                     320
Leu Glu Ser Cys Gly Leu Glu Pro Gly Asp Val Asp Ala Val Glu Ala
                325             330             335
His Gly Thr Gly Thr Ala Leu Gly Asp Pro Ile Glu Ala Asn Ala Leu
                340             345             350
Leu Asp Thr Tyr Gly Arg Asp Arg Asp Ala Asp Arg Pro Leu Trp Leu
            355             360             365
Gly Ser Val Lys Ser Asn Ile Gly His Thr Gln Ala Ala Ala Gly Val
        370             375             380
Thr Gly Leu Leu Lys Val Val Leu Ala Leu Arg Asn Gly Glu Leu Pro
385             390             395                     400
Ala Thr Leu His Val Glu Glu Pro Thr Pro His Val Asp Trp Ser Ser
                405             410             415
Gly Gly Val Ala Leu Leu Ala Gly Asn Gln Pro Trp Arg Arg Gly Glu
            420             425             430
Arg Thr Arg Arg Ala Arg Val Ser Ala Phe Gly Ile Ser Gly Thr Asn
            435             440             445
Ala His Val Ile Val Glu Glu Ala Pro Glu Arg Glu His Arg Glu Thr
        450             455             460
Thr Ala His Asp Gly Arg Pro Val Pro Leu Val Val Ser Ala Arg Thr
465             470             475                     480
Thr Ala Ala Leu Arg Ala Gln Ala Ala Gln Ile Ala Glu Leu Leu Glu
                485             490             495
Arg Pro Asp Ala Asp Leu Ala Gly Val Gly Leu Gly Leu Ala Thr Thr
            500             505             510
Arg Ala Arg His Glu His Arg Ala Ala Val Val Ala Ser Thr Arg Glu
            515             520             525
Glu Ala Val Arg Gly Leu Arg Glu Ile Ala Ala Gly Ala Ala Thr Ala
            530             535             540
Asp Ala Val Val Glu Gly Val Thr Glu Val Asp Gly Arg Asn Val Val
545             550             555                     560
Phe Leu Phe Pro Gly Gln Gly Ser Gln Trp Ala Gly Met Gly Ala Glu
                565             570             575
Leu Leu Ser Ser Ser Pro Val Phe Ala Gly Lys Ile Arg Ala Cys Asp
```

-continued

|  |  |  | 580 |  |  |  | 585 |  |  |  | 590 |  |  |  |
|---|---|---|---|---|---|---|---|---|---|---|---|---|---|---|
| Glu | Ser | Met 595 | Ala | Pro | Met | Gln | Asp 600 | Trp | Lys | Val | Ser | Val 605 | Leu | Arg |
| Gln | Ala | Pro 610 | Gly | Ala | Pro | Gly 615 | Leu | Asp | Arg | Val | Asp 620 | Val | Gln | Pro |
| Val 625 | Leu | Phe | Ala | Val | Met 630 | Val | Ser | Leu | Ala | Glu 635 | Leu | Trp | Arg | Ser | Tyr 640 |
| Gly | Val | Glu | Pro | Ala 645 | Ala | Val | Val | Gly | His 650 | Ser | Gln | Gly | Glu | Ile | Ala 655 |
| Ala | Ala | His | Val 660 | Ala | Gly | Ala | Leu | Thr 665 | Leu | Glu | Asp | Ala | Ala 670 | Lys | Leu |
| Val | Val | Gly 675 | Arg | Ser | Arg | Leu | Met 680 | Arg | Ser | Leu | Ser | Gly 685 | Glu | Gly | Gly |
| Met | Ala 690 | Ala | Val | Ala | Leu | Gly 695 | Glu | Ala | Ala | Val | Arg 700 | Glu | Arg | Leu | Arg |
| Pro 705 | Trp | Gln | Asp | Arg | Leu 710 | Ser | Val | Ala | Ala | Val 715 | Asn | Gly | Pro | Arg | Ser 720 |
| Val | Val | Val | Ser | Gly 725 | Glu | Pro | Gly | Ala | Leu 730 | Arg | Ala | Phe | Ser | Glu 735 | Asp |
| Cys | Ala | Ala | Glu 740 | Gly | Ile | Arg | Val | Arg 745 | Asp | Ile | Asp | Val | Asp 750 | Tyr | Ala |
| Ser | His | Ser 755 | Pro | Gln | Ile | Glu | Arg 760 | Val | Arg | Glu | Glu | Leu 765 | Leu | Glu | Thr |
| Thr | Gly 770 | Asp | Ile | Ala | Pro | Arg 775 | Pro | Ala | Arg | Val | Thr 780 | Phe | His | Ser | Thr |
| Val 785 | Glu | Ser | Arg | Ser | Met 790 | Asp | Gly | Thr | Glu | Leu 795 | Asp | Ala | Arg | Tyr | Trp 800 |
| Tyr | Arg | Asn | Leu | Arg 805 | Glu | Thr | Val | Arg | Phe 810 | Ala | Asp | Ala | Val | Thr 815 | Arg |
| Leu | Ala | Glu | Ser 820 | Gly | Tyr | Asp | Ala | Phe 825 | Ile | Glu | Val | Ser | Pro 830 | His | Pro |
| Val | Val | Val 835 | Gln | Ala | Val | Glu | Glu 840 | Ala | Val | Glu | Glu | Ala 845 | Asp | Gly | Ala |
| Glu | Asp 850 | Ala | Val | Val | Val | Gly 855 | Ser | Leu | His | Arg | Asp 860 | Gly | Gly | Asp | Leu |
| Ser 865 | Ala | Phe | Leu | Arg | Ser 870 | Met | Ala | Thr | Ala | His 875 | Val | Ser | Gly | Val | Asp 880 |
| Ile | Arg | Trp | Asp | Val 885 | Ala | Leu | Pro | Gly | Ala 890 | Ala | Pro | Phe | Ala | Leu 895 | Pro |
| Thr | Tyr | Pro | Phe 900 | Gln | Arg | Lys | Arg | Tyr 905 | Trp | Leu | Gln | Pro | Ala 910 | Ala | Pro |
| Ala | Ala | Ala 915 | Ser | Asp | Glu | Leu | Ala 920 | Tyr | Arg | Val | Ser | Trp 925 | Thr | Pro | Ile |
| Glu | Lys 930 | Pro | Glu | Ser | Gly | Asn 935 | Leu | Asp | Gly | Asp | Trp 940 | Leu | Val | Val | Thr |
| Pro 945 | Leu | Ile | Ser | Pro | Glu 950 | Trp | Thr | Glu | Met | Leu 955 | Cys | Glu | Ala | Ile | Asn 960 |
| Ala | Asn | Gly | Gly | Arg 965 | Ala | Leu | Arg | Cys | Glu 970 | Val | Asp | Thr | Ser | Ala 975 | Ser |
| Arg | Thr | Glu | Met 980 | Ala | Gln | Ala | Val | Ala 985 | Gln | Ala | Gly | Thr | Gly 990 | Phe | Arg |
| Gly | Val | Leu | Ser 995 | Leu | Leu | Ser | Ser | Asp 1000 | Glu | Ser | Ala | Cys | Arg 1005 | Pro | Gly |

```
Val Pro Ala Gly Ala Val Gly Leu Leu Thr Leu Val Gln Ala Leu Gly
    1010                1015                    1020

Asp Ala Gly Val Asp Ala Pro Val Trp Cys Leu Thr Gln Gly Ala Val
    1025                1030                    1035                1040

Arg Thr Pro Ala Asp Asp Leu Ala Arg Pro Ala Gln Thr Thr Ala
                    1045                1050                1055

His Gly Phe Ala Gln Val Ala Gly Leu Glu Leu Pro Gly Arg Trp Gly
                1060                1065                1070

Gly Val Val Asp Leu Pro Glu Ser Val Asp Ala Ala Leu Arg Leu
            1075                1080                1085

Leu Val Ala Val Leu Arg Gly Gly Arg Ala Glu Asp His Leu Ala
            1090                1095                1100

Val Arg Asp Gly Arg Leu His Gly Arg Arg Val Val Arg Ala Ser Leu
1105                1110                    1115                1120

Pro Gln Ser Gly Ser Arg Ser Trp Thr Pro His Gly Thr Val Leu Val
                    1125                1130                1135

Thr Gly Ala Ala Ser Pro Val Gly Asp Gln Leu Val Arg Trp Leu Ala
                    1140                1145                1150

Asp Arg Gly Ala Glu Arg Leu Val Leu Ala Gly Ala Cys Pro Gly Asp
                1155                1160                1165

Asp Leu Leu Ala Ala Val Glu Glu Ala Gly Ala Ser Ala Val Val Cys
    1170                1175                1180

Ala Gln Asp Ala Ala Ala Leu Arg Glu Ala Leu Gly Asp Glu Pro Val
1185                1190                    1195                1200

Thr Ala Leu Val His Ala Gly Thr Leu Thr Asn Phe Gly Ser Ile Ser
                    1205                1210                1215

Glu Val Ala Pro Glu Glu Phe Ala Glu Thr Ile Ala Ala Lys Thr Ala
                1220                1225                1230

Leu Leu Ala Val Leu Asp Glu Val Leu Gly Asp Arg Ala Val Glu Arg
            1235                1240                1245

Glu Val Tyr Cys Ser Ser Val Ala Gly Ile Trp Gly Gly Ala Gly Met
                1250                1255                1260

Ala Ala Tyr Ala Ala Gly Ser Ala Tyr Leu Asp Ala Leu Ala Glu His
1265                1270                    1275                1280

His Arg Ala Arg Gly Arg Ser Cys Thr Ser Val Ala Trp Thr Pro Trp
                    1285                1290                1295

Ala Leu Pro Gly Gly Ala Val Asp Asp Gly Tyr Leu Arg Glu Arg Gly
                1300                1305                1310

Leu Arg Ser Leu Ser Ala Asp Arg Ala Met Arg Thr Trp Glu Arg Val
            1315                1320                1325

Leu Ala Ala Gly Pro Val Ser Val Ala Val Ala Asp Val Asp Trp Pro
            1330                1335                1340

Val Leu Ser Glu Gly Phe Ala Ala Thr Arg Pro Thr Ala Leu Phe Ala
1345                1350                    1355                1360

Glu Leu Ala Gly Arg Gly Gly Gln Ala Glu Ala Glu Pro Asp Ser Gly
                    1365                1370                1375

Pro Thr Gly Glu Pro Ala Gln Arg Leu Ala Gly Leu Ser Pro Asp Glu
                1380                1385                1390

Gln Gln Glu Asn Leu Leu Glu Leu Val Ala Asn Ala Val Ala Glu Val
            1395                1400                1405

Leu Gly His Glu Ser Ala Ala Glu Ile Asn Val Arg Arg Ala Phe Ser
        1410                1415                1420

Glu Leu Gly Leu Asp Ser Leu Asn Ala Met Ala Leu Arg Lys Arg Leu
    1425                1430                1435                1440
```

```
Ser Ala Ser Thr Gly Leu Arg Leu Pro Ala Ser Leu Val Phe Asp His
                1445                1450                1455

Pro Thr Val Thr Ala Leu Ala Gln His Leu Arg Ala Arg Leu Val Gly
                1460                1465                1470

Asp Ala Asp Gln Ala Ala Val Arg Val Gly Ala Ala Asp Glu Ser
                1475                1480                1485

Glu Pro Ile Ala Ile Val Gly Ile Gly Cys Arg Phe Pro Gly Gly Ile
    1490                1495                1500

Gly Ser Pro Glu Gln Leu Trp Arg Val Leu Ala Glu Gly Ala Asn Leu
1505                1510                1515                1520

Thr Thr Gly Phe Pro Ala Asp Arg Gly Trp Asp Ile Gly Arg Leu Tyr
                1525                1530                1535

His Pro Asp Pro Asp Asn Pro Gly Thr Ser Tyr Val Asp Lys Gly Gly
                1540                1545                1550

Phe Leu Thr Asp Ala Ala Asp Phe Asp Pro Gly Phe Phe Gly Ile Thr
                1555                1560                1565

Pro Arg Glu Ala Leu Ala Met Asp Pro Gln Gln Arg Leu Met Leu Glu
                1570                1575                1580

Thr Ala Trp Glu Ala Val Glu Arg Ala Gly Ile Asp Pro Asp Ala Leu
1585                1590                1595                1600

Arg Gly Thr Asp Thr Gly Val Phe Val Gly Met Asn Gly Gln Ser Tyr
                1605                1610                1615

Met Gln Leu Leu Ala Gly Glu Ala Glu Arg Val Asp Gly Tyr Gln Gly
                1620                1625                1630

Leu Gly Asn Ser Ala Ser Val Leu Ser Gly Arg Ile Ala Tyr Thr Phe
                1635                1640                1645

Gly Trp Glu Gly Pro Ala Leu Thr Val Asp Thr Ala Cys Ser Ser Ser
                1650                1655                1660

Leu Val Gly Ile His Leu Ala Met Gln Ala Leu Arg Arg Gly Glu Cys
1665                1670                1675                1680

Ser Leu Ala Leu Ala Gly Gly Val Thr Val Met Ser Asp Pro Tyr Thr
                1685                1690                1695

Phe Val Asp Phe Ser Thr Gln Arg Gly Leu Ala Ser Asp Gly Arg Cys
                1700                1705                1710

Lys Ala Phe Ser Ala Arg Ala Asp Gly Phe Ala Leu Ser Glu Gly Val
                1715                1720                1725

Ala Ala Leu Val Leu Glu Pro Leu Ser Arg Ala Arg Ala Asn Gly His
                1730                1735                1740

Gln Val Leu Ala Val Leu Arg Gly Ser Ala Val Asn Gln Asp Gly Ala
1745                1750                1755                1760

Ser Asn Gly Leu Ala Ala Pro Asn Gly Pro Ser Gln Glu Arg Val Ile
                1765                1770                1775

Arg Gln Ala Leu Ala Ala Ser Gly Val Pro Ala Ala Asp Val Asp Val
                1780                1785                1790

Val Glu Ala His Gly Thr Gly Thr Glu Leu Gly Asp Pro Ile Glu Ala
                1795                1800                1805

Gly Ala Leu Ile Ala Thr Tyr Gly Gln Asp Arg Asp Arg Pro Leu Arg
                1810                1815                1820

Leu Gly Ser Val Lys Thr Asn Ile Gly His Thr Gln Ala Ala Ala Gly
1825                1830                1835                1840

Ala Ala Gly Val Ile Lys Val Val Leu Ala Met Arg His Gly Met Leu
                1845                1850                1855

Pro Arg Ser Leu His Ala Asp Glu Leu Ser Pro His Ile Asp Trp Glu
```

-continued

```
                   1860                    1865                    1870
Ser  Gly  Ala  Val  Glu  Val  Leu  Arg  Glu  Glu  Val  Pro  Trp  Pro  Ala  Gly
               1875                    1880                    1885
Glu  Arg  Pro  Arg  Arg  Ala  Gly  Val  Ser  Ser  Phe  Gly  Val  Ser  Gly  Thr
               1890                    1895                    1900
Asn  Ala  His  Val  Ile  Val  Glu  Glu  Ala  Pro  Ala  Glu  Gln  Glu  Ala  Ala
1905                              1910                    1915                    1920
Arg  Thr  Glu  Arg  Gly  Pro  Leu  Pro  Phe  Val  Leu  Ser  Gly  Arg  Ser  Glu
               1925                    1930                    1935
Ala  Val  Val  Ala  Ala  Gln  Ala  Arg  Ala  Leu  Ala  Glu  His  Leu  Arg  Asp
               1940                    1945                    1950
Thr  Pro  Glu  Leu  Gly  Leu  Thr  Asp  Ala  Ala  Trp  Thr  Leu  Ala  Thr  Gly
               1955                    1960                    1965
Arg  Ala  Arg  Phe  Asp  Val  Arg  Ala  Ala  Val  Leu  Gly  Asp  Asp  Arg  Ala
               1970                    1975                    1980
Gly  Val  Cys  Ala  Glu  Leu  Asp  Ala  Leu  Ala  Glu  Gly  Arg  Pro  Ser  Ala
1985                              1990                    1995                    2000
Asp  Ala  Val  Ala  Pro  Val  Thr  Ser  Ala  Pro  Arg  Lys  Pro  Val  Leu  Val
               2005                    2010                    2015
Phe  Pro  Gly  Gln  Gly  Ala  Gln  Trp  Val  Gly  Met  Ala  Arg  Asp  Leu  Leu
               2020                    2025                    2030
Glu  Ser  Ser  Glu  Val  Phe  Ala  Glu  Ser  Met  Ser  Arg  Cys  Ala  Glu  Ala
               2035                    2040                    2045
Leu  Ser  Pro  His  Thr  Asp  Trp  Lys  Leu  Leu  Asp  Val  Val  Arg  Gly  Asp
               2050                    2055                    2060
Gly  Gly  Pro  Asp  Pro  His  Glu  Arg  Val  Asp  Val  Leu  Gln  Pro  Val  Leu
2065                              2070                    2075                    2080
Phe  Ser  Ile  Met  Val  Ser  Leu  Ala  Glu  Leu  Trp  Arg  Ala  His  Gly  Val
               2085                    2090                    2095
Thr  Pro  Ala  Ala  Val  Val  Gly  His  Ser  Gln  Gly  Glu  Ile  Ala  Ala  Ala
               2100                    2105                    2110
His  Val  Ala  Gly  Ala  Leu  Ser  Leu  Glu  Ala  Ala  Ala  Lys  Val  Val  Ala
               2115                    2120                    2125
Leu  Arg  Ser  Gln  Val  Leu  Arg  Glu  Leu  Asp  Asp  Gln  Gly  Gly  Met  Val
               2130                    2135                    2140
Ser  Val  Gly  Ala  Ser  Arg  Asp  Glu  Leu  Glu  Thr  Val  Leu  Ala  Arg  Trp
2145                              2150                    2155                    2160
Asp  Gly  Arg  Val  Ala  Val  Ala  Ala  Val  Asn  Gly  Pro  Gly  Thr  Ser  Val
               2165                    2170                    2175
Val  Ala  Gly  Pro  Thr  Ala  Glu  Leu  Asp  Glu  Phe  Phe  Ala  Glu  Ala  Glu
               2180                    2185                    2190
Ala  Arg  Glu  Met  Lys  Pro  Arg  Arg  Ile  Ala  Val  Arg  Tyr  Ala  Ser  His
               2195                    2200                    2205
Ser  Pro  Glu  Val  Ala  Arg  Ile  Glu  Asp  Arg  Leu  Ala  Ala  Glu  Leu  Gly
               2210                    2215                    2220
Thr  Ile  Thr  Ala  Val  Arg  Gly  Ser  Val  Pro  Leu  His  Ser  Thr  Val  Thr
2225                              2230                    2235                    2240
Gly  Glu  Val  Ile  Asp  Thr  Ser  Ala  Met  Asp  Ala  Ser  Tyr  Trp  Tyr  Arg
               2245                    2250                    2255
Asn  Leu  Arg  Arg  Pro  Val  Leu  Phe  Glu  Gln  Ala  Val  Arg  Gly  Leu  Val
               2260                    2265                    2270
Glu  Gln  Gly  Phe  Asp  Thr  Phe  Val  Glu  Val  Ser  Pro  His  Pro  Val  Leu
               2275                    2280                    2285
```

```
Leu Met Ala Val Glu Glu Thr Ala Glu His Ala Gly Ala Glu Val Thr
2290                2295                2300
Cys Val Pro Thr Leu Arg Arg Glu Gln Ser Gly Pro His Glu Phe Leu
2305                2310                2315                2320
Arg Asn Leu Leu Arg Ala His Val His Gly Val Gly Ala Asp Leu Arg
                2325                2330                2335
Pro Ala Val Ala Gly Gly Arg Pro Ala Glu Leu Pro Thr Tyr Pro Phe
                2340                2345                2350
Glu His Gln Arg Phe Trp Pro Arg Pro His Arg Pro Ala Asp Val Ser
                2355                2360                2365
Ala Leu Gly Val Arg Gly Ala Glu His Pro Leu Leu Ala Ala Val
                2370                2375                2380
Asp Val Pro Gly His Gly Gly Ala Val Phe Thr Gly Arg Leu Ser Thr
2385                2390                2395                2400
Asp Glu Gln Pro Trp Leu Ala Glu His Val Val Gly Gly Arg Thr Leu
                2405                2410                2415
Val Pro Gly Ser Val Leu Val Asp Leu Ala Leu Ala Ala Gly Glu Asp
                2420                2425                2430
Val Gly Leu Pro Val Leu Glu Leu Val Leu Gln Arg Pro Leu Val
                2435                2440                2445
Leu Ala Gly Ala Gly Ala Leu Leu Arg Met Ser Val Gly Ala Pro Asp
                2450                2455                2460
Glu Ser Gly Arg Arg Thr Ile Asp Val His Ala Ala Glu Asp Val Ala
2465                2470                2475                2480
Asp Leu Ala Asp Ala Gln Trp Ser Gln His Ala Thr Gly Thr Leu Ala
                2485                2490                2495
Gln Gly Val Ala Ala Gly Pro Arg Asp Thr Glu Gln Trp Pro Pro Glu
                2500                2505                2510
Asp Ala Val Arg Ile Pro Leu Asp Asp His Tyr Asp Gly Leu Ala Glu
                2515                2520                2525
Gln Gly Tyr Glu Tyr Gly Pro Ser Phe Gln Ala Leu Arg Ala Ala Trp
                2530                2535                2540
Arg Lys Asp Asp Ser Val Tyr Ala Glu Val Ser Ile Ala Ala Asp Glu
2545                2550                2555                2560
Glu Gly Tyr Ala Phe His Pro Val Leu Leu Asp Ala Val Ala Gln Thr
                2565                2570                2575
Leu Ser Leu Gly Ala Leu Gly Glu Pro Gly Gly Gly Lys Leu Pro Phe
                2580                2585                2590
Ala Trp Asn Thr Val Thr Leu His Ala Ser Gly Ala Thr Ser Val Arg
                2595                2600                2605
Val Val Ala Thr Pro Ala Gly Ala Asp Ala Met Ala Leu Arg Val Thr
                2610                2615                2620
Asp Pro Ala Gly His Leu Val Ala Thr Val Asp Ser Leu Val Val Arg
2625                2630                2635                2640
Ser Thr Gly Glu Lys Trp Glu Gln Pro Glu Pro Arg Gly Gly Glu Gly
                2645                2650                2655
Glu Leu His Ala Leu Asp Trp Gly Arg Leu Ala Glu Pro Gly Ser Thr
                2660                2665                2670
Gly Arg Val Val Ala Ala Asp Ala Ser Asp Leu Asp Ala Val Leu Arg
                2675                2680                2685
Ser Gly Glu Pro Glu Pro Asp Ala Val Leu Val Arg Tyr Glu Pro Glu
                2690                2695                2700
Gly Asp Asp Pro Arg Ala Ala Ala Arg His Gly Val Leu Trp Ala Ala
                2705                2710                2715                2720
```

```
Ala Leu Val Arg Arg Trp Leu Glu Gln Glu Glu Leu Pro Gly Ala Thr
                2725                2730                2735
Leu Val Ile Ala Thr Ser Gly Ala Val Thr Val Ser Asp Asp Asp Ser
                2740                2745                2750
Val Pro Glu Pro Gly Ala Ala Ala Met Trp Gly Val Ile Arg Cys Ala
                2755                2760                2765
Gln Ala Glu Ser Pro Asp Arg Phe Val Leu Leu Asp Thr Asp Ala Glu
                2770                2775                2780
Pro Gly Met Leu Pro Ala Val Pro Asp Asn Pro Gln Leu Ala Leu Arg
2785                2790                2795                2800
Gly Asp Asp Val Phe Val Pro Arg Leu Ser Pro Leu Ala Pro Ser Ala
                2805                2810                2815
Leu Thr Leu Pro Ala Gly Thr Gln Arg Leu Val Pro Gly Asp Gly Ala
                2820                2825                2830
Ile Asp Ser Val Ala Phe Glu Pro Ala Pro Asp Val Glu Gln Pro Leu
                2835                2840                2845
Arg Ala Gly Glu Val Arg Val Asp Val Arg Ala Thr Gly Val Asn Phe
                2850                2855                2860
Arg Asp Val Leu Leu Ala Leu Gly Met Tyr Pro Gln Lys Ala Asp Met
2865                2870                2875                2880
Gly Thr Glu Ala Ala Gly Val Val Thr Ala Val Gly Pro Asp Val Asp
                2885                2890                2895
Ala Phe Ala Pro Gly Asp Arg Val Leu Gly Leu Phe Gln Gly Ala Phe
                2900                2905                2910
Ala Pro Ile Ala Val Thr Asp His Arg Leu Leu Ala Arg Val Pro Asp
                2915                2920                2925
Gly Trp Ser Asp Ala Asp Ala Ala Ala Val Pro Ile Ala Tyr Thr Thr
                2930                2935                2940
Ala His Tyr Ala Leu His Asp Leu Ala Gly Leu Arg Ala Gly Gln Ser
2945                2950                2955                2960
Val Leu Ile His Ala Ala Ala Gly Gly Val Gly Met Ala Ala Val Ala
                2965                2970                2975
Leu Ala Arg Arg Ala Gly Ala Glu Val Leu Ala Thr Ala Gly Pro Ala
                2980                2985                2990
Lys His Gly Thr Leu Arg Ala Leu Gly Leu Asp Asp Glu His Ile Ala
                2995                3000                3005
Ser Ser Arg Glu Thr Gly Phe Ala Arg Lys Phe Arg Glu Arg Thr Gly
                3010                3015                3020
Gly Arg Gly Val Asp Val Val Leu Asn Ser Leu Thr Gly Glu Leu Leu
3025                3030                3035                3040
Asp Glu Ser Ala Asp Leu Leu Ala Glu Asp Gly Val Phe Val Glu Met
                3045                3050                3055
Gly Lys Thr Asp Leu Arg Asp Ala Gly Asp Phe Arg Gly Arg Tyr Ala
                3060                3065                3070
Pro Phe Asp Leu Gly Glu Ala Gly Asp Asp Arg Leu Gly Glu Ile Leu
                3075                3080                3085
Arg Glu Val Val Gly Leu Leu Gly Ala Gly Glu Leu Asp Arg Leu Pro
                3090                3095                3100
Val Ser Ala Trp Glu Leu Gly Ser Ala Pro Ala Ala Leu Gln His Met
3105                3110                3115                3120
Ser Arg Gly Arg His Val Gly Lys Leu Val Leu Thr Gln Pro Ala Pro
                3125                3130                3135
Val Asp Pro Asp Gly Thr Val Leu Ile Thr Gly Gly Thr Gly Thr Leu
```

-continued

```
                       3140                         3145                         3150
Gly  Arg  Leu  Leu  Ala  Arg  His  Leu  Val  Thr  Glu  His  Gly  Val  Arg  His
                3155                         3160                         3165
Leu  Leu  Leu  Val  Ser  Arg  Arg  Gly  Ala  Asp  Ala  Pro  Gly  Ser  Asp  Glu
           3170                         3175                         3180
Leu  Arg  Ala  Glu  Ile  Glu  Asp  Leu  Gly  Ala  Ser  Ala  Glu  Ile  Ala  Ala
3185                         3190                         3195                         3200
Cys  Asp  Thr  Ala  Asp  Arg  Asp  Ala  Leu  Ser  Ala  Leu  Leu  Asp  Gly  Leu
                     3205                         3210                         3215
Pro  Arg  Pro  Leu  Thr  Gly  Val  Val  His  Ala  Ala  Gly  Val  Leu  Ala  Asp
                3220                         3225                         3230
Gly  Leu  Val  Thr  Ser  Ile  Asp  Glu  Pro  Ala  Val  Glu  Gln  Val  Leu  Arg
                3235                         3240                         3245
Ala  Lys  Val  Asp  Ala  Ala  Trp  Asn  Leu  His  Glu  Leu  Thr  Ala  Asn  Thr
           3250                         3255                         3260
Gly  Leu  Ser  Phe  Phe  Val  Leu  Phe  Ser  Ser  Ala  Ala  Ser  Val  Leu  Ala
3265                         3270                         3275                         3280
Gly  Pro  Gly  Gln  Gly  Val  Tyr  Ala  Ala  Ala  Asn  Glu  Ser  Leu  Asn  Ala
                3285                         3290                         3295
Leu  Ala  Ala  Leu  Arg  Arg  Thr  Arg  Gly  Leu  Pro  Ala  Lys  Ala  Leu  Gly
                3300                         3305                         3310
Trp  Gly  Leu  Trp  Ala  Gln  Ala  Ser  Glu  Met  Thr  Ser  Gly  Leu  Gly  Asp
                3315                         3320                         3325
Arg  Ile  Ala  Arg  Thr  Gly  Val  Ala  Ala  Leu  Pro  Thr  Glu  Arg  Ala  Leu
           3330                         3335                         3340
Ala  Leu  Phe  Asp  Ser  Ala  Leu  Arg  Arg  Gly  Gly  Glu  Val  Val  Phe  Pro
3345                         3350                         3355                         3360
Leu  Ser  Ile  Asn  Arg  Ser  Ala  Leu  Arg  Arg  Ala  Glu  Phe  Val  Pro  Glu
                     3365                         3370                         3375
Val  Leu  Arg  Gly  Met  Val  Arg  Ala  Lys  Leu  Arg  Ala  Ala  Gly  Gln  Ala
                3380                         3385                         3390
Glu  Ala  Ala  Gly  Pro  Asn  Val  Val  Asp  Arg  Leu  Ala  Gly  Arg  Ser  Glu
           3395                         3400                         3405
Ser  Asp  Gln  Val  Ala  Gly  Leu  Ala  Glu  Leu  Val  Arg  Ser  His  Ala  Ala
           3410                         3415                         3420
Ala  Val  Ser  Gly  Tyr  Gly  Ser  Ala  Asp  Gln  Leu  Pro  Glu  Arg  Lys  Ala
3425                         3430                         3435                         3440
Phe  Lys  Asp  Leu  Gly  Phe  Asp  Ser  Leu  Ala  Ala  Val  Glu  Leu  Arg  Asn
                     3445                         3450                         3455
Arg  Leu  Gly  Thr  Ala  Thr  Gly  Val  Arg  Leu  Pro  Ser  Thr  Leu  Val  Phe
                3460                         3465                         3470
Asp  His  Pro  Thr  Pro  Leu  Ala  Val  Ala  Glu  His  Leu  Arg  Asp  Arg  Leu
                3475                         3480                         3485
Phe  Ala  Ala  Ser  Pro  Ala  Val  Asp  Ile  Gly  Asp  Arg  Leu  Asp  Glu  Leu
           3490                         3495                         3500
Glu  Lys  Ala  Leu  Glu  Ala  Leu  Ser  Ala  Glu  Asp  Gly  His  Asp  Asp  Val
3505                         3510                         3515                         3520
Gly  Gln  Arg  Leu  Glu  Ser  Leu  Leu  Arg  Arg  Trp  Asn  Ser  Arg  Arg  Ala
                3525                         3530                         3535
Asp  Ala  Pro  Ser  Thr  Ser  Ala  Ile  Ser  Glu  Asp  Ala  Ser  Asp  Asp  Glu
                3540                         3545                         3550
Leu  Phe  Ser  Met  Leu  Asp  Gln  Arg  Phe  Gly  Gly  Gly  Glu  Asp  Leu
           3555                         3560                         3565
```

( 2 ) INFORMATION FOR SEQ ID NO:5:

( i ) SEQUENCE CHARACTERISTICS:
        ( A ) LENGTH: 3170 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Ser Gly Asp Asn Gly Met Thr Glu Glu Lys Leu Arg Arg Tyr Leu
 1               5                  10                  15
Lys Arg Thr Val Thr Glu Leu Asp Ser Val Thr Ala Arg Leu Arg Glu
             20                  25                  30
Val Glu His Arg Ala Gly Glu Pro Ile Ala Ile Val Gly Met Ala Cys
                 35                  40                  45
Arg Phe Pro Gly Asp Val Asp Ser Pro Glu Ser Phe Trp Glu Phe Val
         50                  55                  60
Ser Gly Gly Gly Asp Ala Ile Ala Glu Ala Pro Ala Asp Arg Gly Trp
 65                  70                  75                  80
Glu Pro Asp Pro Asp Ala Arg Leu Gly Gly Met Leu Ala Ala Ala Gly
                 85                  90                  95
Asp Phe Asp Ala Gly Phe Phe Gly Ile Ser Pro Arg Glu Ala Leu Ala
                100                 105                 110
Met Asp Pro Gln Gln Arg Ile Met Leu Glu Ile Ser Trp Glu Ala Leu
            115                 120                 125
Glu Arg Ala Gly His Asp Pro Val Ser Leu Arg Gly Ser Ala Thr Gly
        130                 135                 140
Val Phe Thr Gly Val Gly Thr Val Asp Tyr Gly Pro Arg Pro Asp Glu
145                 150                 155                 160
Ala Pro Asp Glu Val Leu Gly Tyr Val Gly Thr Gly Thr Ala Ser Ser
                165                 170                 175
Val Ala Ser Gly Arg Val Ala Tyr Cys Leu Gly Leu Glu Gly Pro Ala
                180                 185                 190
Met Thr Val Asp Thr Ala Cys Ser Ser Gly Leu Thr Ala Leu His Leu
            195                 200                 205
Ala Met Glu Ser Leu Arg Arg Asp Glu Cys Gly Leu Ala Leu Ala Gly
        210                 215                 220
Gly Val Thr Val Met Ser Ser Pro Gly Ala Phe Thr Glu Phe Arg Ser
225                 230                 235                 240
Gln Gly Gly Leu Ala Ala Asp Gly Arg Cys Lys Pro Phe Ser Lys Ala
                245                 250                 255
Ala Asp Gly Phe Gly Leu Ala Glu Gly Ala Gly Val Leu Val Leu Gln
                260                 265                 270
Arg Leu Ser Ala Ala Arg Arg Glu Gly Arg Pro Val Leu Ala Val Leu
            275                 280                 285
Arg Gly Ser Ala Val Asn Gln Asp Gly Ala Ser Asn Gly Leu Thr Ala
        290                 295                 300
Pro Ser Gly Pro Ala Gln Gln Arg Val Ile Arg Arg Ala Leu Glu Asn
305                 310                 315                 320
Ala Gly Val Arg Ala Gly Asp Val Asp Tyr Val Glu Ala His Gly Thr
                325                 330                 335
Gly Thr Arg Leu Gly Asp Pro Ile Glu Val His Ala Leu Leu Ser Thr
            340                 345                 350
Tyr Gly Ala Glu Arg Asp Pro Asp Asp Pro Leu Trp Ile Gly Ser Val
        355                 360                 365
```

-continued

| Lys | Ser | Asn | Ile | Gly | His | Thr | Gln | Ala | Ala | Ala | Gly | Val | Ala | Gly | Val |
|     | 370 |     |     |     |     | 375 |     |     |     | 380 |     |     |     |     |     |

| Met | Lys | Ala | Val | Leu | Ala | Leu | Arg | His | Gly | Glu | Met | Pro | Arg | Thr | Leu |
| 385 |     |     |     |     | 390 |     |     |     | 395 |     |     |     |     |     | 400 |

| His | Phe | Asp | Glu | Pro | Ser | Pro | Gln | Ile | Glu | Trp | Asp | Leu | Gly | Ala | Val |
|     |     |     |     | 405 |     |     |     |     | 410 |     |     |     |     | 415 |     |

| Ser | Val | Val | Ser | Gln | Ala | Arg | Ser | Trp | Pro | Ala | Gly | Glu | Arg | Pro | Arg |
|     |     |     | 420 |     |     |     |     | 425 |     |     |     |     | 430 |     |     |

| Arg | Ala | Gly | Val | Ser | Ser | Phe | Gly | Ile | Ser | Gly | Thr | Asn | Ala | His | Val |
|     |     | 435 |     |     |     |     | 440 |     |     |     |     | 445 |     |     |     |

| Ile | Val | Glu | Glu | Ala | Pro | Glu | Ala | Asp | Glu | Pro | Glu | Pro | Ala | Pro | Asp |
|     | 450 |     |     |     |     | 455 |     |     |     | 460 |     |     |     |     |     |

| Ser | Gly | Pro | Val | Pro | Leu | Val | Leu | Ser | Gly | Arg | Asp | Glu | Gln | Ala | Met |
| 465 |     |     |     |     | 470 |     |     |     |     | 475 |     |     |     |     | 480 |

| Arg | Ala | Gln | Ala | Gly | Arg | Leu | Ala | Asp | His | Leu | Ala | Arg | Glu | Pro | Arg |
|     |     |     |     | 485 |     |     |     |     | 490 |     |     |     |     | 495 |     |

| Asn | Ser | Leu | Arg | Asp | Thr | Gly | Phe | Thr | Leu | Ala | Thr | Arg | Arg | Ser | Ala |
|     |     |     |     | 500 |     |     |     |     | 505 |     |     |     |     | 510 |     |

| Trp | Glu | His | Arg | Ala | Val | Val | Val | Gly | Asp | Arg | Asp | Asp | Ala | Leu | Ala |
|     |     |     | 515 |     |     |     |     | 520 |     |     |     |     | 525 |     |     |

| Gly | Leu | Arg | Ala | Val | Ala | Asp | Gly | Arg | Ile | Ala | Asp | Arg | Thr | Ala | Thr |
|     |     | 530 |     |     |     |     |     | 535 |     |     |     |     | 540 |     |     |

| Gly | Gln | Ala | Arg | Thr | Arg | Arg | Gly | Val | Ala | Met | Val | Phe | Pro | Gly | Gln |
| 545 |     |     |     |     | 550 |     |     |     |     | 555 |     |     |     |     | 560 |

| Gly | Ala | Gln | Trp | Gln | Gly | Met | Ala | Arg | Asp | Leu | Leu | Arg | Glu | Ser | Gln |
|     |     |     |     | 565 |     |     |     |     | 570 |     |     |     |     | 575 |     |

| Val | Phe | Ala | Asp | Ser | Ile | Arg | Asp | Cys | Glu | Arg | Ala | Leu | Ala | Pro | His |
|     |     |     | 580 |     |     |     |     | 585 |     |     |     |     | 590 |     |     |

| Val | Asp | Trp | Ser | Leu | Thr | Asp | Leu | Leu | Ser | Gly | Ala | Arg | Pro | Leu | Asp |
|     |     |     | 595 |     |     |     |     | 600 |     |     |     |     | 605 |     |     |

| Arg | Val | Asp | Val | Val | Gln | Pro | Ala | Leu | Phe | Ala | Val | Met | Val | Ser | Leu |
|     |     | 610 |     |     |     |     | 615 |     |     |     |     | 620 |     |     |     |

| Ala | Ala | Leu | Trp | Arg | Ser | His | Gly | Val | Glu | Pro | Ala | Ala | Val | Val | Gly |
| 625 |     |     |     |     | 630 |     |     |     |     | 635 |     |     |     |     | 640 |

| His | Ser | Gln | Gly | Glu | Ile | Ala | Ala | Ala | His | Val | Ala | Gly | Ala | Leu | Thr |
|     |     |     |     | 645 |     |     |     |     | 650 |     |     |     |     | 655 |     |

| Leu | Glu | Asp | Ala | Ala | Lys | Leu | Val | Ala | Val | Arg | Ser | Arg | Val | Leu | Ala |
|     |     |     |     | 660 |     |     |     |     | 665 |     |     |     |     | 670 |     |

| Arg | Leu | Gly | Gly | Gln | Gly | Gly | Met | Ala | Ser | Phe | Gly | Leu | Gly | Thr | Glu |
|     |     |     | 675 |     |     |     |     | 680 |     |     |     |     | 685 |     |     |

| Gln | Ala | Ala | Glu | Arg | Ile | Gly | Arg | Phe | Ala | Gly | Ala | Leu | Ser | Ile | Ala |
|     | 690 |     |     |     |     | 695 |     |     |     |     | 700 |     |     |     |     |

| Ser | Val | Asn | Gly | Pro | Arg | Ser | Val | Val | Val | Ala | Gly | Glu | Ser | Gly | Pro |
| 705 |     |     |     |     | 710 |     |     |     |     | 715 |     |     |     |     | 720 |

| Leu | Asp | Glu | Leu | Ile | Ala | Glu | Cys | Glu | Ala | Glu | Gly | Ile | Thr | Ala | Arg |
|     |     |     |     | 725 |     |     |     |     | 730 |     |     |     |     | 735 |     |

| Arg | Ile | Pro | Val | Asp | Tyr | Ala | Ser | His | Ser | Pro | Gln | Val | Glu | Ser | Leu |
|     |     |     | 740 |     |     |     |     | 745 |     |     |     |     | 750 |     |     |

| Arg | Glu | Glu | Leu | Leu | Thr | Glu | Leu | Ala | Gly | Ile | Ser | Pro | Val | Ser | Ala |
|     |     | 755 |     |     |     |     | 760 |     |     |     |     | 765 |     |     |     |

| Asp | Val | Ala | Leu | Tyr | Ser | Thr | Thr | Thr | Gly | Gln | Pro | Ile | Asp | Thr | Ala |
|     | 770 |     |     |     |     | 775 |     |     |     |     | 780 |     |     |     |     |

| Thr | Met | Asp | Thr | Ala | Tyr | Trp | Tyr | Ala | Asn | Leu | Arg | Glu | Gln | Val | Arg |

```
785                     790                     795                     800

Phe  Gln  Asp  Ala  Thr  Arg  Gln  Leu  Ala  Glu  Ala  Gly  Phe  Asp  Ala  Phe
                    805                     810                     815

Val  Glu  Val  Ser  Pro  His  Pro  Val  Leu  Thr  Val  Gly  Ile  Glu  Ala  Thr
                    820                     825                     830

Leu  Asp  Ser  Ala  Leu  Pro  Ala  Asp  Ala  Gly  Ala  Cys  Val  Val  Gly  Thr
                    835                     840                     845

Leu  Arg  Arg  Asp  Arg  Gly  Gly  Leu  Ala  Asp  Phe  His  Thr  Ala  Leu  Gly
850                     855                     860

Glu  Ala  Tyr  Ala  Gln  Gly  Val  Glu  Val  Asp  Trp  Ser  Pro  Ala  Phe  Ala
865                     870                     875                     880

Asp  Ala  Arg  Pro  Val  Glu  Leu  Pro  Val  Tyr  Pro  Phe  Gln  Arg  Gln  Arg
                    885                     890                     895

Tyr  Trp  Leu  Pro  Ile  Pro  Thr  Gly  Gly  Arg  Ala  Arg  Asp  Glu  Asp  Asp
                    900                     905                     910

Asp  Trp  Arg  Tyr  Gln  Val  Val  Trp  Arg  Glu  Ala  Glu  Trp  Glu  Ser  Ala
                    915                     920                     925

Ser  Leu  Ala  Gly  Arg  Val  Leu  Leu  Val  Thr  Gly  Pro  Gly  Val  Pro  Ser
                    930                     935                     940

Glu  Leu  Ser  Asp  Ala  Ile  Arg  Ser  Gly  Leu  Glu  Gln  Ser  Gly  Ala  Thr
945                     950                     955                     960

Val  Leu  Thr  Cys  Asp  Val  Glu  Ser  Arg  Ser  Thr  Ile  Gly  Thr  Ala  Leu
                    965                     970                     975

Glu  Ala  Ala  Asp  Thr  Asp  Ala  Leu  Ser  Thr  Val  Val  Ser  Leu  Leu  Ser
                    980                     985                     990

Arg  Asp  Gly  Glu  Ala  Val  Asp  Pro  Ser  Leu  Asp  Ala  Leu  Ala  Leu  Val
                    995                     1000                    1005

Gln  Ala  Leu  Gly  Ala  Ala  Gly  Val  Glu  Ala  Pro  Leu  Trp  Val  Leu  Thr
                    1010                    1015                    1020

Arg  Asn  Ala  Val  Gln  Val  Ala  Asp  Gly  Glu  Leu  Val  Asp  Pro  Ala  Gln
                    1025                    1030                    1035                    1040

Ala  Met  Val  Gly  Gly  Leu  Gly  Arg  Val  Val  Gly  Ile  Glu  Gln  Pro  Gly
                    1045                    1050                    1055

Arg  Trp  Gly  Gly  Leu  Val  Asp  Leu  Val  Asp  Ala  Asp  Ala  Ala  Ser  Ile
                    1060                    1065                    1070

Arg  Ser  Leu  Ala  Ala  Val  Leu  Ala  Asp  Pro  Arg  Gly  Glu  Glu  Gln  Val
                    1075                    1080                    1085

Ala  Ile  Arg  Ala  Asp  Gly  Ile  Lys  Val  Ala  Arg  Leu  Val  Pro  Ala  Pro
                    1090                    1095                    1100

Ala  Arg  Ala  Ala  Arg  Thr  Arg  Trp  Ser  Pro  Arg  Gly  Thr  Val  Leu  Val
1105                    1110                    1115                    1120

Thr  Gly  Gly  Thr  Gly  Gly  Ile  Gly  Ala  His  Val  Ala  Arg  Trp  Leu  Ala
                    1125                    1130                    1135

Arg  Ser  Gly  Ala  Glu  His  Leu  Val  Leu  Leu  Gly  Arg  Arg  Gly  Ala  Asp
                    1140                    1145                    1150

Ala  Pro  Gly  Ala  Ser  Glu  Leu  Arg  Glu  Glu  Leu  Thr  Ala  Leu  Gly  Thr
                    1155                    1160                    1165

Gly  Val  Thr  Ile  Ala  Ala  Cys  Asp  Val  Ala  Asp  Arg  Ala  Arg  Leu  Glu
                    1170                    1175                    1180

Ala  Val  Leu  Ala  Ala  Glu  Arg  Ala  Glu  Gly  Arg  Thr  Val  Ser  Ala  Val
1185                    1190                    1195                    1200

Met  His  Ala  Ala  Gly  Val  Ser  Thr  Ser  Thr  Pro  Leu  Asp  Asp  Leu  Thr
                    1205                    1210                    1215
```

```
Glu Ala Glu Phe Thr Glu Ile Ala Asp Val Lys Val Arg Gly Thr Val
            1220                1225                1230
Asn Leu Asp Glu Leu Cys Pro Asp Leu Asp Ala Phe Val Leu Phe Ser
            1235                1240                1245
Ser Asn Ala Gly Val Trp Gly Ser Pro Gly Leu Ala Ser Tyr Ala Ala
            1250                1255                1260
Ala Asn Ala Phe Leu Asp Gly Phe Ala Arg Arg Arg Arg Ser Glu Gly
1265                1270                1275                1280
Ala Pro Val Thr Ser Ile Ala Trp Gly Leu Trp Ala Gly Gln Asn Met
            1285                1290                1295
Ala Gly Asp Glu Gly Gly Glu Tyr Leu Arg Ser Gln Gly Leu Arg Ala
            1300                1305                1310
Met Asp Pro Asp Arg Ala Val Glu Glu Leu His Ile Thr Leu Asp His
            1315                1320                1325
Gly Gln Thr Ser Val Ser Val Val Asp Met Asp Arg Arg Arg Phe Val
            1330                1335                1340
Glu Leu Phe Thr Ala Ala Arg His Arg Pro Leu Phe Asp Glu Ile Ala
1345                1350                1355                1360
Gly Ala Arg Ala Glu Ala Arg Gln Ser Glu Gly Pro Ala Leu Ala
            1365                1370                1375
Gln Arg Leu Ala Ala Leu Ser Thr Ala Glu Arg Arg Glu His Leu Ala
            1380                1385                1390
His Leu Ile Arg Ala Glu Val Ala Ala Val Leu Gly His Gly Asp Asp
            1395                1400                1405
Ala Ala Ile Asp Arg Asp Arg Ala Phe Arg Asp Leu Gly Phe Asp Ser
            1410                1415                1420
Met Thr Ala Val Asp Leu Arg Asn Arg Leu Ala Ala Val Thr Gly Val
1425                1430                1435                1440
Arg Glu Ala Ala Thr Val Val Phe Asp His Pro Thr Ile Thr Arg Leu
            1445                1450                1455
Ala Asp His Tyr Leu Glu Arg Leu Val Gly Ala Ala Glu Ala Glu Gln
            1460                1465                1470
Ala Pro Ala Leu Val Arg Glu Val Pro Lys Asp Ala Asp Asp Pro Ile
            1475                1480                1485
Ala Ile Val Gly Met Ala Cys Arg Phe Pro Gly Gly Val His Asn Pro
1490                1495                1500
Gly Glu Leu Trp Glu Phe Ile Val Gly Arg Gly Asp Ala Val Thr Glu
1505                1510                1515                1520
Met Pro Thr Asp Arg Gly Trp Asp Leu Asp Ala Leu Phe Asp Pro Asp
            1525                1530                1535
Pro Gln Arg His Gly Thr Ser Tyr Ser Arg His Gly Ala Phe Leu Asp
            1540                1545                1550
Gly Ala Ala Asp Phe Asp Ala Ala Phe Phe Gly Ile Ser Pro Arg Glu
            1555                1560                1565
Ala Leu Ala Met Asp Pro Gln Gln Arg Gln Val Leu Glu Thr Thr Trp
            1570                1575                1580
Glu Leu Phe Glu Asn Ala Gly Ile Asp Pro His Ser Leu Arg Gly Ser
1585                1590                1595                1600
Asp Thr Gly Val Phe Leu Gly Ala Ala Tyr Gln Gly Tyr Gly Gln Asp
            1605                1610                1615
Ala Val Val Pro Glu Asp Ser Glu Gly Tyr Leu Leu Thr Gly Asn Ser
            1620                1625                1630
Ser Ala Val Val Ser Gly Arg Val Ala Tyr Val Leu Gly Leu Glu Gly
            1635                1640                1645
```

Pro Ala Val Thr Val Asp Thr Ala Cys Ser Ser Ser Leu Val Ala Leu
          1650                1655                1660

His Ser Ala Cys Gly Ser Leu Arg Asp Gly Asp Cys Gly Leu Ala Val
1665                1670                1675                1680

Ala Gly Gly Val Ser Val Met Ala Gly Pro Glu Val Phe Thr Glu Phe
                1685                1690                1695

Ser Arg Gln Gly Gly Leu Ala Val Asp Gly Arg Cys Lys Ala Phe Ser
          1700                1705                1710

Ala Glu Ala Asp Gly Phe Gly Phe Ala Glu Gly Val Ala Val Val Leu
          1715                1720                1725

Leu Gln Arg Leu Ser Asp Ala Arg Arg Ala Gly Arg Gln Val Leu Gly
          1730                1735                1740

Val Val Ala Gly Ser Ala Ile Asn Gln Asp Gly Ala Ser Asn Gly Leu
1745                1750                1755                1760

Ala Ala Pro Ser Gly Val Ala Gln Gln Arg Val Ile Arg Lys Ala Trp
                1765                1770                1775

Ala Arg Ala Gly Ile Thr Gly Ala Asp Val Ala Val Val Glu Ala His
                1780                1785                1790

Gly Thr Gly Thr Arg Leu Gly Asp Pro Val Glu Ala Ser Ala Leu Leu
          1795                1800                1805

Ala Thr Tyr Gly Lys Ser Arg Gly Ser Ser Gly Pro Val Leu Leu Gly
          1810                1815                1820

Ser Val Lys Ser Asn Ile Gly His Ala Gln Ala Ala Ala Gly Val Ala
1825                1830                1835                1840

Gly Val Ile Lys Val Val Leu Gly Leu Asn Arg Gly Leu Val Pro Pro
                1845                1850                1855

Met Leu Cys Arg Gly Glu Arg Ser Pro Leu Ile Glu Trp Ser Ser Gly
                1860                1865                1870

Gly Val Glu Leu Ala Glu Ala Val Ser Pro Trp Pro Pro Ala Ala Asp
                1875                1880                1885

Gly Val Arg Arg Ala Gly Val Ser Ala Phe Gly Val Ser Gly Thr Asn
          1890                1895                1900

Ala His Val Ile Ile Ala Glu Pro Pro Glu Pro Glu Pro Leu Pro Glu
1905                1910                1915                1920

Pro Gly Pro Val Gly Val Leu Ala Ala Ala Asn Ser Val Pro Val Leu
                1925                1930                1935

Leu Ser Ala Arg Thr Glu Thr Ala Leu Ala Ala Gln Ala Arg Leu Leu
                1940                1945                1950

Glu Ser Ala Val Asp Asp Ser Val Pro Leu Thr Ala Leu Ala Ser Ala
          1955                1960                1965

Leu Ala Thr Gly Arg Ala His Leu Pro Arg Arg Ala Ala Leu Leu Ala
          1970                1975                1980

Gly Asp His Glu Gln Leu Arg Gly Gln Leu Arg Ala Val Ala Glu Gly
1985                1990                1995                2000

Val Ala Ala Pro Gly Ala Thr Thr Gly Thr Ala Ser Ala Gly Gly Val
                2005                2010                2015

Val Phe Val Phe Pro Gly Gln Gly Ala Gln Trp Glu Gly Met Ala Arg
                2020                2025                2030

Gly Leu Leu Ser Val Pro Val Phe Ala Glu Ser Ile Ala Glu Cys Asp
                2035                2040                2045

Ala Val Leu Ser Glu Val Ala Gly Phe Ser Ala Ser Glu Val Leu Glu
                2050                2055                2060

Gln Arg Pro Asp Ala Pro Ser Leu Glu Arg Val Asp Val Val Gln Pro

-continued

```
       2065                  2070                 2075                  2080
Val Leu Phe Ser Val Met Val Ser Leu Ala Arg Leu Trp Gly Ala Cys
                2085                2090                2095
Gly Val Ser Pro Ser Ala Val Ile Gly His Ser Gln Gly Glu Ile Ala
                2100                2105                2110
Ala Ala Val Val Ala Gly Val Leu Ser Leu Glu Asp Gly Val Arg Val
                2115                2120                2125
Val Ala Leu Arg Ala Lys Ala Leu Arg Ala Leu Ala Gly Lys Gly Gly
                2130                2135                2140
Met Val Ser Leu Ala Ala Pro Gly Glu Arg Ala Arg Ala Leu Ile Ala
2145                2150                2155                2160
Pro Trp Glu Asp Arg Ile Ser Val Ala Ala Val Asn Ser Pro Ser Ser
                2165                2170                2175
Val Val Val Ser Gly Asp Pro Glu Ala Leu Ala Glu Leu Val Ala Arg
                2180                2185                2190
Cys Glu Asp Glu Gly Val Arg Ala Lys Thr Leu Pro Val Asp Tyr Ala
                2195                2200                2205
Ser His Ser Arg His Val Glu Glu Ile Arg Glu Thr Ile Leu Ala Asp
                2210                2215                2220
Leu Asp Gly Ile Ser Ala Arg Arg Ala Ala Ile Pro Leu Tyr Ser Thr
2225                2230                2235                2240
Leu His Gly Glu Arg Arg Asp Gly Ala Asp Met Gly Pro Arg Tyr Trp
                2245                2250                2255
Tyr Asp Asn Leu Arg Ser Gln Val Arg Phe Asp Glu Ala Val Ser Ala
                2260                2265                2270
Ala Val Ala Asp Gly His Ala Thr Phe Val Glu Met Ser Pro His Pro
                2275                2280                2285
Val Leu Thr Ala Ala Val Gln Glu Ile Ala Ala Asp Ala Val Ala Ile
                2290                2295                2300
Gly Ser Leu His Arg Asp Thr Ala Glu Glu His Leu Ile Ala Glu Leu
2305                2310                2315                2320
Ala Arg Ala His Val His Gly Val Ala Val Asp Trp Arg Asn Val Phe
                2325                2330                2335
Pro Ala Ala Pro Pro Val Ala Leu Pro Asn Tyr Pro Phe Glu Pro Gln
                2340                2345                2350
Arg Tyr Trp Leu Ala Pro Glu Val Ser Asp Gln Leu Ala Asp Ser Arg
                2355                2360                2365
Tyr Arg Val Asp Trp Arg Pro Leu Ala Thr Thr Pro Val Asp Leu Glu
                2370                2375                2380
Gly Gly Phe Leu Val His Gly Ser Ala Pro Glu Ser Leu Thr Ser Ala
2385                2390                2395                2400
Val Glu Lys Ala Gly Gly Arg Val Val Pro Val Ala Ser Ala Asp Arg
                2405                2410                2415
Glu Ala Ser Ala Ala Leu Arg Glu Val Pro Gly Glu Val Ala Gly Val
                2420                2425                2430
Leu Ser Val His Thr Gly Ala Ala Thr His Leu Ala Leu His Gln Ser
                2435                2440                2445
Leu Gly Glu Ala Gly Val Arg Ala Pro Leu Trp Leu Val Thr Ser Arg
                2450                2455                2460
Ala Val Ala Leu Gly Glu Ser Glu Pro Val Asp Pro Glu Gln Ala Met
2465                2470                2475                2480
Val Trp Gly Leu Gly Arg Val Met Gly Leu Glu Thr Pro Glu Arg Trp
                2485                2490                2495
```

```
Gly  Gly  Leu  Val  Asp  Leu  Pro  Ala  Glu  Pro  Ala  Pro  Gly  Asp  Gly  Glu
              2500                    2505                    2510

Ala  Phe  Val  Ala  Cys  Leu  Gly  Ala  Asp  Gly  His  Glu  Asp  Gln  Val  Ala
              2515                    2520                    2525

Ile  Arg  Asp  His  Ala  Arg  Tyr  Gly  Arg  Arg  Leu  Val  Arg  Ala  Pro  Leu
              2530                    2535                    2540

Gly  Thr  Arg  Glu  Ser  Ser  Trp  Glu  Pro  Ala  Gly  Thr  Ala  Leu  Val  Thr
2545                     2550                    2555                         2560

Gly  Gly  Thr  Gly  Ala  Leu  Gly  Gly  His  Val  Ala  Arg  His  Leu  Ala  Arg
                    2565                    2570                    2575

Cys  Gly  Val  Glu  Asp  Leu  Val  Leu  Val  Ser  Arg  Arg  Gly  Val  Asp  Ala
                    2580                    2585                    2590

Pro  Gly  Ala  Ala  Glu  Leu  Glu  Ala  Glu  Leu  Val  Ala  Leu  Gly  Ala  Lys
                    2595                    2600                    2605

Thr  Thr  Ile  Thr  Ala  Cys  Asp  Val  Ala  Asp  Arg  Glu  Gln  Leu  Ser  Lys
                    2610                    2615                    2620

Leu  Leu  Glu  Glu  Leu  Arg  Gly  Gln  Gly  Arg  Pro  Val  Arg  Thr  Val  Val
2625                     2630                    2635                         2640

His  Thr  Ala  Gly  Val  Pro  Glu  Ser  Arg  Pro  Leu  His  Glu  Ile  Gly  Glu
                    2645                    2650                    2655

Leu  Glu  Ser  Val  Cys  Ala  Ala  Lys  Val  Thr  Gly  Ala  Arg  Leu  Leu  Asp
                    2660                    2665                    2670

Glu  Leu  Cys  Pro  Asp  Ala  Glu  Thr  Phe  Val  Leu  Phe  Ser  Ser  Gly  Ala
                    2675                    2680                    2685

Gly  Val  Trp  Gly  Ser  Ala  Asn  Leu  Gly  Ala  Tyr  Ser  Ala  Ala  Asn  Ala
                    2690                    2695                    2700

Tyr  Leu  Asp  Ala  Leu  Ala  His  Arg  Arg  Arg  Ala  Glu  Gly  Arg  Ala  Ala
2705                     2710                    2715                         2720

Thr  Ser  Val  Ala  Trp  Gly  Ala  Trp  Ala  Gly  Glu  Gly  Met  Ala  Thr  Gly
                    2725                    2730                    2735

Asp  Leu  Glu  Gly  Leu  Thr  Arg  Arg  Gly  Leu  Arg  Pro  Met  Ala  Pro  Glu
                    2740                    2745                    2750

Arg  Ala  Ile  Arg  Ala  Leu  His  Gln  Ala  Leu  Asp  Asn  Gly  Asp  Thr  Cys
                    2755                    2760                    2765

Val  Ser  Ile  Ala  Asp  Val  Asp  Trp  Glu  Ala  Phe  Ala  Val  Gly  Phe  Thr
2770                     2775                    2780

Ala  Ala  Arg  Pro  Arg  Pro  Leu  Leu  Asp  Glu  Leu  Val  Thr  Pro  Ala  Val
2785                     2790                    2795                         2800

Gly  Ala  Val  Pro  Ala  Val  Gln  Ala  Ala  Pro  Ala  Arg  Glu  Met  Thr  Ser
                    2805                    2810                    2815

Gln  Glu  Leu  Leu  Glu  Phe  Thr  His  Ser  His  Val  Ala  Ala  Ile  Leu  Gly
                    2820                    2825                    2830

His  Ser  Ser  Pro  Asp  Ala  Val  Gly  Gln  Asp  Gln  Pro  Phe  Thr  Glu  Leu
                    2835                    2840                    2845

Gly  Phe  Asp  Ser  Leu  Thr  Ala  Val  Gly  Leu  Arg  Asn  Gln  Leu  Gln  Gln
                    2850                    2855                    2860

Ala  Thr  Gly  Leu  Ala  Leu  Pro  Ala  Thr  Leu  Val  Phe  Glu  His  Pro  Thr
2865                     2870                    2875                         2880

Val  Arg  Arg  Leu  Ala  Asp  His  Ile  Gly  Gln  Gln  Leu  Asp  Ser  Gly  Thr
                    2885                    2890                    2895

Pro  Ala  Arg  Glu  Ala  Ser  Ser  Ala  Leu  Arg  Asp  Gly  Tyr  Arg  Gln  Ala
                    2900                    2905                    2910

Gly  Val  Ser  Gly  Arg  Val  Arg  Ser  Tyr  Leu  Asp  Leu  Leu  Ala  Gly  Leu
                    2915                    2920                    2925
```

Ser Asp Phe Arg Glu His Phe Asp Gly Ser Asp Gly Phe Ser Leu Asp
2930                     2935                 2940

Leu Val Asp Met Ala Asp Gly Pro Gly Glu Val Thr Val Ile Cys Cys
2945                 2950                 2955                 2960

Ala Gly Thr Ala Ala Ile Ser Gly Pro His Glu Phe Thr Arg Leu Ala
            2965                 2970                 2975

Gly Ala Leu Arg Gly Ile Ala Pro Val Arg Ala Val Pro Gln Pro Gly
            2980                 2985                 2990

Tyr Glu Glu Gly Glu Pro Leu Pro Ser Ser Met Ala Ala Val Ala Ala
            2995             3000                 3005

Val Gln Ala Asp Ala Val Ile Arg Thr Gln Gly Asp Lys Pro Phe Val
    3010                 3015             3020

Val Ala Gly His Ser Ala Gly Ala Leu Met Ala Tyr Ala Leu Ala Thr
3025             3030             3035                     3040

Glu Leu Leu Asp Arg Gly His Pro Pro Arg Gly Val Val Leu Ile Asp
            3045                 3050                 3055

Val Tyr Pro Pro Gly His Gln Asp Ala Met Asn Ala Trp Leu Glu Glu
            3060             3065             3070

Leu Thr Ala Thr Leu Phe Asp Arg Glu Thr Val Arg Met Asp Asp Thr
        3075             3080             3085

Arg Leu Thr Ala Leu Gly Ala Tyr Asp Arg Leu Thr Gly Gln Trp Arg
    3090             3095             3100

Pro Arg Glu Thr Gly Leu Pro Thr Leu Leu Val Ser Ala Gly Glu Pro
3105             3110             3115                 3120

Met Gly Pro Trp Pro Asp Asp Ser Trp Lys Pro Thr Trp Pro Phe Glu
            3125             3130             3135

His Asp Thr Val Ala Val Pro Gly Asp His Phe Thr Met Val Gln Glu
        3140             3145             3150

His Ala Asp Ala Ile Ala Arg His Ile Asp Ala Trp Leu Gly Gly Gly
        3155             3160             3165

Asn Ser
3170

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 1a ( x i ) SEQUENCE DESCRIPTION: SEQ ID NO:6:

GGGAGCATGC TCTCGGTGCG CGGCGGCCGC          30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 1b (x i) SEQUENCE DESCRIPTION: SEQ ID NO:7:

GCCCTGCAGC GCGTACTCCG AGGTGGCGGT 30

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i i) HYPOTHETICAL: NO (i x) FEATURE:
        (A) NAME/KEY: PCR primer 2a (x i) SEQUENCE DESCRIPTION: SEQ ID NO:8:

TGGTCTGCAG GCGAGGCCGG ACACCGAGG 29

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i i) HYPOTHETICAL: NO (i x) FEATURE:
        (A) NAME/KEY: PCR primer 2b (x i) SEQUENCE DESCRIPTION: SEQ ID NO:9:

GGAAGAAGTC AAAGTTCCTC GGTCCCTTCT 30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i i) HYPOTHETICAL: NO (i x) FEATURE:
        (A) NAME/KEY: PCR primer 3a (x i) SEQUENCE DESCRIPTION: SEQ ID NO:10:

GCGCGAGCTC GACGACCAGG GCGGCATGGT 30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i i) HYPOTHETICAL: NO (i x) FEATURE:
        (A) NAME/KEY: PCR primer 3b (x i) SEQUENCE DESCRIPTION: SEQ ID NO:11:

GGTGGCATGC TGCGACCACT GCGCGTCGGC 30

(2) INFORMATION FOR SEQ ID NO:12:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i i ) HYPOTHETICAL: NO ( i x ) FEATURE:
    ( A ) NAME/KEY: PCR primer 4a ( x i ) SEQUENCE DESCRIPTION: SEQ ID NO:12:

AGCTGCATGC TCTGGACTGG GGACGGCTAG           30

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 4b ( x i ) SEQUENCE DESCRIPTION: SEQ ID NO:13:

CGCGGGATCC CAGCTCCCAC GCCGATACCG           30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 5a ( x i ) SEQUENCE DESCRIPTION: SEQ ID NO:14:

TGCAGAATTC GCTGGCCGCG CTCTGGCGCT           30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 5b ( x i ) SEQUENCE DESCRIPTION: SEQ ID NO:15:

GAGAGCTGCA GCATGAGCCG CTGCTGCGGG           30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
    ( A ) NAME/KEY: PCR primer 6a ( x i ) SEQUENCE DESCRIPTION: SEQ ID NO:16:

CATGCTGCAG GACTTCAGCC GGATGAACTC    30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 6b ( x i ) SEQUENCE DESCRIPTION: SEQ ID NO:17:

GAGGAAGCTT CCAGCCGGTC CAGTTCGTCC    30

( 2 ) INFORMATION FOR SEQ ID NO:18:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 7a ( x i ) SEQUENCE DESCRIPTION: SEQ ID NO:18:

CGCCCGAATT CGAGGCGCTG GGCGCCCGGA C    31

( 2 ) INFORMATION FOR SEQ ID NO:19:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 7b ( x i ) SEQUENCE DESCRIPTION: SEQ ID NO:19:

CCACCTGCAG CGCGGGACCT TCCAGCCCC    29

( 2 ) INFORMATION FOR SEQ ID NO:20:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 8a ( x i ) SEQUENCE DESCRIPTION: SEQ ID NO:20:

GTGGGTCGCT GCAGACGGTG ACTGCGG    27

( 2 ) INFORMATION FOR SEQ ID NO:21:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 8b ( x i ) SEQUENCE DESCRIPTION: SEQ ID NO:21:

GGTCAAGCTT CGTCGGCGAG CAGCTTCTC 29

( 2 ) INFORMATION FOR SEQ ID NO:22:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 9a ( x i ) SEQUENCE DESCRIPTION: SEQ ID NO:22:

GCGCCGAATT CTCGAGACGG CGTGGGAGGC A 31

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 9b ( x i ) SEQUENCE DESCRIPTION: SEQ ID NO:23:

TTGCGGTACC AGTAGGAGGC GTCCATCGCG 30

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i x ) FEATURE:
        ( A ) NAME/KEY: PCR primer 10a ( x i ) SEQUENCE DESCRIPTION: SEQ ID NO:24:

GCTGGGATCC CGCGGCGCGG GTTGCAGCAC 30

( 2 ) INFORMATION FOR SEQ ID NO:25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (i i i) HYPOTHETICAL: NO (i x) FEATURE:
  (A) NAME/KEY: PCR primer 10b (x i) SEQUENCE DESCRIPTION: SEQ ID NO:25:

CGGAACTCGG TGAGCATGCC GGGACTGCTC                    30

(2) INFORMATION FOR SEQ ID NO:26:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (i i i) HYPOTHETICAL: NO (i x) FEATURE:
    (A) NAME/KEY: PCR primer 11a (x i) SEQUENCE DESCRIPTION: SEQ ID NO:26:

ATGCTCGAGA TCTCGTGGGA GGCGCTGGA                     29

(2) INFORMATION FOR SEQ ID NO:27:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i i) HYPOTHETICAL: NO (i x) FEATURE:
    (A) NAME/KEY: PCR primer 11b (x i) SEQUENCE DESCRIPTION: SEQ ID NO:27:

AGAACTCGGT GAGCATGCCC GGGCCCGCCA                    30

What is claimed is:

1. A method for directing the biosynthesis of a specific erythromycin analog by genetic manipulation of a gene encoding the deoxyerythronolide B synthase function of an erythromycin-producing microorganism, said method comprising the steps of:

(a) isolating a genomic DNA segment comprising the eryA gene of *Saccharopolyspora erythraea;*

(b) identifying discrete fragments of said genomic DNA each encoding a separate polypeptide domain, wherein each domain provides no more than one of the enzymatic activities associated with said deoxyerythronolide B synthase function, said enzymatic activities consisting of β-ketoreductase, dehydratase, acyl carrier protein, enoylreductase, β-ketoacyl ACP synthase and acyltransferase;

(c) altering at least one region of said eryA gene by modifying said DNA fragments to produce at least one alteration of said deoxyerythronolide B synthase function, said alteration selected from the group consisting of (i) inactivation of one or more domains providing enzymatic activity affecting the processing of β-carbonyl groups of polyketide subunits, (ii) addition of one or more domains providing enzymatic activity affecting the processing of β-carbonyl groups of polyketide subunits, (iii) inactivation of one or more domains providing enzymatic activity affecting the condensation of carbon units to a nascent deoxyerythronolide B structure, (iv) addition of domains providing enzymatic activities affecting the length of said deoxyerythronolide B structure, (v) deletion of one or more domains providing one or more enzymatic activities affecting the length of said deoxyerythronolide B structure, and (vi) substitution of one acyltransferase domain with another isologous acyltransferase domain of different specificity;

(d) transforming a cell of said erythromycin-producing microorganism with said altered region of said eryA gene under conditions suitable for the occurrence of a homologous recombination event replacing a corresponding region of said cell's eryA gene with said altered region;

(e) growing a culture of said transformed cell under conditions suitable for the formation of said specific erythromycin analog; and (f) isolating said specific erythromycin analog from said culture.

2. The method of claim 1 wherein said one or more inactivated domains providing enzymatic activity affecting the processing of β-carbonyl groups are selected from the group consisting of β-ketoreductase, dehydratase and enoylreductase.

3. The method of claim 2 wherein said one or more inactivated domains providing enzymatic activity affecting the processing of β-carbonyl groups is β-ketoreductase.

4. The method of claim 2 wherein said one or more inactivated domains providing enzymatic activity affecting the processing of β-carbonyl groups is dehydratase.

5. The method of claim 2 wherein said one or more inactivated domains providing enzymatic activity affecting the processing of β-carbonyl groups is enoylreductase.

6. The method of claim 1 wherein said one or more additional domains providing enzymatic activity affecting the processing of β-carbonyl groups are selected from the group consisting of (a) β-ketoreductase, (b) β-ketoreductase and dehydratase, and (c) β-ketoreductase, dehydratase and enoylreductase.

7. The method of claim 6 wherein said one or more additional domains providing enzymatic activity affecting the processing of β-carbonyl groups is β-ketoreductase.

8. The method of claim 6 wherein said one or more additional domains providing enzymatic activity affecting the processing of β-carbonyl groups is dehydratase.

9. The method of claim 6 wherein said one or more additional domains providing enzymatic activity affecting the processing of β-carbonyl groups is enoylreductase.

10. The method of claim 6 wherein said one or more additional domains providing enzymatic activity affecting the processing of β-carbonyl groups is β-ketoreductase and dehydratase.

11. The method of claim 6 wherein said one or more additional domains providing enzymatic activity affecting the processing of β-carbonyl groups is β-ketoreductase, dehydratase and enoylreductase.

12. The method of claim 1 wherein said one or more inactivated domains providing enzymatic activity affecting the condensation of carbon units to the nascent polyketide structure are selected from the group consisting of β-ketoacyl ACP synthase, acyl carrier protein and acyltransferase.

13. The method of claim 12 wherein said one or more inactivated domains providing enzymatic activity affecting the condensation of carbon units to the nascent polyketide structure is β-ketoacyl ACP synthase.

14. The method of claim 12 wherein said one or more inactivated domains providing enzymatic activity affecting the condensation of carbon units to the nascent polyketide structure is acyl carrier protein.

15. The method of claim 12 wherein said one or more inactivated domains providing enzymatic activity affecting the condensation of carbon units to the nascent polyketide structure is acyltransferase.

16. The method of claim 1 wherein said addition of domains providing enzymatic activities affecting the length of said deoxyerythronolide B results in an increase of said length, and said additional domains are acyltransferase, acyl carrier protein and β-ketoacyl ACP synthase.

17. The method of claim 1 wherein said deletion of one or more domains providing one or more enzymatic activities affecting the length of said deoxyerythronolide B results in a decrease of said length and consists of the deletion of one or more domains between two other domains or groups of domains providing corresponding enzymatic activities.

18. The method of claim 17 wherein said two other domains or groups of domains are selected from the group consisting of β-ketoreductases, dehydratases, acyl carrier proteins, β-ketoacyl ACP synthases and acyltransferases.

19. The method of claim 1 wherein said erythromycin analog is selected from the group consisting of 11-oxo-11-deoxyerythromycin A, 7-hydroxyerythromycin A, 6-deoxy-7-hydroxyerythromycin A, ((14S, 15S)14(1-hydroxyethyl) erythromycin A, 11-epifluoro-15-norerythromycin A, 14-(1-propyl)erythromycin A, and 14-(1-hydroxypropyl) erythromycin A.

20. The method of claim 19 wherein said erythromycin analog is 11-oxo-11-deoxyerythromycin A.

21. The method of claim 19 wherein said erythromycin analog is 7-hydroxyerythromycin A.

22. The method of claim 19 wherein said erythromycin analog is 6-deoxy-7-hydroxyerythromycin A.

23. The method of claim 19 wherein said erythromycin analog is ((14S, 15S)14(1-hydroxyethyl)erythromycin A.

24. The method of claim 19 wherein said erythromycin analog is 11-epifluoro-15-norerythromycin A.

25. The method of claim 19 wherein said erythromycin analog is 14-(1-hydroxypropyl)erythromycin A.

26. The method of claim 19 wherein said erythromycin analog is 14-(1-propyl)erythromycin A.

27. The method of claim 1 wherein said deoxyerythronolide B synthase function comprises the enzymatic activities associated with the formation of 6-deoxyerythronolide B.

28. The method of claim 1 wherein said isolated genomic DNA segment comprises a gene having the DNA sequence of FIG. 2.

* * * * *